US012686720B2

(12) United States Patent
Lugovskoy et al.

(10) Patent No.: US 12,686,720 B2
(45) Date of Patent: \*Jul. 21, 2026

(54) BISPECIFIC AGONISTIC ANTIBODIES TO ACTIVIN A RECEPTOR LIKE TYPE 1 (ALK1)

(71) Applicant: DIAGONAL THERAPEUTICS INC., Cambridge, MA (US)

(72) Inventors: Alexey Alexandrovich Lugovskoy, Belmont, MA (US); Jean-Christophe Hus, Concord, MA (US); Melissa Geddie, Arlington, MA (US)

(73) Assignee: DIAGONAL THERAPEUTICS INC., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/297,899

(22) Filed: Aug. 12, 2025

(65) Prior Publication Data

US 2026/0049149 A1       Feb. 19, 2026

Related U.S. Application Data

(60) Division of application No. 19/193,079, filed on Apr. 29, 2025, now Pat. No. 12,473,367, which is a continuation of application No. 18/628,187, filed on Apr. 5, 2024.

(60) Provisional application No. 63/596,899, filed on Nov. 7, 2023, provisional application No. 63/537,318, filed on Sep. 8, 2023, provisional application No. 63/458,044, filed on Apr. 7, 2023.

(51) Int. Cl.
| | |
|---|---|
| *A61K 39/395* | (2006.01) |
| *A61P 3/00* | (2006.01) |
| *C07K 16/28* | (2006.01) |
| *A61K 39/00* | (2006.01) |

(52) U.S. Cl.
CPC ............ *C07K 16/2863* (2013.01); *A61P 3/00* (2018.01); *C07K 16/2896* (2013.01); *A61K 2039/505* (2013.01); *C07K 2317/31* (2013.01); *C07K 2317/53* (2013.01); *C07K 2317/565* (2013.01); *C07K 2317/622* (2013.01); *C07K 2317/75* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,624,821 | A | 4/1997 | Winter et al. |
| 5,731,168 | A | 3/1998 | Carter et al. |
| 5,821,333 | A | 10/1998 | Carter et al. |
| 7,083,784 | B2 | 8/2006 | Dall'Acqua et al. |
| 7,537,762 | B2 | 5/2009 | North et al. |
| 7,592,428 | B1 | 9/2009 | Miyazono et al. |
| 7,612,181 | B2 | 11/2009 | Wu et al. |
| 8,012,704 | B2 | 9/2011 | Miyazono et al. |
| 8,158,584 | B2 | 4/2012 | Grinberg et al. |
| 8,216,805 | B2 | 7/2012 | Carter et al. |
| 8,409,577 | B2 | 4/2013 | Thompson et al. |
| 8,790,647 | B2 | 7/2014 | Greenwood et al. |
| 8,926,976 | B2 | 1/2015 | Corbin et al. |
| 8,969,526 | B2 | 3/2015 | Baehner et al. |
| 9,066,930 | B2 | 6/2015 | Yan et al. |
| 9,212,230 | B2 | 12/2015 | Schuurman et al. |
| 9,499,634 | B2 | 11/2016 | Dixit et al. |
| 10,106,621 | B2 | 10/2018 | Cobbold et al. |
| 10,919,947 | B2 | 2/2021 | Kwon et al. |
| 11,046,780 | B2 | 6/2021 | Satoh et al. |
| 11,136,581 | B2 | 10/2021 | Karthikeyan et al. |
| 11,236,131 | B2 | 2/2022 | Cobbold et al. |
| 11,292,846 | B2 | 4/2022 | Weber et al. |
| 11,440,949 | B2 | 9/2022 | Kumar et al. |
| 2009/0017019 | A1 | 1/2009 | Shields et al. |
| 2009/0258420 | A1 | 10/2009 | Van Vlijmen et al. |
| 2010/0129929 | A1 | 5/2010 | Polakewicz et al. |
| 2010/0233079 | A1 | 9/2010 | Jakob et al. |
| 2010/0331527 | A1 | 12/2010 | Davis et al. |
| 2011/0110944 | A1 | 5/2011 | Steidl et al. |
| 2013/0202594 | A1 | 8/2013 | Bhatt et al. |
| 2014/0154254 | A1 | 6/2014 | Kannan et al. |
| 2014/0193425 | A1 | 7/2014 | Knopf et al. |
| 2014/0294834 | A1 | 10/2014 | Harms et al. |
| 2015/0147327 | A1 | 5/2015 | Wu et al. |
| 2015/0299677 | A1 | 10/2015 | Alimzhanov et al. |
| 2015/0307625 | A1 | 10/2015 | Zhao et al. |
| 2015/0307628 | A1 | 10/2015 | Kim et al. |
| 2017/0095512 | A1 | 4/2017 | Izrael et al. |
| 2019/0048063 | A1 | 2/2019 | Grinberg et al. |
| 2020/0087367 | A1 | 3/2020 | Li et al. |
| 2020/0332013 | A1 | 10/2020 | Weber et al. |

(Continued)

FOREIGN PATENT DOCUMENTS

| | | | |
|---|---|---|---|
| EP | | 2351838 A1 | 8/2011 |
| WO | WO 1998/050431 | A2 | 11/1998 |
| WO | WO 1999/046386 | B1 | 9/1999 |
| WO | WO 1999/051642 | A1 | 10/1999 |
| WO | WO 2004/029207 | A2 | 4/2004 |
| WO | WO 2006/012627 | A2 | 2/2006 |
| WO | WO 2007/024715 | A2 | 3/2007 |
| WO | WO 2008/097541 | A2 | 8/2008 |
| WO | WO 2008/128559 | A1 | 10/2008 |
| WO | WO 2009/139891 | A2 | 11/2009 |
| WO | WO 2010/126169 | A1 | 11/2010 |
| WO | WO 2011/056494 | A1 | 5/2011 |
| WO | WO 2013/064701 | A2 | 5/2013 |

(Continued)

OTHER PUBLICATIONS

Carter, "Bispecific human IgG by design", Immunol. Methods, Feb. 1, 2001, 248(1-2): 7-15.

(Continued)

*Primary Examiner* — Meera Natarajan
(74) *Attorney, Agent, or Firm* — LATHROP GPM LLP; James H. Velema, Esq.; Michael J. Spellberg, Esq.

(57) ABSTRACT

Provided herein are bispecific agonistic antibodies that bind to ALK1, BMPRII, ActRIIA, and/or ActRIIB, and methods of using the same.

30 Claims, 4 Drawing Sheets

Specification includes a Sequence Listing.

(56) References Cited

U.S. PATENT DOCUMENTS

| | | | |
|---|---|---|---|
| 2021/0130867 A1 | 5/2021 | Bahn et al. | |
| 2021/0403549 A1 | 12/2021 | Sessa et al. | |
| 2022/0098329 A1 | 3/2022 | Santich et al. | |
| 2022/0185901 A1 | 6/2022 | Weber et al. | |
| 2022/0242958 A1 | 8/2022 | Roobrouck et al. | |
| 2022/0306735 A1 | 9/2022 | Dekosky et al. | |
| 2022/0347322 A1 | 11/2022 | Wang | |
| 2022/0389096 A1 | 12/2022 | Schonfeld et al. | |
| 2022/0395544 A1 | 12/2022 | Paul et al. | |
| 2023/0075244 A1 | 3/2023 | Marambaud | |
| 2023/0220085 A1 | 7/2023 | Yu et al. | |
| 2023/0285506 A1 | 9/2023 | Li et al. | |
| 2023/0365703 A1 | 11/2023 | Wang et al. | |
| 2024/0383990 A1 | 11/2024 | Lugovskoy et al. | |
| 2025/0002588 A1 | 1/2025 | Lugovskoy et al. | |
| 2025/0257140 A1 | 8/2025 | Lugovskoy et al. | |

FOREIGN PATENT DOCUMENTS

| | | |
|---|---|---|
| WO | WO 2013/136186 A2 | 1/2017 |
| WO | WO 2017/004563 A1 | 5/2019 |
| WO | WO 2019/086331 A2 | 5/2019 |
| WO | WO 2021/174198 A1 | 9/2021 |
| WO | WO 2022/149113 A1 | 7/2022 |
| WO | WO 2023/016568 A1 | 2/2023 |
| WO | WO 2023/030433 A1 | 3/2023 |
| WO | WO 2023/141327 A2 | 7/2023 |
| WO | WO 2024/086852 A1 | 4/2024 |
| WO | WO 2024/211807 A1 | 10/2024 |
| WO | WO 2024/211896 A2 | 10/2024 |

OTHER PUBLICATIONS

Geddie et al., "Development of disulfide-stabilized Fabs for targeting of antibody-directed nanotherapeutics", mABs, Jun. 2022, 14(1): 1-10.

Gunasekaran et al., "Enhancing antibody Fc heterodimer formation through electrostatic steering effects: applications to bispecific molecules and monovalent IgG" J Biol Chem, Apr. 16, 2010, 285(25): 19637-19646.

Harris et al., "A bispecific antibody agonist of the IL-2 heterodimeric receptor preferentially promotes in vivo expansion of CD8 and NK cells", Scientific Reports, Dec. 1, 2021, 11(1): 1-5.

Holliger et al., "Diabodies": small bivalent and bispecific antibody fragments, Proc. Natl. Acad. Sci. USA, Jul. 15, 1993, 90: 6444-6448.

International Search Report and Written Opinion for PCT International Patent Application No. PCT/US2024/023386, mailed Jul. 29, 2024.

International Search Report and Written Opinion for PCT International Patent Application No. PCT/US2024/023406, mailed Jul. 22, 2024.

Jakob et al., "Structure reveals function of the dual variable domain immunoglobulin(DVD-Ig™ molecule)", MABS, May 1, 2013, 5(3): 358-363.

Klein et al., "Progress in overcoming the chain association issue in bispecific heterodimeric IgG antibodies", mAbs, Nov. 1, 2012, 4(6): 653-663.

Labrijn et al., "Efficient generation of stable bispecific IgG1 by controlled Fab-arm exchange", PNAS, Mar. 26, 2013, 110(13): 5145-5150.

Lewis et al., "Generation of bispecific IgG antibodies by structure-based design of an orthogonal Fab interface", Nature Biotechnology, Feb. 2014, 32(2): 191-198.

Muda et al., "Therapeutic assessment of SEED: a new engineered antibody platform designed to generate mono- and bispecific antibodies", PEDS, May 2011, 24(5): 447-454.

Ntumba et al., "BMP9/ALK1 inhibits neovascularization in mouse models of age-related macular degeneration", Oncotarget, Aug. 10, 2016, 7(35): 55957-55969.

Poljak, "Production and structure of diabodies", Structure, Dec. 15, 1994, 2(12): 1121-1123.

Ridgway et al., "'Knobs-into-holes' engineering of antibody CH3 domains for heavy chain heterodimerization", Protein Engineering, Jul. 1996, 9(7): 617-621.

Ruiz et al., "A mouse model of hereditary hemorrhagic telangiectasia generated by transmammary-delivered immunoblocking of BMP9 and BMP10", Scientific Reports, Nov. 22, 2016, 6: 37366.

Shim et al. "Bispecific Antibodies and Antibody-Drug Conjugates for Cancer Therapy: Technological Considerations", Biomolecules, Feb. 26, 2020, 10(3): 360.

Spiess et al., "Bispecific antibodies with natural architecture produced by co-culture of bacteria expressing two distinct half-antibodies", Nature Biotechnology, Jul. 13, 2013, 31: 753-758.

Wranik et al., LUZ-Y, a Novel Platform for the Mammalian Cell Production of Full-length IgG-bispecific Antibodies, J Biol Chem, Dec. 21, 2012, 287(52): 43331-43339.

Wu et al., "Simultaneous targeting of multiple disease mediators by a dual-variable-domain immunoglobulin", Nature Biotechnol., Nov. 2007, 25(11): 1290-1297.

International Search Report and Written Opinion for PCT International Patent Application No. PCT/US2025/050338, mailed May 11, 2026.

Goff et al., "A Phase I Study of the Anti-Activin Receptor-Like Kinase 1 (ALK-1) Monoclonal Antibody PF-03446962 in Patients with Advanced Solid Tumors", Cancer Therapy: Clinical, May 1, 2016, 22(9): 2146-2154.

Yeoh et al., "Potential of Phage Display Antibody Technology for Cardiovascular Disease Immunotherapy", Journal of Cardiovascular Translational Research, 2022, 15: 360-380, Epublished Aug. 31, 2021.

FIG. 3A          FIG. 3B

BISPECIFIC AGONISTIC ANTIBODIES TO ACTIVIN A RECEPTOR LIKE TYPE 1 (ALK1)

RELATED APPLICATIONS

This application is a divisional of U.S. patent application Ser. No. 19/193,079, filed Apr. 29, 2025, which is a continuation of U.S. patent application Ser. No. 18/628,187, filed Apr. 5, 2024, which claims priority to U.S. Provisional Patent Application Ser. Nos. 63/458,044, filed Apr. 7, 2023; 63/537,318, filed Sep. 8, 2023; and 63/596,899, filed Nov. 7, 2023, the entire disclosures of which are hereby incorporated herein by reference.

SEQUENCE LISTING

The instant application contains a Sequence Listing which has been submitted electronically in XML format and is hereby incorporated by reference in its entirety. Said XML file, created on Jul. 17, 2025, is named 767823_DGT9-005CONDV_ST26.xml, and is 263,156 bytes in size.

BACKGROUND

Hereditary hemorrhagic telangiectasia (HHT), also known as Osler-Weber-Rendu disease, is an autosomal dominant genetic disease characterized by vascular malformations (arteriovenous malformations; AVMs) in multiple organs caused by an absent capillary network. The most common symptoms of HHT are epistaxis (nose bleeds), telangiectasis, and visceral lesions. About 25-40% of patients have progressive disease and AVMs can result in acute life-threatening hemorrhages and emboli in patients. The majority (>85%) of HHT patients are heterozygous for loss of function (LOF) mutations in the endoglin (ENG, HHT1) or activin A receptor like type 1 (ALK1, HHT2) genes. HHT1 and HHT2 patients develop very similar clinical symptoms that result from sporadic vascular malformations, but tissues affected are different. HHT1 patients, accounting for about 61% of HHT, are more prone to pulmonary arteriovenous malformations (PAVMs) and cerebral arteriovenous malformations (CAVMs), Whereas HHT2 patients, accounting for about a third of patients (37%), are more prone to complications from liver AVMs and pulmonary hypertension. Hepatic involvement can lead to secondary portal hypertension which can require liver transplant and lead to heart failure. Pulmonary involvement in these patients can lead to pulmonary arterial hypertension (PAH). Activin receptor-like kinase 1 (ALK1) and endoglin are endothelial cell (EC)-restricted receptor of the large TGF-β family. Members of the TGF-β family act on many, if not all, cell types within the body, producing diverse and complex cellular outcomes, such as growth arrest, immune suppression, differentiation, apoptosis, and specification of developmental cell fate during embryogenesis and pathogenesis. Activation of the endothelial cell-restricted TGF-β type I receptor ALK1 results from the binding of several different ligands of the TGF-β family, including bone morphogenetic protein (BMP) 9, BMP10, and TGF-β.

TGF-beta signaling requires the recruitment of type I and type II receptors in a multimeric complex to initiate signaling. Endoglin is the type III receptor which delivers BMP9 and 10 to type I and type II receptors at endothelial cell membrane. A dimeric ligand molecule facilitates the assembly of a heteromeric complex of type II and type I receptors, wherein the constitutively active kinase domain of the type II receptor trans-phosphorylates and activates the kinase domain of the type I receptor. The type I receptor is then able to imitate signaling via multiple signaling cascades, including the SMADs, which translocate to the nucleus and activate the transcription of target genes.

Defective signaling in ALK1 mediated pathway is also a hallmark of familial and sporadic PAH patients, which leads to endothelial dysfunction, i.e., apoptosis, proliferation, interaction with smooth muscle cells (SMC) and transdifferentiation. Over time, vasculature remodeling obstructs small pulmonary arteries, resulting in increased pulmonary vascular resistance and pulmonary pressures. This leads to reduced cardiac output, right heart failure, and ultimately death.

SUMMARY

The present disclosure improves upon the prior art by providing heteromeric antibodies which can effectively cross-link the ALK1 receptor to a receptor selected from BMPRII, ActRIIA, and ActRIIB and thereby activate SMAD signaling.

In one aspect, provided herein is a multispecific binding protein comprising a first binding moiety which binds specifically to human ALK1 and a second binding moiety which binds specifically to a target selected from BMPRII, ActRIIA, and ActRIIB, wherein: (a) the multispecific binding protein is capable of inducing signaling by inducing proximity between ALK1 and BMPRII, ActRIIA, or ActRIIB; and (b) at least one modified hinge region.

In some embodiments, the first modified hinge region comprises: (a) an upper hinge region of up to 7 amino acids in length or is absent; and (b) a lower hinge region, wherein the lower hinge region is linked to the N-terminus of a first constant region. In some embodiments, the multispecific binding protein further comprises a second modified hinge region linked to the N-terminus of a second constant region. In some embodiments, the second modified hinge region comprises (a) an upper hinge region of up to 7 amino acids in length or is absent; and (b) a lower hinge region, wherein the lower hinge region is linked to the N-terminus of the second constant region. In some embodiments, the upper hinge region of the first and the second modified hinge region are the same sequence. In some embodiments the upper hinge region of the first and the second modified hinge regions are different sequences.

In some embodiments the upper hinge region comprises an amino acid sequence derived from an upper hinge region of a human IgG antibody. In some embodiments, the IgG antibody is selected from IgG1, IgG2, IgG3, and IgG4. In some embodiments, the IgG antibody is IgG1. In some embodiments, the upper hinge region comprises an amino acid sequence of SEQ ID NO: 1. In some embodiments, the upper hinge region comprises an amino acid sequence of SEQ ID NO: 2. In some embodiments, the IgG antibody is IgG4. In some embodiments, the upper hinge region comprises an amino acid sequence of SEQ ID NO: 3. In some embodiments, the upper hinge is absent.

In some embodiments, the first heavy chain constant region and/or the second heavy chain constant region comprise a human IgG1, IgG2, IgG3, or IgG4. In some embodiments, the first heavy chain constant region and/or the second heavy chain constant region comprise an amino acid sequence of SEQ ID NO: 10.

In some embodiments, at least one heavy chain constant region comprises a substitution at amino acid position 234, according to EU numbering. In some embodiments, the substitution at amino acid position 234 is an alanine (A). In some embodiments, at least one heavy chain constant region comprises a substitution at amino acid position 235, according to EU numbering. In some embodiments, the substitution at amino acid position 235 is an alanine (A). In some embodiments, at least one heavy chain constant region comprises a substitution at amino acid position 237 according to EU numbering. In some embodiments, the substitution at amino acid position 237 is an alanine (A). In some embodiments, at least one heavy chain constant region comprises one or more substitutions at amino acid positions 234, 235, or 237, according to EU numbering. In some embodiments, the substitution at amino acid position 234 is an alanine (A), the substitution at amino acid position 235 is an alanine (A), and the substitution at amino acid position 237 is an alanine (A).

In some embodiments, the heavy chain constant region comprises heterodimerization mutations to promote heterodimerization of the first binding moiety with the second binding moiety. In some embodiments, the heterodimerization mutations are Knob-in-Hole (KIH) mutations. In some embodiments, the first heavy chain constant region comprises an amino acid substitution at position 366, 368, or 407 which produced a hole, and the second heavy chain constant region comprises an amino acid substitution at position 366 which produce a knob. In some embodiments, the first heavy chain constant region comprises the amino acid substitution T366S, L368A, or Y407V, and the second heavy chain constant region comprises the amino acid substitution T366W.

In some embodiments, the heterodimerization mutations are charge stabilization mutations. In some embodiments, the first heavy chain constant region comprises the amino acid substitution N297K, and the second heavy chain constant region comprises the amino acid substitution N297D. In some embodiments, the first heavy chain constant region comprises the amino acid substitution T299K, and the second heavy chain constant region comprises the amino acid substitution T299D.

In some embodiments, the heterodimerization mutations comprise an engineered disulfide bond. In some embodiments, the engineered disulfide bond is formed by a first heavy chain constant region comprising the amino acid substitution Y349C, and a second heavy chain constant region comprising the amino acid substitution S354C. In some embodiments, the engineered disulfide bond is formed by a C-terminal extension peptide fused to the C-terminus of each of the first heavy chain constant region and the second heavy chain constant region. In some embodiments, the first heavy chain constant region C-terminal extension comprises the amino acid sequence GEC, and the second heavy chain constant region C-terminal extension comprises the amino acid sequence SCDKT(SEQ ID NO:178).

In some embodiments, at least one heavy chain constant region comprises one or more mutations to promote increased half-life. In some embodiments, at least one heavy chain constant region comprises one or more substitutions at amino acid positions 252, 254, or 256, according to EU numbering. In some embodiments: the substitution at amino acid position 252 is a tyrosine (Y), the substitution at amino acid position 254 is a threonine (T), and the substitution at amino acid position 256 is a glutamic acid (E).

In some embodiments, the first binding moiety that binds specifically to human ALK1 is selected from a single chain Fv (scFv), VHH, Fab, F(ab')2, or a single domain antibody. In some embodiments, the second binding moiety that binds specifically to a target selected from BMPRII, ActRIIA, and ActRIIB is selected from a single chain Fv (scFv), VHH, Fab, F(ab')2, or a single domain antibody.

In some embodiments, the multispecific binding protein comprises from N-terminus to C-terminus: (ai) a first polypeptide chain comprising a first antigen binding domain, a first modified hinge region, and a first constant region; and (bi) a second polypeptide chain comprising a second antigen binding domain, a second modified hinge region, and a second constant region; (aii) a first polypeptide chain comprising a second antigen binding domain, a first antigen binding domain, a first modified hinge region, and a first constant region; and (bii) a second polypeptide chain comprising a second modified hinge region, and a second constant region; or (aiii) a first polypeptide chain comprising a first modified hinge region, and a first constant region; and (biii) a second polypeptide chain comprising a second antigen binding domain, a first antigen binding domain, a second modified hinge region, and a second constant region. In some embodiments, (a) the first binding moiety comprises an VHH domain and the second moiety comprises a VHH domain; (b) the first binding moiety comprises a Fab domain and the second binding moiety comprises a VHH domain; (c) the first binding moiety comprises a VHH domain and the second binding moiety comprises a Fab domain; (d) the first binding moiety comprises a Fab domain and the second binding moiety comprises a Fab domain; (e) the first binding moiety comprises a Fab domain and the second binding moiety comprises an scFv; (f) the first binding moiety comprises a scFv and the second binding moiety comprises a Fab domain; (g) the first binding moiety comprises a scFv and the second binding moiety comprises a scFv; (h) the first binding moiety comprises a scFv and the second binding moiety comprises a VHH; or (i) the first binding moiety comprises a VHH and the second binding moiety comprises a scFv.

In some embodiments, the multispecific binding protein comprises a first and a second polypeptide chain, wherein: said first polypeptide chain comprises VH1-(HX1)n-VH2-C—(HX2)n, wherein: VH1 is a first heavy chain variable domain; VH2 is a second heavy chain variable domain; C is a heavy chain constant domain; HX1 is a linker; HX2 is an Fc region; and n is independently 0 or 1; and said second polypeptide chain comprises VL1-(LX1)n-VL2-C-(LX2)n, wherein: VL1 is a first light chain variable domain; VL2 is a second light chain variable domain; C is a light chain constant domain; LX1 is a linker; LX2 does not comprise an Fc region; and n is independently 0 or 1.

In some embodiments, VH1 binds specifically to human ALK1 and VH2 binds specifically to a target selected from BMPRII, ActRIIA, and ActRIIB.

In some embodiments, VL1 binds specifically to human ALK1 and VL2 binds specifically to a target selected from BMPRII, ActRIIA, and ActRIIB.

In some embodiments, VH1 binds specifically to a target selected from BMPRII, ActRIIA, and ActRIIB and VH2 binds specifically to human ALK1.

In some embodiments, VL1 binds specifically to a target selected from BMPRII, ActRIIA, and ActRIIB and VL2 binds specifically to human ALK1.

In some embodiments, linker HX1 comprises an amino acid sequence of PLAP(SEQ ID NO:2) or PAPNLLGGP (SEQ ID NO:157).

In some embodiments, linker LX1 comprises an amino acid sequence of PLAP(SEQ ID NO:2) or PAPNLLGGP (SEQ ID NO:157).

In some embodiments, linker HX1 comprises an amino acid sequence of PLAP(SEQ ID NO:2) and linker LX1 comprises an amino acid sequence of PLAP(SEQ ID NO:2) or PAPNLLGGP(SEQ ID NO:157).

In some embodiments, the first and/or the second antigen binding domain is truncated at the C-terminal end adjacent to the upper hinge domain. In some embodiments, the C-terminal end adjacent to the upper hinge domain is truncated by at least one residue. In some embodiments, the C-terminal end adjacent to the upper hinge domain is truncated by at least two residues. In certain embodiments, the C terminal SS amino acids in a VH domain are truncated.

In some embodiments, the multispecific binding protein comprises a first polypeptide chain of any one of SEQ ID NOs: 136-141 and a second polypeptide chain of any one of SEQ ID NOs: 142-145.

In one aspect, the disclosure provides a multispecific binding protein comprising at least a first polypeptide chain, wherein:

said first polypeptide chain comprises a first variable
        heavy chain domain (VH1) linked to a second variable
        heavy chain domain (VH2) via at least one modified
        hinge region; and
    the VH1 binds specifically to ALK1 and the VH2 binds
        specifically to a target selected from BMPRII, ActRIIA,
        and ActRIIB.

In some embodiments, one or both of VH1 and VH2 are VH domains or VHH domains.

In some embodiments, the multispecific binding protein further comprises a second polypeptide chain, wherein said second polypeptide chain comprises a first variable light chain domain (VL1) linked to a second variable light chain domain (VL2), and wherein VL1 binds specifically to ALK1 and the VL2 binds specifically to a target selected from BMPRII, ActRIIA, and ActRIIB.

In some embodiments, the VL1 is linked to the VL2 via at least one modified hinge region.

In some embodiments, one or both of VH1 and VH2 is truncated at the C-terminal end.

In some embodiments, the C-terminal end is truncated by at least one residue.

In some embodiments, the C-terminal end is truncated by at least two residues.

In some embodiments, the SS amino acid residues of the C-terminal end are deleted.

In some embodiments, the multispecific binding protein comprises a first polypeptide chain of VH1-HX1-VH2-C-Fc, wherein:

VH1 is a first heavy chain variable domain;
    VH2 is a second heavy chain variable domain;
    C is a heavy chain constant domain;
    HX1 is a modified hinge region linker; and
    Fc is an Fc region; and
    a second polypeptide chain of VL1-LX1-VL2-C,
    wherein:
    VL1 is a first light chain variable domain;
    VL2 is a second light chain variable domain;
    C is a light chain constant domain; and
    LX1 is a modified hinge region linker.

In some embodiments, the modified hinge region comprises or consists of an amino acid sequence of PLAP(SEQ ID NO:2) or PAPNLLGGP(SEQ ID NO:157).

In some embodiments, the binding moiety which binds specifically to ALK1 is cross reactive with human ALK1 and mouse ALK1.

In some embodiments, the binding moiety which binds specifically to ActRIIA is cross reactive with ActRIIB.

In another aspect, provided herein is a multispecific binding protein comprising a first binding moiety which binds specifically to ALK1 and a second binding moiety which binds specifically to a target selected from BMPRII, ActRIIA, and ActRIIB, wherein: (a) the multispecific binding protein is capable of inducing signaling by inducing proximity between ALK1 and BMPRII, ActRIIA, or ActRIIB; and (b) at least one modified hinge region, wherein the at least one modified hinge region comprises: (i) an upper hinge region of up to 7 amino acids in length or is absent; and (ii) a lower hinge region, wherein the lower hinge region is linked to the N-terminus of the first heavy chain constant region.

In another aspect, provided herein is a multispecific binding protein comprising at least a first polypeptide chain, wherein said first polypeptide chain comprises a first variable heavy chain domain (VH1) linked to a second variable heavy chain domain (VH2) via at least one modified hinge region, wherein: the VH1 binds specifically to a target selected from BMPRII, ActRIIA, and ActRIIB and the VH2 binds specifically to ALK1; or the VH1 binds specifically to ALK1 and the VH2 binds specifically to a target selected from BMPRII, ActRIIA, and ActRIIB.

In some embodiments, one or both of VH1 and VH2 are VH domains or VHH domains.

In some embodiments, the multispecific binding protein further comprises a second polypeptide chain, wherein said second polypeptide chain comprises a first variable light chain domain (VL1) linked to a second variable light chain domain (VL2), wherein: the VL1 binds specifically to a target selected from BMPRII, ActRIIA, and ActRIIB and the VL2 binds specifically to a ALK1; or the VL1 binds specifically to ALK1 and the VL2 binds specifically to a target selected from BMPRII, ActRIIA, and ActRIIB.

In some embodiments, the VL1 is linked to the VL2 via at least one modified hinge region.

In some embodiments, one or both of VH1 and VH2 is truncated at the C-terminal end.

In some embodiments, the C-terminal end is truncated by at least one residue.

In some embodiments, the C-terminal end is truncated by at least two residues.

In some embodiments, the SS amino acid residues of the C-terminal end are deleted.

In some embodiments, the multispecific binding protein comprises: a first polypeptide chain of VH1-HX1-VH2-C-Fc, wherein:

VH1 is a first heavy chain variable domain;
    VH2 is a second heavy chain variable domain;
    C is a heavy chain constant domain;
    HX1 is a modified hinge region linker; and
    Fc is an Fc region; and
    a second polypeptide chain of VL1-LX1-VL2-C,
    wherein:
    VL1 is a first light chain variable domain;
    VL2 is a second light chain variable domain;
    C is a light chain constant domain; and
    LX1 is a modified hinge region linker.

In some embodiments, the modified hinge region comprises: i) an upper hinge region of up to 7 amino acids in length or is absent; and ii) a lower hinge region.

In some embodiments, the modified hinge region comprises or consists of an amino acid sequence of PLAP(SEQ ID NO:2) or PAPNLLGGP(SEQ ID NO:157).

In some embodiments, the VH binding to ALK1 comprises an HCDR1 amino acid sequence of SYAMS(SEQ ID NO:158), an HCDR2 amino acid sequence of NINQDGSEKNYVDSMRG(SEQ ID NO:159), and an HCDR3 amino acid sequence of EFDY(SEQ ID NO:160);

and the VL binding to ALK1 comprises an LCDR1 amino acid sequence of SGSSSNIGSNYVY(SEQ ID NO:161), an LCDR2 amino acid sequence of GNNKRPS(SEQ ID NO:162), and an LCDR3 amino acid sequence of AAWDD-SLNGRV(SEQ ID NO:163).

In some embodiments, the VH binding to ALK1 comprises an HCDR1 amino acid sequence of SYWMS(SEQ ID NO:164), an HCDR2 amino acid sequence of NINQDGSEKYYVDSMRG(SEQ ID NO:165), and an HCDR3 amino acid sequence of EYDY(SEQ ID NO:166); and the VL binding to ALK1 comprises an LCDR1 amino acid sequence of SGSSSNIGSNYVY(SEQ ID NO:161), an LCDR2 amino acid sequence of GNNKRPS(SEQ ID NO:162), and an LCDR3 amino acid sequence of AAWDD-SLNGRV(SEQ ID NO:163).

In some embodiments, the VH binding to ALK1 comprises an HCDR1 amino acid sequence of SYWMS(SEQ ID NO:164), an HCDR2 amino acid sequence of NIKQDGSEKNYVDSMRG(SEQ ID NO:167), and an HCDR3 amino acid sequence of EFDF(SEQ ID NO:168); and the VL binding to ALK1 comprises an LCDR1 amino acid sequence of SGSSSNIGSNYVY(SEQ ID NO:161), an LCDR2 amino acid sequence of GNNKRPS(SEQ ID NO:162), and an LCDR3 amino acid sequence of AAWDD-SLNGRV(SEQ ID NO:163).

In some embodiments, the VH binding to BMPRII comprises an HCDR1 amino acid sequence of DYYMT(SEQ ID NO:169), an HCDR2 amino acid sequence of SISGGSTYY-ADSRKG(SEQ ID NO:170), and an HCDR3 amino acid sequence of DFGVAGWFGQYGMDV(SEQ ID NO:171); and the VL binding to BMPRII comprises an LCDR1 amino acid sequence of TGSSSNIGAGYDVH(SEQ ID NO:172), an LCDR2 amino acid sequence of RSNQRPS(SEQ ID NO:173), and an LCDR3 amino acid sequence of SSYAG-NYNLV(SEQ ID NO:174).

In some embodiments, the VH binding to BMPRII comprises an HCDR1 amino acid sequence of DYYMN(SEQ ID NO:175), an HCDR2 amino acid sequence of SISGGSTYY-ADSVKG(SEQ ID NO:176), and an HCDR3 amino acid sequence of DFGVAGWFGQFGMDV(SEQ ID NO:177); and the VL binding to BMPRII comprises an LCDR1 amino acid sequence of TGSSSNIGAGYDVH(SEQ ID NO:172), an LCDR2 amino acid sequence of RSNQRPS(SEQ ID NO:173), and an LCDR3 amino acid sequence of SSYAG-NYNLV(SEQ ID NO:174).

In some embodiments, the VH binding to BMPRII comprises an HCDR1 amino acid sequence of DYYMN(SEQ ID NO:175), an HCDR2 amino acid sequence of SISGGSTYY-ADSVKG(SEQ ID NO:176), and an HCDR3 amino acid sequence of DFGVAGWFGYYGMDV(SEQ ID NO:179); and the VL binding to BMPRII comprises an LCDR1 amino acid sequence of TGSSSNIGAGYDVH(SEQ ID NO:172), an LCDR2 amino acid sequence of RSNQRPS(SEQ ID NO:173), and an LCDR3 amino acid sequence of SSYAG-NYNLV(SEQ ID NO:174).

In some embodiments, the VH binding to ALK1 comprises an HCDR1 amino acid sequence of SYAMS(SEQ ID NO:158), an HCDR2 amino acid sequence of NINQDGSEKNYVDSMRG(SEQ ID NO:159), and an HCDR3 amino acid sequence of EFDY(SEQ ID NO:160); and the VL binding to ALK1 comprises an LCDR1 amino acid sequence of SGSSSNIGSNYVY(SEQ ID NO:161), an LCDR2 amino acid sequence of GNNKRPS(SEQ ID NO:162), and an LCDR3 amino acid sequence of AAWDD-SLNGRV(SEQ ID NO:163); and the VH binding to BMPRII comprises an HCDR1 amino acid sequence of DYYMT (SEQ ID NO:169), an HCDR2 amino acid sequence of SISGGSTYYADSRKG(SEQ ID NO:170), and an HCDR3 amino acid sequence of DFGVAGWFGQYGMDV(SEQ ID NO:171); and the VL binding to BMPRII comprises an LCDR1 amino acid sequence of TGSSSNIGAGYDVH (SEQ ID NO:172), an LCDR2 amino acid sequence of RSNQRPS(SEQ ID NO:173), and an LCDR3 amino acid sequence of SSYAGNYNLV(SEQ ID NO:174).

In some embodiments, the VH binding to ALK1 comprises an HCDR1 amino acid sequence of SYWMS(SEQ ID NO:164), an HCDR2 amino acid sequence of NINQDGSEKYYVDSMRG(SEQ ID NO:165), and an HCDR3 amino acid sequence of EYDY(SEQ ID NO:166); and the VL binding to ALK1 comprises an LCDR1 amino acid sequence of SGSSSNIGSNYVY(SEQ ID NO:161), an LCDR2 amino acid sequence of GNNKRPS(SEQ ID NO:162), and an LCDR3 amino acid sequence of AAWDD-SLNGRV(SEQ ID NO:163); and the VH binding to BMPRII comprises an HCDR1 amino acid sequence of DYYMN (SEQ ID NO:175), an HCDR2 amino acid sequence of SISGGSTYYADSVKG(SEQ ID NO:176), and an HCDR3 amino acid sequence of DFGVAGWFGQFGMDV(SEQ ID NO:177); and the VL binding to BMPRII comprises an LCDR1 amino acid sequence of TGSSSNIGAGYDVH (SEQ ID NO:172), an LCDR2 amino acid sequence of RSNQRPS(SEQ ID NO:173), and an LCDR3 amino acid sequence of SSYAGNYNLV(SEQ ID NO:174).

In some embodiments, the VH binding to ALK1 comprises an HCDR1 amino acid sequence of SYWMS(SEQ ID NO:164), an HCDR2 amino acid sequence of NIKQDGSEKNYVDSMRG(SEQ ID NO:167), and an HCDR3 amino acid sequence of EFDF(SEQ ID NO:168); and the VL binding to ALK1 comprises an LCDR1 amino acid sequence of SGSSSNIGSNYVY(SEQ ID NO:161), an LCDR2 amino acid sequence of GNNKRPS(SEQ ID NO:162), and an LCDR3 amino acid sequence of AAWDD-SLNGRV(SEQ ID NO:163); and the VH binding to BMPRII comprises an HCDR1 amino acid sequence of DYYMN (SEQ ID NO:175), an HCDR2 amino acid sequence of SISGGSTYYADSVKG(SEQ ID NO:176), and an HCDR3 amino acid sequence of DFGVAGWFGYYGMDV(SEQ ID NO:179); and the VL binding to BMPRII comprises an LCDR1 amino acid sequence of TGSSSNIGAGYDVH (SEQ ID NO:172), an LCDR2 amino acid sequence of RSNQRPS(SEQ ID NO:173), and an LCDR3 amino acid sequence of SSYAGNYNLV(SEQ ID NO:174).

In some embodiments, the VH binding to ALK1 comprises an amino acid sequence of EVQLLESGG-GLVQPGGSLRLSCAASGFTFSSYAMSWVRQAPGK-GLEWVANINQDGSEKNYV
DSMRGRFTISRDNSKNTLYLQMNSLRAEDTAVYY-CAREFDYWGQGTLVTVSS(SEQ ID NO:180), or an amino acid sequence with at least 90%, at least 91%, at least 92%, at least 93%, at least 94%, at least 95%, at least 96%, at least 97%, at least 98%, or at least 99% identity thereto; and the VL binding to ALK1 comprises an amino acid sequence of QSVLAQPPSASGTPGQRVTISCSGSSSNIG-SNYVYWYQQLPGTAPKLLIYGNNKRPSGVPDRF
SGSKSGTSASLAISGLRSEDEADYYCAAWDDSLN-GRVFGGGTKLTVL(SEQ ID NO:181), or an amino acid sequence with at least 90%, at least 91%, at least 92%, at least 93%, at least 94%, at least 95%, at least 96%, at least 97%, at least 98%, or at least 99% identity thereto.

In some embodiments, the VH binding to ALK1 comprises an amino acid sequence of EVQLLESGG-GLVQPGGSLRLSCAASGFTFSSYWMSWVRQAPGK-GLEWVANINQDGSEKYYV
DSMRGRFTISRDNSKNTLYLQMNSLRAEDTAVYY- CAREYDYWGQGTLVTVSS(SEQ ID NO:182), or an amino acid sequence with at least 90%, at least 91%, at least 92%, at least 93%, at least 94%, at least 95%, at least 96%, at least 97%, at least 98%, or at least 99% identity thereto; and the VL binding to ALK1 comprises an amino acid sequence of QSVLAQPPSASGTPGQRVTISCSGSSSNIG-SNYVYWYQQLPGTAPKLLIYGNNKRPSGVPDRF SGSKSGTSASLAISGLRSEDEADYYCAAWDDSLN-GRVFGGGTKLTVL(SEQ ID NO:181), or an amino acid sequence with at least 90%, at least 91%, at least 92%, at least 93%, at least 94%, at least 95%, at least 96%, at least 97%, at least 98%, or at least 99% identity thereto.

In some embodiments, the VH binding to ALK1 comprises an amino acid sequence of EVQLLESGG-GLVQPGGSLRLSCAASGFTFSSYWMSWVRQAPGK-GLEWVANIKQDGSEKNYV DSMRGRFTISRDNSKNTLYLQMNSLRAEDTAVYY-CAREFDFWGQGTLVTVSS(SEQ ID NO:183), or an amino acid sequence with at least 90%, at least 91%, at least 92%, at least 93%, at least 94%, at least 95%, at least 96%, at least 97%, at least 98%, or at least 99% identity thereto; and the VL binding to ALK1 comprises an amino acid sequence of QSVLAQPPSASGTPGQRVTISCSGSSSNIG-SNYVYWYQQLPGTAPKLLIYGNNKRPSGVPDRF SGSKSGTSASLAISGLRSEDEADYYCAAWDDSLN-GRVFGGGTKLTVL(SEQ ID NO:181), or an amino acid sequence with at least 90%, at least 91%, at least 92%, at least 93%, at least 94%, at least 95%, at least 96%, at least 97%, at least 98%, or at least 99% identity thereto.

In some embodiments, the VH binding to BMPRII comprises an amino acid sequence of EVQLLESGG-GLVQPGGSLRLSCAASGFTFSDYYMTWIRQAPGK-GLEWVSSISGGSTYYADSR KGRFTISRDNSENTLYLQMNSLRAEDTAVYY-CARDFGVAGWFGQYGMDVWGQGTLVTVSS(S EQ ID NO:184), or an amino acid sequence with at least 90%, at least 91%, at least 92%, at least 93%, at least 94%, at least 95%, at least 96%, at least 97%, at least 98%, or at least 99% identity thereto; and the VL binding to BMPRII comprises an amino acid sequence of QSVLTQPP-SASGTPGQRVTISCTGSSSNI-GAGYDVHWYQQLPGTAPKLLIYRSNQRPSGVPDR FSGSKSGTSASLAISGLRSEDEADYYCSSYAG-NYNLVFGGGTKLTVL(SEQ ID NO:185), or an amino acid sequence with at least 90%, at least 91%, at least 92%, at least 93%, at least 94%, at least 95%, at least 96%, at least 97%, at least 98%, or at least 99% identity thereto; or In some embodiments, the VH binding to BMPRII comprises an amino acid sequence of EVQLLESGG-GLVQPGGSLRLSCAASGFTFSDYYMNWIRQAPGK-GLEWVSSISGGSTYYADSV KGRFTISRDNSENTLYLQMNSLRAEDTAVYY-CARDFGVAGWFGQFGMDVWGQGTLVTVSS(S EQ ID NO:186), or an amino acid sequence with at least 90%, at least 91%, at least 92%, at least 93%, at least 94%, at least 95%, at least 96%, at least 97%, at least 98%, or at least 99% identity thereto; and the VL binding to BMPRII comprises an amino acid sequence of QSVLTQPP-SASGTPGQRVTISCTGSSSNI-GAGYDVHWYQQLPGTAPKLLIYRSNQRPSGVPDR FSGSKSGTSASLAISGLRSEDEADYYCSSYAG-NYNLVFGGGTKLTVL(SEQ ID NO:185), or an amino acid sequence with at least 90%, at least 91%, at least 92%, at least 93%, at least 94%, at least 95%, at least 96%, at least 97%, at least 98%, or at least 99% identity thereto; or In some embodiments, the VH binding to BMPRII comprises an amino acid sequence of EVQLLESGG- GLVQPGGSLRLSCAASGFTFSDYYMNWIRQAPGK-GLEWVSSISGGSTYYADSV KGRFTISRDNSENTLYLQMNSLRAEDTAVYY-CARDFGVAGWFGYYGMDVWGQGTLVTVSS(S EQ ID NO:187), or an amino acid sequence with at least 90%, at least 91%, at least 92%, at least 93%, at least 94%, at least 95%, at least 96%, at least 97%, at least 98%, or at least 99% identity thereto; and the VL binding to BMPRII comprises an amino acid sequence of QSVLTQPP-SASGTPGQRVTISCTGSSSNI-GAGYDVHWYQQLPGTAPKLLIYRSNQRPSGVPDR FSGSKSGTSASLAISGLRSEDEADYYCSSYAG-NYNLVFGGGTKLTVL(SEQ ID NO:185), or an amino acid sequence with at least 90%, at least 91%, at least 92%, at least 93%, at least 94%, at least 95%, at least 96%, at least 97%, at least 98%, or at least 99% identity thereto.

In some embodiments, the VH binding to ALK1 comprises an amino acid sequence of EVQLLESGG-GLVQPGGSLRLSCAASGFTFSSYAMSWVRQAPGK-GLEWVANINQDGSEKNYV DSMRGRFTISRDNSKNTLYLQMNSLRAEDTAVYY-CAREFDYWGQGTLVTVSS(SEQ ID NO:180), or an amino acid sequence with at least 90%, at least 91%, at least 92%, at least 93%, at least 94%, at least 95%, at least 96%, at least 97%, at least 98%, or at least 99% identity thereto; the VL binding to ALK1 comprises an amino acid sequence of QSVLAQPPSASGTPGQRVTISCSGSSSNIG-SNYVYWYQQLPGTAPKLLIYGNNKRPSGVPDRF SGSKSGTSASLAISGLRSEDEADYYCAAWDDSLN-GRVFGGGTKLTVL(SEQ ID NO:181), or an amino acid sequence with at least 90%, at least 91%, at least 92%, at least 93%, at least 94%, at least 95%, at least 96%, at least 97%, at least 98%, or at least 99% identity thereto, the VH binding to BMPRII comprises an amino acid sequence of EVQLLESGGGLVQPGGSLRLS-CAASGFTFSDYYMTWIRQAPGKGLEWVSSISGG-STYYADSR KGRFTISRDNSENTLYLQMNSLRAED-TAVYYCARDFGVAGWFGQYGMDVWGQGTLVTVSS(S EQ ID NO:184), or an amino acid sequence with at least 90%, at least 91%, at least 92%, at least 93%, at least 94%, at least 95%, at least 96%, at least 97%, at least 98%, or at least 99% identity thereto; and the VL binding to BMPRII comprises an amino acid sequence of QSVLTQPP-SASGTPGQRVTISCTGSSSNI-GAGYDVHWYQQLPGTAPKLLIYRSNQRPSGVPDR FSGSKSGTSASLAISGLRSEDEADYYCSSYAG-NYNLVFGGGTKLTVL(SEQ ID NO:185), or an amino acid sequence with at least 90%, at least 91%, at least 92%, at least 93%, at least 94%, at least 95%, at least 96%, at least 97%, at least 98%, or at least 99% identity thereto.

In some embodiments, the VH binding to ALK1 comprises an amino acid sequence of EVQLLESGG-GLVQPGGSLRLSCAASGFTFSSYWMSWVRQAPGK-GLEWVANINQDGSEKYYV DSMRGRFTISRDNSKNTLYLQMNSLRAEDTAVYY-CAREYDYWGQGTLVTVSS(SEQ ID NO:182), or an amino acid sequence with at least 90%, at least 91%, at least 92%, at least 93%, at least 94%, at least 95%, at least 96%, at least 97%, at least 98%, or at least 99% identity thereto; the VL binding to ALK1 comprises an amino acid sequence of QSVLAQPPSASGTPGQRVTISCSGSSSNIG-SNYVYWYQQLPGTAPKLLIYGNNKRPSGVPDRF SGSKSGTSASLAISGLRSEDEADYYCAAWDDSLN-GRVFGGGTKLTVL(SEQ ID NO:181), or an amino acid sequence with at least 90%, at least 91%, at least 92%, at least 93%, at least 94%, at least 95%, at least 96%, at least 97%, at least 98%, or at least 99% identity thereto; and the VH binding to BMPRII comprises an amino acid sequence of EVQLLESGGGLVQPGGSLRLS-CAASGFTFSDYYMNWIRQAPGKGLEWVSSISGG-STYYADSV KGRFTISRDNSENTLYLQMNSLRAED-TAVYYCARDFGVAGWFGQFGMDVWGQGTLVTVSS(SEQ ID NO:186), or an amino acid sequence with at least 90%, at least 91%, at least 92%, at least 93%, at least 94%, at least 95%, at least 96%, at least 97%, at least 98%, or at least 99% identity thereto; and the VL binding to BMPRII comprises an amino acid sequence of QSVLTQPP-SASGTPGQRVTISCTGSSSNI-GAGYDVHWYQQLPGTAPKLLIYRSNQRPSGVPDR FSGSKSGTSASLAISGLRSEDEADYYCSSYAG-NYNLVFGGGTKLTVL(SEQ ID NO:185), or an amino acid sequence with at least 90%, at least 91%, at least 92%, at least 93%, at least 94%, at least 95%, at least 96%, at least 97%, at least 98%, or at least 99% identity thereto.

In some embodiments, the VH binding to ALK1 comprises an amino acid sequence of EVQLLESGG-GLVQPGGSLRLSCAASGFTFSSYWMSWVRQAPGK-GLEWVANIKQDGSEKNYV DSMRGRFTISRDNSKNTLYLQMNSLRAEDTAVYY-CAREFDFWGQGTLVTVSS(SEQ ID NO:183), or an amino acid sequence with at least 90%, at least 91%, at least 92%, at least 93%, at least 94%, at least 95%, at least 96%, at least 97%, at least 98%, or at least 99% identity thereto; the VL binding to ALK1 comprises an amino acid sequence of QSVLAQPPSASGTPGQRVTISCSGSSSNIG-SNYVYWYQQLPGTAPKLLIYGNNKRPSGVPDRF SGSKSGTSASLAISGLRSEDEADYYCAAWDDSLN-GRVFGGGTKLTVL(SEQ ID NO:181), or an amino acid sequence with at least 90%, at least 91%, at least 92%, at least 93%, at least 94%, at least 95%, at least 96%, at least 97%, at least 98%, or at least 99% identity thereto; and the VH binding to BMPRII comprises an amino acid sequence of EVQLLESGGGLVQPGGSLRLS-CAASGFTFSDYYMNWIRQAPGKGLEWVSSISGG-STYYADSV KGRFTISRDNSENTLYLQMNSLRAED-TAVYYCARDFGVAGWFGYYGMDVWGQGTLVTVSS(SEQ ID NO:187), or an amino acid sequence with at least 90%, at least 91%, at least 92%, at least 93%, at least 94%, at least 95%, at least 96%, at least 97%, at least 98%, or at least 99% identity thereto; and the VL binding to BMPRII comprises an amino acid sequence of QSVLTQPP-SASGTPGQRVTISCTGSSSNI-GAGYDVHWYQQLPGTAPKLLIYRSNQRPSGVPDR FSGSKSGTSASLAISGLRSEDEADYYCSSYAG-NYNLVFGGGTKLTVL(SEQ ID NO:185), or an amino acid sequence with at least 90%, at least 91%, at least 92%, at least 93%, at least 94%, at least 95%, at least 96%, at least 97%, at least 98%, or at least 99% identity thereto.

In some embodiments, the first polypeptide chain comprises an amino acid sequence selected from the group consisting of SEQ ID NO: 136-142, and the second polypeptide chain comprises an amino acid sequence selected from the group consisting of SEQ ID NO: 143-146.

In some embodiments, the first polypeptide chain comprises an amino acid sequence of SEQ ID NO: 137, or an amino acid sequence with at least 90%, at least 91%, at least 92%, at least 93%, at least 94%, at least 95%, at least 96%, at least 97%, at least 98%, or at least 99% identity thereto, and the second polypeptide chain comprises an amino acid sequence of SEQ ID NO: 146, or an amino acid sequence with at least 90%, at least 91%, at least 92%, at least 93%, at least 94%, at least 95%, at least 96%, at least 97%, at least 98%, or at least 99% identity thereto.

In some embodiments, the first polypeptide chain comprises an amino acid sequence of SEQ ID NO: 138, or an amino acid sequence with at least 90%, at least 91%, at least 92%, at least 93%, at least 94%, at least 95%, at least 96%, at least 97%, at least 98%, or at least 99% identity thereto, and the second polypeptide chain comprises an amino acid sequence of SEQ ID NO: 146, or an amino acid sequence with at least 90%, at least 91%, at least 92%, at least 93%, at least 94%, at least 95%, at least 96%, at least 97%, at least 98%, or at least 99% identity thereto.

In some embodiments, the first polypeptide chain comprises an amino acid sequence of SEQ ID NO: 139, or an amino acid sequence with at least 90%, at least 91%, at least 92%, at least 93%, at least 94%, at least 95%, at least 96%, at least 97%, at least 98%, or at least 99% identity thereto, and the second polypeptide chain comprises an amino acid sequence of SEQ ID NO: 146, or an amino acid sequence with at least 90%, at least 91%, at least 92%, at least 93%, at least 94%, at least 95%, at least 96%, at least 97%, at least 98%, or at least 99% identity thereto.

In some embodiments, the first polypeptide chain comprises an amino acid sequence of SEQ ID NO: 140, or an amino acid sequence with at least 90%, at least 91%, at least 92%, at least 93%, at least 94%, at least 95%, at least 96%, at least 97%, at least 98%, or at least 99% identity thereto, and the second polypeptide chain comprises an amino acid sequence of SEQ ID NO: 146, or an amino acid sequence with at least 90%, at least 91%, at least 92%, at least 93%, at least 94%, at least 95%, at least 96%, at least 97%, at least 98%, or at least 99% identity thereto.

In some embodiments, the first polypeptide chain comprises an amino acid sequence of SEQ ID NO: 141, or an amino acid sequence with at least 90%, at least 91%, at least 92%, at least 93%, at least 94%, at least 95%, at least 96%, at least 97%, at least 98%, or at least 99% identity thereto, and the second polypeptide chain comprises an amino acid sequence of SEQ ID NO: 146, or an amino acid sequence with at least 90%, at least 91%, at least 92%, at least 93%, at least 94%, at least 95%, at least 96%, at least 97%, at least 98%, or at least 99% identity thereto.

In some embodiments, the first polypeptide chain comprises an amino acid sequence of SEQ ID NO: 142, or an amino acid sequence with at least 90%, at least 91%, at least 92%, at least 93%, at least 94%, at least 95%, at least 96%, at least 97%, at least 98%, or at least 99% identity thereto, and the second polypeptide chain comprises an amino acid sequence of SEQ ID NO: 146, or an amino acid sequence with at least 90%, at least 91%, at least 92%, at least 93%, at least 94%, at least 95%, at least 96%, at least 97%, at least 98%, or at least 99% identity thereto.

In some embodiments, the first polypeptide chain comprises an amino acid sequence of SEQ ID NO: 68, or an amino acid sequence with at least 90%, at least 91%, at least 92%, at least 93%, at least 94%, at least 95%, at least 96%, at least 97%, at least 98%, or at least 99% identity thereto, and the second polypeptide chain comprises an amino acid sequence of SEQ ID NO: 69, or an amino acid sequence with at least 90%, at least 91%, at least 92%, at least 93%, at least 94%, at least 95%, at least 96%, at least 97%, at least 98%, or at least 99% identity thereto.

In some embodiments, the first polypeptide chain comprises an amino acid sequence of SEQ ID NO: 70, or an amino acid sequence with at least 90%, at least 91%, at least 92%, at least 93%, at least 94%, at least 95%, at least 96%, at least 97%, at least 98%, or at least 99% identity thereto, and the second polypeptide chain comprises an amino acid sequence of SEQ ID NO: 71, or an amino acid sequence with at least 90%, at least 91%, at least 92%, at least 93%, at least 94%, at least 95%, at least 96%, at least 97%, at least 98%, or at least 99% identity thereto.

In some embodiments, the first polypeptide chain comprises an amino acid sequence of SEQ ID NO: 72, or an amino acid sequence with at least 90%, at least 91%, at least 92%, at least 93%, at least 94%, at least 95%, at least 96%, at least 97%, at least 98%, or at least 99% identity thereto, and the second polypeptide chain comprises an amino acid sequence of SEQ ID NO: 73, or an amino acid sequence with at least 90%, at least 91%, at least 92%, at least 93%, at least 94%, at least 95%, at least 96%, at least 97%, at least 98%, or at least 99% identity thereto.

In some embodiments, the first polypeptide chain comprises an amino acid sequence of SEQ ID NO: 74, or an amino acid sequence with at least 90%, at least 91%, at least 92%, at least 93%, at least 94%, at least 95%, at least 96%, at least 97%, at least 98%, or at least 99% identity thereto, and the second polypeptide chain comprises an amino acid sequence of SEQ ID NO: 75, or an amino acid sequence with at least 90%, at least 91%, at least 92%, at least 93%, at least 94%, at least 95%, at least 96%, at least 97%, at least 98%, or at least 99% identity thereto.

In one aspect, the disclosure provides a multispecific binding protein comprising a first polypeptide chain and a second polypeptide chain, wherein the first polypeptide chain and second polypeptide chain each comprise, from N-terminus to C-terminus, a first single chain variable fragment (scFv) linked to a second scFv, wherein: the first scFv binds specifically to a target selected from BMPRII, ActRIIA, and ActRIIB and the second scFv binds specifically to ALK1; or the first scFv binds specifically to ALK1 and the second scFv binds specifically to a target selected from BMPRII, ActRIIA, and ActRIIB.

In some embodiments, the first scFv is linked to the second scFv via at least one modified hinge region.

In some embodiments, the scFv binding to ALK1 comprises: a VH domain comprising an HCDR1 amino acid sequence of SYAMS(SEQ ID NO:158), an HCDR2 amino acid sequence of NINQDGSEKNYVDSMRG(SEQ ID NO:159), and an HCDR3 amino acid sequence of EFDY(SEQ ID NO:160); and a VL binding to ALK1 comprises an LCDR1 amino acid sequence of SGSSSNIGSNYVY(SEQ ID NO:161), an LCDR2 amino acid sequence of GNNKRPS(SEQ ID NO:162), and an LCDR3 amino acid sequence of AAWDDSLNGRV(SEQ ID NO:163).

In some embodiments, the scFv binding to ALK1 comprises: a VH domain comprising an an HCDR1 amino acid sequence of SYWMS(SEQ ID NO:164), an HCDR2 amino acid sequence of NINQDGSEKYYVDSMRG(SEQ ID NO:165), and an HCDR3 amino acid sequence of EYDY(SEQ ID NO:166); and a VL domain comprising an an LCDR1 amino acid sequence of SGSSSNIGSNYVY(SEQ ID NO:161), an LCDR2 amino acid sequence of GNNKRPS(SEQ ID NO:162), and an LCDR3 amino acid sequence of AAWDDSLNGRV(SEQ ID NO:163).

In some embodiments, the scFv binding to ALK1 comprises: a VH domain comprising an HCDR1 amino acid sequence of SYWMS(SEQ ID NO:164), an HCDR2 amino acid sequence of NIKQDGSEKNYVDSMRG(SEQ ID NO:167), and an HCDR3 amino acid sequence of EFDF(SEQ ID NO:168); and a VL domain comprising an LCDR1 amino acid sequence of SGSSSNIGSNYVY(SEQ ID NO:161), an LCDR2 amino acid sequence of GNNKRPS(SEQ ID NO:162), and an LCDR3 amino acid sequence of AAWDDSLNGRV(SEQ ID NO:163).

In some embodiments, the scFv binding to BMPRII comprises: a VH domain comprising an HCDR1 amino acid sequence of DYYMT(SEQ ID NO:169), an HCDR2 amino acid sequence of SISGGSTYYADSRKG(SEQ ID NO:170), and an HCDR3 amino acid sequence of DFGVAGWFGQYGMDV(SEQ ID NO:171); and a VL domain comprising an LCDR1 amino acid sequence of TGSSSNIGAGYDVH(SEQ ID NO:172), an LCDR2 amino acid sequence of RSNQRPS(SEQ ID NO:173), and an LCDR3 amino acid sequence of SSYAGNYNLV(SEQ ID NO:174).

In some embodiments, the scFv binding to BMPRII comprises: a VH domain comprising an HCDR1 amino acid sequence of DYYMN(SEQ ID NO:175), an HCDR2 amino acid sequence of SISGGSTYYADSVKG(SEQ ID NO:176), and an HCDR3 amino acid sequence of DFGVAGWFGQFGMDV(SEQ ID NO:177); and a VL domain comprising an LCDR1 amino acid sequence of TGSSSNIGAGYDVH(SEQ ID NO:172), an LCDR2 amino acid sequence of RSNQRPS(SEQ ID NO:173), and an LCDR3 amino acid sequence of SSYAGNYNLV(SEQ ID NO:174); or In some embodiments, the scFv binding to BMPRII comprises: a VH domain comprising an HCDR1 amino acid sequence of DYYMN(SEQ ID NO:175), an HCDR2 amino acid sequence of SISGGSTYYADSVKG(SEQ ID NO:176), and an HCDR3 amino acid sequence of DFGVAGWFGYYGMDV(SEQ ID NO:179); and a VL domain comprising an LCDR1 amino acid sequence of TGSSSNIGAGYDVH(SEQ ID NO:172), an LCDR2 amino acid sequence of RSNQRPS(SEQ ID NO:173), and an LCDR3 amino acid sequence of SSYAGNYNLV(SEQ ID NO:174).

In some embodiments, the scFv binding to ALK1 comprises: a VH domain comprising an HCDR1 amino acid sequence of SYAMS(SEQ ID NO:158), an HCDR2 amino acid sequence of NINQDGSEKNYVDSMRG(SEQ ID NO:159), and an HCDR3 amino acid sequence of EFDY(SEQ ID NO:160); and a VL binding to ALK1 comprises an LCDR1 amino acid sequence of SGSSSNIGSNYVY(SEQ ID NO:161), an LCDR2 amino acid sequence of GNNKRPS(SEQ ID NO:162), and an LCDR3 amino acid sequence of AAWDDSLNGRV(SEQ ID NO:163); and the scFv binding to BMPRII comprises: a VH domain comprising an HCDR1 amino acid sequence of DYYMT(SEQ ID NO:169), an HCDR2 amino acid sequence of SISGGSTYYADSRKG(SEQ ID NO:170), and an HCDR3 amino acid sequence of DFGVAGWFGQYGMDV(SEQ ID NO:171); and a VL domain comprising an LCDR1 amino acid sequence of TGSSSNIGAGYDVH(SEQ ID NO:172), an LCDR2 amino acid sequence of RSNQRPS(SEQ ID NO:173), and an LCDR3 amino acid sequence of SSYAGNYNLV(SEQ ID NO:174).

In some embodiments, the scFv binding to ALK1 comprises: a VH domain comprising an an HCDR1 amino acid sequence of SYWMS(SEQ ID NO:164), an HCDR2 amino acid sequence of NINQDGSEKYYVDSMRG(SEQ ID NO:165), and an HCDR3 amino acid sequence of EYDY(SEQ ID NO:166); and a VL domain comprising an LCDR1 amino acid sequence of SGSSSNIGSNYVY(SEQ ID NO:161), an LCDR2 amino acid sequence of GNNKRPS(SEQ ID NO:162), and an LCDR3 amino acid sequence of AAWDDSLNGRV(SEQ ID NO:163); and the scFv binding to BMPRII comprises: a VH domain comprising an HCDR1 amino acid sequence of DYYMN(SEQ ID NO:175), an HCDR2 amino acid sequence of SISGGSTYYADSVKG(SEQ ID NO:176), and an HCDR3 amino acid sequence of DFGVAGWFGQFGMDV(SEQ ID NO:177); and a VL domain comprising an LCDR1 amino acid sequence of TGSSSNIGAGYDVH(SEQ ID NO:172), an LCDR2 amino acid sequence of RSNQRPS(SEQ ID NO:173), and an LCDR3 amino acid sequence of SSYAGNYNLV(SEQ ID NO:174).

In some embodiments, the scFv binding to ALK1 comprises: a VH domain comprising an HCDR1 amino acid sequence of SYWMS(SEQ ID NO:164), an HCDR2 amino acid sequence of NIKQDGSEKNYVDSMRG(SEQ ID NO:167), and an HCDR3 amino acid sequence of EFDF (SEQ ID NO:168); and a VL domain comprising an LCDR1 amino acid sequence of SGSSSNIGSNYVY(SEQ ID NO:161), an LCDR2 amino acid sequence of GNNKRPS (SEQ ID NO:162), and an LCDR3 amino acid sequence of AAWDDSLNGRV(SEQ ID NO:163); and the scFv binding to BMPRII comprises: a VH domain comprising an HCDR1 amino acid sequence of DYYMN(SEQ ID NO:175), an HCDR2 amino acid sequence of SISGGSTYYADSVKG (SEQ ID NO:176), and an HCDR3 amino acid sequence of DFGVAGWFGYYGMDV(SEQ ID NO:179); and a VL domain comprising an LCDR1 amino acid sequence of TGSSSNIGAGYDVH(SEQ ID NO:172), an LCDR2 amino acid sequence of RSNQRPS(SEQ ID NO:173), and an LCDR3 amino acid sequence of SSYAGNYNLV(SEQ ID NO:174).

In some embodiments, the scFv binding to ALK1 comprises: a VH domain comprising an amino acid sequence of EVQLLESGGGLVQPGGSLRLSCAASGFTFSSYAM-SWVRQAPGKGLEWVANINQDGSEKNYV DSMR-GRFTISRDNSKNTLYLQMNSLRAEDTAVYY-CAREFDYWGQGTLVTVSS(SEQ ID NO:180), or an amino acid sequence with at least 90%, at least 91%, at least 92%, at least 93%, at least 94%, at least 95%, at least 96%, at least 97%, at least 98%, or at least 99% identity thereto; and a VL domain comprising an amino acid sequence of QSVLAQPPSASGTPGQRVTISCSGSSSNIG-SNYVYWYQQLPGTAPKLLIYGNNKRPSGVPDRF SGSKSGTSASLAISGLRSEDEADYYCAAWDDSLN-GRVFGGGTKLTVL(SEQ ID NO:181), or an amino acid sequence with at least 90%, at least 91%, at least 92%, at least 93%, at least 94%, at least 95%, at least 96%, at least 97%, at least 98%, or at least 99% identity thereto.

In some embodiments, the scFv binding to BMPRII comprises: a VH domain comprising an amino acid sequence of EVQLLESGGGLVQPGGSLRLS-CAASGFTFSDYYMTWIRQAPGKGLEWVSSISGG-STYYADSR KGRFTISRDNSENTLYLQMNSLRAED-TAVYYCARDFGVAGWFGQYGMDVWGQGTLVTVSS(SEQ ID NO:184), or an amino acid sequence with at least 90%, at least 91%, at least 92%, at least 93%, at least 94%, at least 95%, at least 96%, at least 97%, at least 98%, or at least 99% identity thereto; and a VL domain comprising an amino acid sequence of QSVLTQPP-SASGTPGQRVTISCTGSSSNI-GAGYDVHWYQQLPGTAPKLLIYRSNQRPSGVPDR FSGSKSGTSASLAISGLRSEDEADYYCSSYAG-NYNLVFGGGTKLTVL(SEQ ID NO:185), or an amino acid sequence with at least 90%, at least 91%, at least 92%, at least 93%, at least 94%, at least 95%, at least 96%, at least 97%, at least 98%, or at least 99% identity thereto.

In some embodiments, the scFv binding to ALK1 comprises an amino acid sequence of SEQ ID NO: 120, or an amino acid sequence with at least 90%, at least 91%, at least 92%, at least 93%, at least 94%, at least 95%, at least 96%, at least 97%, at least 98%, or at least 99% identity thereto.

In some embodiments, the scFv binding to ALK1 comprises an amino acid sequence of SEQ ID NO: 122, or an amino acid sequence with at least 90%, at least 91%, at least 92%, at least 93%, at least 94%, at least 95%, at least 96%, at least 97%, at least 98%, or at least 99% identity thereto.

In some embodiments, the scFv binding to BMPRII comprises an amino acid sequence of SEQ ID NO: 121, or an amino acid sequence with at least 90%, at least 91%, at least 92%, at least 93%, at least 94%, at least 95%, at least 96%, at least 97%, at least 98%, or at least 99% identity thereto.

In some embodiments, the scFv binding to ALK1 comprises an amino acid sequence of SEQ ID NO: 123, or an amino acid sequence with at least 90%, at least 91%, at least 92%, at least 93%, at least 94%, at least 95%, at least 96%, at least 97%, at least 98%, or at least 99% identity thereto.

In some embodiments, the first and second polypeptide chain each comprise an amino acid sequence of any one of SEQ ID Nos: 60-63, or an amino acid sequence with at least 90%, at least 91%, at least 92%, at least 93%, at least 94%, at least 95%, at least 96%, at least 97%, at least 98%, or at least 99% identity thereto.

In some embodiments, wherein the multispecific binding protein is capable of inducing signaling by inducing proximity between ALK1 and BMPRII, ActRIIA, or ActRIIB.

In some embodiments, the multispecific binding protein has greater agonist activity compared to a multispecific binding protein that lacks at least one modified hinge region.

In some embodiments, the multispecific binding protein induces at least about 35% of the activity of BMP9.

In some embodiments, the activity of BMP9 is determined by measuring phosphorylated SMAD1 (pSMAD1) levels in cells incubated with the multispecific binding protein and/or in cells incubated with BMP9.

In some embodiments, the melting temperature onset of unfolding (Tonset) of the multispecific binding protein is at least about 55° C.

In some embodiments, the melting temperature thermal transition midpoint (Tm) of the multispecific binding protein is at least about 64° C.

In some embodiments, the Tonset and Tm of the multispecific binding protein is determined by differential scanning calorimetry (DSC).

In some embodiments, the multispecific binding protein is capable of stimulating expression of ID1 in a cell.

In some embodiments, expression of ID1 in the cell is at least 50% relative to ID1 expression from a cell incubated with BMP9.

In some embodiments, the first polypeptide chain further comprises a heavy chain constant region.

In some embodiments, the heavy chain constant region comprises a substitution at amino acid position 234, according to EU numbering.

In some embodiments, the substitution at amino acid position 234 is an alanine (A).

In some embodiments, the heavy chain constant region comprises a substitution at amino acid position 235, according to EU numbering.

In some embodiments, the substitution at amino acid position 235 is an alanine (A).

In some embodiments, the heavy chain constant region comprises a substitution at amino acid position 237 according to EU numbering.

In some embodiments, the substitution at amino acid position 237 is an alanine (A).

In some embodiments, the heavy chain constant region comprises one or more substitutions at amino acid positions 234, 235, or 237, according to EU numbering.

In some embodiments, the substitution at amino acid position 234 is an alanine (A), the substitution at amino acid position 235 is an alanine (A), and the substitution at amino acid position 237 is an alanine (A).

In some embodiments, the heavy chain constant region comprises heterodimerization mutations to promote heterodimerization of the first binding moiety with the second binding moiety.

In some embodiments, the heterodimerization mutations are Knob-in-Hole (KIH) mutations.

In some embodiments, the first heavy chain constant region comprises an amino acid substitution at position 366, 368, or 407 which produced a hole, and the second heavy chain constant region comprises an amino acid substitution at position 366 which produce a knob.

In some embodiments, the first heavy chain constant region comprises the amino acid substitution T366S, L368A, or Y407V, and the second heavy chain constant region comprises the amino acid substitution T366W.

In some embodiments, the heterodimerization mutations are charge stabilization mutations.

In some embodiments, the first heavy chain constant region comprises the amino acid substitution N297K, and the second heavy chain constant region comprises the amino acid substitution N297D.

In some embodiments, the first heavy chain constant region comprises the amino acid substitution T299K, and the second heavy chain constant region comprises the amino acid substitution T299D.

In some embodiments, the heterodimerization mutations comprise an engineered disulfide bond.

In some embodiments, the engineered disulfide bond is formed by a first heavy chain constant region comprising the amino acid substitution Y349C, and a second heavy chain constant region comprising the amino acid substitution S354C.

In some embodiments, the engineered disulfide bond is formed by a C-terminal extension peptide fused to the C-terminus of each of the first heavy chain constant region and the second heavy chain constant region.

In some embodiments, the first heavy chain constant region C-terminal extension comprises the amino acid sequence GEC, and the second heavy chain constant region C-terminal extension comprises the amino acid sequence SCDKT(SEQ ID NO:178).

In some embodiments, at least one heavy chain constant region comprises one or more mutations to promote increased half-life.

In some embodiments, at least one heavy chain constant region comprises one or more substitutions at amino acid positions 252, 254, or 256, according to EU numbering.

In some embodiments, the substitution at amino acid position 252 is a tyrosine (Y), the substitution at amino acid position 254 is a threonine (T), and the substitution at amino acid position 256 is a glutamic acid (E).

In some embodiments, at least one heavy chain constant region comprises one or more substitutions at amino acid positions 428 or 434, according to EU numbering.

In some embodiments, at least one heavy chain constant region comprises a M428L and N434S substitution, according to EU numbering.

In one aspect, the disclosure provides a pharmaceutical composition comprising the multispecific binding protein described herein and a pharmaceutically acceptable carrier.

In one aspect, the disclosure provides an isolated nucleic acid molecule encoding the multispecific binding protein described herein.

In one aspect, the disclosure provides an expression vector comprising the nucleic acid molecule described herein.

In one aspect, the disclosure provides a host cell comprising the expression vector described herein.

In one aspect, the disclosure provides a method for treating a disease or disorder in a subject, comprising administering to a subject in need thereof the multispecific binding protein described herein.

In some embodiments, the disease or disorder is a vascular disease or disorder.

In some embodiments, the vascular disease or disorder is hereditary hemorrhagic telangiectasia (HHT).

In some embodiments, the vascular disease or disorder is pulmonary arterial hypertension (PAH).

In some embodiments, the multispecific binding protein is for use as a medicament.

In one aspect, the disclosure provides a method for inducing signaling between ALK1 and BMPRII, ActRIIA, or ActRIIB in a subject, comprising administering to the subject the multispecific binding protein described herein.

In some embodiments, the multispecific binding protein is capable of inducing signaling by inducing proximity between ALK1 and BMPRII, ActRIIA, or ActRIIB.

In some embodiments, the multispecific binding protein has greater agonist activity compared to a multispecific binding protein that lacks at least one modified hinge region.

In some embodiments, the multispecific binding protein induces at least about 35% of the activity of BMP9.

In some embodiments, the activity of BMP9 is determined by measuring phosphorylated SMAD1 (pSMAD1) levels in cells incubated with the multispecific binding protein and/or in cells incubated with BMP9.

BRIEF DESCRIPTION OF THE DRAWINGS

FIG. 3A-3C are graphs depicting arteriovenous malformations (AVMs) in the retina in a HHT mouse model. FIG. 3A illustrates mice treated with control (no bispecific antibody) compared to DGL288 (15 mg/kg/day). Mice treated with DGL288 did not form detectable AVMs compared to control. FIG. 3B illustrates that mice treated with 1 mg/kg/day OF DGL292 did not form AVMs compared to the mice treated with control. FIG. 3C demonstrates that DGL288 given at a dose of 1 mg/kg/day also did not form AVMs compared to mice treated with control.

DETAILED DESCRIPTION

Figure 1:
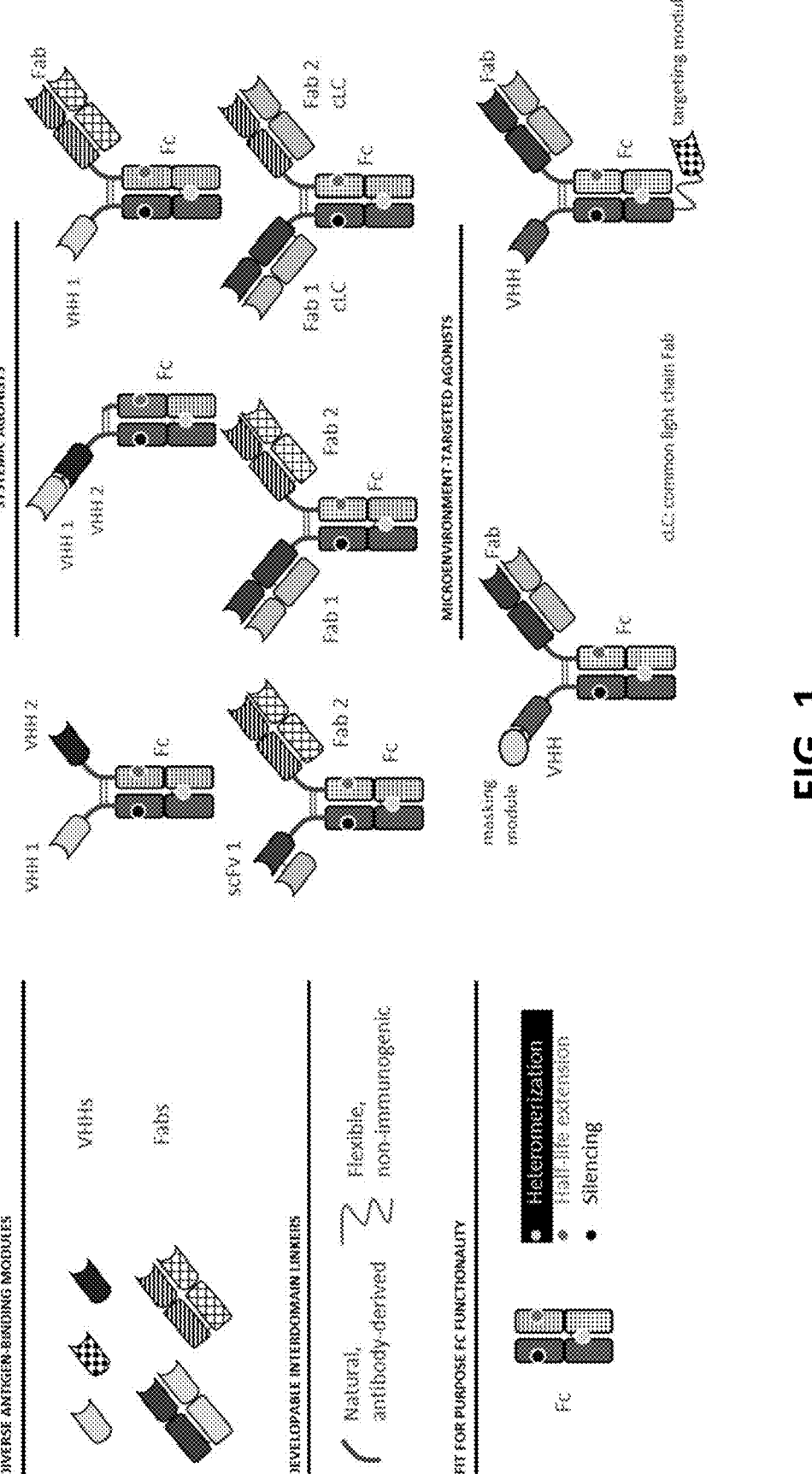
FIG. 1 is an illustration depicting certain exemplary embodiments of the formats of the bispecific antibodies described herein.
Figure 2:
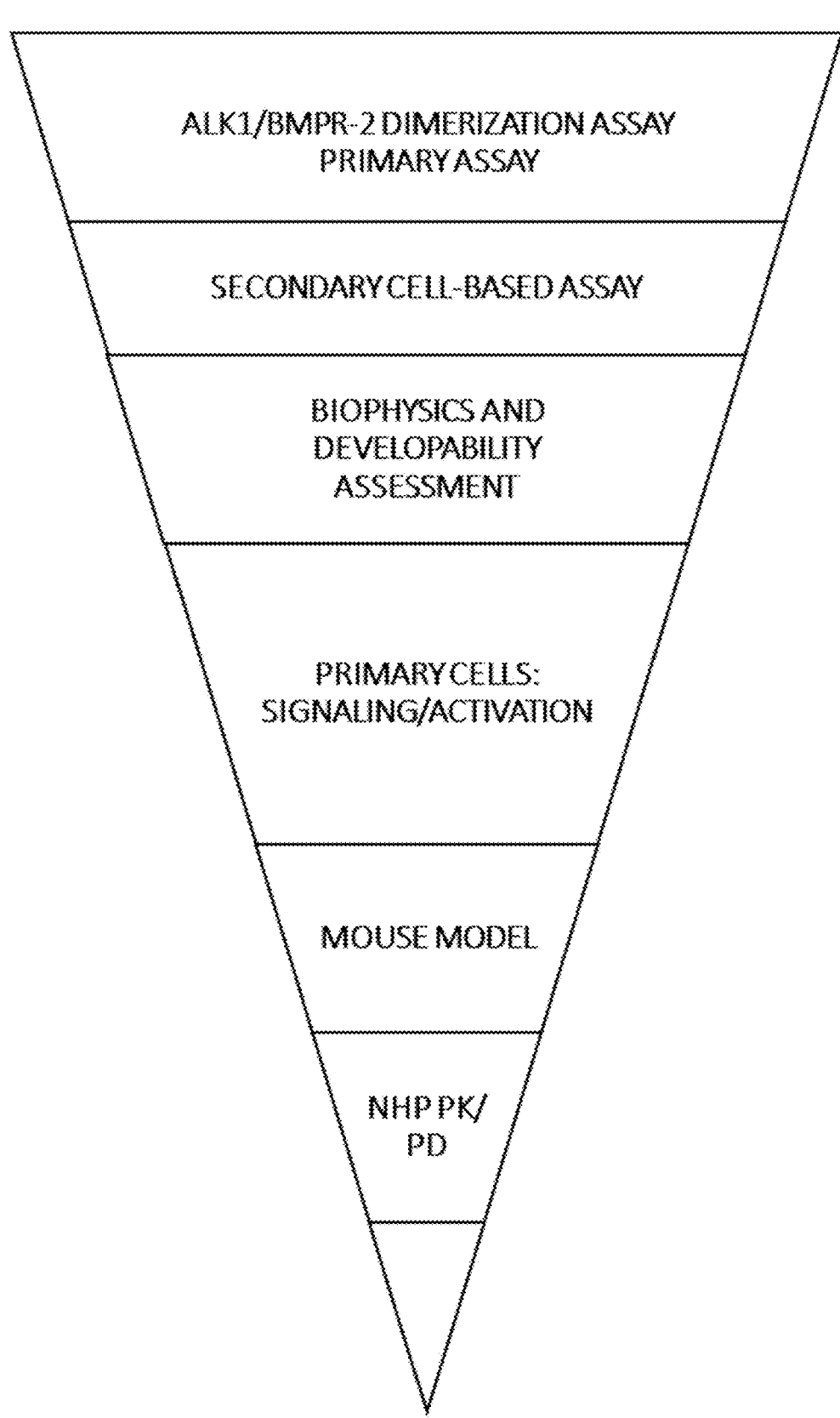
FIG. 2 is a schematic diagram depicting the workflow for characterization of the bispecific antibodies of the present disclosure.

Before the present disclosure is described, it is to be understood that this disclosure is not limited to particular methods and experimental conditions described, as such methods and conditions may vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs.

Although any methods and materials similar or equivalent to those described herein can be used in the practice of the present disclosure, exemplary methods and materials are now described. All publications mentioned herein are incorporated herein by reference to describe in their entirety.

As used herein, the terms "antibody" and "antibodies" include full-length antibodies, antigen-binding fragments of full-length antibodies, and molecules comprising antibody CDRs, VH regions, and/or VL regions. Examples of antibodies include, without limitation, monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single chain antibodies or single-chain Fvs (scFv), camelized antibodies, affibodies, common light chain antibodies, Fab fragments, F(ab')2 fragments, disulfide-linked Fvs (sdFv), anti-idiotypic (anti-Id) antibodies (including, e.g., anti-anti-Id antibodies), dual variable domains (DVD), and antigen-binding fragments of any of the above. In certain embodiments, antibodies described herein refer to polyclonal antibody populations. Antibodies can be of any type (e.g., IgG, IgE, IgM, IgD, IgA or IgY), any class (e.g., IgG1, IgG2, IgG3, IgG4, IgA1 or IgA2), or any subclass (e.g., IgG2a or IgG2b) of immunoglobulin molecule. In certain embodiments, antibodies described herein are IgG antibodies, or a class (e.g., human IgG1 or IgG4) or subclass thereof. As used herein, the terms "VH" and "VL" refer to antibody heavy and light chain variable domain, respectively, as described in Kabat et al., (1991) Sequences of Proteins of Immunological Interest (NIH Publication No. 91-3242, Bethesda), which is herein incorporated by reference in its entirety.

As used herein, the term "VHH" refers to the heavy chain variable domain of a camelid heavy chain-only antibody (HCAb) and humanized variants thereof, as described in Hamers-Casterman C. et al., Nature (1993) 363:446-8.10.1038/363446a0, which is incorporated by reference herein in its entirety.

As used herein, the term "VH/VL Pair" refers to a combination of a VH and a VL that together form the binding site for an antigen.

As used herein, the term "heavy chain" when used in reference to an antibody can refer to any distinct type, e.g., alpha (a), delta (b), epsilon (E), gamma (γ), and mu (p), based on the amino acid sequence of the constant domain, which give rise to IgA, IgD, IgE, IgG, and IgM classes of antibodies, respectively, including subclasses of IgG, e.g., IgG1, IgG2, IgG3, and IgG4.

As used herein, the term "full-length antibody heavy chain" refers to an antibody heavy chain comprising, from N to C terminal, a VH, a CH1 region, a hinge region, a CH2 domain and a CH3 domain.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain. As used herein, the term "complementarity determining region" or "CDR" refers to sequences of amino acids within antibody variable regions, which confer antigen specificity and binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" or "FR" are known in the art to refer to the non-CDR portions of the variable regions of the heavy and light chains. In general, there are four FRs in each heavy chain variable region (FR-H1, FR-H2, FR-H3, and FR-H4), and four FRs in each light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD. ("Kabat" numbering scheme), Al-Lazikani et al., (1997) JMB 273, 927-948 ("Chothia" numbering scheme), MacCallum et al., J. Mol. Biol. 262: 732-745 (1996), "Antibody-antigen interactions: Contact analysis and binding site topography," J. Mol. Biol. 262, 732-745. ("Contact" numbering scheme), Lefranc M. P. et al., "IMGT unique numbering for immunoglobulin and T cell receptor variable domains and Ig superfamily V-like domains," Dev. Comp. Immunol., 2003 January; 27(1):55-77 ("IMGT" numbering scheme), and Honegger A. and Pluckthun A., "Yet another numbering scheme for immunoglobulin variable domains: an automatic modeling and analysis tool," J. Mol. Biol., 2001 Jun. 8; 309(3):657-70, (AHo numbering scheme).

The boundaries of a given CDR or FR may vary depending on the scheme used for identification. For example, the Kabat scheme is based on sequence alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

As used herein, the term "single chain variable fragment" (scFv) refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The term "human antibody," as used herein, is intended to include antibodies having variable and constant regions derived from human germline immunoglobulin sequences. The human mAbs of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "multispecific antigen-binding molecules," as used herein refers to bispecific, trispecific or multispecific antigen-binding molecules, and antigen-binding fragments thereof. Multispecific antigen-binding molecules may be specific for different epitopes of one target polypeptide or may contain antigen-binding domains specific for epitopes of more than one target polypeptide. A multispecific antigen-binding molecule can be a single multifunctional polypep-tide, or it can be a multimeric complex of two or more polypeptides that are covalently or non-covalently associ-ated with one another. The term "multispecific antigen-binding molecules" includes antibodies of the present dis-closure that may be linked to or co-expressed with another functional molecule, e.g., another peptide or protein. For example, an antibody or fragment thereof can be function-ally linked (e.g., by chemical coupling, genetic fusion, non-covalent association or otherwise) to one or more other molecular entities, such as a protein or fragment thereof to produce a bi-specific or a multispecific antigen-binding molecule with a second binding specificity. According to the present disclosure, the term "multispecific antigen-binding molecules" also includes bispecific, trispecific or multispe-cific antibodies or antigen-binding fragments thereof. In certain exemplary embodiments, an antibody of the present disclosure is functionally linked to another antibody or antigen-binding fragment thereof to produce a bispecific antibody with a second binding specificity.

The term "valency" or "valent", as used herein, denotes the presence of a number of binding sites in an antibody molecule. For example, the term bivalent indicates the presence of two binding sites. In some embodiments, the antibody molecule could be multivalent. As such, the term trivalent indicates three binding sites; the term tetravalent indicates four binding sites. In some embodiments, there may be more than four binding sites. In some embodiments, the binding sites may bind to the same antigen. In some embodiments, the binding sites bind to different antigens.

In some embodiments, the multivalent antibody mol-ecules of the invention are multi-chain molecules with one or more binding sites in each chain.

For example, in one embodiment, the multivalent binding molecule is a bivalent molecule with one binding site (e.g., a VHH or scFV) in a first chain and a second binding site in a second chain. In another embodiment, the multivalent binding molecule is a bivalent molecule with two binding sites in a first chain and no binding sites in the second chain.

In another embodiment, the multivalent binding molecule is a trivalent molecule with one binding site (e.g., a VHH or scFV) in a first chain and a second and third binding site in a second chain. In another embodiment, the multivalent binding molecule is a trivalent molecule with three binding sites in a first chain and no binding sites in a second chain.

In another embodiment, the multivalent binding molecule is a tetravalent molecule with two binding sites in a first chain and two binding sites in a second chain. In another embodiment, the multivalent binding molecule is a tetrava-lent molecule with three binding sites in a first chain and one binding site in a second chain. In another embodiment, the multivalent binding molecule is a tetravalent molecule with four binding sites in a first chain and no binding sites in a second chain.

In exemplary embodiments, the heteromeric antibodies of the present disclosure are bispecific antibodies. Bispecific antibodies can be monoclonal, e.g., human or humanized, antibodies that have binding specificities for at least two different antigens.

Methods for making bispecific antibodies are well-known. Traditionally, the recombinant production of bispe-cific antibodies was based on the co-expression of two immunoglobulin heavy chain/light chain pairs, where the two heavy chains have different specificities (Milstein et al., Nature 305:537 (1983)). Because of the random assortment of immunoglobulin heavy and light chains, the hybridomas (quadromas) produce a potential mixture of ten different antibody molecules, of which only one has the correct bispecific structure. The purification of the correct molecule is usually accomplished by affinity chromatography steps. More modern techniques for generating bispecific antibod-ies employ heterodimerization domains that favor desired pairing of heavy chain from the antibody with a first specificity to the heavy chain of an antibody with a second specificity.

Antibody variable domains with the desired binding specificities can be fused to immunoglobulin constant domain sequences. The fusion typically is with an immu-noglobulin heavy chain constant domain, comprising at least part of the hinge, CH2, and CH3 regions. It may have the first heavy chain constant region (CH1) containing the site necessary for light chain binding present in at least one of the fusions. DNAs encoding the immunoglobulin heavy chain fusions and, if desired, the immunoglobulin light chain, are inserted into separate expression vectors, and are co-transformed into a suitable host organism. For further details of generating bispecific antibodies see, for example Suresh et al., Meth. Enzymol. 121:210 (1986).

As used herein, the term "Fc" refers to a polypeptide comprising a CH2 domain and a CH3 domain, wherein the C-terminus of the CH2 domain is linked (directly or indi-rectly) to the N-terminus of the CH3 domain. The term "Fc polypeptide" includes an antibody heavy chain linked to an antibody light chain by disulfide bonds (e.g., to form a half-antibody).

In certain embodiments, an Fc chain begins in the hinge region just upstream of the papain cleavage site and ends at the C-terminus of the antibody. Accordingly, a complete Fc chain comprises at least a hinge domain, a CH2 domain, and a CH3 domain. In certain embodiments, an Fc chain com-prises at least one of: a hinge (e.g., upper, middle, and/or lower hinge region) domain, a CH2 domain, a CH3 domain, a CH4 domain, or a variant, portion, or fragment thereof. In certain embodiments, an Fc domain comprises a complete Fc chain (i.e., a hinge domain, a CH2 domain, and a CH3 domain). In certain embodiments, an Fc chain comprises a hinge domain (or portion thereof) fused to a CH3 domain (or portion thereof). In certain embodiments, an Fc chain comprises a CH2 domain (or portion thereof) fused to a CH3 domain (or portion thereof). In certain embodiments, an Fc chain consists of a CH3 domain or portion thereof. In certain embodiments, an Fc chain consists of a hinge domain (or portion thereof) and a CH3 domain (or portion thereof). In certain embodiments, an Fc chain consists of a CH2 domain (or portion thereof) and a CH3 domain. In certain embodiments, an Fc chain consists of a hinge domain (or portion thereof) and a CH2 domain (or portion thereof). In certain embodiments, an Fc chain lacks at least a portion of a CH2 domain (e.g., all or part of a CH2 domain). An Fc chain herein generally refers to a polypeptide comprising all or part of the Fc chain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc chain may be derived from an immunoglobulin of any species and/or any subtype, including, but not limited to, a human IgG1, IgG2, IgG3, IgG4, IgD, IgA, IgE, or IgM antibody. The Fc domain encompasses native Fc and Fc variant molecules. As with Fc variants and native Fc's, the term Fc chain includes molecules in monomeric or multimeric form, whether digested from whole antibody or produced by other means. In some embodiment, the Fc chain comprises the carboxy-terminal portions of both heavy chains held together by disulfides. In certain embodiments, an Fc chain consists of a CH2 domain and a CH3 domain.

In some embodiments, an Fc polypeptide comprises part or all of a wild-type hinge sequence (generally at its N-terminal). In some embodiments, an Fc polypeptide does not comprise a functional or wild-type hinge sequence.

As used herein, the term "CH1 domain" refers to the first constant domain of an antibody heavy chain (e.g., amino acid positions 118-215 of human IgG1, according to the EU index). The term includes naturally occurring CH1 domains and engineered variants of naturally occurring CH1 domains (e.g., CH1 domains comprising one or more amino acid insertions, deletions, substitutions, or modifications relative to a naturally occurring CH1 domain).

As used herein, the term "CH2 domain" refers to the second constant domain of an antibody heavy chain (e.g., amino acid positions 231-340 of human IgG1, according to the EU index). The term includes naturally occurring CH2 domains and engineered variants of naturally occurring CH2 domains (e.g., CH2 domains comprising one or more amino acid insertions, deletions, substitutions, or modifications relative to a naturally occurring CH2 domain).

As used herein, the term "CH3 domain" refers to the third constant domain of an antibody heavy chain (e.g., amino acid positions 341-447 of human IgG1, according to the EU index). The term includes naturally occurring CH3 domains and engineered variants of naturally occurring CH3 domains (e.g., CH3 domains comprising one or more amino acid insertions, deletions, substitutions, or modifications relative to a naturally occurring CH3 domain).

As used herein, the term "hinge region" refers to the portion of an antibody heavy chain comprising the cysteine residues (e.g., the cysteine residues at amino acid positions 226 and 229 of human IgG1, according to the EU index) that mediate disulfide bonding between two heavy chains in an intact antibody. The term includes naturally occurring hinge regions and engineered variants of naturally occurring hinge regions (e.g., hinge regions comprising one or more amino acid insertions, deletions, substitutions, or modifications relative to a naturally occurring hinge regions). An exemplary full-length IgG1 hinge region comprises amino acid positions 216-230 of human IgG1, according to the EU index. A hinge region may consist of at least 2 (e.g., 5, 10, 15, 20, 40, 60 or more) amino acids which result in a flexible or semi-flexible linkage between adjacent variable regions and/or constant domains in a single polypeptide molecule. In some embodiments, the hinge region is an immunoglobulin-like hinge region. In some embodiments, the immunoglobulin-like hinge region can be from or derived from any IgG1, IgG2, IgG3, or IgG4 subtype, or from IgA, IgE, IgD or IgM, including chimeric forms thereof, e.g., a chimeric IgG1/2 hinge region.

In some embodiments, the hinge region can be from the human IgG1 subtype extending from amino acid 216 to amino acid 230 according to the numbering system of the EU index, or from amino acid 226 to amino acid 243 according to the numbering system of Kabat. Those skilled in the art may differ in their understanding of the exact amino acids corresponding to the various domains of the IgG molecule. Thus, the N-terminal or C-terminal of the domains outlined above may extend or be shortened by 1, 2, 3, 4, 5, 6, 7, 8, 9, or even 10 amino acids.

The term "upper hinge" as used herein typically refers to the last residue of the CH1 domain up to but not including the first inter-heavy chain cysteine. The upper hinge can sometimes be defined as the N-terminal sequence from position 216 to position 225 according to the Kabat EU numbering system of an IgG1 antibody (Kabat et al., Sequences of Proteins of Immunological Interest, 5th Ed. Public Health Service, National Institute of Health, Bethesda, Md., 1991). The term "middle hinge" refers to the region extending from the first inter-heavy chain cysteine to a proline residue adjacent to the carboxyl-end of the last middle hinge cysteine. The middle hinge can be the N-terminal sequence from position 226 to position 230 according to the Kabat EU numbering system. The term "lower hinge" refers to a highly conserved 7-8 amino acids. The lower hinge can be defined as the sequence from position 231 to 238 according the Kabat EU numbering system of an IgG1 antibody. In some embodiments, the antibody according to the present invention effectively comprises an upper, a middle, and a lower hinge.

As used herein, the term "a modified hinge region" refers to a hinge region in which alterations are made in one or more of the characteristics of the hinge, including, but not limited to, flexibility, length, conformation, charge and hydrophobicity relative to a wild-type hinge. The modified hinge regions disclosed herein may be generated by methods well known in the art, such as, for example introducing a modification into a wild-type hinge. In some embodiments, the hinge region may be modified by one or more amino acids. Modifications which may be utilized to generate a modified hinge region include, but are not limited to, amino acid insertions, deletions, substitutions, and rearrangements. Said modifications of the hinge and the modified hinge regions disclosed are referred to herein jointly as "hinge modifications of the invention", "modified hinge(s) of the invention" or simply "hinge modifications" or "modified hinge(s)." The modified hinge regions disclosed herein may be incorporated into a molecule of choice including, but not limited to, antibodies and fragments thereof. In some embodiments, the hinge region may be truncated and contain only a portion of the full hinge region.

As demonstrated herein, molecules comprising a modified hinge may exhibit altered (e.g., enhanced) agonistic activity when compared to a molecule having the same amino acid sequence except for the modified hinge, such as, for example, a molecule having the same amino acid sequence except comprising a wild type hinge. In some embodiments, the antibody comprises a modified hinge region wherein the upper hinge region is up to 7 amino acids in length. In some embodiments, the upper hinge region is absent. In some embodiments, the modified hinge is a modified IgG1 linker. In some embodiments, the modified IgG1 hinge is derived from the sequence PLAPDKTHT (SEQ ID NO: 1). In some embodiments, the modified IgG1 hinge comprises the sequence PLAP (SEQ ID NO: 2). In some embodiments, the modified IgG1 hinge comprises the sequence DKTHT (SEQ ID NO: 5). In some embodiments, the modified hinge is a modified IgG4 hinge. In some embodiments, the modified IgG1 hinge comprises the sequence EKSYGPP (SEQ ID NO: 4). In some embodiments, the modified hinge is a Gly/Ser hinge. In some embodiments, the Gly/Ser hinge comprises the sequence GGGGSGGGGSGGGGSGGGGS (SEQ ID NO: 3). In some embodiments, the C-terminal residues of the variable domain adjacent to the upper hinge are truncated. In some embodiments, at least one residue of the variable domain adjacent to the upper hinge is truncated. In some embodiments, at least two residues of the variable domain adjacent to the upper hinge is truncated.

The modified hinge region of the disclosure may be used as a linker to attach one or more antigen binding domains of the disclosure. In certain embodiments, a first variable heavy chain domain (VH1) linked to a second variable heavy chain domain (VH2) via at least one modified hinge region. In certain embodiments, a first variable light chain domain (VL1) linked to a second variable light chain domain (VL2) via at least one modified hinge region. The VH1 and VL1 associate to form a first antigen binding domain and the VH2 and VL2 associate to form a second antigen binding domain. In other embodiments, a first scFv is linked to a second scFv via at least one modified hinge region.

In certain embodiments, the multispecific binding proteins of the disclosure (i.e., multispecific binding proteins having at least a first antigen binding protein and a second antigen binding protein) have greater agonist activity compared to a multispecific binding protein that lacks at least one modified hinge region. For example, but in no way limiting, a multispecific binding protein having a VH1 linked to a VH2 via at least one modified hinge region and/or a VL1 linked to a VL2 via at least one modified hinge region may possess greater agonist activity of a target receptor pair (e.g., ALK1 and any one of BMPRII, ActRIIA, and ActRIIB), than the same multispecific binding protein that does not have the at least one modified hinge region.

As used herein, the term "EU index" refers to the EU numbering convention for the constant regions of an antibody, as described in Edelman, G M. et al., Proc. Natl. Acad. USA, 63, 78-85 (1969) and Kabat et al., Sequences of Proteins of Immunological Interest, U.S. Dept. Health and Human Services, 5th edition, 1991, each of which is herein incorporated by reference in its entirety. All numbering of amino acid positions of the Fc polypeptides, or fragments thereof, used herein is according to the EU index. As used herein, the term "linker" refers to 0-100 contiguous amino acid residues. The linkers are, present or absent, and same or different. Linkers comprised in a protein or a polypeptide may all have the same amino acid sequence or may have different amino acid sequences.

In some embodiments, the term "linker" refers to 1-100 contiguous amino acid residues. Typically, a linker provides flexibility and spatial separation between two amino acids or between two polypeptide domains. A linker may be inserted between VH, VL, CH and/or CL domains to provide sufficient flexibility and mobility for the domains of the light and heavy chains depending on the format of the molecule. A linker is typically inserted at the transition between variable domains between variable and knockout domain, or between variable and constant domains, respectively, at the amino sequence level. The transition between domains can be identified because the approximate sizes of the immunoglobulin domains are well understood. The precise location of a domain transition can be determined by locating peptide stretches that do not form secondary structural elements such as beta-sheets or alpha-helices as demonstrated by experimental data or as can be determined by techniques of modeling or secondary structure prediction.

As used herein, the term "specifically binds," "specifically binding," "binding specificity" or "specifically recognized" refers that an antigen binding protein or antigen-binding fragment thereof that exhibits appreciable affinity for an antigen (e.g., a BMPR Type I receptor or BMPR Type II receptor antigen) and does not exhibit significant cross reactivity to a target that is not a BMPR Type I receptor or a BMPR Type II receptor protein. As used herein, the term "affinity" refers to the strength of the interaction between an antigen binding protein or antigen-binding fragment thereof antigen binding site and the epitope to which it binds. In certain exemplary embodiments, affinity is measured by surface plasmon resonance (SPR), e.g., in a Biacore instrument. As readily understood by those skilled in the art, an antigen binding protein affinity may be reported as a dissociation constant (KD) in molarity (M). The antigen binding protein or antigen-binding fragment thereof of the disclosure have KD values in the range of about $10^{-5}$ M to about $10^{-12}$ M (i.e., low micromolar to picomolar range), about $10^{-7}$ M to $10^{-11}$ M, about $10^{-8}$ M to about $10^{-10}$ M, about $10^{-9}$ M. In certain embodiments, the antigen binding protein or antigen-binding fragment thereof has a binding affinity of about $10^{-5}$ M, $10^{-6}$ M, $10^{-7}$ M, $10^{-8}$ M, $10^{-9}$ M, $10^{-10}$ M, $10^{-11}$ M, or $10^{-12}$ M. In certain embodiments, the antigen binding protein or antigen-binding fragment thereof has a binding affinity of about $10^{-7}$ M to about $10^{-9}$ M (nanomolar range).

Specific binding can be determined according to any art-recognized means for determining such binding. In some embodiments, specific binding is determined by competitive binding assays (e.g., ELISA) or Biacore assays. In certain embodiments, the assay is conducted at about 20° C., 25° C., 30° C., or 37° C.

As used herein, "administer" or "administration" refers to the act of injecting or otherwise physically delivering a substance as it exists outside the body (e.g., an isolated binding polypeptide provided herein) into a patient, such as by, but not limited to, pulmonary (e.g., inhalation), mucosal (e.g., intranasal), intradermal, intravenous, intramuscular delivery and/or any other method of physical delivery described herein or known in the art. When a disease, or a symptom thereof, is being managed or treated, administration of the substance typically occurs after the onset of the disease or symptoms thereof. When a disease, or symptom thereof, is being prevented, administration of the substance typically occurs before the onset of the disease or symptoms thereof and may be continued chronically to defer or reduce the appearance or magnitude of disease-associated symptoms.

As used herein, the term "composition" is intended to encompass a product containing the specified ingredients (e.g., an isolated binding polypeptide provided herein) in, optionally, the specified amounts, as well as any product which results, directly or indirectly, from combination of the specified ingredients in, optionally, the specified amounts.

"Effective amount" means the amount of active pharmaceutical agent (e.g., an isolated binding polypeptide of the present disclosure) sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

As used herein, the terms "subject" and "patient" are used interchangeably. As used herein, a subject can be a mammal, such as a non-primate (e.g., cows, pigs, horses, cats, dogs, rats, mice, etc.) or a primate (e.g., monkey and human). In certain embodiments, the term "subject," as used herein, refers to a vertebrate, such as a mammal. Mammals include, without limitation, humans, non-human primates, wild animals, feral animals, farm animals, sport animals, and pets.

As used herein, the term "therapy" refers to any protocol, method and/or agent that can be used in the prevention, management, treatment and/or amelioration of a disease or a symptom related thereto. In some embodiments, the term "therapy" refers to any protocol, method and/or agent that can be used in the modulation of an immune response to an infection in a subject or a symptom related thereto. In some embodiments, the terms "therapies" and "therapy" refer to a biological therapy, supportive therapy, and/or other therapies useful in the prevention, management, treatment and/or amelioration of a disease or a symptom related thereto, known to one of skill in the art such as medical personnel. In other embodiments, the terms "therapies" and "therapy" refer to a biological therapy, supportive therapy, and/or other therapies useful in the modulation of an immune response to an infection in a subject or a symptom related thereto known to one of skill in the art such as medical personnel.

As used herein, the terms "treat," "treatment" and "treating" refer to the reduction or amelioration of the progression, severity, and/or duration of a disease or a symptom related thereto, resulting from the administration of one or more therapies (including, but not limited to, the administration of one or more prophylactic or therapeutic agents, such as an isolated binding polypeptide provided herein). The term "treating," as used herein, can also refer to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

The term "about" or "approximately" means within about 20%, such as within about 10%, within about 5%, or within about 1% or less of a given value or range.

BMPR Type I Receptors and BMPR Type II Receptors

Bone morphogenetic protein (BMP) Type I and Type II receptors are serine-threonine kinase transmembrane signal transduction proteins that regulate a vast array of ligand-dependent cell-fate decisions with temporal and spatial fidelity during development and postnatal life. The activation of the receptors, induced by first binding to their ligand (BMPs) and then heterodimerizing, triggers intracellular signaling that is initiated by phosphorylation of receptor-regulated SMAD1, 5, and 8 (R-SMADs). These activated R-SMADs form heteromeric complexes with SMAD4, which engage in specific transcriptional responses.

As used herein, the term "ALK1" refers to the activin A receptor like type 1, a BMP Type I receptor. Alternative terms for ALK1 include ACVRLK1, Serine/threonine-protein kinase receptor R3, TGF-B superfamily receptor type 1, and HHT2. The ALK1 protein is encoded by the gene ACVRL1. The ALK1 protein comprises human, murine, and further mammalian homologues. Sequence(s) for human ALK1 are accessible via UniProt Identifier P37023 (ACVL1 HUMAN), for instance human isoform P37023-1. Sequence (s) for murine ALK1 are accessible via UniProt Identifier Q61288 (ACVL1 MOUSE). The term "ALK1" may encompass different isoforms and variants that may exist for different species and are all comprised by the term ALK1. In addition, the term "ALK1" may include synthetic variants of the ALK1 protein produced, e.g. by introducing at least one mutation. The protein ALK1 may furthermore be subject to various modifications, e.g., synthetic or naturally occurring modifications. Naturally occurring mutations in the ALK1 gene are associated with hereditary hemorrhagic telangiectasia (HHT) type 2, wherein patients suffer pulmonary hypertension, daily epistaxis, strokes, and emboli.

The term "BMPRII" refers to the protein Bone morphogenetic protein receptor type 2. Alternative names comprise BMP type-2 receptor, Bone morphogenetic protein receptor type II, BMP type II receptor, BMR2, PPH1, BMPR3, BRK-3, POVD1, T-ALK, BMPRII and BMPR-II. The BMPRII protein is encoded by the gene BMPR2. The BMPRII protein comprises human, murine, and further mammalian homologues. Sequence(s) for human BMPRII are accessible via UniProt Identifier Q13873 (BMPRII HUMAN), for instance human isoform 1 (identifier: QI 3873-1), and human isoform 2 (identifier: Q13873-2). Sequence(s) for murine BMPRII are accessible via UniProt Identifier 035607 (BMPRII MOUSE). Different isoforms and variants may exist for the different species and are all comprised by the term BMPRII. In addition, synthetic variants of the BMPRII protein may be generated, e.g. by introducing at least one mutation, and are comprised by the term BMPRII. The protein BMPRII may furthermore be subject to various modifications, e.g., synthetic or naturally occurring modifications.

As used herein, the term "ActRIIA" refers to a family of activin receptor type IIA (ActRIIA) proteins from any species and variants derived from such ActRIIA proteins by mutagenesis or other modification. Reference to ActRIIA herein is understood to be a reference to any one of the currently identified forms. Members of the ActRIIA family are generally transmembrane proteins, composed of a ligand-binding extracellular domain comprising a cysteine-rich region, a transmembrane domain, and a cytoplasmic domain with predicted serine/threonine kinase activity. The term "ActRIIA" includes polypeptides comprising any naturally occurring polypeptide of an ActRIIA family member as well as any variants thereof (including mutants, fragments, fusions, and peptidomimetic forms) that retain a useful activity.

As used herein, the term "ActRIIB" refers to a family of activin receptor type IIB (ActRIIB) proteins from any species and variants derived from such ActRIIB proteins by mutagenesis or other modification. Reference to ActRIIB herein is understood to be a reference to any one of the currently identified forms. Members of the ActRIIB family are generally transmembrane proteins, composed of a ligand-binding extracellular domain comprising a cysteine-rich region, a transmembrane domain, and a cytoplasmic domain with predicted serine/threonine kinase activity. The term "ActRIIA" includes polypeptides comprising any naturally occurring polypeptide of an ActRIIB family member as well as any variants thereof (including mutants, fragments, fusions, and peptidomimetic forms) that retain a useful activity. Examples of such variant ActRIIB polypeptides are provided throughout the present disclosure as well as in International Patent Application Publication Nos. WO 2006/012627 and WO 2008/097541, which are incorporated herein by reference in its entirety.

ALK1/BMPRII, ActRIIA or ActRIIB Bispecific Antibodies

Bispecific antibodies as provided herein promote the heterodimerization of ALK1 and a BMP Type II receptor, such as BMPRII, ActRIIA, and ActRIIB. Bispecific antibodies according to the current invention can be produced with high yields. The bispecific antibodies or their binding domains can be easily maturated, or screening approaches can be used to detect binders with optimized binding capabilities. For bispecific antibodies, each binding site can be optimized individually. Finally, even in the absence of downstream signaling, e.g. due to a genetic defect, an antibody approach could still be able to rescue the ALK1/BMPRII, ALK1/ActRIIA, or the ALK1 ActRIIB signaling cascade.

The antibodies disclosed herein specifically bind to ALK1 and BMPRII, ActRIIA, or ActRIIB; i.e., they bind to their targets with an affinity that is higher (e.g., at least two-fold higher) than their binding affinity for an irrelevant antigen (e.g., bovine serum albumin (BSA), casein).

As used herein, the term "inducing proximity" between ALK1 and BMPRII, ActRIIA, or ActRIIB refers to bringing ALK1 and any one of BMPRII, ActRIIA, or ActRIIB together such that the ALK1/BMPRII, ALK1/ActRIIA, or the ALK1/ActRIIB signaling cascade is stimulated. In certain embodiments, the proximity induced by the multispecific binding proteins of the disclosure is the same or similar to the proximity induced when BMP9 brings ALK1 and BMPRII together. Stimulation of the ALK1/BMPRII, ALK1/ActRIIA, or the ALK1/ActRIIB signaling cascade may be detected through any of the downstream results of said signaling cascade, including, but not limited to, detection of phosphorylated SMAD proteins (e.g. pSMAD1, pSMAD5, and/or pSMAD8), and detection of gene expression associated with said signaling cascade. Genes that have been previously shown to be upregulated from the ALK1/BMPRII, ALK1/ActRIIA, or the ALK1/ActRIIB signaling cascade include, but are not limited to, ID1, ID3, and TMEM100.

The bispecific antibodies of the disclosure are exemplified by numerous ALK1/BMPRII bispecific antibodies in the working examples, however the technical effect of the exemplified bispecific antibodies (i.e., inducing agonism) is expected to extend to ALK1/ActRIIA and ALK1/ActRIIB bispecific antibodies as well. One of skill in the art will appreciate that the technical effect of inducing proximity between ALK1 and BMPRII with a ALK1/BMPRII bispecific antibody, and the subsequent activation of the receptor complex, will extend to ALK1/ActRIIA and ALK1/ActRIIB bispecific antibodies that also induce proximity between ALK1 and ActRIIA and ALK1 and ActRIIB.

The bispecific antibodies of the disclosure may employ at least one modified hinge region. The modified hinge region serves as a linker to connect different domains of the bispecific antibody. In certain embodiments, the modified hinge region links a first variable heavy chain domain (VH1) to a second variable heavy chain domain (VH2), and/or the modified hinge region links a first variable light chain domain (VL1) linked to a second variable light chain domain (VL2). In another embodiment, the modified hinge region links a first scFv to a second scFv. In certain embodiments, the modified hinge region comprises; i) an upper hinge region of up to 7 amino acids in length or is absent;

and ii) a lower hinge region. In certain embodiments, the modified hinge region comprises or consists of an amino acid sequence of PLAP(SEQ ID NO:2) or PAPNLLGGP (SEQ ID NO:157).

The bispecific antibodies of the disclosure (e.g., multi-specific binding proteins) have greater agonist activity compared to a bispecific antibody that lacks at least one modified hinge region. Agonist activity may be measured using a specific receptor potency assay (e.g., Pathhunter U2OS dimerization assay (DiscoverX) Potency assays (e.g., Pathhunter) involve a cell line (e.g., U2OS) that expresses the target receptors of interest. The binding of the bispecific antibodies to the receptors triggers a signaling cascade leading to the expression of a reporter gene which can be quantified.

The bispecific antibodies of the disclosure (e.g., multi-specific binding proteins) induce at least about 35% of the activity of BMP9. In certain embodiments, bispecific antibodies of the disclosure (e.g., multispecific binding proteins) induce at least about 40% of the activity of BMP9. In certain embodiments, bispecific antibodies of the disclosure (e.g., multispecific binding proteins) induce at least about 40% of the activity of BMP9. In certain embodiments, bispecific antibodies of the disclosure (e.g., multispecific binding proteins) induce at least about 45% of the activity of BMP9. In certain embodiments, bispecific antibodies of the disclosure (e.g., multispecific binding proteins) induce at least about 50% of the activity of BMP9. In certain embodiments, bispecific antibodies of the disclosure (e.g., multispecific binding proteins) induce at least about 55% of the activity of BMP9. In certain embodiments, bispecific antibodies of the disclosure (e.g., multispecific binding proteins) induce at least about 60% of the activity of BMP9. In certain embodiments, bispecific antibodies of the disclosure (e.g., multispecific binding proteins) induce at least about 65% of the activity of BMP9. In certain embodiments, bispecific antibodies of the disclosure (e.g., multispecific binding proteins) induce at least about 70% of the activity of BMP9. In certain embodiments, bispecific antibodies of the disclosure (e.g., multispecific binding proteins) induce at least about 75% of the activity of BMP9. In certain embodiments, bispecific antibodies of the disclosure (e.g., multispecific binding proteins) induce at least about 80% of the activity of BMP9.

In certain embodiments, the activity of BMP9 is determined by measuring phosphorylated SMAD1 (pSMAD1) levels, measuring phosphorylated SMAD5 (pSMAD5) levels, and/or measuring phosphorylated SMAD8 (pSMAD8) levels in cells incubated with the multispecific binding protein and/or in cells incubated with BMP9. Phosphorylated SMAD levels (i.e., pSMAD1, pSMAD5, and pSMAD8) may be detected using an enzyme-linked immunosorbent assay (ELISA). Briefly, a first population of cells (e.g., HUVEC cells) is incubated with a bispecific antibody of the disclosure and a second population of cells (e.g., HUVEC cells) is incubated with BMP9. Following an incubation time, cells are lysed and the cell lysate is analyzed using an antibody against the phosphorylated SMAD protein (i.e., pSMAD1, pSMAD5, or pSMAD8). Antibody binding is detected (such as through a fluorescent signal) and quantified. The level of the phosphorylated SMAD protein in the first population of cells is then compared to the level of the phosphorylated SMAD protein in the second population of cells to determine the % activity of the bispecific antibody relative to BMP9.

The bispecific antibodies of the disclosure (e.g., multi-specific binding proteins) are capable of stimulating expression of a gene selected from ID1, ID3, and TMEM100 in a cell. The expression of ID1, ID3, and/or TMEM100 in the cell is at least 50% relative to ID1, ID3, and/or TMEM100 expression from a cell incubated with BMP9. In certain embodiments, the expression of ID1, ID3, and/or TMEM100 in the cell is at least equal to ID1, ID3, and/or TMEM100 expression from a cell incubated with BMP9. In certain embodiments, the expression of ID1, ID3, and/or TMEM100 in the cell is at least 1.5-fold greater than ID1, ID3, and/or TMEM100 expression from a cell incubated with BMP9. In certain embodiments, the expression of ID1, ID3, and/or TMEM100 in the cell is at least 2-fold greater than ID1, ID3, and/or TMEM100 expression from a cell incubated with BMP9. In certain embodiments, the expression of ID1, ID3, and/or TMEM100 in the cell is at least 3-fold greater than ID1, ID3, and/or TMEM100 expression from a cell incubated with BMP9. In certain embodiments, the expression of ID1, ID3, and/or TMEM100 in the cell is at least 4-fold greater than ID1, ID3, and/or TMEM100 expression from a cell incubated with BMP9. In certain embodiments, the expression of ID1, ID3, and/or TMEM100 in the cell is at least 5-fold greater than ID1, ID3, and/or TMEM100 expression from a cell incubated with BMP9. In certain embodiments, the expression of ID1, ID3, and/or TMEM100 in the cell is at least 6-fold greater than ID1, ID3, and/or TMEM100 expression from a cell incubated with BMP9.

Detection of ID1, ID3, and TMEM100 expression may be achieved using standard molecular biology techniques and PCR. Briefly, a first population of cells (e.g., HUVEC cells or HMEC-1 cells) is incubated with a bispecific antibody of the disclosure and a second population of cells (e.g., HUVEC cells or HMEC-1 cells) is incubated with BMP9. Following an incubation time, mRNA from the cells is isolated, cDNA is generated, and PCR is performed to detect the levels of ID1, ID3, and/or TMEM100 relative to a control gene, such as GAPDH. The level of ID1, ID3, and/or TMEM100 in the first population of cells is then compared to the level of ID1, ID3, and/or TMEM100 in the second population of cells.

Thermostability

Certain bispecific antibodies of the disclosure (e.g., multispecific binding proteins) possess improved thermostability relative to other antibodies of the disclosure. For example, bispecific antibodies designated DGL947 (comprising a first polypeptide chain of SEQ ID NO: 139 and a second polypeptide chain of SEQ ID NO: 146) and DGL949 (comprising a first polypeptide chain of SEQ ID NO: 141 and a second polypeptide chain of SEQ ID NO: 146) possess improved thermostability relative to bispecific antibodies designated DGL945 and DGL1146. As used herein, improved thermostability" refers to a higher melting temperature. The melting temperature may be the melting temperature onset of unfolding (Tonset) and/or the melting temperature thermal transition midpoint (Tm).

In certain embodiments, the melting temperature onset of unfolding (Tonset) of the bispecific antibodies of the disclosure is at least about 50° C., at least about 51° C., at least about 52° C., at least about 53° C., at least about 54° C., at least about 55° C., at least about 56° C., at least about 57° C., at least about 58° C., at least about 59° C., or at least about 60° C.

In certain embodiments, the melting temperature thermal transition midpoint (Tm) of the bispecific antibodies of the disclosure is at least about 63° C., at least about 64° C., at least about 65° C., at least about 66° C., at least about 67° C., at least about 68° C., at least about 69° C., at least about 70° C., at least about 71° C., or at least about 72° C.

The Tonset and Tm of the bispecific antibodies of the disclosure is determined by differential scanning calorimetry (DSC).

In some embodiments according to the first aspect, the bispecific antibodies specifically bind an extracellular domain of ALK1 and/or an extracellular domain of BMPRII, ActRIIA, OR ActRIIB. In some embodiments, the ALK1 is human ALK1 or a fragment thereof, and/or the BMPRII, ActRIIA, or ActRIIB is human BMPRII, ActRIIA, or ActRIIB or a fragment thereof. In some embodiments, the bispecific antibody binds an extracellular domain of human ALK1 or a fragment thereof and/or an extracellular domain of human BMPRII or a fragment thereof.

In some embodiments, the bispecific antibody binds to ALK1 with a Kd of at most about $10^{-4}$ M to about $10^{-13}$ M (e.g., $10^{-4}$ M, $10^{-4.5}$ M, $10^{-5}$ M, $10^{-5.5}$ M, $10^{-6}$ M, $10^{-6.5}$ M, $10^{-7}$ M, $10^{-7.5}$ M, $10^{-8}$ M, $10^{-8.5}$ M, $10^{-9}$ M, $10^{-9.5}$ M, $10^{-10}$ M, $10^{-10.5}$ M, $10^{-11}$ M, $10^{-11.5}$ M, $10^{-12}$ M, $10^{-12.5}$ M, $10^{-13}$ M).

In some embodiments, the bispecific antibody binds to BMPRII, ActRIIA, or ActRIIB with a Kd of at most about $10^{-4}$ M to about $10^{-13}$ M (e.g., $10^{-4}$ M, $10^{-4.5}$ M, $10^{-5}$ M, $10^{-5.5}$ M, $10^{-6}$ M, $10^{-6.5}$ M, $10^{-7}$ M, $10^{-7.5}$ M, $10^{-8}$ M, $10^{-8.5}$ M, $10^{-9}$ M, $10^{-9.5}$ M, $10^{-10}$ M, $10^{-10.5}$ M, $10^{-11}$ M, $10^{-11.5}$ M, $10^{-12}$ M, $10^{-12.5}$ M, $10^{-13}$ M).

In some embodiments, the bispecific antibody binds to ALK1 and BMPRII or ALK1 and ActRIIA or ALK1 and ActRIIB with a Kd of at most about $10^{-4}$ M to about $10^{-13}$ M (e.g., $10^{-4}$ M, $10^{-4.5}$ M, $10^{-5}$ M, $10^{-5.5}$ M, $10^{-6}$ M, $10^{-6.5}$ M, $10^{-7}$ M, $10^{-7.5}$ M, $10^{-8}$ M, $10^{-8.5}$ M, $10^{-9}$ M, $10^{-9.5}$ M, $10^{-10}$ M, $10^{-10.5}$ M, $10^{-11}$ M, $10^{-11.5}$ M, $10^{-12}$ M, $10^{-12.5}$ M, $10^{-13}$ M).

The Kd of antibody binding to an antigen can be assayed using any method known in the art including, for example, immunoassays such as enzyme-linked immunospecific assay (ELISA), Bimolecular Interaction Analysis (BIA) (e.g., Sjolander & Urbaniczky; Anal. Chem. 63:2338-2345, 1991; Szabo, et al., Curr. Opin. Struct. Biol. 5:699-705, 1995), and fluorescence-activated cell sorting (FACS) for quantification of antibody binding to cells that express an antigen. BIA is a technology for analyzing bispecific interactions in real time, without labeling any of the interactants (e.g., BIACORE™). Changes in the optical phenomenon surface plasmon resonance (SPR) can be used as an indication of real-time reactions between biological molecules.

In some embodiments, the antibody according to the current invention, in addition to binding domains for ALK1 and BMPRII, ActRIIA, or ActRIIB further comprises a binding domain for a ligand of the ALK1/BMPRII, ALK1/ActRIIA, or ALK1/ActRIIB receptor, or for another molecule involved in ALK1/BMPRII, ALK1/ActRIIA, or ALK1/ActRIIB signaling.

In some embodiments, the binding moiety which binds specifically to ALK1 is cross reactive with human ALK1 and mouse ALK1.

In some embodiments, the binding moiety which binds specifically to ActRIIA is cross reactive with ActRIIB.

Except if there is an obvious incompatibility for a person skilled in the art, each of the embodiments describing the binding capabilities can be combined with each of the embodiments describing the format of the antibody.

Binding Domains

One component of the multispecific binding protein of the present disclosure is a binding domain or binding specificity which binds a first cell surface target and a second cell surface target. In certain embodiments, the first cell surface target is a first receptor subunit, and the second cell surface target is the receptor subunit.

Any type of binding moiety that specifically binds to a specific receptor subunit can be employed in the multispecific binding proteins disclosed herein. In certain embodiments, the binding moiety comprises an antibody variable domain. Exemplary binding moieties comprising an antibody variable domain include, without limitation, a VH, a VL, a VHH, a VH/VL pair, an scFv, a diabody, or a Fab. Other suitable binding moiety formats include, without limitation, lipocalins (see e.g., Gebauer M. et al., 2012, Method Enzymol. 503:157-188, which is incorporated by reference herein in its entirety), adnectins (see e.g., Lipovsek D., 2011, Protein Eng. Des. Sel. 24:3-9, which is incorporated by reference herein in its entirety), avimers (see e.g., Silverman J, et al., 2005, Nat. Biotechnol. 23:1556-1561, which is incorporated by reference herein in its entirety), fynomers (see e.g., Schlatter D, et al., 2012, mAbs 4:497-508, which is incorporated by reference herein in its entirety), kunitz domains (see e.g., Hosse R. J. et al., 2006, Protein Sci. 15:14-27, which is incorporated by reference herein in its entirety), knottins (see e.g., Kintzing J. R. et al., 2016, Curr. Opin. Chem. Biol. 34:143-150, which is incorporated by reference herein in its entirety), affibodies (see e.g., Feldwisch J. et al., 2010 J. Mol. Biol. 398:232-247, which is incorporated by reference herein in its entirety), and DARPins (see e.g., Pluckthun A., 2015, Annu. Rev. Pharmacol. Toxicol. 55:489-511, which is incorporated by reference herein in its entirety).

In certain embodiments, the binding domain comprises the heavy and/or light chain variable regions of a conventional antibody or antigen binding fragment thereof (e.g., a Fab or scFv), wherein the term "conventional antibody" is used herein to describe heterotetrameric antibodies containing heavy and light immunoglobulin chains arranged according to the "Y" configuration. Such conventional antibodies may derive from any suitable species including but not limited to antibodies of llama, alpaca, camel, mouse, rat, rabbit, goat, hamster, chicken, monkey, or human origin. In certain exemplary embodiments, the conventional antibody comprises a heavy chain variable domain (VH) and a light chain variable domain (VL) wherein the VH and/or VL domains or one or more complementarity determining regions (CDRs) thereof are derived from the same antibodies. In certain embodiments, the conventional antibody antigen binding region may be referred to as a "Fab" (Fragment antigen-binding). The Fab comprises one constant and one variable domain from each of heavy chain and light chain. The variable heavy and light chains contain the CDRs responsible for antigen binding.

In other embodiments, the specific receptor subunit binding subunit comprises at least a CDR or VHH domain of a VHH antibody or Nanobody®. VHH antibodies, which are camelid-derived heavy chain antibodies, are composed of two heavy chains and are devoid of light chains (Hamers-Casterman, et al. Nature. 1993; 363; 446-8). Each heavy chain of the VHH antibody has a variable domain at the N-terminus, and these variable domains are referred to in the art as "VHH" domains in order to distinguish them from the variable domains of the heavy chains of the conventional antibodies i.e., the VH domains. Similar to conventional antibodies, the VHH domains of the molecule comprise HCDR1, HCDR2 and HCDR3 regions which confer antigen binding specificity and therefore VHH antibodies or fragments such as isolated VHH domains, are suitable as components of the multispecific binding proteins of the present disclosure.

Multispecific Binding Proteins

In certain embodiments, the first and second binding domains disclosed herein can be paired together or operatively linked to generate a multispecific binding protein which is capable of cross-linking a first and a second subunits of the given receptor (e.g., a BMP Type I receptor and a BMP type II receptor). In some embodiments, the first specific binding domain (e.g., VHH or scFv) is operatively linked (directly or indirectly) to the N and/or C terminus of a first Fc domain or polypeptide, and the second specific binding domain is operatively linked to the N and/or C terminus of second Fc domain or polypeptide, such that the first Fc domain and the second Fc domain facilitate heterodimerization of the first and second specific binding domains.

In certain exemplary embodiments, the multispecific binding proteins of the disclosure are agonistic to any given signaling pathway, i.e., they are not antagonistic to the ALK1 pathway. In some embodiments, agonism may be measured using a specific receptor potency assay (e.g., Pathhunter U2OS dimerization assay (DiscoverX) Potency assays (e.g., Pathhunter) involve a cell line (e.g., U2OS) that expresses the target receptors of interest. The binding of the bispecific antibodies to the receptors triggers a signaling cascade leading to the expression of a reporter gene which can be quantified.

In certain embodiments, the multispecific binding protein comprises a dual variable domain format. "Dual variable domain" ("DVD") binding proteins of the disclosure comprise two or more antigen binding sites and are tetravalent or multivalent binding proteins. The DVDs of the disclosure are multispecific, i.e., capable of binding ALK1 and one of BMPRII, ActRIIA, and ActRIIB. A DVD binding protein comprising two heavy chain DVD polypeptides and two light chain DVD polypeptides is referred to as a "DVD immunoglobulin" or "DVD-Ig". Each half of a DVD-Ig comprises a heavy chain DVD polypeptide and a light chain DVD polypeptide, and two or more antigen binding sites. Each binding site comprises a heavy chain variable domain and a light chain variable domain with a total of six CDRs involved in antigen binding per antigen binding site.

A description of the design, expression, and characterization of DVD-Ig molecules is provided in PCT Publication No. WO 2007/024715; U.S. Pat. No. 7,612,181; and Wu et al., Nature Biotechnol., 25: 1290-1297 (2007). An example of such DVD-Ig molecules comprises a heavy chain that comprises the structural formula VD1-(X1)n-VD2-C—(X2) n, wherein VD1 is a first heavy chain variable domain, VD2 is a second heavy chain variable domain, C is a heavy chain constant domain, X1 is a linker with the proviso that it is not CH1, X2 is an Fc region, and n is 0 or 1; and a light chain that comprises the structural formula VD1-(X1)n-VD2-C—(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1. Such a DVD-Ig may comprise two such heavy chains and two such light chains, wherein each chain comprises variable domains linked in tandem without an intervening constant region between variable regions, wherein a heavy chain and a light chain associate to form tandem functional antigen binding sites, and a pair of heavy and light chains may associate with another pair of heavy and light chains to form a tetrameric binding protein with four functional antigen binding sites. In another example, a DVD-Ig molecule may comprise heavy and light chains that each comprise three variable domains (VD1, VD2, VD3) linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

In an embodiment, the disclosure provides a binding protein comprising first and second polypeptide chains, wherein said first polypeptide chain comprises a first VD1-(X1)n-VD2-C—(X2)n, wherein: VD1 is a first heavy chain variable domain; VD2 is a second heavy chain variable domain; C is a heavy chain constant domain; X1 is a linker with the proviso that it is not CH1; X2 is an Fc region; and n is independently 0 or 1; and wherein said second polypeptide chain comprises a second VD1-(X1)n-VD2-C—(X2)n, wherein: VD1 is a first light chain variable domain; VD2 is a second light chain variable domain; C is a light chain constant domain; X1 is a linker with the proviso that it is not CH1; X2 does not comprise an Fc region; and n is independently 0 or 1.

With respect to constructing DVD-Ig or other binding protein molecules, a "linker" is used to denote a single amino acid or a polypeptide ("linker polypeptide") comprising two or more amino acid residues joined by peptide bonds and used to link one or more antigen binding portions. Such linker polypeptides are well known in the art (see, e.g., Holliger et al., Proc. Natl. Acad. Sci. USA, 90: 6444-6448 (1993); Poljak, R. J., Structure, 2: 1121-1123 (1994)). Flexible linkers may be employed, which are generally composed of small, non-polar (e.g. Gly) or polar (e.g. Ser or Thr) amino acids. Exemplary flexible linkers include, but are not limited to, GGGGSG (SEQ ID NO: 188), GGSGG (SEQ ID NO: 189), GGGGSGGGGS (SEQ ID NO: 190), GGSGGGGSG (SEQ ID NO: 191), GGSGGGGSGS (SEQ ID NO: 192), GGSGGGGSGGGGS (SEQ ID NO: 193), GGGGSGGGGSGGGG (SEQ ID NO: 194), GGGGSGGGGSGGGGS (SEQ ID NO: 195), and RADAAAAGGGGSGGGGSGGGGSGGGGS (SEQ ID NO: 196).

Alternatively, rigid linkers may be employed to join one or more antigen binding proteins. Said rigid linkers may allow for the maintenance of fixed distances between linked antigen binding proteins, thereby promoting the activity of each individual protein. Rigid linkers may employ one of more proline amino acids to confer the rigidity. Exemplary rigid linkers include, but are not limited to, ASTKGP (SEQ ID NO: 197), ASTKGPSVFPLAP (SEQ ID NO: 198), TVAAP (SEQ ID NO: 199), RTVAAP (SEQ ID NO: 200), TVAAPSVFIFPP (SEQ ID NO: 201), RTVAAPSVFIFPP (SEQ ID NO: 202), AKTTPKLEEGEFSEAR (SEQ ID NO: 203), AKTTPKLEEGEFSEARV (SEQ ID NO: 204), AKTTPKLGG (SEQ ID NO: 205), SAKTTPKLGG (SEQ ID NO: 206), SAKTTP (SEQ ID NO: 207), RADAAP (SEQ ID NO: 208), RADAAPTVS (SEQ ID NO: 209), RADAAAAGGPGS (SEQ ID NO: 210), SAKTTPKLEEGEFSEARV (SEQ ID NO: 211), ADAAP (SEQ ID NO: 212), ADAAPTVSIFPP (SEQ ID NO: 213), QPKAAP (SEQ ID NO: 214), QPKAAPSVTLFPP (SEQ ID NO: 215), AKTTPP (SEQ ID NO: 216), AKTTPPSVT-PLAP (SEQ ID NO: 217), AKTTAP (SEQ ID NO: 218), AKTTAPSVYPLAP (SEQ ID NO: 219), GENKVEYAPAL-MALS (SEQ ID NO: 220), GPAKELTPLKEAKVS (SEQ ID NO: 221), and GHEAAAVMQVQYPAS (SEQ ID NO:222).

In certain embodiments, the linker comprises a modified hinge region as described herein.

In certain embodiments, the linker comprises or consists of PLAP(SEQ ID NO:2), PAPNLLGGP(SEQ ID NO:157), PLAPDKTHT(SEQ ID NO:1), EKSYGPP(SEQ ID NO:4), or DKTHT(SEQ ID NO:5).

In certain embodiments, the multispecific binding protein comprises a first and a second polypeptide chain, wherein:
  said first polypeptide chain comprises VH1-(HX1)n-VH2-C—(HX2)n, wherein:
  VH1 is a first heavy chain variable domain; VH2 is a second heavy chain variable domain; C is a heavy chain constant domain; HX1 is a linker; HX2 is an Fc region; and n is independently 0 or 1; and
  said second polypeptide chain comprises VL1-(LX1)n-VL2-C-(LX2)n, wherein:
  VL1 is a first light chain variable domain; VL2 is a second light chain variable domain; C is a light chain constant domain; LX1 is a linker; LX2 does not comprise an Fc region; and n is independently 0 or 1.

In certain embodiments, VH1 binds specifically to human ALK1 and VH2 binds specifically to a target selected from BMPRII, ActRIIA, and ActRIIB.

In certain embodiments, VL1 binds specifically to human ALK1 and VL2 binds specifically to a target selected from BMPRII, ActRIIA, and ActRIIB.

In certain embodiments, VH1 binds specifically to a target selected from BMPRII, ActRIIA, and ActRIIB and VH2 binds specifically to human ALK1.

In certain embodiments, VL1 binds specifically to a target selected from BMPRII, ActRIIA, and ActRIIB and VL2 binds specifically to human ALK1.

In certain embodiments, linker HX1 comprises an amino acid sequence of PLAP(SEQ ID NO:2) or PAPNLLGGP (SEQ ID NO:157).

In certain embodiments, linker LX1 comprises an amino acid sequence of PLAP(SEQ ID NO:2) or PAPNLLGGP (SEQ ID NO:157).

In certain embodiments, linker HX1 comprises an amino acid sequence of PLAP(SEQ ID NO:2) and linker LX1 comprises an amino acid sequence of PLAP(SEQ ID NO:2) or PAPNLLGGP(SEQ ID NO:157).

In certain embodiments, the multispecific binding protein comprises two polypeptide chains of VH1-(HX1)n-VH2-C—(HX2)n and two polypeptide chains of VL1-(LX1)n-VL2-C-(LX2)n.

In certain embodiments, for (HX1)n, n is 1 and for (HX2)n, n is 1.

In certain embodiments, for (LX1)n, n is 1 and for (LX2)n, n is 0.

In certain embodiments, the multispecific binding protein comprises a first and a second polypeptide chain, wherein:
  said first polypeptide chain comprises VH1-(HX1)n-VH2-C-Fc, wherein:
  VH1 is a first heavy chain variable domain; VH2 is a second heavy chain variable domain; C is a heavy chain constant domain; HX1 is a linker; Fc is an Fc region; and n is independently 0 or 1; and
  said second polypeptide chain comprises VL1-(LX1)n-VL2-C, wherein:
  VL1 is a first light chain variable domain; VL2 is a second light chain variable domain; C is a light chain constant domain; LX1 is a linker; and n is independently 0 or 1.

Non-DVD-Ig Formats

In another aspect of the disclosure, the multispecific binding protein comprises from N-terminus to C-terminus:

ai) a first polypeptide chain comprising a first antigen binding domain, a first linker (e.g., a modified hinge region), and a first constant region; and bi) a second polypeptide chain comprising a second antigen binding domain, a second linker (e.g., a modified hinge region), and a second constant region;

aii) a first polypeptide chain comprising a second antigen binding domain, a first antigen binding domain, a first linker (e.g., a modified hinge region), and a first constant region; and bii) a second polypeptide chain comprising a second linker (e.g., a modified hinge region) or the absence of a linker, and a second constant region;

aiii) a first polypeptide chain comprising a first linker (e.g., a modified hinge region) or the absence of a linker, and a first constant region; and biii) a second polypeptide chain comprising a second antigen binding domain, a first antigen binding domain, a second linker (e.g., a modified hinge region), and a second constant region; or aiv) a first polypeptide chain comprising a first antigen binding domain, an optional first linker (e.g., a modified hinge region), a second antigen binding domain, an optional second linker (e.g., a modified hinge region), and a first constant region; and biv) a second polypeptide chain comprising a third antigen binding domain, an optional third linker (e.g., a modified hinge region), a fourth antigen binding domain, an optional fourth linker (e.g., a modified hinge region), and a second constant region.

In certain embodiments, the first antigen binding domain comprises an scFv, VHH, Fab, F(ab')2, or a single domain antibody.

In certain embodiments, the second antigen binding domain comprises an scFv, VHH, Fab, F(ab')2, or a single domain antibody.

In certain embodiments, the third antigen binding domain comprises an scFv, VHH, Fab, F(ab')2, or a single domain antibody.

In certain embodiments, the fourth antigen binding domain comprises an scFv, VHH, Fab, F(ab')2, or a single domain antibody.

In certain embodiments, any one or more of the first antigen binding domain, second antigen binding domain, third antigen binding domain, and fourth antigen binding domain comprise an scFv, VHH, Fab, F(ab')2, or a single domain antibody.

In certain embodiments, the first antigen binding domain, second antigen binding domain, third antigen binding domain, and fourth antigen binding domain each comprise an scFv.

The Fc polypeptides employed in the multispecific binding proteins of the disclosure generally comprise a CH2 domain and a CH3 domain, wherein the C-terminus of the CH2 domain is linked (directly or indirectly) to the N-terminus of the CH3 domain. Any naturally occurring or variant CH2 and/or CH3 domain can be used. For example, in certain embodiments, the CH2 and/or CH3 domain is a naturally occurring CH2 or CH3 domain from an IgG1, IgG2, IgG3, IgG4, IgA1, or IgA2 antibody heavy chain, e.g., a human IgG1, IgG2, IgG3, IgG4, IgA1, or IgA2 antibody heavy chain. The CH2 and CH3 domains can be from the same or different antibody heavy chains. In certain embodiments, the Fc polypeptide comprises a CH2 and CH3 domain-containing portion from a single antibody heavy chain. In certain embodiments, the CH2 and/or CH3 domain is a variant of a naturally occurring CH2 or CH3 domain, respectively. In certain embodiments, the CH2 and/or CH3 domain is a variant comprising one or more amino acid insertions, deletion, substitutions, or modifications relative to a naturally occurring CH2 or CH3 domain, respectively. In certain embodiments, the CH2 and/or CH3 domain is a chimera of one or more CH2 or CH3 domains, respectively. In certain embodiments, the CH2 domain comprises amino acid positions 231-340 of a naturally occurring hinge region (e.g., human IgG1), according to the EU index. In certain embodiments, the CH3 domain comprises amino acid positions 341-447 of a naturally occurring hinge region (e.g., human IgG1), according to the EU index.

In certain embodiments, the Fc polypeptides further comprise a hinge region, wherein the C-terminus of hinge region is linked (directly or indirectly) to the N-terminus of the CH2 domain. For example, in certain embodiments, the hinge region is a naturally occurring hinge region from an IgG1, IgG2, IgG3, IgG4, IgA1, or IgA2 antibody heavy chain, e.g., a human IgG1, IgG2, IgG3, IgG4, IgA1, or IgA2 antibody heavy chain. The hinge region can be from the same or different antibody heavy chain than the CH2 and/or CH3 domains. In certain embodiments, the hinge region is a variant comprising one or more amino acid insertions, deletion, substitutions, or modifications relative to a naturally occurring hinge region. In certain embodiments, the hinge region is a chimera of one or more hinge regions. In certain embodiments, the hinge region comprises amino acid positions 226-229 of a naturally occurring hinge region (e.g., human IgG1), according to the EU index. In certain embodiments, the hinge region comprises amino acid positions 216-230 of a naturally occurring hinge region (e.g., human IgG1), according to the EU index. In certain embodiments, the hinge region comprises amino acid positions 216-230 of a naturally occurring hinge region (e.g., human IgG1), according to the EU index. In certain embodiments, the hinge region is a variant IgG4 hinge region comprising a serine (S) at amino acid position 228, according to the EU index.

In certain embodiments, the Fc polypeptides further comprise a CH1 domain, wherein the C-terminus of CH1 domain is linked (directly or indirectly) to the N-terminus of the hinge region. For example, in certain embodiments, the CH1 domain is a naturally occurring CH1 domain from an IgG1, IgG2, IgG3, IgG4, IgA1, or IgA2 antibody heavy chain, e.g., a human IgG1, IgG2, IgG3, IgG4, IgA1, or IgA2 antibody heavy chain. The CH1 domain can be from the same or different antibody heavy chain than the hinge region, CH2 domain and/or CH3 domain. In certain embodiments, the CH1 domain is a variant comprising one or more amino acid insertions, deletions, substitutions, or modifications relative to a naturally occurring CH1 domain. In certain embodiments, the CH1 domain is a chimera of one or more CH1 domain. In certain embodiments, the CH1 domain comprises amino acid positions 118-215 of a naturally occurring hinge region (e.g., human IgG1), according to the EU index.

In certain embodiment, the Fc polypeptide lacks a CH1 domain or comprises mutations in a CH1 domain or heavy chain variable domain that prevent association of the heavy chain with an antibody light chain. In certain embodiments, the antibody heavy chain lacks a portion of a hinge region.

Heterodimerization Motifs

In certain exemplary embodiments, the first and second Fc domains are further engineered to enhance heterodimerization of the first specific and second specific binding domains and minimize the effects of incorrect chain pairing (i.e., pairing of a BMP Type I receptor and a BMP Type II receptor).

Any art-recognized approach that addresses the problem of incorrect chain pairing can be employed to improve desired multispecific antibody production. For instance, US2010/0254989 A1 describes the construction of bispecific cMet—ErbB1 antibodies, where the VH and VL of the individual antibodies are fused genetically via a GlySer linker. For bispecific antibodies including an Fc domain, mutations may be introduced into the Fc to promote the correct heterodimerization of the Fc portion. Several such approaches are reviewed in Klein et al. (mAbs (2012) 4:6, 1-11), the contents of which are incorporated herein by reference in their entirety.

In certain embodiments, the first specific and second specific binding specificities of the multispecific antibody are heterodimerized through knobs-into-holes (KiH) pairing of Fc domains. This dimerization technique utilizes "protuberances" or "knobs" with "cavities" or "holes" engineered into the interface of CH3 domains. Where a suitably positioned and dimensioned knob or hole exists at the interface of either the first or second CH3 domain, it is only necessary to engineer a corresponding hole or knob, respectively, at the adjacent interface, thus promoting and strengthening Fc domain pairing in the CH3/CH3 domain interface. The IgG Fc domain that is fused to the VHH is provided with a knob, and the IgG Fc domain of the conventional antibody is provided with a hole designed to accommodate the knob, or vice-versa. A "knob" refers to an at least one amino acid side chain, typically a larger side chain, that protrudes from the interface of the CH3 portion of a first Fc domain. The protrusion creates a "knob" which is complementary to and received by a "hole" in the CH3 portion of a second Fc domain. The "hole" is an at least one amino acid side chain, typically a smaller side chain, which recedes from the interface of the CH3 portion of the second Fc domain. This technology is described, for example, in U.S. Pat. Nos. 5,821,333; 5,731,168 and 8,216,805; Ridgway et al. Protein Engineering (1996) 9:617-621); and Carter P. J. Immunol. Methods (2001) 248: 7-15, which are herein incorporated by reference.

Exemplary amino acid residues that may act as the knob include arginine (R), phenylalanine (F), tyrosine (Y) or tryptophan (W). An existing amino acid residue in the CH3 domain may be replaced or substituted with a knob amino acid residue. Preferred amino acids to substitute may include any amino acids with a small side chain, such as alanine (A), asparagine (N), aspartic acid (D), glycine (G), serine (S), threonine (T), or valine (V).

Exemplary amino acid residues that may act as the hole include alanine (A), serine (S), threonine (T), or valine (V). An existing amino acid residue in the CH3 domain may be replaced or substituted with a hole amino acid residue. Preferred amino acids to substitute may include any amino acids with a large side chain, such as arginine (R), phenylalanine (F), tyrosine (Y) or tryptophan (W).

The CH3 domain is preferably derived from a human IgG1 antibody. Exemplary amino acid substitutions to the CH3 domain include Y349C, S354C, T366S, T366Y, T366W, F405A, F405W, Y407T, Y407A, Y407V, T394S, or combinations thereof. A preferred exemplary combination is S354C, T366Y or T366W for the knob mutation on a first CH3 domain and Y349C, T366S, L368A, Y407T or Y407V for the hole mutation on a second CH3 domain.

In certain embodiments, the two Fc domains of the antigen binding construct are heterodimerized through Fab arm exchange (FAE). A human IgG1 possessing a P228S hinge mutation may contain an F405L or K409R CH3 domain mutation. Mixing of the two antibodies with a reducing agent leads to FAE. This technology is described in U.S. Pat. No. 9,212,230 and Labrijn A. F. PNAS (2013) 110(13):5145-5150, which are incorporated herein by reference.

In other embodiments, the two Fc domains of the antigen binding construct are heterodimerized through electrostatic steering effects. This dimerization technique utilizes electrostatic steering to promote and strengthen Fc domain pairing in the CH3/CH3 domain interface. The charge complementarity between two CH3 domains is altered to favor heterodimerization (opposite charge pairing) over homodimerization (same charge pairing). In this method, the electrostatic repulsive forces prevent homodimerization. Certain exemplary amino acid residue substitutions which confer electrostatic steering effects include K409D, K392D, and/or K370D in a first CH3 domain and D399K, E356K, and/or E357K in a second CH3 domain. This technology is described in US Patent Publication No. 2014/0154254 A1 and Gunasekaran K. JBC (2010) 285(25):19637-19646, which are incorporated herein by reference.

In other embodiments, the charge complementarity is formed by a first Fc domain comprising a N297K and/or a T299K mutation, and a second Fc domain comprising a N297D and/or a T299D mutation.

In an aspect of the invention, the two Fc domains of the antigen binding construct are heterodimerized through hydrophobic interaction effects. This dimerization technique utilizes hydrophobic interactions instead of electrostatic ones to promote and strengthen Fc domain pairing in the CH3/CH3 domain interface. Exemplary amino acid residue substitution may include K409W, K360E, Q347E, Y349S, and/or S354C in a first CH3 domain and D399V, F405T, Q347R, E357W, and/or Y349C in a second CH3 domain. Preferred pairs of amino acid residue substitutions between a first CH3 domain and a second CH3 domain include K409W:D399V, K409W:F405T, K360E:Q347R, Y349S:E357W, and S354C:Y349C. This technology is described in US Patent Publication No. 2015/0307628 A1.

In an aspect of the invention, heterodimerization can be mediated through the use of leucine zipper fusions. Leucine zipper domains fused to the C terminus of each CH3 domain of the antibody chains force heterodimerization. This technology is described in Wranik B. JBC (2012) 287(52): 43331-43339.

In an aspect of the invention, heterodimerization can be mediated through the use of a Strand Exchange Engineered Domain (SEED) body. CH3 domains derived from an IgG and IgA format force heterodimerization. This technology is described in Muda M. PEDS (2011) 24(5): 447-454.

In other embodiments, the heterodimerization motif may comprise non-native, disulfide bonds formed by engineered cysteine residues. In certain embodiments, the first set of disulfide may comprise a Y349C mutation in the first Fc domain and a S354C mutation in the second Fc domain. In other embodiment, an engineered disulfide bond may be introduced by fusion a C-terminal extension peptide with an engineered cysteine residue to the C-terminus of each of the two Fc domains. In certain embodiments, the first Fc domain may comprise the substitution of the carboxyl-terminal as "PGK" with "GEC", and the second Fc domain may comprise the substitution of the carboxyl terminal amino acids "PGK" with "KSCDKT" (SEQ ID NO:223).

In yet another approach, the multispecific antibodies may employ the CrossMab principle (as reviewed in Klein et al.), which involves domain swapping between heavy and light chains so as to promote the formation of the correct pairings. Yet another approach involves engineering the interfaces between the paired VH-VL domains or paired CH1-CL domains of the heavy and light chains so as to increase the affinity between the heavy chain and its cognate light chain (Lewis et al. Nature Biotechnology (2014) 32: 191-198).

An alternative approach to the production of multispecific antibody preparations having the correct antigen specificity has been the development of methods that enrich for antibodies having the correct heavy chain-light chain pairings. For example, Spiess et al. (Nature Biotechnology (2013) 31: 753-758) describe a method for the production of a MET-EGFR bispecific antibody from a co-culture of bacteria expressing two distinct half-antibodies.

Methods have also been described wherein the constant region of at least one of the heavy chains of a bispecific antibody is mutated so as to alter its binding affinity for an affinity agent, for example Protein A. This allows correctly paired heavy chain heterodimers to be isolated based on a purification technique that exploits the differential binding of the two heavy chains to an affinity agent (see US2010/0331527, WO2013/136186).

International patent application no. PCT/EP2012/071866 (WO2013/064701) addresses the problem of incorrect chain pairing using a method for multispecific antibody isolation based on the use of anti-idiotypic binding agents, in particular anti-idiotypic antibodies. The anti-idiotype binding agents are employed in a two-step selection method in which a first agent is used to capture antibodies having a VH-VL domain pairing specific for a first antigen and a second agent is subsequently used to capture antibodies also having a second VH-VL domain pairing specific for a second antigen.

In yet another embodiment, the multispecific antibody employs a first binding specificity having a conventional Fab binding region and a second binding specificity comprising a single domain antibody (VHH) binding region. The heterodimerization method employed forces the binding of the heavy chain region of the Fab and the full, heavy chain only, of the VHH. Because the VHH chain does not associate with light chains, the light chain region of the Fab portion will only associate with its corresponding heavy chain.

In certain other embodiments, the multispecific binding protein described herein further comprises a common light chain. The term "common light chain" as used herein refers to a light chain which is capable of pairing with a first heavy chain of an antibody which binds to a first antigen in order to form a binding site specifically binding to said first antigen and which is also capable of pairing with a second heavy chain of an antibody which binds to a second antigen in order to form a binding site specifically binding to said second antigen. A common light chain is a polypeptide comprising in N-terminal to C-terminal direction an antibody light chain variable domain (VL), and an antibody light chain constant domain (CL), which is herein also abbreviated as "VL-CL". Multispecific binding proteins with a common light chain require heterodimerization of the distinct heavy chains. In certain embodiments, the heterodimerization methods listed above may be used with a common light chain. In certain exemplary embodiments, the heterodimerization motif may comprise non-native, disulfide bonds formed by engineered cysteine residues. Adding disulfide bonds, both between the heavy and light chain of an antibody has been shown to improve stability. Additionally, disulfide bonds have also been used as a solution to improve light-chain pairing within bispecific antibodies (Geddie M. L. et al, mABs (2022) 14(1)).

Unless otherwise stated, all antibody constant region numbering employed herein corresponds to the EU numbering scheme, as described in Edelman et al. (Proc. Natl. Acad. Sci. 63(1): 78-85. 1969).

Additional methods of heterodimerization of heavy and/or light chains and the generation and purification of asymmetric antibodies are known in the art. See, for example, Klein C. mAbs (2012) 4(6): 653-663, and U.S. Pat. No. 9,499,634, each of which is incorporated herein by reference.

Effector Function Mutations

As discussed above, multispecific binding proteins of the disclosure can be provided in various isotypes and with different constant regions. The Fc region of the multispecific binding primarily determines its effector function in terms of Fc binding, antibody-dependent cell-mediated cytotoxicity (ADCC) activity, complement dependent cytotoxicity (CDC) activity, and antibody-dependent cell phagocytosis (ADCP) activity. These "cellular effector functions", as distinct from effector T cell function, involve the recruitment of cells bearing Fc receptors to the site of the target cells, resulting in killing of the antibody-bound cell.

An antibody according to the present invention may be one that exhibits reduced effector function. In certain embodiments, the one or more mutations reduces one or more of antibody dependent cellular cytotoxicity (ADCC), antibody dependent cellular phagocytosis (ADCP), or complement dependent cytotoxicity (CDC). In certain embodiments, an antibody according to the present invention may lack ADCC, ADCP and/or CDC activity. In either case, an antibody according to the present invention may comprise, or may optionally lack, an Fc region that binds to one or more types of Fc receptor. Use of different antibody formats, and the presence or absence of FcR binding and cellular effector functions, allow the antibody to be tailored for use in particular therapeutic purposes as discussed elsewhere herein.

In certain embodiments, the first and the second Fc domain comprise one or more mutations that reduces Fc effector function. In certain embodiments, the first Fc domain and the second Fc domain each comprise a L234A and L235A mutation. These IgG1 mutations are also known as the "LALA" mutations and are described in further detail in Xu et al. (Cell Immunol. 2000; 200:16-26). In certain embodiments the first Fc domain and the second Fc domain each comprise a L234A, L235A, G237A, and/or P329G mutation. The Fc domain amino acid positions referred to herein are based on EU antibody numbering. Alternatively, an antibody may have a constant region which is effector null. An antibody may have a heavy chain constant region that does not bind Fcγ receptors, for example the constant region may comprise a L235E mutation. Another optional mutation for a heavy chain constant region is S228P, which increases stability. A heavy chain constant region may be an IgG4 comprising both the L235E mutation and the S228P mutation. This "IgG4-PE" heavy chain constant region is effector null. A disabled IgG1 heavy chain constant region is also effector null. A disabled IgG1 heavy chain constant region may contain alanine at position 234, 235 and/or 237 (EU index numbering), e.g., it may be an IgG1 sequence comprising the L234A, L235A and/or G237A mutations ("LALAGA").

Human IgG1 constant regions containing specific mutations or altered glycosylation on residue Asn297 (e.g., N297Q, N297D, and N297K, EU index numbering) have been shown to reduce binding to Fc receptors.

In other embodiments, it may be desirable to enhance the binding of the Fc region of a multispecific antibody to human Fc gamma receptor IIIA (FcgRIIIA) relative to that of the Fc region of a corresponding naturally occurring antibody. In certain embodiments, a constant region may be engineered for enhanced ADCC and/or CDC and/or ADCP. The potency of Fc-mediated effects may be enhanced by engineering the Fc domain by various established techniques. Such methods increase the affinity for certain Fc-receptors, thus creating potential diverse profiles of activation enhancement. This can be achieved by modification of one or several amino acid residues. Example mutations are one or more of the residues selected from 239, 332 and 330 for human IgG1 constant regions (or the equivalent positions in other IgG isotypes). An antibody may thus comprise a human IgG1 constant region having one or more mutations independently selected from S239D, I332E and A330L (EU index numbering).

Increased affinity for Fc receptors can also be achieved by altering the natural glycosylation profile of the Fc domain by, for example, generating under fucosylated or de-fucosylated variants. Non-fucosylated antibodies harbor a tri-mannosyl core structure of complex-type N-glycans of Fc without fucose residue. These glycoengineered antibodies that lack core fucose residue from the Fc N-glycans may exhibit stronger ADCC than fucosylated equivalents due to enhancement of FcγRIIIA binding capacity. For example, to increase ADCC, residues in the hinge region can be altered to increase binding to FcγRIIIA. Thus, an antibody may comprise a human IgG heavy chain constant region that is a variant of a wild-type human IgG heavy chain constant region. In certain embodiments, the variant human IgG heavy chain constant region binds to human Fcγ receptors selected from the group consisting of FcγRIIB and FcγRIIA with higher affinity than the wild type human IgG heavy chain constant region binds to the human FcγRIIIA. The antibody may comprise a human IgG heavy chain constant region that is a variant of a wild type human IgG heavy chain constant region, wherein the variant human IgG heavy chain constant region binds to human FcγRIIB with higher affinity than the wild type human IgG heavy chain constant region binds to human FcγRIIB. The variant human IgG heavy chain constant region can be a variant human IgG1, a variant human IgG2, or a variant human IgG4 heavy chain constant region. In one embodiment, the variant human IgG heavy chain constant region comprises one or more amino acid mutations selected from G236D, P238D, S239D, S267E, L328F, and L328E (EU index numbering system). In another embodiment, the variant human IgG heavy chain constant region comprises a set of amino acid mutations selected from the group consisting of: S267E and L328F; P238D and L328E; P238D and one or more substitutions selected from the group consisting of E233D, G237D, H268D, P271 G, and A330R; P238D, E233D, G237D, H268D, P271G, and A330R; G236D and S267E; S239D and S267E; V262E, S267E, and L328F; and V264E, S267E, and L328F (EU index numbering system).

The enhancement of CDC may be achieved by amino acid changes that increase affinity for C1q, the first component of the classic complement activation cascade. Another approach is to create a chimeric Fc domain created from human IgG1 and human IgG3 segments that exploit the higher affinity of IgG3 for C1q. Antibodies of the present invention may comprise mutated amino acids at residues 329, 331 and/or 322 to alter the C1q binding and/or reduced or abolished CDC activity. In another embodiment, the antibodies or antibody fragments disclosed herein may contain Fc regions with modifications at residues 231 and 239, whereby the amino acids are replaced to alter the ability of the antibody to fix complement. In one embodiment, the antibody or fragment has a constant region comprising one or more mutations selected from E345K, E430G, R344D and D356R, in particular a double mutation comprising R344D and D356R (EU index numbering system).

The functional properties of the multispecific binding proteins may be further tuned by combining amino acid substitutions that alter Fc binding affinity with amino acid substitutions that affect binding to FcRn. Binding proteins with amino acid substitutions that affect binding to FcRn (also referred to herein as "FcRn variants") may in certain situations also increase serum half-life in vivo as compared to an unmodified binding protein. As will be appreciated, any combination of Fc and FcRn variants may be used to tune clearance of the antigen-antibody complex. Suitable FcRn variants that may be combined with any of the Fc variants described herein that include without limitation N434A, N434S, M428L, V308F, V259I, M428L/N434S, V259I/V308F, Y436I/M428L, Y436I/N434S, Y436V/N434S, Y436V/M428L, M252Y, M252Y/S254T/T256E, and V259I/V308F/M428L.

Expression of Antigen-Binding Proteins

In one aspect, polynucleotides encoding the binding proteins (e.g., antigen-binding proteins and antigen-binding fragments thereof) disclosed herein are provided. Methods of making binding proteins comprising expressing these polynucleotides are also provided.

Polynucleotides encoding the binding proteins disclosed herein are typically inserted in an expression vector for introduction into host cells that may be used to produce the desired quantity of the binding proteins. Accordingly, in certain aspects, the disclosure provides expression vectors comprising polynucleotides disclosed herein and host cells comprising these vectors and polynucleotides.

The term "vector" or "expression vector" is used herein to mean vectors used in accordance with the present disclosure as a vehicle for introducing into and expressing a desired gene in a cell. As known to those skilled in the art, such vectors may readily be selected from the group consisting of plasmids, phages, viruses and retroviruses. In general, vectors compatible with the disclosure will comprise a selection marker, appropriate restriction sites to facilitate cloning of the desired gene and the ability to enter and/or replicate in eukaryotic or prokaryotic cells.

Numerous expression vector systems may be employed for the purposes of this disclosure. For example, one class of vector utilizes DNA elements which are derived from animal viruses such as bovine papilloma virus, polyoma virus, adenovirus, vaccinia virus, baculovirus, retroviruses (RSV, MMTV or MOMLV), or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed or introduced into the same cell by co-transformation. Additional elements may also be needed for optimal synthesis of mRNA. These elements may include signal sequences, splice signals, as well as transcriptional promoters, enhancers, and termination signals. In some embodiments, the cloned variable region genes are inserted into an expression vector along with the heavy and light chain constant region genes (e.g., human constant region genes) synthesized as discussed above.

In other embodiments, the binding proteins may be expressed using polycistronic constructs. In such expression systems, multiple gene products of interest such as heavy and light chains of antibodies may be produced from a single polycistronic construct. These systems advantageously use an internal ribosome entry site (IRES) to provide relatively high levels of polypeptides in eukaryotic host cells. Compatible IRES sequences are disclosed in U.S. Pat. No. 6,193,980, which is incorporated by reference herein in its entirety for all purposes. Those skilled in the art will appreciate that such expression systems may be used to effectively produce the full range of polypeptides disclosed in the instant application.

More generally, once a vector or DNA sequence encoding a binding protein, e.g. an antibody or fragment thereof, has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "Mammalian Expression Vectors" Chapter 24.2, pp. 470-472 Vectors, Rodriguez and Denhardt, Eds. (Butterworths, Boston, Mass. 1988). Plasmid introduction into the host can be by electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

As used herein, the term "transformation" shall be used in a broad sense to refer to the introduction of DNA into a recipient host cell that changes the genotype.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of antibody unless it is clearly specified otherwise. In other words, recovery of polypeptide from the "cells" may mean either from spun down whole cells, from supernatant of lysed cells culture, or from the cell culture containing both the medium and the suspended cells.

In one embodiment, a host cell line used for antibody expression is of mammalian origin. Those skilled in the art can determine particular host cell lines which are best suited for the desired gene product to be expressed therein. Exemplary host cell lines include, but are not limited to, GS-CHO and CHO-K1 (Chinese Hamster Ovary lines), DG44 and DUXB11 (Chinese Hamster Ovary lines, DHFR minus), HELA (human cervical carcinoma), CV-1 (monkey kidney line), COS (a derivative of CV-1 with SV40 T antigen), R1610 (Chinese hamster fibroblast) BALBC/3T3 (mouse fibroblast), HEK (human kidney line), SP2/O (mouse myeloma), BFA-1c1BPT (bovine endothelial cells), RAJI (human lymphocyte), 293 (human kidney). In one embodiment, the cell line provides for altered glycosylation, e.g., afucosylation, of the antibody expressed therefrom (e.g., PER.C6® (Crucell) or FUT8-knock-out CHO cell lines (POTELLIGENT® cells) (Biowa, Princeton, N.J.)). In one embodiment, NS0 cells may be used. CHO cells are particularly useful. Host cell lines are typically available from commercial services, e.g., the American Tissue Culture Collection, or from authors of published literature.

In vitro production allows scale-up to give large amounts of the desired polypeptides. Techniques for mammalian cell cultivation under tissue culture conditions are known in the art and include homogeneous suspension culture, e.g., in an airlift reactor or in a continuous stirrer reactor, or immobilized or entrapped cell culture, e.g., in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose and/or (immuno-) affinity chromatography.

Genes encoding the binding proteins featured in the disclosure can also be expressed in non-mammalian cells such as bacteria or yeast or plant cells. In this regard, it will be appreciated that various unicellular non-mammalian microorganisms such as bacteria can also be transformed, i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the binding proteins can become part of inclusion bodies. In some embodiments, the binding proteins are then isolated, purified and assembled into functional molecules. In some embodiments, the binding proteins of the disclosure are expressed in a bacterial host cell. In some embodiments, the bacterial host cell is transformed with an expression vector comprising a nucleic acid molecule encoding a binding protein of the disclosure.

In addition to prokaryotes, eukaryotic microbes may also be used. *Saccharomyces cerevisiae*, or common baker's yeast, is the most commonly used among eukaryotic microbes, although a number of other strains are commonly available. For expression in *Saccharomyces*, the plasmid YRp7, for example (Stinchcomb et al., Nature, 282:39 (1979); Kingsman et al., Gene, 7:141 (1979); Tschemper et al., Gene, 10:157 (1980)), is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trp1 lesion as a characteristic of the yeast host cell genome then provides an effective environment for detecting transformation by growth in the absence of tryptophan.

Formulations/Pharmaceutical Compositions

In certain embodiments, a pharmaceutical composition comprising a pharmaceutically acceptable carrier and a therapeutically effective amount of an antigen-binding protein described herein is provided. Some embodiments include pharmaceutical compositions comprising a therapeutically effective amount of any one of the binding proteins as described herein, or a binding protein-drug conjugate, in admixture with a pharmaceutically or physiologically acceptable formulation agent selected for suitability with the mode of administration.

Acceptable formulation materials are typically non-toxic to recipients at the dosages and concentrations employed.

In some embodiments, the pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclo-dextrin, or hydroxypropyl-beta-cyclodextrin), fillers, mono-saccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic poly-mers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylpara-ben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides, e.g., sodium or potassium chloride, or mannitol sorbitol), delivery vehicles, diluents, excipients and/or pharmaceutical adjuvants (see, e.g., REMINGTON'S PHARMACEUTICAL SCIENCES (18th Ed., A. R. Gennaro, ed., Mack Publishing Company 1990), and sub-sequent editions of the same, incorporated herein by refer-ence for any purpose).

In some embodiments the optimal pharmaceutical com-position will be determined by a skilled artisan depending upon, for example, the intended route of administration, delivery format, and desired dosage. Such compositions can influence the physical state, stability, rate of in vivo release, and rate of in vivo clearance of the binding protein.

In some embodiments the primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exem-plary pharmaceutical compositions comprise Tris buffer of about pH 7.0-8.5, or acetate buffer of about pH 4.0-5.5, which can further include sorbitol or a suitable substitute. In one embodiment of the disclosure, binding protein compo-sitions can be prepared for storage by mixing the selected composition having the desired degree of purity with optional formulation agents in the form of a lyophilized cake or an aqueous solution. Further, the binding protein can be formulated as a lyophilizate using appropriate excipients such as sucrose.

In some embodiments, the pharmaceutical compositions of the disclosure can be selected for parenteral delivery or subcutaneous delivery. Alternatively, the compositions can be selected for inhalation or for delivery through the diges-tive tract, such as orally. The preparation of such pharma-ceutically acceptable compositions is within the skill of the art.

In some embodiments, the formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use can be in the form of a pyrogen-free, parenterally acceptable, aqueous solution comprising the desired binding protein in a pharmaceutically acceptable vehicle. A particularly suitable vehicle for par-enteral injection is sterile distilled water in which a binding protein is formulated as a sterile, isotonic solution, properly preserved. Yet another preparation can involve the formu-lation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, a binding protein can be formulated as a dry powder for inhalation. Binding protein inhalation solutions can also be formulated with a propellant for aerosol delivery. In yet another embodiment, solutions can be nebulized.

It is also contemplated that certain formulations can be administered orally. In one embodiment of the disclosure, multispecific binding proteins that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the binding protein. Diluents, flavorings, low melting point waxes, vegetable oils, lubricants, suspending agents, tablet disintegrating agents, and binders can also be employed.

Another pharmaceutical composition can involve an effective quantity of multispecific binding proteins in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phos-phate; or binding agents, such as starch, gelatin, or acacia; or lubricating agents such as magnesium stearate, stearic acid, or talc.

Additional pharmaceutical compositions of the disclosure will be evident to those skilled in the art, including formu-lations involving binding proteins in sustained- or con-trolled-delivery formulations. Techniques for formulating a variety of other sustained- or controlled-delivery means, such as liposome carriers, bio-erodible microparticles or porous beads and depot injections, are also known to those skilled in the art. Additional examples of sustained-release preparations include semipermeable polymer matrices in the form of shaped articles, e.g., films, or microcapsules. Sus-tained release matrices can include polyesters, hydrogels, polylactides, copolymers of L-glutamic acid and gamma ethyl-L-glutamate, poly(2-hydroxyethyl-methacrylate), eth-ylene vinyl acetate, or poly-D(−)-3-hydroxybutyric acid.

Sustained-release compositions can also include liposomes, which can be prepared by any of several methods known in the art.

In some embodiments, pharmaceutical compositions are to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper that can be pierced by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

The disclosure also encompasses kits for producing a single dose administration unit. The kits can each contain both a first container having a dried multispecific binding protein and a second container having an aqueous formulation. Also included within the scope of this disclosure are kits containing single and multi-chambered pre-filled syringes (e.g., liquid syringes and lyosyringes).

The effective amount of a binding protein pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding protein is being used, the route of administration, and the size (body weight, body surface, or organ size) and condition (the age and general health) of the patient. Accordingly, the clinician can titer the dosage and modify the route of administration to obtain the optimal therapeutic effect.

Dosing frequency will depend upon the pharmacokinetic parameters of the binding protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions can be administered by bolus injection or continuously by infusion, or by implantation device.

In some embodiments, the composition can also be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

Multispecific binding proteins disclosed herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma and are herein incorporated by reference in their entireties). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

A multispecific binding protein disclosed herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the heterodimeric protein alone or in combination with other pharmaceutically acceptable excipients can also be administered.

Transdermal patches, including iontophoretic and electrophoretic devices, are well known to those of skill in the art, and can be used to administer a heterodimeric protein. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957, all of which are herein incorporated by reference in their entireties.

In certain embodiments, a pharmaceutical composition comprising a multispecific binding protein described herein is a lyophilized powder, which can be reconstituted for administration as solutions, emulsions and other mixtures. It may also be reconstituted and formulated as solids or gels. The lyophilized powder is prepared by dissolving heterodimeric protein described herein, or a pharmaceutically acceptable derivative thereof, in a suitable solvent. In certain embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agents. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined. Multispecific binding proteins provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874, all of which are herein incorporated by reference in their entireties. In a specific embodiment, a heterodimeric protein described herein is targeted to a tumor.

Methods of Treatment/Use

Another aspect of the disclosure is a multispecific antibody and/or an antigen-binding protein as described herein for use as a medicament.

In a particular embodiment, a method of treating a disorder through the activation of BMP Type I receptors and BMP Type II receptors is provided, the method comprising administering to a subject in need thereof an effective amount of an antigen-binding protein described herein.

The binding proteins can be employed in any known assay method, such as competitive binding assays, direct and indirect sandwich assays, and immunoprecipitation assays for the detection and quantitation of one or more target antigens. The binding proteins will bind the one or more target antigens with an affinity that is appropriate for the assay method being employed.

For diagnostic applications, in some embodiments, binding proteins can be labeled with a detectable moiety. The detectable moiety can be any one that is capable of producing, either directly or indirectly, a detectable signal. For example, the detectable moiety can be a radioisotope, such as $^{3}H$, $^{14}C$ $^{32}P$, $^{35}$, $^{125}I$, $^{99}Tc$, $^{111}In$, or $^{67}Ga$; a fluorescent or chemiluminescent compound, such as fluorescein isothiocyanate, rhodamine, or luciferin; or an enzyme, such as alkaline phosphatase, β-galactosidase, or horseradish peroxidase.

The binding proteins are also useful for in vivo imaging. A binding protein labeled with a detectable moiety can be administered to an animal, e.g., into the bloodstream, and the presence and location of the labeled antibody in the host assayed. The binding protein can be labeled with any moiety that is detectable in an animal, whether by nuclear magnetic resonance, radiology, or other detection means known in the art.

The disclosure also relates to a kit comprising a binding protein and other reagents useful for detecting target antigen levels in biological samples. Such reagents can include a detectable label, blocking serum, positive and negative control samples, and detection reagents. In some embodiments, the kit comprises a composition comprising any binding protein, polynucleotide, vector, vector system, and/or host cell described herein. In some embodiments, the kit comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing a condition and may have a sterile access port (for example the container may be an intravenous solution bag or a vial having a stopper that can be pierced by a hypodermic injection needle). In some embodiments, the label or package insert indicates that the composition is used for preventing, diagnosing, and/or treating the condition of choice. Alternatively, or additionally, the article of manufacture or kit may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In some embodiments, the present disclosure relates to a method of preventing and/or treating a disease or disorder (e.g., cancer). In some embodiments, the method comprises administering to a patient a therapeutically effective amount of at least one of the binding proteins, or pharmaceutical compositions related thereto, described herein. In some embodiments, the patient is a human.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present disclosure has been described with reference to the specific embodiments thereof, it should be understood by those skilled in the art that various changes may be made and equivalents may be substituted without departing from the true spirit and scope of the disclosure. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present disclosure. All such modifications are intended to be within the scope of the claims appended hereto. Having now described certain embodiments in detail, the same will be more clearly understood by reference to the following examples, which are included for purposes of illustration only and are not intended to be limiting.

EXAMPLES

Example 1. Bispecific Antibodies to BMPR Type I and Type II Receptors with Optimized Hinges, Linkers and Valencies Bispecific antibodies targeting the BMRP Type I receptor ALK1 and BMPR Type II receptor BMPRII were designed, with sequences provided below. Some constructs include upper hinge variants: hinge 1=no upper hinge; hinge 3=an upper hinge sequence of PLAP (SEQ ID NO: 2); hinge 6=an upper hinge sequence of DKTHT (SEQ ID NO: 5).

Three-dimensional structures of BMP10 in complex with ALK1 and BMPRII (PDB ID 7PPC) was used in combination with structural models from AlphaFold2 AF-P37023-F1-model_v4 (ALK1), AF-Q13873-F1-model_v4 (BMPRII) and a model from Agnew et al. (DOI: 10.1038/s41467-021-25248-5) to construct a model of the intra and extra cellular domains of the BMPRII/ALK1/BMP9 active tetrameric receptor complex that enables phosphorylation of the GS domain and activation of SMADs. We predicted that tetravalent format of agonistic antibodies would facilitate the predicted tetrameric receptor assembly, required for signaling of ALK1/BMPRII complex.

The DIAGONAL platform predicted epitopes on ALK1 and BMPRII that binders could target to engage the receptor in this tetravalent format. Those predictions were used to design CDRs of the binding modules of the DGL molecules and connecting linkers compatible with the geometrical constraints of tetravalent antibody formats.

Antibodies were transiently transfected using the Expi293 (Thermo) system according to the manufacturer's instructions. Cells were harvested six days post transfection and harvested using batch purification with mabSelect resin. Purity of the final product was assessed using SDS-PAGE and analytical gel filtration.

TABLE 1

| Hinge variant and Fc domain sequences | | |
|---|---|---|
| | SEQ ID NO | SEQUENCE |
| Hinge 2 | 1 | PLAPDKTHT |
| Hinge 3 | 2 | PLAP |
| Hinge 4 | 3 | GGGGSGGGGSGGGGSGGGGS |
| Hinge 5 | 4 | EKSYGPP |
| Hinge 6 | 5 | DKTHT |
| Middle and Lower Hinge | 6 | CPPCPAPELLG |
| Hinge 3 + Middle and Lower | 7 | PLAPCPPCPAPELLG |
| Hinge 6 + Middle and Lower | 8 | DKTHTCPPCPAPELLG |
| Hinge 5 + Middle and Lower | 9 | EKSYGPPCPPCPAPELLG |
| Wildtype Fc domain | 10 | GPSVFLFPPKPKDTLMISRTPEVTCVVVDVSH EDPEVKFNWYVDGVEVHNAKTKPREEQYNS TYRVVSVLTVLHQDWLNGKEYKCKVSNKALP APIEKTISKAKGQPREPQVYTLPPSRDELTKN QVSLTCLVKGFYPSDIAVEWESNGQPENNYK TTPPVLDSDGSFFLYSKLTVDKSRWQQGNVF SCSVMHEALHNHYTQKSLSLSPG |
| Hinge 3 + Fc domain | 11 | PLAPCPPCPAPELLGGPSVFLFPPKPKDTL MISRTPEVTCVVVDVSHEDPEVKFNWYVDGV EVHNAKTKPREEQYNSTYRVVSVLTVLHQDW LNGKEYKCKVSNKALPAPIEKTISKAKGQPRE PQVYTLPPSRDELTKNQVSLTCLVKGFYPSDI AVEWESNGQPENNYKTTPPVLDSDGSFFLYS KLTVDKSRWQQGNVFSCSVMHEALHNHYTQ KSLSLSPG |
| Hinge 6 + Fc domain | 12 | DKTHTCPPCPAPELLGGPSVFLFPPKPKDT LMISRTPEVTCVVVDVSHEDPEVKFNWYVDG VEVHNAKTKPREEQYNSTYRVVSVLTVLHQD WLNGKEYKCKVSNKALPAPIEKTISKAKGQPR EPQVYTLPPSRDELTKNQVSLTCLVKGFYPSD IAVEWESNGQPENNYKTTPPVLDSDGSFFLYS KLTVDKSRWQQGNVFSCSVMHEALHNHYTQ KSLSLSPG |
| Hinge 5 + Fc domain | 13 | EKSYGPPCPPCPAPELLGGPSVFLFPPKPK DTLMISRTPEVTCVVVDVSHEDPEVKFNWYV DGVEVHNAKTKPREEQYNSTYRVVSVLTVLH QDWLNGKEYKCKVSNKALPAPIEKTISKAKGQ PREPQVYTLPPSRDELTKNQVSLTCLVKGFYP SDIAVEWESNGQPENNYKTTPPVLDSDGSFF LYSKLTVDKSRWQQGNVFSCSVMHEALHNH YTQKSLSLSPG |

TABLE 1-continued

| Hinge variant and Fc domain sequences | | |
|---|---|---|
| | SEQ ID NO | SEQUENCE |
| Middle + Lower hinge and Fc domain | 14 | CPPCPAPELLGGPSVFLFPPKPKDTLMISRT PEVTCVVVDVSHEDPEVKFNWYVDGVEVHNA KTKPREEQYNSTYRVVSVLTVLHQDWLNGKE YKCKVSNKALPAPIEKTISKAKGQPREPQVYTL PPSRDELTKNQVSLTCLVKGFYPSDIAVEWES NGQPENNYKTTPPVLDSDGSFFLYSKLTVDKS RWQQGNVFSCSVMHEALHNHYTQKSLSLSP G |

TABLE 2

| Bispecific antibodies to ALK1 and BMPRII constructs | |
|---|---|
| Antibody Designation | Amino acid sequence |
| DGL284 | GDEMGTDIQMTQSPSSLSASVGDRVTITCRASQSISSYLNWYQQKPG KAPKLLIYAASSLQSGVPSRFSGSGSGTDFTLTISSLQPEDFATYYCQ QSYSTPRTFGQGTKVDIKEGKSSGSGSESKASQVQLQESGPGLVKP SQTLSLTCTVSGGSISSDDYYWSIRQTPGKGLEWIGYIYYSGITYYN PSLKSRVTISVDTSKNQFSLKLSSVTAADTAVYYCAREGCNDGVCYN GVFDYWGQGTLVTVSSSGGGSGGGGSGGGGSGGGGSGGGGDG GGGSGGGTQSALTQPASVSGSPGQSITISCTGTSSDVGGYKSVSWYQ QHPGKAPKLMIYDVSNRPSGVSDRFSGSKSGNTASLTISGLQAEDEA DYYCSSYTSSSSLWVFGGGTKLTVLGEGKSSGSGSESKASQVQLVQ SGAEVKKPGSSVKVSCKASGGTFSSYAISWVRQAPGQGLEWMGRII PILGIANYAQKFQGRVTMTEDTSTDTAYMELSSLRSEDTAVYYCATDL WGVGADWGQGTLVTVSSGSGGGGDGGGGSGDKTHTCPPCPAPEL LGGPSVFLFPPKPKDTLMISRTPEVTCVVVDVSHEDPEVKFNWYVDG VEVHNAKTKPREEQYNSTYRVVSVLTVLHQDWLNGKEYKCKVSNKA LPAPIEKTISKAKGQPREPQVYTLPPSREELTKNQVSLTCLVKGFYPS DIAVEWESNGQPENNYKTTPPVLDSDGSFFLYSKLTVDKSRWQQGN VFSCSVMHEALHNHYTQKSLSLSPGS (SEQ ID NO: 15) |
| DGL266 | EVQLLESGGGLVQPGGSLRLSCAASGFTFSIYAMSWVRQAPGKGLE WVSAISGSGGSTYYADSVKGRFTISRDNSKNTLYLQMNSLRAEDTAV YYCARDFDYWGQGTLVTVTSSGGGGSGGGGSGGGGSQSVLTQPP SASGTPGQRVTISCSGSSSNIGSNYVYWYQQLPGTAPKLLIYGNINRP SGVPDRFSGSKSGTSASLAISGLRSEDEADYYCAAWDDSLNGRVFG GGTKLTVLGGGGSGGGGSGGGGSGVECPPCPAPPVAGPSVFLFPP KPKDTLMISRTPEVTCVVVDVSHEDPEVQFNWYVDGVEVHNAKTKP REEQFNSTFRVVSVLTVVHQDWLNGKEYKCKVSNKGLPAPIEKTISKT KGQPREPQVYTLPPCREEMTKNQVSLWCLVKGFYPSDIAVEWESNG QPENNYKTTPPMLDSDGSFFLYSKLTVDKSRWQQGNVFSCSVMHEA LHNHYTQKSLSLSPG (SEQ ID NO: 16) EVQLLESGGGLVQPGGSLRLSCAASGFTFSNAWMNWVRQAPGKGL EWVSSISSSSSYIYYADSVKGRFTISRDNSKNTLYLQMNSLRAEDTAV YYCARAVAAGGMFWGLDQWGQGTLVTVTSSGGGGSGGGGSGGGG GSQSVLTQPPSASGTPGQRVTISCSGSRSNIGSNSVHWYQQLPGTA PKLLIYGNSNRPSGVPDRFSGSKSGTSASLAISGLRSEDEADYYCQS YDSSLNDHVVFGGGTKLTVLGGGGSGGGGSGGGGSGVECPPCPAP PVAGPSVFLFPPKPKDTLMISRTPEVTCVVVDVSHEDPEVQFNWYVD GVEVHNAKTKPREEQFNSTFRVVSVLTVVHQDWLNGKEYKCKVSNK GLPAPIEKTISKTKGQPREPQVCTLPPSREEMTKNQVSLSCAVKGFYP SDIAVEWESNGQPENNYKTTPPMLDSDGSFFLVSKLTVDKSRWQQG NVFSCSVMHEALHNHYTQKSLSLSPG (SEQ ID NO: 17) |
| DGL267 | EVQLLESGGGLVQPGGSLRLSCAASGFTFSSYAMSWVRQAPGKGLE WVANINQDGSEKNYVDSMRGRFTISRDNSKNTLYLQMNSLRAEDTA VYYCAREFDYWGQGTLVTVTSSGGGGSGGGGSGGGGSQSVLAQP PSASGTPGQRVTISCSGSSSNIGSNYVYWYQQLPGTAPKLLIYGNNK RPSGVPDRFSGSKSGTSASLAISGLRSEDEADYYCAAWDDSLNGRV FGGGTKLTVLGGGGSGGGGSGGGGSGVECPPCPAPPVAGPSVFLF PPKPKDTLMISRTPEVTCVVVDVSHEDPEVQFNWYVDGVEVHNAKT KPREEQFNSTFRVVSVLTVVHQDWLNGKEYKCKVSNKGLPAPIEKTI SKTKGQPREPQVYTLPPCREEMTKNQVSLWCLVKGFYPSDIAVEWE SNGQPENNYKTTPPMLDSDGSFFLYSKLTVDKSRWQQGNVFSCSV MHEALHNHYTQKSLSLSPG (SEQ ID NO: 18) EVQLLESGGGLVQPGGSLRLSCAASGFTFSDYYMTWIRQAPGKGLE WVSSISGGSTYYADSRKGRFTISRDNSENTLYLQMNSLRAEDTAVYY CARDFGVAGWFGQYGMDVWGQGTLVTVSSGGGGSGGGGSGGGG SQSVLTQPPSASGTPGQRVTISCTGSSSNIGAGYDVHWYQQLPGTA |

TABLE 2-continued

Bispecific antibodies to ALK1 and BMPRII constructs

| Antibody Designation | Amino acid sequence |
|---|---|
| | PKLLIYRSNQRPSGVPDRFSGSKSGTSASLAISGLRSEDEADYYCSSY AGNYNLVFGGGTKLTVLGGGGSGGGGSGGGGSGVECPPCPAPPVA GPSVFLFPPKPKDTLMISRTPEVTCVVVDVSHEDPEVQFNWYVDGVE VHNAKTKPREEQFNSTFRVVSVLTVVHQDWLNGKEYKCKVSNKGLP APIEKTISKTKGQPREPQVCTLPPSREEMTKNQVSLSCAVKGFYPSDI AVEWESNGQPENNYKTTPPMLDSDGSFFLVSKLTVDKSRWQQGNV FSCSVMHEALHNHYTQKSLSLSPG (SEQ ID NO: 19) |
| DGL268 | EVQLLESGGGLVQPGGSLRLSCAASGFTFSIYAMSWVRQAPGKGLE WVSAISGSGGSTYYADSVKGRFTISRDNSKNTLYLQMNSLRAEDTAV YYCARDFDYWGQGTLVTVTSSGGGGSGGGGSGGGGSQSVLTQPP SASGTPGQRVTISCSGSSSNIGSNYVYWYQQLPGTAPKLLIYGNINRP SGVPDRFSGSKSGTSASLAISGLRSEDEADYYCAAWDDSLNGRVFG GGTKLTVLGGGGSGGGGSGGGGSGVECPPCPAPPVAGPSVFLFPP KPKDTLMISRTPEVTCVVVDVSHEDPEVQFNWYVDGVEVHNAKTKP REEQFNSTFRVVSVLTVVHQDWLNGKEYKCKVSNKGLPAPIEKTISKT KGQPREPQVYTLPPCREEMTKNQVSLWCLVKGFYPSDIAVEWESNG QPENNYKTTPPMLDSDGSFFLYSKLTVDKSRWQQGNVFSCSVMHEA LHNHYTQKSLSLSPG (SEQ ID NO: 20) EVQLLESGGGLVQPGGSLRLSCAASGFTFSIYAMSWVRQAPGKGLE WVSAISGSGGSTYYADSVKGRFTISRDNSKNTLYLQMNSLRAEDTAV YYCARDFDYWGQGTLVTVTSSGGGGSGGGGSGGGGSQSVLTQPP SASGTPGQRVTISCSGSSSNIGSNYVYWYQQLPGTAPKLLIYGNINRP SGVPDRFSGSKSGTSASLAISGLRSEDEADYYCAAWDDSLNGRVFG GGTKLTVLGGGGSGGGGSGGGGSGVECPPCPAPPVAGPSVFLFPP KPKDTLMISRTPEVTCVVVDVSHEDPEVQFNWYVDGVEVHNAKTKP REEQFNSTFRVVSVLTVVHQDWLNGKEYKCKVSNKGLPAPIEKTISKT KGQPREPQVCTLPPSREEMTKNQVSLSCAVKGFYPSDIAVEWESNG QPENNYKTTPPMLDSDGSFFLVSKLTVDKSRWQQGNVFSCSVMHEA LHNHYTQKSLSLSPG (SEQ ID NO: 21) |
| DGL269 | EVQLLESGGGLVQPGGSLRLSCAASGFTFSNAWMNWVRQAPGKGL EWVSSISSSSSYIYYADSVKGRFTISRDNSKNTLYLQMNSLRAEDTAV YYCARAVAAGGMFWGLDQWGQGTLVTVTSSGGGGSGGGGSGGG GSQSVLTQPPSASGTPGQRVTISCSGSRSNIGSNSVHWYQQLPGTA PKLLIYGNSNRPSGVPDRFSGSKSGTSASLAISGLRSEDEADYYCQS YDSSLNDHVVFGGGTKLTVLGGGGSGGGGSGGGGSGVECPPCPAP PVAGPSVFLFPPKPKDTLMISRTPEVTCVVVDVSHEDPEVQFNWYVD GVEVHNAKTKPREEQFNSTFRVVSVLTVVHQDWLNGKEYKCKVSNK GLPAPIEKTISKTKGQPREPQVYTLPPCREEMTKNQVSLWCLVKGFY PSDIAVEWESNGQPENNYKTTPPMLDSDGSFFLYSKLTVDKSRWQQ GNVFSCSVMHEALHNHYTQKSLSLSPG (SEQ ID NO: 22) EVQLLESGGGLVQPGGSLRLSCAASGFTFSNAWMNWVRQAPGKGL EWVSSISSSSSYIYYADSVKGRFTISRDNSKNTLYLQMNSLRAEDTAV YYCARAVAAGGMFWGLDQWGQGTLVTVTSSGGGGSGGGGSGGG GSQSVLTQPPSASGTPGQRVTISCSGSRSNIGSNSVHWYQQLPGTA PKLLIYGNSNRPSGVPDRFSGSKSGTSASLAISGLRSEDEADYYCQS YDSSLNDHVVFGGGTKLTVLGGGGSGGGGSGGGGSGVECPPCPAP PVAGPSVFLFPPKPKDTLMISRTPEVTCVVVDVSHEDPEVQFNWYVD GVEVHNAKTKPREEQFNSTFRVVSVLTVVHQDWLNGKEYKCKVSNK GLPAPIEKTISKTKGQPREPQVCTLPPSREEMTKNQVSLSCAVKGFYP SDIAVEWESNGQPENNYKTTPPMLDSDGSFFLVSKLTVDKSRWQQG NVFSCSVMHEALHNHYTQKSLSLSPG (SEQ ID NO: 23) |
| DGL270 | EVQLLESGGGLVQPGGSLRLSCAASGFTFSSYAMSWVRQAPGKGLE WVANINQDGSEKNYVDSMRGRFTISRDNSKNTLYLQMNSLRAEDTA VYYCAREFDYWGQGTLVTVTSSGGGGSGGGGGGGGSQSVLAQP PSASGTPGQRVTISCSGSSSNIGSNYVYWYQQLPGTAPKLLIYGNNK RPSGVPDRFSGSKSGTSASLAISGLRSEDEADYYCAAWDDSLNGRV FGGGTKLTVLGGGGSGGGGSGGGGSGVECPPCPAPPVAGPSVFLF PPKPKDTLMISRTPEVTCVVVDVSHEDPEVQFNWYVDGVEVHNAKT KPREEQFNSTFRVVSVLTVVHQDWLNGKEYKCKVSNKGLPAPIEKTI SKTKGQPREPQVYTLPPCREEMTKNQVSLWCLVKGFYPSDIAVEWE SNGQPENNYKTTPPMLDSDGSFFLYSKLTVDKSRWQQGNVFSCSV MHEALHNHYTQKSLSLSPG (SEQ ID NO: 24) EVQLLESGGGLVQPGGSLRLSCAASGFTFSSYAMSWVRQAPGKGLE WVANINQDGSEKNYVDSMRGRFTISRDNSKNTLYLQMNSLRAEDTA VYYCAREFDYWGQGTLVTVTSSGGGGSGGGGSGGGGSQSVLAQP PSASGTPGQRVTISCSGSSSNIGSNYVYWYQQLPGTAPKLLIYGNNK RPSGVPDRFSGSKSGTSASLAISGLRSEDEADYYCAAWDDSLNGRV FGGGTKLTVLGGGGSGGGGSGGGGSGVECPPCPAPPVAGPSVFLF |

TABLE 2-continued

<u>Bispecific antibodies to ALK1 and BMPRII constructs</u>

| Antibody Designation | Amino acid sequence |
|---|---|
|  | PPKPKDTLMISRTPEVTCVVVDVSHEDPEVQFNWYVDGVEVHNAKT<br>KPREEQFNSTFRVVSVLTVVHQDWLNGKEYKCKVSNKGLPAPIEKTI<br>SKTKGQPREPQVCTLPPSREEMTKNQVSLSCAVKGFYPSDIAVEWE<br>SNGQPENNYKTTPPMLDSDGSFFLVSKLTVDKSRWQQGNVFSCSV<br>MHEALHNHYTQKSLSLSPG (SEQ ID NO: 25) |
| DGL271 | EVQLLESGGGLVQPGGSLRLSCAASGFTFSDYYMTWIRQAPGKGLE<br>WVSSISGGSTYYADSRKGRFTISRDNSENTLYLQMNSLRAEDTAVYY<br>CARDFGVAGWFGQYGMDVWGQGTLVTVSSGGGGSGGGGSGGGG<br>SQSVLTQPPSASGTPGQRVTISCTGSSSNIGAGYDVHWYQQLPGTA<br>PKLLIYRSNQRPSGVPDRFSGSKSGTSASLAISGLRSEDEADYYCSSY<br>AGNYNLVFGGGTKLTVLGGGGSGGGGSGGGGSGVECPPCPAPPVA<br>GPSVFLFPPKPKDTLMISRTPEVTCVVVDVSHEDPEVQFNWYVDGVE<br>VHNAKTKPREEQFNSTFRVVSVLTVVHQDWLNGKEYKCKVSNKGLP<br>APIEKTISKTKGQPREPQVYTLPPCREEMTKNQVSLWCLVKGFYPSDI<br>AVEWESNGQPENNYKTTPPMLDSDGSFFLYSKLTVDKSRWQQGNV<br>FSCSVMHEALHNHYTQKSLSLSPG (SEQ ID NO: 26)<br>EVQLLESGGGLVQPGGSLRLSCAASGFTFSDYYMTWIRQAPGKGLE<br>WVSSISGGSTYYADSRKGRFTISRDNSENTLYLQMNSLRAEDTAVYY<br>CARDFGVAGWFGQYGMDVWGQGTLVTVSSGGGGSGGGGSGGGG<br>SQSVLTQPPSASGTPGQRVTISCTGSSSNIGAGYDVHWYQQLPGTA<br>PKLLIYRSNQRPSGVPDRFSGSKSGTSASLAISGLRSEDEADYYCSSY<br>AGNYNLVFGGGTKLTVLGGGGSGGGGSGGGGSGVECPPCPAPPVA<br>GPSVFLFPPKPKDTLMISRTPEVTCVVVDVSHEDPEVQFNWYVDGVE<br>VHNAKTKPREEQFNSTFRVVSVLTVVHQDWLNGKEYKCKVSNKGLP<br>APIEKTISKTKGQPREPQVCTLPPSREEMTKNQVSLSCAVKGFYPSDI<br>AVEWESNGQPENNYKTTPPMLDSDGSFFLVSKLTVDKSRWQQGNV<br>FSCSVMHEALHNHYTQKSLSLSPG (SEQ ID NO: 27) |
| DGL272 | EVQLLESGGGLVQPGGSLRLSCAASGFTFSIYAMSWVRQAPGKGLE<br>WVSAISGSGGSTYYADSVKGRFTISRDNSKNTLYLQMNSLRAEDTAV<br>YYCARDFDYWGQGTLVTVSSGGGGSGGGGSGGGGSQSVLTQPP<br>SASGTPGQRVTISCSGSSSNIGSNYVYWYQQLPGTAPKLLIYGNINRP<br>SGVPDRFSGSKSGTSASLAISGLRSEDEADYYCAAWDDSLNGRVFG<br>GGTKLTVLDKTHTCPPCPAPEAAGAPSVFLFPPKPKDTLMISRTPEVT<br>CVVVDVSHEDPEVKFNWYVDGVEVHNAKTKPREEQYNSTYRVVSVL<br>TVLHQDWLNGKEYKCKVSNKALPAPIEKTISKAKGQPREPQVYTLPP<br>CRDELTKNQVSLWCLVKGFYPSDIAVEWESNGQPENNYKTTPPVLD<br>SDGSFFLYSKLTVDKSRWQQGNVFSCSVMHEALHNHYTQKSLSLSP<br>GEPEA (SEQ ID NO: 28)<br>EVQLLESGGGLVQPGGSLRLSCAASGFTFSNAWMNWVRQAPGKGL<br>EWVSSISSSSSYIYYADSVKGRFTISRDNSKNTLYLQMNSLRAEDTAV<br>YYCARAVAAGGMFWGLDQWGQGTLVTVTSSGGGGSGGGGSGGGG<br>GSQSVLTQPPSASGTPGQRVTISCSGSRSNIGSNSVHWYQQLPGTA<br>PKLLIYGNSNRPSGVPDRFSGSKSGTSASLAISGLRSEDEADYYCQS<br>YDSSLNDHVVFGGGTKLTVLDKTHTCPPCPAPEAAGAPSVFLFPPKP<br>KDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKG<br>QPREPQVCTLPPSRDELTKNQVSLSCAVKGFYPSDIAVEWESNGQP<br>ENNYKTTPPVLDSDGSFFLVSKLTVDKSRWQQGNVFSCSVMHEALH<br>NHYTQKSLSLSPGWSHPQFEK (SEQ ID NO: 29) |
| DGL273 | EVQLLESGGGLVQPGGSLRLSCAASGFTFSIYAMSWVRQAPGKGLE<br>WVSAISGSGGSTYYADSVKGRFTISRDNSKNTLYLQMNSLRAEDTAV<br>YYCARDFDYWGQGTLVTVSSGGGGSGGGGSGGGGSQSVLTQPP<br>SASGTPGQRVTISCSGSSSNIGSNYVYWYQQLPGTAPKLLIYGNINRP<br>SGVPDRFSGSKSGTSASLAISGLRSEDEADYYCAAWDDSLNGRVFG<br>GGTKLTVLCPPCPAPEAAGAPSVFLFPPKPKDTLMISRTPEVTCVVVD<br>VSHEDPEVKFNWYVDGVEVHNAKTKPREEQYNSTYRVVSVLTVLHQ<br>DWLNGKEYKCKVSNKALPAPIEKTISKAKGQPREPQVYTLPPCRDEL<br>TKNQVSLWCLVKGFYPSDIAVEWESNGQPENNYKTTPPVLDSDGSF<br>FLYSKLTVDKSRWQQGNVFSCSVMHEALHNHYTQKSLSLSPGEPEA<br>(SEQ ID NO: 30)<br>EVQLLESGGGLVQPGGSLRLSCAASGFTFSNAWMNWVRQAPGKGL<br>EWVSSISSSSSYIYYADSVKGRFTISRDNSKNTLYLQMNSLRAEDTAV<br>YYCARAVAAGGMFWGLDQWGQGTLVTVTSSGGGGSGGGGSGGGG<br>GSQSVLTQPPSASGTPGQRVTISCSGSRSNIGSNSVHWYQQLPGTA<br>PKLLIYGNSNRPSGVPDRFSGSKSGTSASLAISGLRSEDEADYYCQS<br>YDSSLNDHVVFGGGTKLTVLCPPCPAPEAAGAPSVFLFPPKPKDTLMI<br>SRTPEVTCVVVDVSHEDPEVKFNWYVDGVEVHNAKTKPREEQYNST<br>YRVVSVLTVLHQDWLNGKEYKCKVSNKALPAPIEKTISKAKGQPREP<br>QVCTLPPSRDELTKNQVSLSCAVKGFYPSDIAVEWESNGQPENNYKT<br>TPPVLDSDGSFFLVSKLTVDKSRWQQGNVFSCSVMHEALHNHYTQK<br>SLSLSPGWSHPQFEK (SEQ ID NO: 31) |

TABLE 2-continued

Bispecific antibodies to ALK1 and BMPRII constructs

| Antibody Designation | Amino acid sequence |
|---|---|
| DGL274 | EVQLLESGGGLVQPGGSLRLSCAASGFTFSIYAMSWVRQAPGKGLE WVSAISGSGGSTYYADSVKGRFTISRDNSKNTLYLQMNSLRAEDTAV YYCARDFDYWGQGTLVTVTSSGGGGSGGGGSGGGGSQSVLTQPP SASGTPGQRVTISCSGSSSNIGSNYVYWYQQLPGTAPKLLIYGNINRP SGVPDRFSGSKSGTSASLAISGLRSEDEADYYCAAWDDSLNGRVFG GGTKLTVLPLAPCPPCPAPEAAGAPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPPC RDELTKNQVSLWCLVKGFYPSDIAVEWESNGQPENNYKTTPPVLDS DGSFFLYSKLTVDKSRWQQGNVFSCSVMHEALHNHYTQKSLSLSPG EPEA (SEQ ID NO: 32) EVQLLESGGGLVQPGGSLRLSCAASGFTFSNAWMNWVRQAPGKGL EWVSSISSSSSYIYYADSVKGRFTISRDNSKNTLYLQMNSLRAEDTAV YYCARAVAAGGMFWGLDQWGQGTLVTVTSSGGGGSGGGGSGGGG GSQSVLTQPPSASGTPGQRVTISCSGSRSNIGSNSVHWYQQLPGTA PKLLIYGNSNRPSGVPDRFSGSKSGTSASLAISGLRSEDEADYYCQS YDSSLNDHVVFGGGTKLTVLPLAPCPPCPAPEAAGAPSVFLFPPKPK DTLMISRTPEVTCVVVDVSHEDPEVKFNWYVDGVEVHNAKTKPREE QYNSTYRVVSVLTVLHQDWLNGKEYKCKVSNKALPAPIEKTISKAKG QPREPQVCTLPPSRDELTKNQVSLSCAVKGFYPSDIAVEWESNGQP ENNYKTTPPVLDSDGSFFLVSKLTVDKSRWQQGNVFSCSVMHEALH NHYTQKSLSLSPGWSHPQFEK (SEQ ID NO: 33) |
| DGL275 | EVQLLESGGGLVQPGGSLRLSCAASGFTFSSYAMSWVRQAPGKGLE WVANINQDGSEKNYVDSMRGRFTISRDNSKNTLYLQMNSLRAEDTA VYYCAREFDYWGQGTLVTVTSSGGGGSGGGGSGGGGSQSVLAQP PSASGTPGQRVTISCSGSSSNIGSNYVYWYQQLPGTAPKLLIYGNNK RPSGVPDRFSGSKSGTSASLAISGLRSEDEADYYCAAWDDSLNGRV FGGGTKLTVLDKTHTCPPCPAPEAAGAPSVFLFPPKPKDTLMISRTPE VTCVVVDVSHEDPEVKFNWYVDGVEVHNAKTKPREEQYNSTYRVVS VLTVLHQDWLNGKEYKCKVSNKALPAPIEKTISKAKGQPREPQVYTLP PCRDELTKNQVSLWCLVKGFYPSDIAVEWESNGQPENNYKTTPPVL DSDGSFFLYSKLTVDKSRWQQGNVFSCSVMHEALHNHYTQKSLSLS PGEPEA (SEQ ID NO: 34) EVQLLESGGGLVQPGGSLRLSCAASGFTFSDYYMTWIRQAPGKGLE WVSSISGGSTYYADSRKGRFTISRDNSENTLYLQMNSLRAEDTAVYY CARDFGVAGWFGQYGMDVWGQGTLVTVSSGGGGSGGGGSGGGG SQSVLTQPPSASGTPGQRVTISCTGSSSNIGAGYDVHWYQQLPGTA PKLLIYRSNQRPSGVPDRFSGSKSGTSASLAISGLRSEDEADYYCSSY AGNYNLVFGGGTKLTVLDKTHTCPPCPAPEAAGAPSVFLFPPKPKDT LMISRTPEVTCVVVDVSHEDPEVKFNWYVDGVEVHNAKTKPREEQY NSTYRVVSVLTVLHQDWLNGKEYKCKVSNKALPAPIEKTISKAKGQP REPQVCTLPPSRDELTKNQVSLSCAVKGFYPSDIAVEWESNGQPEN NYKTTPPVLDSDGSFFLVSKLTVDKSRWQQGNVFSCSVMHEALHNH YTQKSLSLSPGWSHPQFEK (SEQ ID NO: 35) |
| DGL276 | EVQLLESGGGLVQPGGSLRLSCAASGFTFSSYAMSWVRQAPGKGLE WVANINQDGSEKNYVDSMRGRFTISRDNSKNTLYLQMNSLRAEDTA VYYCAREFDYWGQGTLVTVTSSGGGGSGGGGSGGGGSQSVLAQP PSASGTPGQRVTISCSGSSSNIGSNYVYWYQQLPGTAPKLLIYGNNK RPSGVPDRFSGSKSGTSASLAISGLRSEDEADYYCAAWDDSLNGRV FGGGTKLTVLCPPCPAPEAAGAPSVFLFPPKPKDTLMISRTPEVTCVV VDVSHEDPEVKFNWYVDGVEVHNAKTKPREEQYNSTYRVVSVLTVL HQDWLNGKEYKCKVSNKALPAPIEKTISKAKGQPREPQVYTLPPCRD ELTKNQVSLWCLVKGFYPSDIAVEWESNGQPENNYKTTPPVLDSDG SFFLYSKLTVDKSRWQQGNVFSCSVMHEALHNHYTQKSLSLSPGEP EA (SEQ ID NO: 36) EVQLLESGGGLVQPGGSLRLSCAASGFTFSDYYMTWIRQAPGKGLE WVSSISGGSTYYADSRKGRFTISRDNSENTLYLQMNSLRAEDTAVYY CARDFGVAGWFGQYGMDVWGQGTLVTVSSGGGGSGGGGSGGGG SQSVLTQPPSASGTPGQRVTISCTGSSSNIGAGYDVHWYQQLPGTA PKLLIYRSNQRPSGVPDRFSGSKSGTSASLAISGLRSEDEADYYCSSY AGNYNLVFGGGTKLTVLCPPCPAPEAAGAPSVFLFPPKPKDTLMISRT PEVTCVVVDVSHEDPEVKFNWYVDGVEVHNAKTKPREEQYNSTYRV VSVLTVLHQDWLNGKEYKCKVSNKALPAPIEKTISKAKGQPREPQVC TLPPSRDELTKNQVSLSCAVKGFYPSDIAVEWESNGQPENNYKTTPP VLDSDGSFFLVSKLTVDKSRWQQGNVFSCSVMHEALHNHYTQKSLS LSPGWSHPQFEK (SEQ ID NO: 37) |
| DGL277 | EVQLLESGGGLVQPGGSLRLSCAASGFTFSSYAMSWVRQAPGKGLE WVANINQDGSEKNYVDSMRGRFTISRDNSKNTLYLQMNSLRAEDTA VYYCAREFDYWGQGTLVTVTSSGGGGSGGGGSGGGGSQSVLAQP PSASGTPGQRVTISCSGSSSNIGSNYVYWYQQLPGTAPKLLIYGNNK RPSGVPDRFSGSKSGTSASLAISGLRSEDEADYYCAAWDDSLNGRV FGGGTKLTVLPLAPCPPCPAPEAAGAPSVFLFPPKPKDTLMISRTPEV |

TABLE 2-continued

---

Bispecific antibodies to ALK1 and BMPRII constructs

---

| Antibody Designation | Amino acid sequence |
|---|---|
| | TCVVVDVSHEDPEVKFNWYVDGVEVHNAKTKPREEQYNSTYRVVSV LTVLHQDWLNGKEYKCKVSNKALPAPIEKTISKAKGQPREPQVYTLPP CRDELTKNQVSLWCLVKGFYPSDIAVEWESNGQPENNYKTTPPVLD SDGSFFLYSKLTVDKSRWQQGNVFSCSVMHEALHNHYTQKSLSLSP GEPEA (SEQ ID NO: 38) EVQLLESGGGLVQPGGSLRLSCAASGFTFSDYYMTWIRQAPGKGLE WVSSISGGGSTYYADSRKGRFTISRDNSENTLYLQMNSLRAEDTAVYY CARDFGVAGWFGQYGMDVWGQGTLVTVSSGGGGGGGGSGGGG SQSVLTQPPSASGTPGQRVTISCTGSSSNIGAGYDVHWYQQLPGTA PKLLIYRSNQRPSGVPDRFSGSKSGTSASLAISGLRSEDEADYYCSSY AGNYNLVFGGGTKLTVLPLAPCPPCPAPEAAGAPSVFLFPPKPKDTL MISRTPEVTCVVVDVSHEDPEVKFNWYVDGVEVHNAKTKPREEQYN STYRVVSVLTVLHQDWLNGKEYKCKVSNKALPAPIEKTISKAKGQPRE PQVCTLPPSRDELTKNQVSLSCAVKGFYPSDIAVEWESNGQPENNY KTTPPVLDSDGSFFLVSKLTVDKSRWQQGNVFSCSVMHEALHNHYT QKSLSLSPGWSHPQFEK (SEQ ID NO: 39) |
| DGL278 | EVQLLESGGGLVQPGGSLRLSCAASGFTFSIYAMSWVRQAPGKGLE WVSAISGSGGSTYYADSVKGRFTISRDNSKNTLYLQMNSLRAEDTAV YYCARDFDYWGQGTLVTVTSSASTKGPSVFPLAPSSKSTSGGTAAL GCLVKDYFPEPVTVSWNSGALTSGVHTFPAVLQSSGLYSLSSVVTVP SSSLGTQTYICNVNHKPSNTKVDKKVEPKSCDKTHTCPPCPAPEAAG APSVFLFPPKPKDTLMISRTPEVTCVVVDVSHEDPEVKFNWYVDGVE VHNAKTKPREEQYNSTYRVVSVLTVLHQDWLNGKEYKCKVSNKALP APIEKTISKAKGQPREPQVYTLPPCRDELTKNQVSLWCLVKGFYPSDI AVEWESNGQPENNYKTTPPVLDSDGSFFLYSKLTVDKSRWQQGNVF SCSVMHEALHNHYTQKSLSLSPGEPEA (SEQ ID NO: 40) QSVLTQPPSASGTPGQRVTISCSGSSSNIGSNYVYWYQQLPGTAPKL LIYGNINRPSGVPDRFSGSKSGTSASLAISGLRSEDEADYYCAAWDD SLNGRVFGGGTKLTVLGQPKAAPSVTLFPPSSEELQANKATLVCLISD FYPGAVTVAWKADSSPVKAGVETTTPSKQSNNKYAASSYLSLTPEQ WKSHRSYSCQVTHEGSTVEKTVAPTECS (SEQ ID NO: 41) EVQLLESGGGLVQPGGSLRLSCAASGFTFSIYAMSWVRQAPGKGLE WVSAISGSGGSTYYADSVKGRFTISRDNSKNTLYLQMNSLRAEDTAV YYCARDFDYWGQGTLVTVTSSGGGGSGGGGSGGGGSQSVLTQPP SASGTPGQRVTISCSGSSSNIGSNYVYWYQQLPGTAPKLLIYGNINRP SGVPDRFSGSKSGTSASLAISGLRSEDEADYYCAAWDDSLNGRVFG GGTKLTVLDKTHTCPPCPAPEAAGAPSVFLFPPKPKDTLMISRTPEVT CVVVDVSHEDPEVKFNWYVDGVEVHNAKTKPREEQYNSTYRVVSVL TVLHQDWLNGKEYKCKVSNKALPAPIEKTISKAKGQPREPQVCTLPP SRDELTKNQVSLSCAVKGFYPSDIAVEWESNGQPENNYKTTPPVLDS DGSFFLVSKLTVDKSRWQQGNVFSCSVMHEALHNHYTQKSLSLSPG KWSHPQFEK (SEQ ID NO: 42) |
| DGL279 | EVQLLESGGGLVQPGGSLRLSCAASGFTFSNAWMNWVRQAPGKGL EWVSSISSSSSYIYYADSVKGRFTISRDNSKNTLYLQMNSLRAEDTAV YYCARAVAAGGMFWGLDQWGQGTLVTVTSSASTKGPSVFPLAPSS KSTSGGTAALGCLVKDYFPEPVTVSWNSGALTSGVHTFPAVLQSSGL YSLSSVVTVPSSSLGTQTYICNVNHKPSNTKVDKKVEPKSCDKTHTC PPCPAPEAAGAPSVFLFPPKPKDTLMISRTPEVTCVVVDVSHEDPEV KFNWYVDGVEVHNAKTKPREEQYNSTYRVVSVLTVLHQDWLNGKEY KCKVSNKALPAPIEKTISKAKGQPREPQVYTLPPCRDELTKNQVSLW CLVKGFYPSDIAVEWESNGQPENNYKTTPPVLDSDGSFFLYSKLTVD KSRWQQGNVFSCSVMHEALHNHYTQKSLSLSPGEPEA (SEQ ID NO: 43) QSVLTQPPSASGTPGQRVTISCSGSRSNIGSNSVHWYQQLPGTAPKL LIYGNSNRPSGVPDRFSGSKSGTSASLAISGLRSEDEADYYCQSYDS SLNDHVVFGGGTKLTVLGQPKAAPSVTLFPPSSEELQANKATLVCLIS DFYPGAVTVAWKADSSPVKAGVETTTPSKQSNNKYAASSYLSLTPEQ WKSHRSYSCQVTHEGSTVEKTVAPTECS (SEQ ID NO: 44) EVQLLESGGGLVQPGGSLRLSCAASGFTFSNAWMNWVRQAPGKGL EWVSSISSSSSYIYYADSVKGRFTISRDNSKNTLYLQMNSLRAEDTAV YYCARAVAAGGMFWGLDQWGQGTLVTVTSSGGGGSGGGGSGGG GSQSVLTQPPSASGTPGQRVTISCSGSRSNIGSNSVHWYQQLPGTA PKLLIYGNSNRPSGVPDRFSGSKSGTSASLAISGLRSEDEADYYCQS YDSSLNDHVVFGGGTKLTVLDKTHTCPPCPAPEAAGAPSVFLFPPKP KDTLMISRTPEVTCVVVDVSHEDPEVKFNWYVDGVEVHNAKTKPREE QYNSTYRVVSVLTVLHQDWLNGKEYKCKVSNKALPAPIEKTISKAKG QPREPQVCTLPPSRDELTKNQVSLSCAVKGFYPSDIAVEWESNGQP ENNYKTTPPVLDSDGSFFLVSKLTVDKSRWQQGNVFSCSVMHEALH NHYTQKSLSLSPGKWSHPQFEK (SEQ ID NO: 45) |
| DGL280 | EVQLLESGGGLVQPGGSLRLSCAASGFTFSSYAMSWVRQAPGKGLE WVANINQDGSEKNYVDSMRGRFTISRDNSKNTLYLQMNSLRAEDTA VYYCAREFDYWGQGTLVTVTSSASTKGPSVFPLAPSSKSTSGGTAAL |

TABLE 2-continued

Bispecific antibodies to ALK1 and BMPRII constructs

| Antibody Designation | Amino acid sequence |
|---|---|
| | GCLVKDYFPEPVTVSWNSGALTSGVHTFPAVLQSSGLYSLSSVVTVP SSSLGTQTYICNVNHKPSNTKVDKKVEPKSCDKTHTCPPCPAPEAAG APSVFLFPPKPKDTLMISRTPEVTCVVVDVSHEDPEVKFNWYVDGVE VHNAKTKPREEQYNSTYRVVSVLTVLHQDWLNGKEYKCKVSNKALP APIEKTISKAKGQPREPQVYTLPPCRDELTKNQVSLWCLVKGFYPSDI AVEWESNGQPENNYKTTPPVLDSDGSFFLYSKLTVDKSRWQQGNVF SCSVMHEALHNHYTQKSLSLSPGEPEA (SEQ ID NO: 46) QSVLAQPPSASGTPGQRVTISCSGSSSNIGSNYVYWYQQLPGTAPKL LIYGNNKRPSGVPDRFSGSKSGTSASLAISGLRSEDEADYYCAAWDD SLNGRVFGGGTKLTVLGQPKAAPSVTLFPPSSEELQANKATLVCLISD FYPGAVTVAWKADSSPVKAGVETTTPSKQSNNKYAASSYLSLTPEQ WKSHRSYSCQVTHEGSTVEKTVAPTECS (SEQ ID NO: 47) EVQLLESGGGLVQPGGSLRLSCAASGFTFSSYAMSWVRQAPGKGLE WVANINQDGSEKNYVDSMRGRFTISRDNSKNTLYLQMNSLRAEDTA VYYCAREFDYWGQGTLVTVTSSGGGGSGGGGSGGGGSQSVLAQP PSASGTPGQRVTISCSGSSSNIGSNYVYWYQQLPGTAPKLLIYGNNK RPSGVPDRFSGSKSGTSASLAISGLRSEDEADYYCAAWDDSLNGRV FGGGTKLTVLDKTHTCPPCPAPEAAGAPSVFLFPPKPKDTLMISRTPE VTCVVVDVSHEDPEVKFNWYVDGVEVHNAKTKPREEQYNSTYRVVS VLTVLHQDWLNGKEYKCKVSNKALPAPIEKTISKAKGQPREPQVCTLP PSRDELTKNQVSLSCAVKGFYPSDIAVEWESNGQPENNYKTTPPVLD SDGSFFLVSKLTVDKSRWQQGNVFSCSVMHEALHNHYTQKSLSLSP GKWSHPQFEK (SEQ ID NO: 48) |
| DGL281 | EVQLLESGGGLVQPGGSLRLSCAASGFTFSDYYMTWIRQAPGKGLE WVSSISGGSTYYADSRKGRFTISRDNSENTLYLQMNSLRAEDTAVYY CARDFGVAGWFGQYGMDVWGQGTLVTVSSASTKGPSVFPLAPSSK STSGGTAALGCLVKDYFPEPVTVSWNSGALTSGVHTFPAVLQSSGLY SLSSVVTVPSSSLGTQTYICNVNHKPSNTKVDKKVEPKSCDKTHTCP PCPAPEAAGAPSVFLFPPKPKDTLMISRTPEVTCVVVDVSHEDPEVKF NWYVDGVEVHNAKTKPREEQYNSTYRVVSVLTVLHQDWLNGKEYK CKVSNKALPAPIEKTISKAKGQPREPQVYTLPPCRDELTKNQVSLWCL VKGFYPSDIAVEWESNGQPENNYKTTPPVLDSDGSFFLYSKLTVDKS RWQQGNVFSCSVMHEALHNHYTQKSLSLSPGEPEA (SEQ ID NO: 49) QSVLTQPPSASGTPGQRVTISCTGSSSNIGAGYDVHWYQQLPGTAP KLLIYRSNQRPSGVPDRFSGSKSGTSASLAISGLRSEDEADYYCSSYA GNYNLVFGGGTKLTVLGQPKAAPSVTLFPPSSEELQANKATLVCLISD FYPGAVTVAWKADSSPVKAGVETTTPSKQSNNKYAASSYLSLTPEQ WKSHRSYSCQVTHEGSTVEKTVAPTECS (SEQ ID NO: 50) EVQLLESGGGLVQPGGSLRLSCAASGFTFSDYYMTWIRQAPGKGLE WVSSISGGSTYYADSRKGRFTISRDNSENTLYLQMNSLRAEDTAVYY CARDFGVAGWFGQYGMDVWGQGTLVTVSSGGGGSGGGGSGGGG SQSVLTQPPSASGTPGQRVTISCTGSSSNIGAGYDVHWYQQLPGTA PKLLIYRSNQRPSGVPDRFSGSKSGTSASLAISGLRSEDEADYYCSSY AGNYNLVFGGGTKLTVLDKTHTCPPCPAPEAAGAPSVFLFPPKPKDT LMISRTPEVTCVVVDVSHEDPEVKFNWYVDGVEVHNAKTKPREEQY NSTYRVVSVLTVLHQDWLNGKEYKCKVSNKALPAPIEKTISKAKGQP REPQVCTLPPSRDELTKNQVSLSCAVKGFYPSDIAVEWESNGQPEN NYKTTPPVLDSDGSFFLVSKLTVDKSRWQQGNVFSCSVMHEALHNH YTQKSLSLSPGKWSHPQFEK (SEQ ID NO: 51) |
| DGL282 | EVQLLESGGGLVQPGGSLRLSCAASGFTFSIYAMSWVRQAPGKGLE WVSAISGSGGSTYYADSVKGRFTISRDNSKNTLYLQMNSLRAEDTAV YYCARDFDYWGQGTLVTVTSSASVAAPSVFIFPPSDEQLKSGTASVV CLLNNFYPREAKVQWKVDNALQSGNSQESVTEQDSKDSTYSLSSTL TLSKADYEKHKVYACEVTHQGLSSPVTKSFNRGECDKTHTCPPCPAP EAAGAPSVFLFPPKPKDTLMISRTPEVTCVVVDVSHEDPEVKFNWYV DGVEVHNAKTKPREEQYNSTYRVVSVLTVLHQDWLNGKEYKCKVSN KALPAPIEKTISKAKGQPREPQVCTLPPSRDELTKNQVSLSCAVKGFY PSDIAVEWESNGQPENNYKTTPPVLDSDGSFFLVSKLTVDKSRWQQ GNVFSCSVMHEALHNHYTQKSLSLSPGWSHPQFEK (SEQ ID NO: 52) QSVLTQPPSASGTPGQRVTISCSGSSSNIGSNYVYWYQQLPGTAPKL LIYGNINRPSGVPDRFSGSKSGTSASLAISGLRSEDEADYYCAAWDD SLNGRVFGGGTKLTVLSSASTKGPSVFPLAPSSKSTSGGTAALGCLV KDYFPEPVTVSWNSGALTSGVHTFPAVLQSSGLYSLSSVVTVPSSSL GTQTYICNVNHKPSNTKVDKKVEPKSC (SEQ ID NO: 53) EVQLLESGGGLVQPGGSLRLSCAASGFTFSNAWMNWVRQAPGKGL EWVSSISSSSSYIYYADSVKGRFTISRDNSKNTLYLQMNSLRAEDTAV YYCARAVAAGGMFWGLDQWGQGTLVTVTSSASTKGPSVFPLAPSS KSTSGGTAALGCLVKDYFPEPVTVSWNSGALTSGVHTFPAVLQSSGL YSLSSVVTVPSSSLGTQTYICNVNHKPSNTKVDKKVEPKSCDKTHTC PPCPAPEAAGAPSVFLFPPKPKDTLMISRTPEVTCVVVDVSHEDPEV KFNWYVDGVEVHNAKTKPREEQYNSTYRVVSVLTVLHQDWLNGKEY |

TABLE 2-continued

Bispecific antibodies to ALK1 and BMPRII constructs

| Antibody Designation | Amino acid sequence |
|---|---|
| | KCKVSNKALPAPIEKTISKAKGQPREPQVYTLPPCRDELTKNQVSLW CLVKGFYPSDIAVEWESNGQPENNYKTTPPVLDSDGSFFLYSKLTVD KSRWQQGNVFSCSVMHEALHNHYTQKSLSLSPGEPEA (SEQ ID NO: 54) |
| | QSVLTQPPSASGTPGQRVTISCSGSRSNIGSNSVHWYQQLPGTAPKL LIYGNSNRPSGVPDRFSGSKSGTSASLAISGLRSEDEADYYCQSYDS SLNDHVVFGGGTKLTVLGQPKAAPSVTLFPPSSEELQANKATLVCLIS DFYPGAVTVAWKADSSPVKAGVETTTPSKQSNNKYAASSYLSLTPEQ WKSHRSYSCQVTHEGSTVEKTVAPTECS (SEQ ID NO: 55) |
| DGL283 | EVQLLESGGGLVQPGGSLRLSCAASGFTFSSYAMSWVRQAPGKGLE WVANINQDGSEKNYVDSMRGRFTISRDNSKNTLYLQMNSLRAEDTA VYYCAREFDYWGQGTLVTVTSSASVAAPSVFIFPPSDEQLKSGTASV VCLLNNFYPREAKVQWKVDNALQSGNSQESVTEQDSKDSTYSLSST LTLSKADYEKHKVYACEVTHQGLSSPVTKSFNRGECDKTHTCPPCPA PEAAGAPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVCTLPPSRDELTKNQVSLSCAVGF YPSDIAVEWESNGQPENNYKTTPPVLDSDGSFFLVSKLTVDKSRWQ QGNVFSCSVMHEALHNHYTQKSLSLSPGWSHPQFEK (SEQ ID NO: 56) |
| | QSVLAQPPSASGTPGQRVTISCSGSSSNIGSNYVYWYQQLPGTAPKL LIYGNNKRPSGVPDRFSGSKSGTSASLAISGLRSEDEADYYCAAWDD SLNGRVFGGGTKLTVLSSASTKGPSVFPLAPSSKSTSGGTAALGCLV KDYFPEPVTVSWNSGALTSGVHTFPAVLQSSGLYSLSSVVTVPSSSL GTQTYICNVNHKPSNTKVDKKVEPKSC (SEQ ID NO: 57) |
| | EVQLLESGGGLVQPGGSLRLSCAASGFTFSDYYMTWIRQAPGKGLE WVSSISGGSTYYADSRKGRFTISRDNSENTLYLQMNSLRAEDTAVYY CARDFGVAGWFGQYGMDVWGQGTLVTVSSASTKGPSVFPLAPSSK STSGGTAALGCLVKDYFPEPVTVSWNSGALTSGVHTFPAVLQSSGLY SLSSVVTVPSSSLGTQTYICNVNHKPSNTKVDKKVEPKSCDKTHTCP PCPAPEAAGAPSVFLFPPKPKDTLMISRTPEVTCVVVDVSHEDPEVKF NWYVDGVEVHNAKTKPREEQYNSTYRVVSVLTVLHQDWLNGKEYK CKVSNKALPAPIEKTISKAKGQPREPQVYTLPPCRDELTKNQVSLWCL VKGFYPSDIAVEWESNGQPENNYKTTPPVLDSDGSFFLYSKLTVDKS RWQQGNVFSCSVMHEALHNHYTQKSLSLSPGEPEA (SEQ ID NO: 58) |
| | QSVLTQPPSASGTPGQRVTISCTGSSSNIGAGYDVHWYQQLPGTAP KLLIYRSNQRPSGVPDRFSGSKSGTSASLAISGLRSEDEADYYCSSYA GNYNLVFGGGTKLTVLGQPKAAPSVTLFPPSSEELQANKATLVCLISD FYPGAVTVAWKADSSPVKAGVETTTPSKQSNNKYAASSYLSLTPEQ WKSHRSYSCQVTHEGSTVEKTVAPTECS (SEQ ID NO: 59) |
| DGL285 | EVQLLESGGGLVQPGGSLRLSCAASGFTFSIYAMSWVRQAPGKGLE WVSAISGSGGSTYYADSVKGRFTISRDNSKNTLYLQMNSLRAEDTAV YYCARDFDYWGQGTLVTVTSSGGGGSGGGGSGGGGSQSVLTQPP SASGTPGQRVTISCSGSSSNIGSNYVYWYQQLPGTAPKLLIYGNINRP SGVPDRFSGSKSGTSASLAISGLRSEDEADYYCAAWDDSLNGRVFG GGTKLTVLDKGPSVFPLAPEPKSSEVQLLESGGGLVQPGGSLRLSCA ASGFTFSNAWMNWVRQAPGKGLEWVSSISSSSSYIYYADSVKGRFTI SRDNSKNTLYLQMNSLRAEDTAVYYCARAVAAGGMFWGLDQWGQG TLVTVTSSGGGGSGGGGSGGGGSQSVLTQPPSASGTPGQRVTISCS GSRSNIGSNSVHWYQQLPGTAPKLLIYGNSNRPSGVPDRFSGSKSG TSASLAISGLRSEDEADYYCQSYDSSLNDHVVFGGGTKLTVLDKTHT CPPCPAPEAAGAPSVFLFPPKPKDTLMISRTPEVTCVVVDVSHEDPE VKFNWYVDGVEVHNAKTKPREEQYNSTYRVVSVLTVLHQDWLNGKE YKCKVSNKALPAPIEKTISKAKGQPREPQVYTLPPSRDELTKNQVSLT CLVKGFYPSDIAVEWESNGQPENNYKTTPPVLDSDGSFFLYSKLTVD KSRWQQGNVFSCSVMHEALHNHYTQKSLSLSPG (SEQ ID NO: 60) |
| DGL286 | EVQLLESGGGLVQPGGSLRLSCAASGFTFSNAWMNWVRQAPGKGL EWVSSISSSSSYIYYADSVKGRFTISRDNSKNTLYLQMNSLRAEDTAV YYCARAVAAGGMFWGLDQWGQGTLVTVTSSGGGGSGGGGSGGGG GSQSVLTQPPSASGTPGQRVTISCSGSRSNIGSNSVHWYQQLPGTA PKLLIYGNSNRPSGVPDRFSGSKSGTSASLAISGLRSEDEADYYCQS YDSSLNDHVVFGGGTKLTVLDKGPSVFPLAPEPKSSEVQLLESGGGL VQPGGSLRLSCAASGFTFSIYAMSWVRQAPGKGLEWVSAISGSGGS TYYADSVKGRFTISRDNSKNTLYLQMNSLRAEDTAVYYCARDFDYW GQGTLVTVTSSGGGGSGGGGSGGGGSQSVLTQPPSASGTPGQRVT ISCSGSSSNIGSNYVYWYQQLPGTAPKLLIYGNINRPSGVPDRFSGSK SGTSASLAISGLRSEDEADYYCAAWDDSLNGRVFGGGTKLTVLDKTH TCPPCPAPEAAGAPSVFLFPPKPKDTLMISRTPEVTCVVVDVSHEDP |

TABLE 2-continued

Bispecific antibodies to ALK1 and BMPRII constructs

| Antibody Designation | Amino acid sequence |
|---|---|
| | EVKFNWYVDGVEVHNAKTKPREEQYNSTYRVVSVLTVLHQDWLNGK EYKCKVSNKALPAPIEKTISKAKGQPREPQVYTLPPSRDELTKNQVSL TCLVKGFYPSDIAVEWESNGQPENNYKTTPPVLDSDGSFFLYSKLTV DKSRWQQGNVFSCSVMHEALHNHYTQKSLSLSPG (SEQ ID NO: 61) |
| DGL287 | EVQLLESGGGLVQPGGSLRLSCAASGFTFSSYAMSWVRQAPGKGLE WVANINQDGSEKNYVDSMRGRFTISRDNSKNTLYLQMNSLRAEDTA VYYCAREFDYWGQGTLVTVTSSGGGGSGGGGSGGGGSQSVLAQP PSASGTPGQRVTISCSGSSSNIGSNYVYWYQQLPGTAPKLLIYGNNK RPSGVPDRFSGSKSGTSASLAISGLRSEDEADYYCAAWDDSLNGRV FGGGTKLTVLDKGPSVFPLAPEPKSSEVQLLESGGGLVQPGGSLRLS CAASGFTFSDYYMTWIRQAPGKGLEWVSSISGGSTYYADSRKGRFTI SRDNSENTLYLQMNSLRAEDTAVYYCARDFGVAGWFGQYGMDVWG QGTLVTVSSGGGGSGGGGSGGGGSQSVLTQPPSASGTPGQRVTIS CTGSSSNIGAGYDVHWYQQLPGTAPKLLIYRSNQRPSGVPDRFSGS KSGTSASLAISGLRSEDEADYYCSSYAGNYNLVFGGGTKLTVLDKTH TCPPCPAPEAAGAPSVFLFPPKPKDTLMISRTPEVTCVVVDVSHEDP EVKFNWYVDGVEVHNAKTKPREEQYNSTYRVVSVLTVLHQDWLNGK EYKCKVSNKALPAPIEKTISKAKGQPREPQVYTLPPSRDELTKNQVSL TCLVKGFYPSDIAVEWESNGQPENNYKTTPPVLDSDGSFFLYSKLTV DKSRWQQGNVFSCSVMHEALHNHYTQKSLSLSPG (SEQ ID NO: 62) |
| DGL288 | EVQLLESGGGLVQPGGSLRLSCAASGFTFSDYYMTWIRQAPGKGLE WVSSISGGSTYYADSRKGRFTISRDNSENTLYLQMNSLRAEDTAVYY CARDFGVAGWFGQYGMDVWGQGTLVTVSSGGGGSGGGGSGGGG SQSVLTQPPSASGTPGQRVTISCTGSSSNIGAGYDVHWYQQLPGTA PKLLIYRSNQRPSGVPDRFSGSKSGTSASLAISGLRSEDEADYYCSSY AGNYNLVFGGGTKLTVLDKGPSVFPLAPEPKSSEVQLLESGGGLVQP GGSLRLSCAASGFTFSSYAMSWVRQAPGKGLEWVANINQDGSEKN YVDSMRGRFTISRDNSKNTLYLQMNSLRAEDTAVYYCAREFDYWGQ GTLVTVTSSGGGGSGGGGSGGGGSQSVLAQPPSASGTPGQRVTIS CSGSSSNIGSNYVYWYQQLPGTAPKLLIYGNNKRPSGVPDRFSGSKS GTSASLAISGLRSEDEADYYCAAWDDSLNGRVFGGGTKLTVLDKTHT CPPCPAPEAAGAPSVFLFPPKPKDTLMISRTPEVTCVVVDVSHEDPE VKFNWYVDGVEVHNAKTKPREEQYNSTYRVVSVLTVLHQDWLNGKE YKCKVSNKALPAPIEKTISKAKGQPREPQVYTLPPSRDELTKNQVSLT CLVKGFYPSDIAVEWESNGQPENNYKTTPPVLDSDGSFFLYSKLTVD KSRWQQGNVFSCSVMHEALHNHYTQKSLSLSPG (SEQ ID NO: 63) |
| PRO003 | EVQLLESGGGLVQPGGSLRLSCAASGFTFSIYAMSWVRQAPGKGLE WVSAISGSGGSTYYADSVKGRFTISRDNSKNTLYLQMNSLRAEDTAV YYCARDFDYWGQGTLVTVTSSGGGGSGGGGSGGGGSQSVLTQPP SASGTPGQRVTISCSGSSSNIGSNYVYWYQQLPGTAPKLLIYGNINRP SGVPDRFSGSKSGTSASLAISGLRSEDEADYYCAAWDDSLNGRVFG GGTKLTVLDKTHTCPPCPAPEAAGAPSVFLFPPKPKDTLMISRTPEVT CVVVDVSHEDPEVKFNWYVDGVEVHNAKTKPREEQYNSTYRVVSVL TVLHQDWLNGKEYKCKVSNKALPAPIEKTISKAKGQPREPQVYTLPP SRDELTKNQVSLTCLVKGFYPSDIAVEWESNGQPENNYKTTPPVLDS DGSFFLYSKLTVDKSRWQQGNVFSCSVMHEALHNHYTQKSLSLSPG GGGGSGGGGSEVQLLESGGGLVQPGGSLRLSCAASGFTFSNAWMN WVRQAPGKGLEWVSSISSSSSYIYYADSVKGRFTISRDNSKNTLYLQ MNSLRAEDTAVYYCARAVAAGGMFWGLDQWGQGTLVTVTSSGGG GSGGGGSGGGGSQSVLTQPPSASGTPGQRVTISCSGSRSNIGSNSV HWYQQLPGTAPKLLIYGNSNRPSGVPDRFSGSKSGTSASLAISGLRS EDEADYYCQSYDSSLNDHVVFGGGTKLTVL (SEQ ID NO: 64) |
| PRO004 | EVQLLESGGGLVQPGGSLRLSCAASGFTFSNAWMNWVRQAPGKGL EWVSSISSSSSYIYYADSVKGRFTISRDNSKNTLYLQMNSLRAEDTAV YYCARAVAAGGMFWGLDQWGQGTLVTVTSSGGGGSGGGGSGGGG GSQSVLTQPPSASGTPGQRVTISCSGSRSNIGSNSVHWYQQLPGTA PKLLIYGNSNRPSGVPDRFSGSKSGTSASLAISGLRSEDEADYYCQS YDSSLNDHVVFGGGTKLTVLDKTHTCPPCPAPEAAGAPSVFLFPPKP KDTLMISRTPEVTCVVVDVSHEDPEVKFNWYVDGVEVHNAKTKPREE QYNSTYRVVSVLTVLHQDWLNGKEYKCKVSNKALPAPIEKTISKAKG QPREPQVYTLPPSRDELTKNQVSLTCLVKGFYPSDIAVEWESNGQPE NNYKTTPPVLDSDGSFFLYSKLTVDKSRWQQGNVFSCSVMHEALHN HYTQKSLSLSPGGGGGSGGGGSEVQLLESGGGLVQPGGSLRLSCA ASGFTFSIYAMSWVRQAPGKGLEWVSAISGSGGSTYYADSVKGRFTI SRDNSKNTLYLQMNSLRAEDTAVYYCARDFDYWGQGTLVTVTSSGG GGSGGGGSGGGGSQSVLTQPPSASGTPGQRVTISCSGSSSNIGSNY VYWYQQLPGTAPKLLIYGNINRPSGVPDRFSGSKSGTSASLAISGLRS EDEADYYCAAWDDSLNGRVFGGGTKLTVL (SEQ ID NO: 65) |
| PRO005 | EVQLLESGGGLVQPGGSLRLSCAASGFTFSSYAMSWVRQAPGKGLE WVANINQDGSEKNYVDSMRGRFTISRDNSKNTLYLQMNSLRAEDTA |

TABLE 2-continued

Bispecific antibodies to ALK1 and BMPRII constructs

| Antibody Designation | Amino acid sequence |
| --- | --- |
| | VYYCAREFDYWGQGTLVTVTSSGGGGSGGGGSGGGGSQSVLAQP PSASGTPGQRVTISCSGSSSNIGSNYVYWYQQLPGTAPKLLIYGNNK RPSGVPDRFSGSKSGTSASLAISGLRSEDEADYYCAAWDDSLNGRV FGGGTKLTVLDKTHTCPPCPAPEAAGAPSVFLFPPKPKDTLMISRTPE VTCVVVDVSHEDPEVKFNWYVDGVEVHNAKTKPREEQYNSTYRVVS VLTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSP GGGGGSGGGGSEVQLLESGGGLVQPGGSLRLSCAASGFTFSDYYM TWIRQAPGKGLEWVSSISGGSTYYADSRKGRFTISRDNSENTLYLQM NSLRAEDTAVYYCARDFGVAGWFGQYGMDVWGQGTLVTVSSGGG GSGGGGSGGGGSQSVLTQPPSASGTPGQRVTISCTGSSSNIGAGYD VHWYQQLPGTAPKLLIYRSNQRPSGVPDRFSGSKSGTSASLAISGLR SEDEADYYCSSYAGNYNLVFGGGTKLTVL (SEQ ID NO: 66) |
| PRO006 | EVQLLESGGGLVQPGGSLRLSCAASGFTFSDYYMTWIRQAPGKGLE WVSSISGGSTYYADSRKGRFTISRDNSENTLYLQMNSLRAEDTAVYY CARDFGVAGWFGQYGMDVWGQGTLVTVSSGGGGSGGGGSGGGG SQSVLTQPPSASGTPGQRVTISCTGSSSNIGAGYDVHWYQQLPGTA PKLLIYRSNQRPSGVPDRFSGSKSGTSASLAISGLRSEDEADYYCSSY AGNYNLVFGGGTKLTVLDKTHTCPPCPAPEAAGAPSVFLFPPKPKDT LMISRTPEVTCVVVDVSHEDPEVKFNWYVDGVEVHNAKTKPREEQY NSTYRVVSVLTVLHQDWLNGKEYKCKVSNKALPAPIEKTISKAKGQP REPQVYTLPPSRDELTKNQVSLTCLVKGFYPSDIAVEWESNGQPENN YKTTPPVLDSDGSFFLYSKLTVDKSRWQQGNVFSCSVMHEALHNHY TQKSLSLSPGGGGGSGGGGSEVQLLESGGGLVQPGGSLRLSCAAS GFTFSSYAMSWVRQAPGKGLEWVANINQDGSEKNYVDSMRGRFTIS RDNSKNTLYLQMNSLRAEDTAVYYCAREFDYWGQGTLVTVTSSGGG GSGGGGSGGGGSQSVLAQPPSASGTPGQRVTISCSGSSSNIGSNYV YWYQQLPGTAPKLLIYGNNKRPSGVPDRFSGSKSGTSASLAISGLRS EDEADYYCAAWDDSLNGRVFGGGTKLTVL (SEQ ID NO: 67) |
| DGL289 | EVQLLESGGGLVQPGGSLRLSCAASGFTFSIYAMSWVRQAPGKGLE WVSAISGSGGSTYYADSVKGRFTISRDNSKNTLYLQMNSLRAEDTAV YYCARDFDYWGQGTLVTVTSSPAPNLLGGPEVQLLESGGGLVQPGG SLRLSCAASGFTFSNAWMNWVRQAPGKGLEWVSSISSSSSYIYYAD SVKGRFTISRDNSKNTLYLQMNSLRAEDTAVYYCARAVAAGGMFWG LDQWGQGTLVTVTSSASTKGPSVFPLAPSSKSTSGGTAALGCLVKDY FPEPVTVSWNSGALTSGVHTFPAVLQSSGLYSLSSVVTVPSSSLGTQ TYICNVNHKPSNTKVDKKVEPKSCDKTHTCPPCPAPEAAGAPSVFLF PPKPKDTLMISRTPEVTCVVVDVSHEDPEVKFNWYVDGVEVHNAKTK PREEQYNSTYRVVSVLTVLHQDWLNGKEYKCKVSNKALPAPIEKTISK AKGQPREPQVYTLPPSRDELTKNQVSLTCLVKGFYPSDIAVEWESNG QPENNYKTTPPVLDSDGSFFLYSKLTVDKSRWQQGNVFSCSVMHEA LHNHYTQKSLSLSPG (SEQ ID NO: 68) QSVLTQPPSASGTPGQRVTISCSGSSSNIGSNYVYWYQQLPGTAPKL LIYGNINRPSGVPDRFSGSKSGTSASLAISGLRSEDEADYYCAAWDD SLNGRVFGGGTKLTVLPAPNLLGGPQSVLTQPPSASGTPGQRVTISC SGSRSNIGSNSVHWYQQLPGTAPKLLIYGNSNRPSGVPDRFSGSKS GTSASLAISGLRSEDEADYYCQSYDSSLNDHVVFGGGTKLTVLGQPK AAPSVTLFPPSSEELQANKATLVCLISDFYPGAVTVAWKADSSPVKAG VETTTPSKQSNNKYAASSYLSLTPEQWKSHRSYSCQVTHEGSTVEK TVAPTECS (SEQ ID NO: 69) |
| DGL290 | EVQLLESGGGLVQPGGSLRLSCAASGFTFSNAWMNWVRQAPGKGL EWVSSISSSSSYIYYADSVKGRFTISRDNSKNTLYLQMNSLRAEDTAV YYCARAVAAGGMFWGLDQWGQGTLVTVTSSPAPNLLGGPEVQLLE SGGGLVQPGGSLRLSCAASGFTFSIYAMSWVRQAPGKGLEWVSAIS GSGGSTYYADSVKGRFTISRDNSKNTLYLQMNSLRAEDTAVYYCARD FDYWGQGTLVTVTSSASTKGPSVFPLAPSSKSTSGGTAALGCLVKDY FPEPVTVSWNSGALTSGVHTFPAVLQSSGLYSLSSVVTVPSSSLGTQ TYICNVNHKPSNTKVDKKVEPKSCDKTHTCPPCPAPEAAGAPSVFLF PPKPKDTLMISRTPEVTCVVVDVSHEDPEVKFNWYVDGVEVHNAKTK PREEQYNSTYRVVSVLTVLHQDWLNGKEYKCKVSNKALPAPIEKTISK AKGQPREPQVYTLPPSRDELTKNQVSLTCLVKGFYPSDIAVEWESNG QPENNYKTTPPVLDSDGSFFLYSKLTVDKSRWQQGNVFSCSVMHEA LHNHYTQKSLSLSPG (SEQ ID NO: 70) QSVLTQPPSASGTPGQRVTISCSGSRSNIGSNSVHWYQQLPGTAPKL LIYGNSNRPSGVPDRFSGSKSGTSASLAISGLRSEDEADYYCQSYDS SLNDHVVFGGGTKLTVLPAPNLLGGPQSVLTQPPSASGTPGQRVTIS CSGSSSNIGSNYVYWYQQLPGTAPKLLIYGNINRPSGVPDRFSGSKS GTSASLAISGLRSEDEADYYCAAWDDSLNGRVFGGGTKLTVLGQPK AAPSVTLFPPSSEELQANKATLVCLISDFYPGAVTVAWKADSSPVKAG VETTTPSKQSNNKYAASSYLSLTPEQWKSHRSYSCQVTHEGSTVEK TVAPTECS (SEQ ID NO: 71) |

TABLE 2-continued

Bispecific antibodies to ALK1 and BMPRII constructs

Antibody
Designation    Amino acid sequence

DGL291         EVQLLESGGGLVQPGGSLRLSCAASGFTFSSYAMSWVRQAPGKGLE
               WVANINQDGSEKNYVDSMRGRFTISRDNSKNTLYLQMNSLRAEDTA
               VYYCAREFDYWGQGTLVTVTSSPAPNLLGGPEVQLLESGGGLVQPG
               GSLRLSCAASGFTFSDYYMTWIRQAPGKGLEWVSSISGGSTYYADS
               RKGRFTISRDNSENTLYLQMNSLRAEDTAVYYCARDFGVAGWFGQY
               GMDVWGQGTLVTVSSASTKGPSVFPLAPSSKSTSGGTAALGCLVKD
               YFPEPVTVSWNSGALTSGVHTFPAVLQSSGLYSLSSVVTVPSSSLGT
               QTYICNVNHKPSNTKVDKKVEPKSCDKTHTCPPCPAPEAAGAPSVFL
               FPPKPKDTLMISRTPEVTCVVVDVSHEDPEVKFNWYVDGVEVHNAKT
               KPREEQYNSTYRVVSVLTVLHQDWLNGKEYKCKVSNKALPAPIEKTIS
               KAKGQPREPQVYTLPPSRDELTKNQVSLTCLVKGFYPSDIAVEWESN
               GQPENNYKTTPPVLDSDGSFFLYSKLTVDKSRWQQGNVFSCSVMHE
               ALHNHYTQKSLSLSPG (SEQ ID NO: 72)
               QSVLAQPPSASGTPGQRVTISCSGSSSNIGSNYVYWYQQLPGTAPKL
               LIYGNNKRPSGVPDRFSGSKSGTSASLAISGLRSEDEADYYCAAWDD
               SLNGRVFGGGTKLTVLPAPNLLGGPQSVLTQPPSASGTPGQRVTISC
               TGSSSNIGAGYDVHWYQQLPGTAPKLLIYRSNQRPSGVPDRFSGSK
               SGTSASLAISGLRSEDEADYYCSSYAGNYNLVFGGGTKLTVLGQPKA
               APSVTLFPPSSEELQANKATLVCLISDFYPGAVTVAWKADSSPVKAGV
               ETTTPSKQSNNKYAASSYLSLTPEQWKSHRSYSCQVTHEGSTVEKT
               VAPTECS (SEQ ID NO: 73)

DGL292         EVQLLESGGGLVQPGGSLRLSCAASGFTFSDYYMTWIRQAPGKGLE
               WVSSISGGSTYYADSRKGRFTISRDNSENTLYLQMNSLRAEDTAVYY
               CARDFGVAGWFGQYGMDVWGQGTLVTVSSPAPNLLGGPEVQLLES
               GGGLVQPGGSLRLSCAASGFTFSSYAMSWVRQAPGKGLEWVANIN
               QDGSEKNYVDSMRGRFTISRDNSKNTLYLQMNSLRAEDTAVYYCAR
               EFDYWGQGTLVTVTSSASTKGPSVFPLAPSSKSTSGGTAALGCLVKD
               YFPEPVTVSWNSGALTSGVHTFPAVLQSSGLYSLSSVVTVPSSSLGT
               QTYICNVNHKPSNTKVDKKVEPKSCDKTHTCPPCPAPEAAGAPSVFL
               FPPKPKDTLMISRTPEVTCVVVDVSHEDPEVKFNWYVDGVEVHNAKT
               KPREEQYNSTYRVVSVLTVLHQDWLNGKEYKCKVSNKALPAPIEKTIS
               KAKGQPREPQVYTLPPSRDELTKNQVSLTCLVKGFYPSDIAVEWESN
               GQPENNYKTTPPVLDSDGSFFLYSKLTVDKSRWQQGNVFSCSVMHE
               ALHNHYTQKSLSLSPG (SEQ ID NO: 74)
               QSVLTQPPSASGTPGQRVTISCTGSSSNIGAGYDVHWYQQLPGTAP
               KLLIYRSNQRPSGVPDRFSGSKSGTSASLAISGLRSEDEADYYCSSYA
               GNYNLVFGGGTKLTVLPAPNLLGGPQSVLAQPPSASGTPGQRVTISC
               SGSSSNIGSNYVYWYQQLPGTAPKLLIYGNNKRPSGVPDRFSGSKS
               GTSASLAISGLRSEDEADYYCAAWDDSLNGRVFGGGTKLTVLGQPK
               AAPSVTLFPPSSEELQANKATLVCLISDFYPGAVTVAWKADSSPVKAG
               VETTTPSKQSNNKYAASSYLSLTPEQWKSHRSYSCQVTHEGSTVEK
               TVAPTECS (SEQ ID NO: 75)

Example 2. Screen for Agonistic Activity

The bispecific antibodies were screened for agonist activity. PathHunter U2Os ALK-1/BMPR-2 dimerization assay was obtained from DiscoverX Corporation (93-0962C3). These cells use Enzyme Fragment Complementation (EFC) technology using R-galactosidase fragments to evaluate protein-protein interactions. Reporter cells were revived and cultured according to supplier's recommendations. Bispecific antibodies were compared to the natural ligands, BMP9 and BMP10.

To perform the assay, cells were detached and removed from the flask with cell detachment reagent (DiscoverX, 92-0009). Cells were spun at 300 g for four minutes and resuspended at a density of 250K/ml in assay plating media (DiscoverX 93-0563R22A). 20 ul of the suspension were plated/well of a 384 well plate and incubated at 37° C. for 24 hours. Bispecifics were made at 5× the final concentration. 12-point titrations using a 1:10 dilution were done to generate curves. 5 ul of the bispecific was added to the 384 well plate and incubated for three hours. 25 ul of flash detection reagent (DiscoverX, 93-0247) was added/well and the plates were read on a Verilux Skan at 60 minutes. Data was analyzed using PRISM.

TABLE 3

Agonist activity of the bispecific antibody constructs

|        | EC50 (nM) | EMAX (RLU) | % Emax BMP9 |
|--------|-----------|------------|-------------|
| BMP9   | 0.02      | 2639991    | 100         |
| BMP10  | 0.1       | 2570138    | 97          |
| DGL266 | 2.0       | 1040871    | 39          |
| DGL267 | 0.9       | 1225023    | 46          |
| DGL268 | 0.1       | 35238      | 1           |
| DGL269 | ND        | −8297      | 0           |
| DGL270 | ND        | 9205       | 0           |
| DGL271 | ND        | 55926      | 2           |
| DGL273 | 4.2       | 1223399    | 46          |
| DGL274 | 1.7       | 1251235    | 47          |
| DGL275 | 0.9       | 1279811    | 48          |
| DGL276 | 1.2       | 1143824    | 43          |
| DGL277 | 1.0       | 1345570    | 51          |
| DGL278 | 14        | 683855     | 26          |
| DGL279 | ND        | ND         | ND          |
| DGL281 | 330       | 1105548    | 42          |
| DGL282 | 170       | 954074     | 36          |
| DGL283 | 28        | 879452     | 33          |
| DGL284 | 1.0       | 1302185    | 49          |
| DGL285 | 0.08      | 1470045    | 56          |

TABLE 3-continued

| | | EMAX | % Emax |
|---|---|---|---|
| | EC50 (nM) | (RLU) | BMP9 |
| DGL286 | 0.2 | 1800963 | 68 |
| DGL287 | 0.04 | 1255425 | 48 |
| DGL288 | 0.07 | 1997935 | 76 |
| DGL289 | 2.4 | 1800109 | 68 |
| DGL290 | 5.3 | 1818708 | 69 |
| DGL291 | 0.2 | 951876 | 36 |
| DGL292 | 0.09 | 1957874 | 74 |
| PRO003 | 0.1 | 1247113 | 47 |
| PRO004 | 0.5 | 1214568 | 46 |
| PRO005 | 0.075 | 931154 | 35 |
| PRO006 | 0.1 | 929009 | 35 |

It was observed that the bispecific antibodies in the tetravalent form (i.e., two binding domains for ALK1 and two binding domains for BMPRII) elicited stronger agonism than bispecific antibodies in a divalent form (i.e., one binding domain for ALK1 and one binding domain for BMPRII). The divalent bispecific antibodies are DGL266-DGL271, which had 0-46% of the activity of BMP9, while the tetravalent bispecific antibodies, such as DGL285-DGL292 consistently yielded higher values. It was unexpectedly discovered that tetravalent bispecific antibodies having, from N-terminus to C-terminus, the BMPRII binding domain then the ALK1 binding domain, had substantially higher agonism relative to tetravalent bispecific antibodies having, from N-terminus to C-terminus, the ALK1 binding domain then the BMPRII binding domain. The data above is recapitulated below to compare bispecific antibodies with the two different orientations.

| ID | ALK1 binder | BMPRII binder | Orientation (N-terminus to C-terminus) | % BMP9 |
|---|---|---|---|---|
| DGL285 | scFv1 | scFv8 | ALK1/BMPRII | 56 |
| DGL286 | scFv1 | scFv8 | BMPRII/ALK1 | 68 |
| DGL287 | scFv29 | scFv36 | ALK1/BMPRII | 48 |
| DGL288 | scFv29 | scFv36 | BMPRII/ALK1 | 76 |
| DGL289 | scFv1 | scFv8 | ALK1/BMPRII | 68 |
| DGL290 | scFv1 | scFv8 | BMPRII/ALK1 | 69 |
| DGL291 | scFv29 | scFv36 | ALK1/BMPRII | 36 |
| DGL292 | scFv29 | scFv36 | BMPRII/ALK1 | 74 |

The effect was observed in a dual scFv tetravalent format and a DVD-Ig format. Bispecific antibodies DGL285-288 are in the dual scFv tetravalent format, and DGL289-292 are in the DVD-Ig format.

The dual scFv tetravalent format comprises two polypeptide chains, each chain, from N-terminus to C-terminus, comprising a first scFv against a first target of either ALK1 or BMPRII, a second scFv against a second target of either ALK1 or BMPRII, and a Fc domain. The first target and second target are different, such that if the first target is BMPRII, the second target is ALK1. A linker, such as the modified hinge described herein, may be used to link the first scFv to the second scFv.

The DVD-Ig format comprises four polypeptide chains. The first and second polypeptide chains each comprise, from N-terminus to C-terminus, a first VH (VH1), a second VH (VH2), and an Fc domain. The third and fourth polypeptide chains each comprise, from N-terminus to C-terminus, a first VL (VL1) and a second VL (VL2). VH1 and VL1 form a first binding domain against a first target of either ALK1 or BMPRII, and VH2 and VL2 form a second binding domain against a second target of either ALK1 or BMPRII. The first target and second target are different, such that if the first target is BMPRII, the second target is ALK1. A linker, such as the modified hinge described herein, may be used to link the VH1 to the VH2 and/or the VL1 to the VL2.

Example 3: Measurement of PSMAD in HUVEC Cells

HUVEC cells from ATCC (CRL-1730) were plated at 15K cells per well of a 96 well plate in 100 ul of complete HUVEC media overnight (F12K (Corning, 10-025-CV), 10% FBS (Gibco, A31605-02), ECGS (30 ug/ml, Corning, 356006), 0.1 mg/ml Heparin (Sigma, H3393), 1× Pen/Strep (Gibco, 15140-122). The following morning, cells were starved for 4 hours by replacing media with 50 ul serum free/ECGS free F12K media. Cells were then treated with 50 ul of serum free/ECGS free media containing 2× concentration dose curve of the bispecifics or BMP ligands. At various time points (5, 15, 30, 60 min) media was removed from cells and 50 ul lysis buffer (Abcam ELISA kit, AB186037) was added per well. After lysis, buffer from four wells were pooled for a single 200 ul lysed sample per condition, which was frozen and later run on ELISAs measuring either total SMAD1 (Abcam, AB186037) or pSMAD1 (Abcam, AB186036). As a negative control, an anti-HEL antibody with LALA-PG mutations (BioXCell, CP149) was used.

TABLE 4

| | Phosphorylation of SMAD1 following treatment with bispecific antibodies. | | |
|---|---|---|---|
| | Concentration of ligand or antibody (nM) | RLU 15 minutes | RLU 60 minutes |
| BMP9 | 1 | 105.7 | 81.8 |
| BMP9 | 0.2 | 102.2 | 83.2 |
| BMP9 | 0.04 | 101.4 | 81.8 |
| BMP9 | 0 | 4.9 | 6.1 |
| DGL286 | 10 | 4.9 | 10.6 |
| DGL286 | 2 | 4.7 | 9.3 |
| DGL286 | 0.4 | 4.4 | 7.0 |
| DGL286 | 0 | 4.6 | 4.5 |
| DGL288 | 10 | 6.7 | 22.7 |
| DGL288 | 2 | 6.5 | 26.9 |
| DGL288 | 0.4 | 4.9 | 35.0 |
| DGL288 | 0 | 4.5 | 4.5 |
| DGL289 | 10 | 4.7 | 6.9 |
| DGL289 | 2 | 4.4 | 5.2 |
| DGL289 | 0.4 | 4.4 | 5.0 |
| DGL289 | 0 | 4.6 | 4.4 |
| DGL292 | 10 | 6.7 | 33.9 |
| DGL292 | 2 | 5.7 | 32.3 |
| DGL292 | 0.4 | 4.6 | 23.7 |
| DGL292 | 0 | 4.6 | 4.4 |
| Control | 10 | 4.7 | 4.5 |
| Control | 2 | 4.8 | 4.6 |
| Control | 0.4 | 4.5 | 4.5 |
| Control | 0 | 4.7 | 4.5 |

Example 4: Measurement of In Vivo Activity

Antibodies were measured for agonistic activity in a mouse model of HHT wherein circulating BMP9/BMP10 were neutralized by anti-BMP9/10 antibodies (Ruiz S, et al, Scientific Reports, 2016 Nov. 22: 5:37366). These mice develop vascular defects in the postnatal retina. Three animals were dosed with either DGL288 or a negative control antibody (Anti-HEL, LALA-PG, BioXCell, CP149) for two days, P3 and P4, at 15 mg/kg/day. BMP9/10 antibodies were dosed on the same days. Analysis was completed on P6. Retinas were dissected and whole-mount prepared, then stained with both isolectin B4 and SMA to label retinal vasculature and detect arteriovenous malformations (AVMs). Results are in FIG. 3A. Mice dosed with DGL288 showed no formation of AVMs, whereas the negative control showed an average of 4.8 AVMs/retina.

Figure 3C:
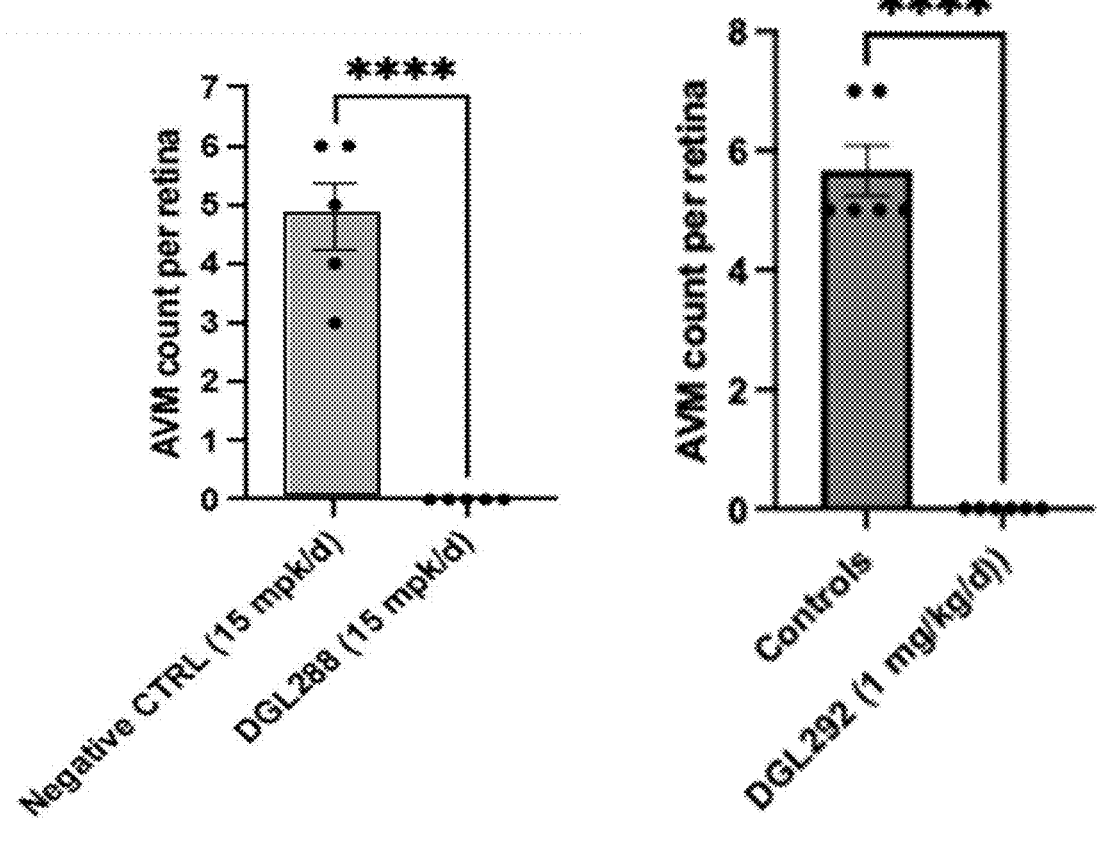
Figure 3C:
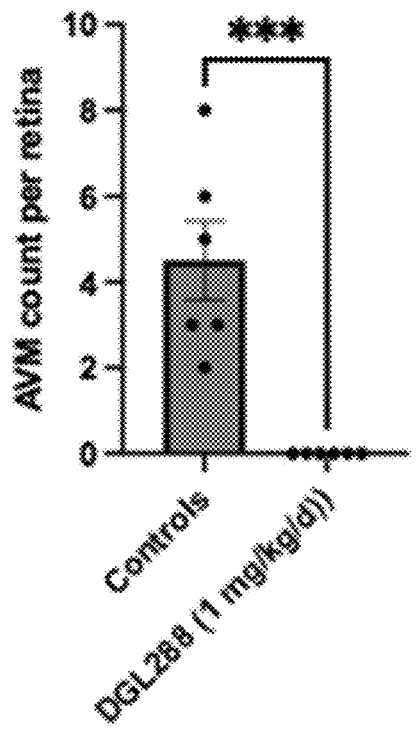

For the second set of experiments, all animals were dosed with BMP9/10 antibodies on P3 and P4. DGL288, DGL292 or PBS control were dosed at 1 mg/kg/day on P4 and P5. Analysis was completed on P6 for DGL288 and the littermate negative control animals, or P7 for DGL292 and littermates dosed with the PBS control. Retinas were dissected and whole-mount prepared, then stained with both isolectin B4 and SMA to detect AVMs. Mice dosed with DGL292 did not form AVMs, compared with an average of 5.7/retina for the controls (FIG. 3B). Mice dosed with DGL288 did not form AVMs, compared with an average of 4.5/retina for the controls (FIG. 3O). No differences in body weight were observed, suggesting that the agonists are well tolerated.

Example 5: Additional Engineering of Binders

Based on structural modeling of the receptor/antibody complex, the binders were engineered to further optimize the complementary regions of the binding to the antigen. Both ALK1 and BMPRII variants were designed for improved potency and/or stability.

TABLE 5

| Optimized ALK1 and BMPRII binders. | |
| --- | --- |
| Alk1_platform_1 | EVQLLESGGGLVQPGGSLRLSCAASGFTFSDYAMSWVRQAPGKGLEW VSAISGSGGVTYYADSVKGRFTISRDNSKNTLYLQMNSLRAEDTAVY YCAREFDWWGQGTLVTVTSSGGGGSGGGGSGGGGSQSVLTQPPSASG TPGQRVTISCSGSSSNIGSNYVYWYQQLPGTAPKLLIYGNINRPSGV PDRFSGSKSGTSASLAISGLRSEDEADYYCAAWDDSLNGRVFGGGTK LTVLDKTHTCPPCPAPEAAGAPSVFLFPPKPKDTLMISRTPEVTCVV VDVSHEDPEVKFNWYVDGVEVHNAKTKPREEQYNSTYRVVSVLTVLH QDWLNGKEYKCKVSNKALPAPIEKTISKAKGQPREPQVYTLPPCRDE LTKNQVSLWCLVKGFYPSDIAVEWESNGQPENNYKTTPPVLDSDGSF FLYSKLTVDKSRWQQGNVFSCSVMHEALHNHYTQKSLSLSPGEPEA (SEQ ID NO: 76) |
| Alk1_platform_2 | EVQLLESGGGLVQPGGSLRLSCAASGFTFSSYAMSWVRQAPGKGLEW VSAISGSGGSTYYADSVKGRFTISRDNSKNTLYLQMNSLRAEDTAVY YCAREFDWWGQGTLVTVTSSGGGGSGGGGSGGGGSQSVLTQPPSASG TPGQRVTISCSGSSSNIGSNYVYWYQQLPGTAPKLLIYGNINRPSGV PDRFSGSKSGTSASLAISGLRSEDEADYYCAAWDDSLNGRVFGGGTK LTVLDKTHTCPPCPAPEAAGAPSVFLFPPKPKDTLMISRTPEVTCVV VDVSHEDPEVKFNWYVDGVEVHNAKTKPREEQYNSTYRVVSVLTVLH QDWLNGKEYKCKVSNKALPAPIEKTISKAKGQPREPQVYTLPPCRDE LTKNQVSLWCLVKGFYPSDIAVEWESNGQPENNYKTTPPVLDSDGSF FLYSKLTVDKSRWQQGNVFSCSVMHEALHNHYTQKSLSLSPGEPEA (SEQ ID NO: 77) |
| Alk1_platform_3 | EVQLLESGGGLVQPGGSLRLSCAASGFTFSDYAMSWVRQAPGKGLEW VSAISGSGGATYYADSVKGRFTISRDNSKNTLYLQMNSLRAEDTAVY YCAREFDYWGQGTLVTVTSSGGGGSGGGGGGGGSQSVLTQPPSASGT PGQRVTISCSGSSSNIGSNYVYWYQQLPGTAPKLLIYGNINRPSGVP DRFSGSKSGTSASLAISGLRSEDEADYYCAAWDDSLNGRVFGGGTKL TVLDKTHTCPPCPAPEAAGAPSVFLFPPKPKDTLMISRTPEVTCVVV DVSHEDPEVKFNWYVDGVEVHNAKTKPREEQYNSTYRVVSVLTVLHQ DWLNGKEYKCKVSNKALPAPIEKTISKAKGQPREPQVYTLPPCRDEL TKNQVSLWCLVKGFYPSDIAVEWESNGQPENNYKTTPPVLDSDGSFF LYSKLTVDKSRWQQGNVFSCSVMHEALHNHYTQKSLSLSPGEPEA (SEQ ID NO: 78) |
| Alk1_platform_4 | EVQLLESGGGLVQPGGSLRLSCAASGFTFSSYAMSWVRQAPGKGLEW VANINQDGSEKNYVDSMRGRFTISRDNSKNTLYLQMNSLRAEDTAVY YCAREFDYWGQGTLVTVTSSGGGGSGGGGSGGGGSQSVLAQPPSASG TPGQRVTISCSGSSSNIGSNYVYWYQQLPGTAPKLLIYGNNKRPSGV PDRFSGSKSGTSASLAISGLRSEDEADYYCAAWDDSLNGRVFGGGTK LTVLDKTHTCPPCPAPEAAGAPSVFLFPPKPKDTLMISRTPEVTCVV VDVSHEDPEVKFNWYVDGVEVHNAKTKPREEQYNSTYRVVSVLTVLH QDWLNGKEYKCKVSNKALPAPIEKTISKAKGQPREPQVYTLPPCRDE LTKNQVSLWCLVKGFYPSDIAVEWESNGQPENNYKTTPPVLDSDGSF FLYSKLTVDKSRWQQGNVFSCSVMHEALHNHYTQKSLSLSPGEPEA (SEQ ID NO: 79) |
| Alk1_platform_5 | EVQLLESGGGLVQPGGSLRLSCAASGFTFSSYAMSWVRQAPGKGLEW VANINQDGSEKNYVDSMRGRFTISRDNSKNTLYLQMNSLRAEDTAVY YCARDYRYWGQGTLVTVTSSGGGGSGGGGSGGGGSQSVLAQPPSASG TPGQRVTISCSGSSSNIGSNYVYWYQQLPGTAPKLLIYGNNKRPSGV PDRFSGSKSGTSASLAISGLRSEDEADYYCAAWDDSLNGRVFGGGTK LTVLDKTHTCPPCPAPEAAGAPSVFLFPPKPKDTLMISRTPEVTCVV |

TABLE 5-continued

Optimized ALK1 and BMPRII binders.

```
                VDVSHEDPEVKFNWYVDGVEVHNAKTKPREEQYNSTYRVVSVLTVLH
                QDWLNGKEYKCKVSNKALPAPIEKTISKAKGQPREPQVYTLPPCRDE
                LTKNQVSLWCLVKGFYPSDIAVEWESNGQPENNYKTTPPVLDSDGSF
                FLYSKLTVDKSRWQQGNVFSCSVMHEALHNHYTQKSLSLSPGEPEA
                (SEQ ID NO: 80)

Alk1_platform_6   EVQLLESGGGLVQPGGSLRLSCAASGFTFSSYAMSWVRQAPGKGLEW
                VANINQDGSEKNYVDSMRGRFTISRDNSKNTLYLQMNSLRAEDTAVY
                YCAREYKYWGQGTLVTVTSSGGGGSGGGGSGGGGSQSVLAQPPSASG
                TPGQRVTISCSGSSSNIGSNYVYWYQQLPGTAPKLLIYGNNKRPSGV
                PDRFSGSKSGTSASLAISGLRSEDEADYYCAAWDDSLNGRVFGGGTK
                LTVLDKTHTCPPCPAPEAAGAPSVFLFPPKPKDTLMISRTPEVTCVV
                VDVSHEDPEVKFNWYVDGVEVHNAKTKPREEQYNSTYRVVSVLTVLH
                QDWLNGKEYKCKVSNKALPAPIEKTISKAKGQPREPQVYTLPPCRDE
                LTKNQVSLWCLVKGFYPSDIAVEWESNGQPENNYKTTPPVLDSDGSF
                FLYSKLTVDKSRWQQGNVFSCSVMHEALHNHYTQKSLSLSPGEPEA
                (SEQ ID NO: 81)

Alk1_platform_7   EVQLLESGGGLVQPGGSLRLSCAASGFTFSSYAMSWVRQAPGKGLEW
                VANINQDGSEKNYVDSMRGRFTISRDNSKNTLYLQMNSLRAEDTAVY
                YCAREYQYWGQGTLVTVTSSGGGGSGGGGSGGGGSQSVLAQPPSASG
                TPGQRVTISCSGSSSNIGSNYVYWYQQLPGTAPKLLIYGNNKRPSGV
                PDRFSGSKSGTSASLAISGLRSEDEADYYCAAWDDSLNGRVFGGGTK
                LTVLDKTHTCPPCPAPEAAGAPSVFLFPPKPKDTLMISRTPEVTCVV
                VDVSHEDPEVKFNWYVDGVEVHNAKTKPREEQYNSTYRVVSVLTVLH
                QDWLNGKEYKCKVSNKALPAPIEKTISKAKGQPREPQVYTLPPCRDE
                LTKNQVSLWCLVKGFYPSDIAVEWESNGQPENNYKTTPPVLDSDGSF
                FLYSKLTVDKSRWQQGNVFSCSVMHEALHNHYTQKSLSLSPGEPEA
                (SEQ ID NO: 82)

Alk1_platform_8   EVQLLESGGGLVQPGGSLRLSCAASGFTFSSYAMSWVRQAPGKGLEW
                VANINQDGSEKNYVDSMRGRFTISRDNSKNTLYLQMNSLRAEDTAVY
                YCARNYQYWGQGTLVTVTSSGGGGSGGGGSGGGGSQSVLAQPPSASG
                TPGQRVTISCSGSSSNIGSNYVYWYQQLPGTAPKLLIYGNNKRPSGV
                PDRFSGSKSGTSASLAISGLRSEDEADYYCAAWDDSLNGRVFGGGTK
                LTVLDKTHTCPPCPAPEAAGAPSVFLFPPKPKDTLMISRTPEVTCVV
                VDVSHEDPEVKFNWYVDGVEVHNAKTKPREEQYNSTYRVVSVLTVLH
                QDWLNGKEYKCKVSNKALPAPIEKTISKAKGQPREPQVYTLPPCRDE
                LTKNQVSLWCLVKGFYPSDIAVEWESNGQPENNYKTTPPVLDSDGSF
                FLYSKLTVDKSRWQQGNVFSCSVMHEALHNHYTQKSLSLSPGEPEA
                (SEQ ID NO: 83)

Alk1_platform_9   EVQLLESGGGLVQPGGSLRLSCAASGFTFSSYAMSWVRQAPGKGLEW
                VANINQDGSEKNYVDSMRGRFTISRDNSKNTLYLQMNSLRAEDTAVY
                YCARNYQFWGQGTLVTVTSSGGGGSGGGGSGGGGSQSVLAQPPSASG
                TPGQRVTISCSGSSSNIGSNYVYWYQQLPGTAPKLLIYGNNKRPSGV
                PDRFSGSKSGTSASLAISGLRSEDEADYYCAAWDDSLNGRVFGGGTK
                LTVLDKTHTCPPCPAPEAAGAPSVFLFPPKPKDTLMISRTPEVTCVV
                VDVSHEDPEVKFNWYVDGVEVHNAKTKPREEQYNSTYRVVSVLTVLH
                QDWLNGKEYKCKVSNKALPAPIEKTISKAKGQPREPQVYTLPPCRDE
                LTKNQVSLWCLVKGFYPSDIAVEWESNGQPENNYKTTPPVLDSDGSF
                FLYSKLTVDKSRWQQGNVFSCSVMHEALHNHYTQKSLSLSPGEPEA
                (SEQ ID NO: 84)

Alk1_platform_10  EVQLLESGGGLVQPGGSLRLSCAASGFTFSIYAMSWVRQAPGKGLEW
                VSAISGSGGSTYYADSVKGRFTISRDNSKNTLYLQMNSLRAEDTAVY
                YCARDGLYWGQGTLVTVTSSGGGGSGGGGSGGGGSQSVLTQPPSASG
                TPGQRVTISCSGSSSNIGSNYVYWYQQLPGTAPKLLIYGNINRPSGV
                PDRFSGSKSGTSASLAISGLRSEDEADYYCAAWDDSLNGRVFGGGTK
                LTVLDKTHTCPPCPAPEAAGAPSVFLFPPKPKDTLMISRTPEVTCVV
                VDVSHEDPEVKFNWYVDGVEVHNAKTKPREEQYNSTYRVVSVLTVLH
                QDWLNGKEYKCKVSNKALPAPIEKTISKAKGQPREPQVYTLPPCRDE
                LTKNQVSLWCLVKGFYPSDIAVEWESNGQPENNYKTTPPVLDSDGSF
                FLYSKLTVDKSRWQQGNVFSCSVMHEALHNHYTQKSLSLSPGEPEA
                (SEQ ID NO: 85)

Alk1_platform_11  EVQLLESGGGLVQPGGSLRLSCAASGFTFSIYAMSWVRQAPGKGLEW
                VSAISGSGGSTYYADSVKGRFTISRDNSKNTLYLQMNSLRAEDTAVY
                YCARNWDYWGQGTLVTVTSSGGGGSGGGGSGGGGSQSVLTQPPSASG
                TPGQRVTISCSGSSSNIGSNYVYWYQQLPGTAPKLLIYGNINRPSGV
                PDRFSGSKSGTSASLAISGLRSEDEADYYCAAWDDSLNGRVFGGGTK
                LTVLDKTHTCPPCPAPEAAGAPSVFLFPPKPKDTLMISRTPEVTCVV
                VDVSHEDPEVKFNWYVDGVEVHNAKTKPREEQYNSTYRVVSVLTVLH
                QDWLNGKEYKCKVSNKALPAPIEKTISKAKGQPREPQVYTLPPCRDE
                LTKNQVSLWCLVKGFYPSDIAVEWESNGQPENNYKTTPPVLDSDGSF
                FLYSKLTVDKSRWQQGNVFSCSVMHEALHNHYTQKSLSLSPGEPEA
                (SEQ ID NO: 86)
```

TABLE 5-continued

Optimized ALK1 and BMPRII binders.

Alk1_platform_12    EVQLLESGGGLVQPGGSLRLSCAASGFTFSIYAMSWVRQAPGKGLEW
                    VSAISGSGGSTYYADSVKGRFTISRDNSKNTLYLQMNSLRAEDTAVY
                    YCARNGLYWGQGTLVTVTSSGGGGSGGGGSGGGGSQSVLTQPPSASG
                    TPGQRVTISCSGSSSNIGSNYVYWYQQLPGTAPKLLIYGNINRPSGV
                    PDRFSGSKSGTSASLAISGLRSEDEADYYCAAWDDSLNGRVFGGGTK
                    LTVLDKTHTCPPCPAPEAAGAPSVFLFPPKPKDTLMISRTPEVTCVV
                    VDVSHEDPEVKFNWYVDGVEVHNAKTKPREEQYNSTYRVVSVLTVLH
                    QDWLNGKEYKCKVSNKALPAPIEKTISKAKGQPREPQVYTLPPCRDE
                    LTKNQVSLWCLVKGFYPSDIAVEWESNGQPENNYKTTPPVLDSDGSF
                    FLYSKLTVDKSRWQQGNVFSCSVMHEALHNHYTQKSLSLSPGEPEA
                    (SEQ ID NO: 87)

Alk1_platform_13    EVQLLESGGGLVQPGGSLRLSCAASGFTFSIYAMSWVRQAPGKGLEW
                    VSAISGSGGSTYYADSVKGRFTISRDNSKNTLYLQMNSLRAEDTAVY
                    YCARNYDFWGQGTLVTVTSSGGGGSGGGGSGGGGSQSVLTQPPSASG
                    TPGQRVTISCSGSSSNIGSNYVYWYQQLPGTAPKLLIYGNINRPSGV
                    PDRFSGSKSGTSASLAISGLRSEDEADYYCAAWDDSLNGRVFGGGTK
                    LTVLDKTHTCPPCPAPEAAGAPSVFLFPPKPKDTLMISRTPEVTCVV
                    VDVSHEDPEVKFNWYVDGVEVHNAKTKPREEQYNSTYRVVSVLTVLH
                    QDWLNGKEYKCKVSNKALPAPIEKTISKAKGQPREPQVYTLPPCRDE
                    LTKNQVSLWCLVKGFYPSDIAVEWESNGQPENNYKTTPPVLDSDGSF
                    FLYSKLTVDKSRWQQGNVFSCSVMHEALHNHYTQKSLSLSPGEPEA
                    (SEQ ID NO: 88)

Alk1_platform_14    EVQLLESGGGLVQPGGSLRLSCAASGFTFSIYAMSWVRQAPGKGLEW
                    VSAISGSGGSTYYADSVKGRFTISRDNSKNTLYLQMNSLRAEDTAVY
                    YCARDYLYWGQGTLVTVTSSGGGGSGGGGSGGGGSQSVLTQPPSASG
                    TPGQRVTISCSGSSSNIGSNYVYWYQQLPGTAPKLLIYGNINRPSGV
                    PDRFSGSKSGTSASLAISGLRSEDEADYYCAAWDDSLNGRVFGGGTK
                    LTVLDKTHTCPPCPAPEAAGAPSVFLFPPKPKDTLMISRTPEVTCVV
                    VDVSHEDPEVKFNWYVDGVEVHNAKTKPREEQYNSTYRVVSVLTVLH
                    QDWLNGKEYKCKVSNKALPAPIEKTISKAKGQPREPQVYTLPPCRDE
                    LTKNQVSLWCLVKGFYPSDIAVEWESNGQPENNYKTTPPVLDSDGSF
                    FLYSKLTVDKSRWQQGNVFSCSVMHEALHNHYTQKSLSLSPGEPEA
                    (SEQ ID NO: 89)

Alk1_platform_15    EVQLLESGGGLVQPGGSLRLSCAASGFTFSSYWMSWVRQAPGKGLEW
                    VANIKQDGSEKNYVDSMRGRFTISRDNSKNTLYLQMNSLRAEDTAVY
                    YCAREYDYWGQGTLVTVTSGGGGSGGGGSGGGGSQSVLAQPPSASGT
                    PGQRVTISCSGSSSNIGSNYVYWYQQLPGTAPKLLIYGNNKRPSGVP
                    DRFSGSKSGTSASLAISGLRSEDEADYYCAAWDDSLNGRVFGGGTKL
                    TVLDKTHTCPPCPAPEAAGAPSVFLFPPKPKDTLMISRTPEVTCVVV
                    DVSHEDPEVKFNWYVDGVEVHNAKTKPREEQYNSTYRVVSVLTVLHQ
                    DWLNGKEYKCKVSNKALPAPIEKTISKAKGQPREPQVYTLPPCRDEL
                    TKNQVSLWCLVKGFYPSDIAVEWESNGQPENNYKTTPPVLDSDGSFF
                    LYSKLTVDKSRWQQGNVFSCSVMHEALHNHYTQKSLSLSPGEPEA
                    (SEQ ID NO: 90)

Alk1_platform_16    EVQLLESGGGLVQPGGSLRLSCAASGFTFSSYWMSWVRQAPGKGLEW
                    VANINQDGSEKYYVDSMRGRFTISRDNSKNTLYLQMNSLRAEDTAVY
                    YCAREYDYWGQGTLVTVTSGGGGSGGGGSGGGGSQSVLAQPPSASGT
                    PGQRVTISCSGSSSNIGSNYVYWYQQLPGTAPKLLIYGNNKRPSGVP
                    DRFSGSKSGTSASLAISGLRSEDEADYYCAAWDDSLNGRVFGGGTKL
                    TVLDKTHTCPPCPAPEAAGAPSVFLFPPKPKDTLMISRTPEVTCVVV
                    DVSHEDPEVKFNWYVDGVEVHNAKTKPREEQYNSTYRVVSVLTVLHQ
                    DWLNGKEYKCKVSNKALPAPIEKTISKAKGQPREPQVYTLPPCRDEL
                    TKNQVSLWCLVKGFYPSDIAVEWESNGQPENNYKTTPPVLDSDGSFF
                    LYSKLTVDKSRWQQGNVFSCSVMHEALHNHYTQKSLSLSPGEPEA
                    (SEQ ID NO: 91)

Alk1_platform_17    EVQLLESGGGLVQPGGSLRLSCAASGFTFSSYWMSWVRQAPGKGLEW
                    VANIKQDGSEKNYVDSMRGRFTISRDNSKNTLYLQMNSLRAEDTAVY
                    YCAREFDFWGQGTLVTVTSGGGGSGGGGSGGGGSQSVLAQPPSASGT
                    PGQRVTISCSGSSSNIGSNYVYWYQQLPGTAPKLLIYGNNKRPSGVP
                    DRFSGSKSGTSASLAISGLRSEDEADYYCAAWDDSLNGRVFGGGTKL
                    TVLDKTHTCPPCPAPEAAGAPSVFLFPPKPKDTLMISRTPEVTCVVV
                    DVSHEDPEVKFNWYVDGVEVHNAKTKPREEQYNSTYRVVSVLTVLHQ
                    DWLNGKEYKCKVSNKALPAPIEKTISKAKGQPREPQVYTLPPCRDEL
                    TKNQVSLWCLVKGFYPSDIAVEWESNGQPENNYKTTPPVLDSDGSFF
                    LYSKLTVDKSRWQQGNVFSCSVMHEALHNHYTQKSLSLSPGEPEA
                    (SEQ ID NO: 92)

ALK1_platform_18    EVQLLESGGGLVQPGGSLRLSCAASGFTFSDYAMSWVRQAPGKGLEW
                    VANINQSGSEKNYVDSMRGRFTISRDNSKNTLYLQMNSLRAEDTAVY
                    YCAREFDWWGQGTLVTVSSSGGGGSGGGGSGGGGSQSVLAQPPSASG
                    TPGQRVTISCSGSSSNIGSNYVYWYQQLPGTAPKLLIYGNNKRPSGV
                    PDRFSGSKSGTSASLAISGLRSEDEADYYCAAWDDSLNGRVFGGGTK
                    LTVLDKTHTCPPCPAPEAAGAPSVFLFPPKPKDTLMISRTPEVTCVV TABLE 5-continued Optimized ALK1 and BMPRII binders.

```
                VDVSHEDPEVKFNWYVDGVEVHNAKTKPREEQYNSTYRVVSVLTVLH
                QDWLNGWCLVKGFYPSDIAVEWESNGQPENNYKTTPPVLDSDGSFFL
                YSKLTVDKSRWQQGNVFSCSVMHEALHNHYTQKSLSLSPGEPEA
                (SEQ ID NO: 93)

ALK1_platform_19  EVQLLESGGGLVQPGGSLRLSCAASGFTFSDYAMSWVRQAPGKGLEW
                VANINQDGSEKNYVDSMRGRFTISRDNSKNTLYLQMNSLRAEDTAVY
                YCAREFDWWGQGTLVTVSSSGGGGSGGGGSGGGGSQSVLAQPPSASG
                TPGQRVTISCSGSSSNIGSNYVYWYQQLPGTAPKLLIYGNNKRPSGV
                PDRFSGSKSGTSASLAISGLRSEDEADYYCAAWDDSLNGRVFGGGTK
                LTVLDKTHTCPPCPAPEAAGAPSVFLFPPKPKDTLMISRTPEVTCVV
                VDVSHEDPEVKFNWYVDGVEVHNAKTKPREEQYNSTYRVVSVLTVLH
                QDWLNGKEYKCKVSNKALPAPIEKTISKAKGQPREPQVYTLPPCRDE
                LTKNQVSLWCLVKGFYPSDIAVEWESNGQPENNYKTTPPVLDSDGSF
                FLYSKLTVDKSRWQQGNVFSCSVMHEALHNHYTQKSLSLSPGEPEA
                (SEQ ID NO: 94)

BMPRII_platform_1  EVQLLESGGGLVQPGGSLRLSCAASGFTFSDYYMTWIRQAPGKGLEW
                VSSISGGSTYYADSRKGRFTISRDNSENTLYLQMNSLRAEDTAVYYC
                ARDFGVAGWFGQYGMDVWGQGTLVTVSSGGGGSGGGGSGGGGSQSVL
                TQPPSASGTPGQRVTISCTGSSSNIGAGYDVHWYQQLPGTAPKLLIY
                RSNQRPSGVPDRFSGSKSGTSASLAISGLRSEDEADYYCSSYAGNYN
                LVFGGGTKLTVLDKTHTCPPCPAPEAAGAPSVFLFPPKPKDTLMISR
                TPEVTCVVVDVSHEDPEVKFNWYVDGVEVHNAKTKPREEQYNSTYRV
                VSVLTVLHQDWLNGKEYKCKVSNKALPAPIEKTISKAKGQPREPQVC
                TLPPSRDELTKNQVSLSCAVKGFYPSDIAVEWESNGQPENNYKTTPP
                VLDSDGSFFLVSKLTVDKSRWQQGNVFSCSVMHEALHNHYTQKSLSL
                SPGWSHPQFEK (SEQ ID NO: 95)

BMPRII_platform_2  EVQLLESGGGLVQPGGSLRLSCAASGFTFSDYYMTWIRQAPGKGLEW
                VSSISGGSTYYADSRKGRFTISRDNSENTLYLQMNSLRAEDTAVYYC
                ARWETSSGGFGSGGLSHWGQGTLVTVSSGGGGSGGGGSGGGGSQSVL
                TQPPSASGTPGQRVTISCTGSSSNIGAGYDVHWYQQLPGTAPKLLIY
                RSNQRPSGVPDRFSGSKSGTSASLAISGLRSEDEADYYCSSYAGNYN
                LVFGGGTKLTVLDKTHTCPPCPAPEAAGAPSVFLFPPKPKDTLMISR
                TPEVTCVVVDVSHEDPEVKFNWYVDGVEVHNAKTKPREEQYNSTYRV
                VSVLTVLHQDWLNGKEYKCKVSNKALPAPIEKTISKAKGQPREPQVC
                TLPPSRDELTKNQVSLSCAVKGFYPSDIAVEWESNGQPENNYKTTPP
                VLDSDGSFFLVSKLTVDKSRWQQGNVFSCSVMHEALHNHYTQKSLSL
                SPGWSHPQFEK (SEQ ID NO: 96)

BMPRII_platform_3  EVQLLESGGGLVQPGGSLRLSCAASGFTFSDYYMTWIRQAPGKGLEW
                VSSISGGSTYYADSRKGRFTISRDNSENTLYLQMNSLRAEDTAVYYC
                ARLTVDGGGYGSGGLDLWGQGTLVTVSSGGGGSGGGGSGGGGSQSVL
                TQPPSASGTPGQRVTISCTGSSSNIGAGYDVHWYQQLPGTAPKLLIY
                RSNQRPSGVPDRFSGSKSGTSASLAISGLRSEDEADYYCSSYAGNYN
                LVFGGGTKLTVLDKTHTCPPCPAPEAAGAPSVFLFPPKPKDTLMISR
                TPEVTCVVVDVSHEDPEVKFNWYVDGVEVHNAKTKPREEQYNSTYRV
                VSVLTVLHQDWLNGKEYKCKVSNKALPAPIEKTISKAKGQPREPQVC
                TLPPSRDELTKNQVSLSCAVKGFYPSDIAVEWESNGQPENNYKTTPP
                VLDSDGSFFLVSKLTVDKSRWQQGNVFSCSVMHEALHNHYTQKSLSL
                SPGWSHPQFEK (SEQ ID NO: 97)

BMPRII_platform_4  EVQLLESGGGLVQPGGSLRLSCAASGFTFSDYYMTWIRQAPGKGLEW
                VSSISGGSTYYADSRKGRFTISRDNSENTLYLQMNSLRAEDTAVYYC
                ARNEVSGGYYGEFGLSLWGQGTLVTVSSGGGGSGGGGSGGGGSQSVL
                TQPPSASGTPGQRVTISCTGSSSNIGAGYDVHWYQQLPGTAPKLLIY
                RSNQRPSGVPDRFSGSKSGTSASLAISGLRSEDEADYYCSSYAGNYN
                LVFGGGTKLTVLDKTHTCPPCPAPEAAGAPSVFLFPPKPKDTLMISR
                TPEVTCVVVDVSHEDPEVKFNWYVDGVEVHNAKTKPREEQYNSTYRV
                VSVLTVLHQDWLNGKEYKCKVSNKALPAPIEKTISKAKGQPREPQVC
                TLPPSRDELTKNQVSLSCAVKGFYPSDIAVEWESNGQPENNYKTTPP
                VLDSDGSFFLVSKLTVDKSRWQQGNVFSCSVMHEALHNHYTQKSLSL
                SPGWSHPQFEK (SEQ ID NO: 98)

BMPRII_platform_5  EVQLLESGGGLVQPGGSLRLSCAASGFTFSDYYMTWIRQAPGKGLEW
                VSSISGGSTYYADSRKGRFTISRDNSENTLYLQMNSLRAEDTAVYYC
                ARNVTSGGYFGSFGLDLWGQGTLVTVSSGGGGSGGGGSGGGGSQSVL
                TQPPSASGTPGQRVTISCTGSSSNIGAGYDVHWYQQLPGTAPKLLIY
                RSNQRPSGVPDRFSGSKSGTSASLAISGLRSEDEADYYCSSYAGNYN
                LVFGGGTKLTVLDKTHTCPPCPAPEAAGAPSVFLFPPKPKDTLMISR
                TPEVTCVVVDVSHEDPEVKFNWYVDGVEVHNAKTKPREEQYNSTYRV
                VSVLTVLHQDWLNGKEYKCKVSNKALPAPIEKTISKAKGQPREPQVC
                TLPPSRDELTKNQVSLSCAVKGFYPSDIAVEWESNGQPENNYKTTPP
                VLDSDGSFFLVSKLTVDKSRWQQGNVFSCSVMHEALHNHYTQKSLSL
                SPGWSHPQFEK (SEQ ID NO: 99)
```

TABLE 5-continued

Optimized ALK1 and BMPRII binders.

```
BMPRII_platform_6    EVQLLESGGGLVQPGGSLRLSCAASGFTFSDYYMTWIRQAPGKGLEW
                     VSSISGGSTYYADSRKGRFTISRDNSENTLYLQMNSLRAEDTAVYYC
                     ARWETSGGYYGSGGLTIWGQGTLVTVSSGGGGSGGGGSGGGGSQSVL
                     TQPPSASGTPGQRVTISCTGSSSNIGAGYDVHWYQQLPGTAPKLLIY
                     RSNQRPSGVPDRFSGSKSGTSASLAISGLRSEDEADYYCSSYAGNYN
                     LVFGGGTKLTVLDKTHTCPPCPAPEAAGAPSVFLFPPKPKDTLMISR
                     TPEVTCVVVDVSHEDPEVKFNWYVDGVEVHNAKTKPREEQYNSTYRV
                     VSVLTVLHQDWLNGKEYKCKVSNKALPAPIEKTISKAKGQPREPQVC
                     TLPPSRDELTKNQVSLSCAVKGFYPSDIAVEWESNGQPENNYKTTPP
                     VLDSDGSFFLVSKLTVDKSRWQQGNVFSCSVMHEALHNHYTQKSLSL
                     SPGWSHPQFEK (SEQ ID NO: 100)

BMPRII_platform_7    EVQLLESGGGLVQPGGSLRLSCAASGFTFSNAWMNWVRQAPGKGLEW
                     VSSISSSSSYIYYADSVKGRFTISRDNSKNTLYLQMNSLRAEDTAVY
                     YCARAVAAGGMFWGLDQWGQGTLVTVTSSGGGGSGGGGSGGGGSQSV
                     LTQPPSASGTPGQRVTISCSGSRSNIGSNSVHWYQQLPGTAPKLLIY
                     GNSNRPSGVPDRFSGSKSGTSASLAISGLRSEDEADYYCQSYDSSLN
                     DHVVFGGGTKLTVLDKTHTCPPCPAPEAAGAPSVFLFPPKPKDTLMI
                     SRTPEVTCVVVDVSHEDPEVKFNWYVDGVEVHNAKTKPREEQYNSTY
                     RVVSVLTVLHQDWLNGKEYKCKVSNKALPAPIEKTISKAKGQPREPQ
                     VCTLPPSRDELTKNQVSLSCAVKGFYPSDIAVEWESNGQPENNYKTT
                     PPVLDSDGSFFLVSKLTVDKSRWQQGNVFSCSVMHEALHNHYTQKSL
                     SLSPGWSHPQFEK (SEQ ID NO: 101)

BMPRII_platform_8    EVQLLESGGGLVQPGGSLRLSCAASGFTFSNAWMNWVRQAPGKGLEW
                     VSSISSSSSYIYYADSVKGRFTISRDNSKNTLYLQMNSLRAEDTAVY
                     YCARSNGSGGSTYPLDLWGQGTLVTVTSSGGGGSGGGGSGGGGSQSV
                     LTQPPSASGTPGQRVTISCSGSRSNIGSNSVHWYQQLPGTAPKLLIY
                     GNSNRPSGVPDRFSGSKSGTSASLAISGLRSEDEADYYCQSYDSSLN
                     DHVVFGGGTKLTVLDKTHTCPPCPAPEAAGAPSVFLFPPKPKDTLMI
                     SRTPEVTCVVVDVSHEDPEVKFNWYVDGVEVHNAKTKPREEQYNSTY
                     RVVSVLTVLHQDWLNGKEYKCKVSNKALPAPIEKTISKAKGQPREPQ
                     VCTLPPSRDELTKNQVSLSCAVKGFYPSDIAVEWESNGQPENNYKTT
                     PPVLDSDGSFFLVSKLTVDKSRWQQGNVFSCSVMHEALHNHYTQKSL
                     SLSPGWSHPQFEK (SEQ ID NO: 102)

BMPRII_platform_9    EVQLLESGGGLVQPGGSLRLSCAASGFTFSNAWMNWVRQAPGKGLEW
                     VSSISSSSSYIYYADSVKGRFTISRDNSKNTLYLQMNSLRAEDTAVY
                     YCARSNGSGGSDYPLDLWGQGTLVTVTSSGGGGSGGGGSGGGGSQSV
                     LTQPPSASGTPGQRVTISCSGSRSNIGSNSVHWYQQLPGTAPKLLIY
                     GNSNRPSGVPDRFSGSKSGTSASLAISGLRSEDEADYYCQSYDSSLN
                     DHVVFGGGTKLTVLDKTHTCPPCPAPEAAGAPSVFLFPPKPKDTLMI
                     SRTPEVTCVVVDVSHEDPEVKFNWYVDGVEVHNAKTKPREEQYNSTY
                     RVVSVLTVLHQDWLNGKEYKCKVSNKALPAPIEKTISKAKGQPREPQ
                     VCTLPPSRDELTKNQVSLSCAVKGFYPSDIAVEWESNGQPENNYKTT
                     PPVLDSDGSFFLVSKLTVDKSRWQQGNVFSCSVMHEALHNHYTQKSL
                     SLSPGWSHPQFEK (SEQ ID NO: 103)

BMPRII_platform_10   EVQLLESGGGLVQPGGSLRLSCAASGFTFSNAWMNWVRQAPGKGLEW
                     VSSISSSSSYIYYADSVKGRFTISRDNSKNTLYLQMNSLRAEDTAVY
                     YCARSNGSGGSTSPLDLWGQGTLVTVTSSGGGGSGGGGSGGGGSQSV
                     LTQPPSASGTPGQRVTISCSGSRSNIGSNSVHWYQQLPGTAPKLLIY
                     GNSNRPSGVPDRFSGSKSGTSASLAISGLRSEDEADYYCQSYDSSLN
                     DHVVFGGGTKLTVLDKTHTCPPCPAPEAAGAPSVFLFPPKPKDTLMI
                     SRTPEVTCVVVDVSHEDPEVKFNWYVDGVEVHNAKTKPREEQYNSTY
                     RVVSVLTVLHQDWLNGKEYKCKVSNKALPAPIEKTISKAKGQPREPQ
                     VCTLPPSRDELTKNQVSLSCAVKGFYPSDIAVEWESNGQPENNYKTT
                     PPVLDSDGSFFLVSKLTVDKSRWQQGNVFSCSVMHEALHNHYTQKSL
                     SLSPGWSHPQFEK (SEQ ID NO: 104)

BMPRII_platform_11   EVQLLESGGGLVQPGGSLRLSCAASGFTFSNAWMNWVRQAPGKGLEW
                     VSSISSSSSYIYYADSVKGRFTISRDNSKNTLYLQMNSLRAEDTAVY
                     YCARAVAGTSMWYGLDQWGQGTLVTVTSSGGGGSGGGGSGGGGSQSV
                     LTQPPSASGTPGQRVTISCSGSRSNIGSNSVHWYQQLPGTAPKLLIY
                     GNSNRPSGVPDRFSGSKSGTSASLAISGLRSEDEADYYCQSYDSSLN
                     DHVVFGGGTKLTVLDKTHTCPPCPAPEAAGAPSVFLFPPKPKDTLMI
                     SRTPEVTCVVVDVSHEDPEVKFNWYVDGVEVHNAKTKPREEQYNSTY
                     RVVSVLTVLHQDWLNGKEYKCKVSNKALPAPIEKTISKAKGQPREPQ
                     VCTLPPSRDELTKNQVSLSCAVKGFYPSDIAVEWESNGQPENNYKTT
                     PPVLDSDGSFFLVSKLTVDKSRWQQGNVFSCSVMHEALHNHYTQKSL
                     SLSPGWSHPQFEK (SEQ ID NO: 105)

BMPRII_platform_12   EVQLLESGGGLVQPGGSLRLSCAASGFTFSNAWMNWVRQAPGKGLEW
                     VSSISSSSSYIYYADSVKGRFTISRDNSKNTLYLQMNSLRAEDTAVY
                     YCARAVGASTVYFGLDQWGQGTLVTVTSSGGGGSGGGGSGGGGSQSV
                     LTQPPSASGTPGQRVTISCSGSRSNIGSNSVHWYQQLPGTAPKLLIY
                     GNSNRPSGVPDRFSGSKSGTSASLAISGLRSEDEADYYCQSYDSSLN
                     DHVVFGGGTKLTVLDKTHTCPPCPAPEAAGAPSVFLFPPKPKDTLMI
```

TABLE 5-continued

Optimized ALK1 and BMPRII binders.

```
                   SRTPEVTCVVVDVSHEDPEVKFNWYVDGVEVHNAKTKPREEQYNSTY
                   RVVSVLTVLHQDWLNGKEYKCKVSNKALPAPIEKTISKAKGQPREPQ
                   VCTLPPSRDELTKNQVSLSCAVKGFYPSDIAVEWESNGQPENNYKTT
                   PPVLDSDGSFFLVSKLTVDKSRWQQGNVFSCSVMHEALHNHYTQKSL
                   SLSPGWSHPQFEK (SEQ ID NO: 106)

BMPRII_platform_13 EVQLLESGGGLVQPGGSLRLSCAASGFTFSNAWMNWVRQAPGKGLEW
                   VSSISSSSSYIYYADSVKGRFTISRDNSKNTLYLQMNSLRAEDTAVY
                   YCARAVAAGGFFWGLDQWGQGTLVTVTSSGGGGSGGGGSGGGGSQSV
                   LTQPPSASGTPGQRVTISCSGSRSNIGSNSVHWYQQLPGTAPKLLIY
                   GNSNRPSGVPDRFSGSKSGTSASLAISGLRSEDEADYYCQSYDSSLN
                   DHVVFGGGTKLTVLDKTHTCPPCPAPEAAGAPSVFLFPPKPKDTLMI
                   SRTPEVTCVVVDVSHEDPEVKFNWYVDGVEVHNAKTKPREEQYNSTY
                   RVVSVLTVLHQDWLNGKEYKCKVSNKALPAPIEKTISKAKGQPREPQ
                   VCTLPPSRDELTKNQVSLSCAVKGFYPSDIAVEWESNGQPENNYKTT
                   PPVLDSDGSFFLVSKLTVDKSRWQQGNVFSCSVMHEALHNHYTQKSL
                   SLSPGWSHPQFEK (SEQ ID NO: 107)

BMPRII_platform_14 EVQLLESGGGLVQPGGSLRLSCAASGFTFSNAWMNWVRQAPGKGLEW
                   VSSISSSSSYIYYADSVKGRFTISRDNSKNTLYLQMNSLRAEDTAVY
                   YCARAVAAGGLFWGLDQWGQGTLVTVTSSGGGGSGGGGSGGGGSQSV
                   LTQPPSASGTPGQRVTISCSGSRSNIGSNSVHWYQQLPGTAPKLLIY
                   GNSNRPSGVPDRFSGSKSGTSASLAISGLRSEDEADYYCQSYDSSLN
                   DHVVFGGGTKLTVLDKTHTCPPCPAPEAAGAPSVFLFPPKPKDTLMI
                   SRTPEVTCVVVDVSHEDPEVKFNWYVDGVEVHNAKTKPREEQYNSTY
                   RVVSVLTVLHQDWLNGKEYKCKVSNKALPAPIEKTISKAKGQPREPQ
                   VCTLPPSRDELTKNQVSLSCAVKGFYPSDIAVEWESNGQPENNYKTT
                   PPVLDSDGSFFLVSKLTVDKSRWQQGNVFSCSVMHEALHNHYTQKSL
                   SLSPGWSHPQFEK (SEQ ID NO: 108)

BMPRII_platform_15 EVQLLESGGGLVQPGGSLRLSCAASGFTFSLAWMNWVRQAPGKGLEW
                   VSSISSSTSYIYYADSVKGRFTISRDNSKNTLYLQMNSLRAEDTAVY
                   YCARAVAAGGMFWGLDQWGQGTLVTVTSSGGGGSGGGGSGGGGSQSV
                   LTQPPSASGTPGQRVTISCSGSRSNIGSNSVHWYQQLPGTAPKLLIY
                   GNSNRPSGVPDRFSGSKSGTSASLAISGLRSEDEADYYCQSYDSSLN
                   DHVVFGGGTKLTVLDKTHTCPPCPAPEAAGAPSVFLFPPKPKDTLMI
                   SRTPEVTCVVVDVSHEDPEVKFNWYVDGVEVHNAKTKPREEQYNSTY
                   RVVSVLTVLHQDWLNGKEYKCKVSNKALPAPIEKTISKAKGQPREPQ
                   VCTLPPSRDELTKNQVSLSCAVKGFYPSDIAVEWESNGQPENNYKTT
                   PPVLDSDGSFFLVSKLTVDKSRWQQGNVFSCSVMHEALHNHYTQKSL
                   SLSPGWSHPQFEK (SEQ ID NO: 109)

BMPRII_platform_16 EVQLLESGGGLVQPGGSLRLSCAASGFTFSLAWMNWVRQAPGKGLEW
                   VSSISSSTSYIYYADSVKGRFTISRDNSKNTLYLQMNSLRAEDTAVY
                   YCARAVAAGGFFWGLDQWGQGTLVTVTSSGGGGSGGGGSGGGGSQSV
                   LTQPPSASGTPGQRVTISCSGSRSNIGSNSVHWYQQLPGTAPKLLIY
                   GNSNRPSGVPDRFSGSKSGTSASLAISGLRSEDEADYYCQSYDSSLN
                   DHVVFGGGTKLTVLDKTHTCPPCPAPEAAGAPSVFLFPPKPKDTLMI
                   SRTPEVTCVVVDVSHEDPEVKFNWYVDGVEVHNAKTKPREEQYNSTY
                   RVVSVLTVLHQDWLNGKEYKCKVSNKALPAPIEKTISKAKGQPREPQ
                   VCTLPPSRDELTKNQVSLSCAVKGFYPSDIAVEWESNGQPENNYKTT
                   PPVLDSDGSFFLVSKLTVDKSRWQQGNVFSCSVMHEALHNHYTQKSL
                   SLSPGWSHPQFEK (SEQ ID NO: 110)

BMPRII_platform_17 EVQLLESGGGLVQPGGSLRLSCAASGFTFSDYYMNWIRQAPGKGLEW
                   VSSISGGSTYYADSVKGRFTISRDNSENTLYLQMNSLRAEDTAVYYC
                   ARDFGVAGWFGQFGMDVWGQGTLVTVSSGGGGSGGGGSGGGGSQSVL
                   TQPPSASGTPGQRVTISCTGSSSNIGAGYDVHWYQQLPGTAPKLLIY
                   RSNQRPSGVPDRFSGSKSGTSASLAISGLRSEDEADYYCSSYAGNYN
                   LVFGGGTKLTVLDKTHTCPPCPAPEAAGAPSVFLFPPKPKDTLMISR
                   TPEVTCVVVDVSHEDPEVKFNWYVDGVEVHNAKTKPREEQYNSTYRV
                   VSVLTVLHQDWLNGKEYKCKVSNKALPAPIEKTISKAKGQPREPQVC
                   TLPPSRDELTKNQVSLSCAVKGFYPSDIAVEWESNGQPENNYKTTPP
                   VLDSDGSFFLVSKLTVDKSRWQQGNVFSCSVMHEALHNHYTQKSLSL
                   SPGWSHPQFEK (SEQ ID NO: 111)

BMPRII_platform_18 EVQLLESGGGLVQPGGSLRLSCAASGFTFSDSYMSWIRQAPGKGLEW
                   VSSISGGSTYYADSVKGRFTISRDNSENTLYLQMNSLRAEDTAVYYC
                   ARDFGVAGYFGQYGMDVWGQGTLVTVSSGGGGSGGGGSGGGGSQSVL
                   TQPPSASGTPGQRVTISCTGSSSNIGAGYDVHWYQQLPGTAPKLLIY
                   RSNQRPSGVPDRFSGSKSGTSASLAISGLRSEDEADYYCSSYAGNYN
                   LVFGGGTKLTVLDKTHTCPPCPAPEAAGAPSVFLFPPKPKDTLMISR
                   TPEVTCVVVDVSHEDPEVKFNWYVDGVEVHNAKTKPREEQYNSTYRV
                   VSVLTVLHQDWLNGKEYKCKVSNKALPAPIEKTISKAKGQPREPQVC
                   TLPPSRDELTKNQVSLSCAVKGFYPSDIAVEWESNGQPENNYKTTPP
                   VLDSDGSFFLVSKLTVDKSRWQQGNVFSCSVMHEALHNHYTQKSLSL
                   SPGWSHPQFEK (SEQ ID NO: 112)
```

TABLE 5-continued

Optimized ALK1 and BMPRII binders.

BMPRII_platform_19 EVQLLESGGGLVQPGGSLRLSCAASGFTFSDYYMNWIRQAPGKGLEW
VSSISGGSTYYADSVKGRFTISRDNSENTLYLQMNSLRAEDTAVYYC
ARDFGVAGWFGYYGMDVWGQGTLVTVSSGGGGSGGGGSGGGGSQSVL
TQPPSASGTPGQRVTISCTGSSSNIGAGYDVHWYQQLPGTAPKLLIY
RSNQRPSGVPDRFSGSKSGTSASLAISGLRSEDEADYYCSSYAGNYN
LVFGGGTKLTVLDKTHTCPPCPAPEAAGAPSVFLFPPKPKDTLMISR
TPEVTCVVVDVSHEDPEVKFNWYVDGVEVHNAKTKPREEQYNSTYRV
VSVLTVLHQDWLNGKEYKCKVSNKALPAPIEKTISKAKGQPREPQVC
TLPPSRDELTKNQVSLSCAVKGFYPSDIAVEWESNGQPENNYKTTPP
VLDSDGSFFLVSKLTVDKSRWQQGNVFSCSVMHEALHNHYTQKSLSL
SPGWSHPQFEK (SEQ ID NO: 113)

BMPRII_platform_20 EVQLLESGGGLVQPGGSLRLSCAASGFTFSDYYMTWIRQAPGKGLEW
VSSISGGSTYYADSRKGRFTISRDNSENTLYLQMNSLRAEDTAVYYC
ARDYGVAGWFGQYGMDVWGQGTLVTVSSGGGGSGGGGSGGGGSQSVL
TQPPSASGTPGQRVTISCTGSSSNIGAGYDVHWYQQLPGTAPKLLIY
RSNQRPSGVPDRFSGSKSGTSASLAISGLRSEDEADYYCSSYAGNYN
LVFGGGTKLTVLDKTHTCPPCPAPEAAGAPSVFLFPPKPKDTLMISR
TPEVTCVVVDVSHEDPEVKFNWYVDGVEVHNAKTKPREEQYNSTYRV
VSVLTVLHQDWLNGKEYKCKVSNKALPAPIEKTISKAKGQPREPQVC
TLPPSRDELTKNQVSLSCAVKGFYPSDIAVEWESNGQPENNYKTTPP
VLDSDGSFFLVSKLTVDKSRWQQGNVFSCSVMHEALHNHYTQKSLSL
SPGWSHPQFEK (SEQ ID NO: 114)

BMPRII_platform_21 EVQLLESGGGLVQPGGSLRLSCAASGFTFSDYYMTWIRQAPGKGLEW
VSSISGGSTYYADSRKGRFTISRDNSENTLYLQMNSLRAEDTAVYYC
ARDFGVSGWFGQYGMDVWGQGTLVTVSSGGGGSGGGGSGGGGSQSVL
TQPPSASGTPGQRVTISCTGSSSNIGAGYDVHWYQQLPGTAPKLLIY
RSNQRPSGVPDRFSGSKSGTSASLAISGLRSEDEADYYCSSYAGNYN
LVFGGGTKLTVLDKTHTCPPCPAPEAAGAPSVFLFPPKPKDTLMISR
TPEVTCVVVDVSHEDPEVKFNWYVDGVEVHNAKTKPREEQYNSTYRV
VSVLTVLHQDWLNGKEYKCKVSNKALPAPIEKTISKAKGQPREPQVC
TLPPSRDELTKNQVSLSCAVKGFYPSDIAVEWESNGQPENNYKTTPP
VLDSDGSFFLVSKLTVDKSRWQQGNVFSCSVMHEALHNHYTQKSLSL
SPGWSHPQFEK (SEQ ID NO: 115)

BMPRII_platform_22 EVQLLESGGGLVQPGGSLRLSCAASGFTFSDYWMTWIRQAPGKGLEW
VSSISGGSTYYADSRKGRFTISRDNSENTLYLQMNSLRAEDTAVYYC
ARDFGVAGWFGQYGMDVWGQGTLVTVSSGGGGSGGGGSGGGGSQSVL
TQPPSASGTPGQRVTISCTGSSSNIGAGYDVHWYQQLPGTAPKLLIY
RSNQRPSGVPDRFSGSKSGTSASLAISGLRSEDEADYYCSSYAGNYN
LVFGGGTKLTVLDKTHTCPPCPAPEAAGAPSVFLFPPKPKDTLMISR
TPEVTCVVVDVSHEDPEVKFNWYVDGVEVHNAKTKPREEQYNSTYRV
VSVLTVLHQDWLNGKEYKCKVSNKALPAPIEKTISKAKGQPREPQVC
TLPPSRDELTKNQVSLSCAVKGFYPSDIAVEWESNGQPENNYKTTPP
VLDSDGSFFLVSKLTVDKSRWQQGNVFSCSVMHEALHNHYTQKSLSL
SPGWSHPQFEK (SEQ ID NO: 116)

BMPRII_platform_23 EVQLLESGGGLVQPGGSLRLSCAASGFTFSDYYMTWIRQAPGKGLEW
VSSISGGTTYYADSRKGRFTISRDNSENTLYLQMNSLRAEDTAVYYC
ARDFGVAGWFGQYGMDVWGQGTLVTVSSGGGGSGGGGSGGGGSQSVL
TQPPSASGTPGQRVTISCTGSSSNIGAGYDVHWYQQLPGTAPKLLIY
RSNQRPSGVPDRFSGSKSGTSASLAISGLRSEDEADYYCSSYAGNYN
LVFGGGTKLTVLDKTHTCPPCPAPEAAGAPSVFLFPPKPKDTLMISR
TPEVTCVVVDVSHEDPEVKFNWYVDGVEVHNAKTKPREEQYNSTYRV
VSVLTVLHQDWLNGKEYKCKVSNKALPAPIEKTISKAKGQPREPQVC
TLPPSRDELTKNQVSLSCAVKGFYPSDIAVEWESNGQPENNYKTTPP
VLDSDGSFFLVSKLTVDKSRWQQGNVFSCSVMHEALHNHYTQKSLSL
SPGWSHPQFEK (SEQ ID NO: 117)

BMPRII_platform_24 EVQLLESGGGLVQPGGSLRLSCAASGFTFSDYWMTWIRQAPGKGLEW
VSSISGGTTYYADSRKGRFTISRDNSENTLYLQMNSLRAEDTAVYYC
ARDYGVAGWFGQYGMDVWGQGTLVTVSSGGGGSGGGGSGGGGSQSVL
TQPPSASGTPGQRVTISCTGSSSNIGAGYDVHWYQQLPGTAPKLLIY
RSNQRPSGVPDRFSGSKSGTSASLAISGLRSEDEADYYCSSYAGNYN
LVFGGGTKLTVLDKTHTCPPCPAPEAAGAPSVFLFPPKPKDTLMISR
TPEVTCVVVDVSHEDPEVKFNWYVDGVEVHNAKTKPREEQYNSTYRV
VSVLTVLHQDWLNGKEYKCKVSNKALPAPIEKTISKAKGQPREPQVC
TLPPSRDELTKNQVSLSCAVKGFYPSDIAVEWESNGQPENNYKTTPP
VLDSDGSFFLVSKLTVDKSRWQQGNVFSCSVMHEALHNHYTQKSLSL
SPGWSHPQFEK (SEQ ID NO: 118)

BMPRII_platform_25 EVQLLESGGGLVQPGGSLRLSCAASGFTFSDYWMTWIRQAPGKGLEW
VSSISGGTTYYADSRKGRFTISRDNSENTLYLQMNSLRAEDTAVYYC
ARDFGVSGWFGQYGMDVWGQGTLVTVSSGGGGSGGGGSGGGGSQSVL
TQPPSASGTPGQRVTISCTGSSSNIGAGYDVHWYQQLPGTAPKLLIY
RSNQRPSGVPDRFSGSKSGTSASLAISGLRSEDEADYYCSSYAGNYN
LVFGGGTKLTVLDKTHTCPPCPAPEAAGAPSVFLFPPKPKDTLMISR TABLE 5-continued Optimized ALK1 and BMPRII binders.

```
            TPEVTCVVVDVSHEDPEVKFNWYVDGVEVHNAKTKPREEQYNSTYRV
            VSVLTVLHQDWLNGKEYKCKVSNKALPAPIEKTISKAGQPREPQVC
            TLPPSRDELTKNQVSLSCAVKGFYPSDIAVEWESNGQPENNYKTTPP
            VLDSDGSFFLVSKLTVDKSRWQQGNVFSCSVMHEALHNHYTQKSLSL
            SPGWSHPQFEK (SEQ ID NO: 119)

scFv_1      EVQLLESGGGLVQPGGSLRLSCAASGFTFSIYAMSWVRQAPGKGLEW
            VSAISGSGGSTYYADSVKGRFTISRDNSKNTLYLQMNSLRAEDTAVY
            YCARDFDYWGQGTLVTVTSSGGGGSGGGGSGGGGSQSVLTQPPSASG
            TPGQRVTISCSGSSSNIGSNYVYWYQQLPGTAPKLLIYGNINRPSGV
            PDRFSGSKSGTSASLAISGLRSEDEADYYCAAWDDSLNGRVFGGGTK
            LTVLDKTHTCPPCPAPEAAGAPSVFLFPPKPKDTLMISRTPEVTCVV
            VDVSHEDPEVKFNWYVDGVEVHNAKTKPREEQYNSTYRVVSVLTVLH
            QDWLNGKEYKCKVSNKALPAPIEKTISKAGQPREPQVYTLPPCRDE
            LTKNQVSLWCLVKGFYPSDIAVEWESNGQPENNYKTTPPVLDSDGSF
            FLYSKLTVDKSRWQQGNVFSCSVMHEALHNHYTQKSLSLSPGEPEA
            (SEQ ID NO: 120)

scFv_8      EVQLLESGGGLVQPGGSLRLSCAASGFTFSNAWMNWVRQAPGKGLEW
            VSSISSSSSYIYYADSVKGRFTISRDNSKNTLYLQMNSLRAEDTAVY
            YCARAVAAGGMFWGLDQWGQGTLVTVTSSGGGGSGGGGSGGGGSQSV
            LTQPPSASGTPGQRVTISCSGSRSNIGSNSVHWYQQLPGTAPKLLIY
            GNSNRPSGVPDRFSGSKSGTSASLAISGLRSEDEADYYCQSYDSSLN
            DHVVFGGGTKLTVLDKTHTCPPCPAPEAAGAPSVFLFPPKPKDTLMI
            SRTPEVTCVVVDVSHEDPEVKFNWYVDGVEVHNAKTKPREEQYNSTY
            RVVSVLTVLHQDWLNGKEYKCKVSNKALPAPIEKTISKAGQPREPQ
            VCTLPPSRDELTKNQVSLSCAVKGFYPSDIAVEWESNGQPENNYKTT
            PPVLDSDGSFFLVSKLTVDKSRWQQGNVFSCSVMHEALHNHYTQKSL
            SLSPGWSHPQFEK (SEQ ID NO: 121)

scFv_29     EVQLLESGGGLVQPGGSLRLSCAASGFTFSSYAMSWVRQAPGKGLEW
            VANINQDGSEKNYVDSMRGRFTISRDNSKNTLYLQMNSLRAEDTAVY
            YCAREFDYWGQGTLVTVTSSGGGGSGGGGSGGGGSQSVLAQPPSASG
            TPGQRVTISCSGSSSNIGSNYVYWYQQLPGTAPKLLIYGNNKRPSGV
            PDRFSGSKSGTSASLAISGLRSEDEADYYCAAWDDSLNGRVFGGGTK
            LTVLDKTHTCPPCPAPEAAGAPSVFLFPPKPKDTLMISRTPEVTCVV
            VDVSHEDPEVKFNWYVDGVEVHNAKTKPREEQYNSTYRVVSVLTVLH
            QDWLNGKEYKCKVSNKALPAPIEKTISKAGQPREPQVYTLPPCRDE
            LTKNQVSLWCLVKGFYPSDIAVEWESNGQPENNYKTTPPVLDSDGSF
            FLYSKLTVDKSRWQQGNVFSCSVMHEALHNHYTQKSLSLSPGEPEA
            (SEQ ID NO: 122)

scFv_36     EVQLLESGGGLVQPGGSLRLSCAASGFTFSDYYMTWIRQAPGKGLEW
            VSSISGGSTYYADSRKGRFTISRDNSENTLYLQMNSLRAEDTAVYYC
            ARDFGVAGWFGQYGMDVWGQGTLVTVSSGGGGSGGGGSGGGGSQSVL
            TQPPSASGTPGQRVTISCTGSSSNIGAGYDVHWYQQLPGTAPKLLIY
            RSNQRPSGVPDRFSGSKSGTSASLAISGLRSEDEADYYCSSYAGNYN
            LVFGGGTKLTVLDKTHTCPPCPAPEAAGAPSVFLFPPKPKDTLMISR
            TPEVTCVVVDVSHEDPEVKFNWYVDGVEVHNAKTKPREEQYNSTYRV
            VSVLTVLHQDWLNGKEYKCKVSNKALPAPIEKTISKAGQPREPQVC
            TLPPSRDELTKNQVSLSCAVKGFYPSDIAVEWESNGQPENNYKTTPP
            VLDSDGSFFLVSKLTVDKSRWQQGNVFSCSVMHEALHNHYTQKSLSL
            SPGWSHPQFEK (SEQ ID NO: 123)
```

TABLE 6

Optimized ALK1 and BMPRII bispecific antibodies.

| Name | Chain 1 | Chain 2 |
|---|---|---|
| DGL621 | Alk1_platform_1 | scFv_8 |
| DGL622 | Alk1_platform_2 | scFv_8 |
| DGL623 | Alk1_platform_3 | scFv_8 |
| DGL624 | Alk1_platform_4 | scFv_8 |
| DGL625 | Alk1_platform_5 | scFv_36 |
| DGL626 | Alk1_platform_6 | scFv_36 |
| DGL627 | Alk1_platform_7 | scFv_36 |
| DGL628 | Alk1_platform_8 | scFv_36 |
| DGL629 | Alk1_platform_9 | scFv_36 |
| DGL630 | Alk1_platform_10 | scFv_8 |
| DGL631 | Alk1_platform_11 | scFv_8 |
| DGL632 | Alk1_platform_12 | scFv_8 |
| DGL633 | Alk1_platform_13 | scFv_8 |
| DGL634 | Alk1_platform_14 | scFv_8 |
| DGL635 | BMPRII_platform_1 | scFv_29 |

TABLE 6-continued

Optimized ALK1 and BMPRII bispecific antibodies.

| Name | Chain 1 | Chain 2 |
|---|---|---|
| DGL636 | BMPRII_platform_2 | scFv_29 |
| DGL637 | BMPRII_platform_3 | scFv_29 |
| DGL638 | BMPRII_platform_4 | scFv_29 |
| DGL639 | BMPRII_platform_5 | scFv_29 |
| DGL640 | BMPRII_platform_6 | scFv_29 |
| DGL641 | BMPRII_platform_7 | scFv_1 |
| DGL642 | BMPRII_platform_8 | scFv_1 |
| DGL643 | BMPRII_platform_9 | scFv_1 |
| DGL644 | BMPRII_platform_10 | scFv_1 |
| DGL645 | BMPRII_platform_11 | scFv_1 |
| DGL646 | BMPRII_platform_12 | scFv_1 |
| DGL647 | BMPRII_platform_13 | scFv_1 |
| DGL648 | BMPRII_platform_14 | scFv_1 |
| DGL649 | BMPRII_platform_15 | scFv_1 |
| DGL650 | BMPRII_platform_16 | scFv_1 |

TABLE 6-continued

Optimized ALK1 and BMPRII bispecific antibodies.

| Name | Chain 1 | Chain 2 |
|---|---|---|
| DGL651 | Alk1_platform_15 | scFv_36 |
| DGL652 | Alk1_platform_16 | scFv_36 |
| DGL653 | Alk1_platform_17 | scFv_36 |
| DGL654 | BMPRII_platform_17 | scFv_29 |
| DGL655 | BMPRII_platform_18 | scFv_29 |
| DGL656 | BMPRII_platform_19 | scFv_29 |
| DGL730 | BMPRII_platform_20 | scFv_29 |
| DGL731 | BMPRII_platform_21 | scFv_29 |
| DGL732 | BMPRII_platform_22 | scFv_29 |
| DGL733 | BMPRII_platform_23 | scFv_29 |
| DGL734 | BMPRII_platform_24 | scFv_29 |
| DGL735 | BMPRII_platform_25 | scFv_29 |
| DGL736 | Alk1_platform_18 | scFv_36 |
| DGL737 | Alk1_platform_19 | scFv_36 |
| DGL860 | ALK1_platform_15 | BMPRII_Platform_17 |
| DGL861 | ALK1_platform_16 | BMPRII_Platform_17 |
| DGL862 | ALK1_platform_17 | BMPRII_Platform_17 |
| DGL863 | ALK1_platform_15 | BMPRII_Platform_18 |
| DGL864 | ALK1_platform_16 | BMPRII_Platform_18 |
| DGL865 | ALK1_platform_17 | BMPRII_Platform_18 |
| DGL866 | ALK1_platform_15 | BMPRII_Platform_19 |
| DGL867 | ALK1_platform_16 | BMPRII_Platform_19 |
| DGL868 | ALK1_platform_17 | BMPRII_Platform_19 |
| DGL869 | scFv29_L1_H3 | scFv36 |
| DGL870 | scFv29_L2_H3 | scFv36 |
| DGL871 | scFv29_L3_H3 | scFv36 |
| DGL872 | scFv29_L4_H3 | scFv36 |
| DGL873 | scFv29_L1 | scFv36 |
| DGL874 | scFv29_L2 | scFv36 |
| DGL875 | scFv29_L3 | scFv36 |
| DGL876 | scFv29_L4 | scFv36 |

TABLE 6-continued

Optimized ALK1 and BMPRII bispecific antibodies.

| Name | Chain 1 | Chain 2 |
|---|---|---|
| DGL877 | scFv29 | scFv36_L1 |
| DGL878 | scFv29 | scFv36_L2 |
| DGL879 | scFv29 | scFv36_L3 |
| DGL880 | scFv29 | scFv36_L4 |
| DGL893 | Alk_platform_15 | BMPRII_platform_21 |
| DGL894 | Alk_platform_15 | BMPRII_platform_22 |
| DGL895 | Alk_platform_15 | BMPRII_platform_23 |
| DGL896 | Alk_platform_15 | BMPRII_platform_25 |
| DGL897 | Alk1_platform_16 | BMPRII_platform_21 |
| DGL898 | Alk1_platform_16 | BMPRII_platform_22 |
| DGL899 | Alk1_platform_16 | BMPRII_platform_23 |
| DGL900 | Alk1_platform_16 | BMPRII_platform_25 |
| DGL901 | Alk1_platform_17 | BMPRII_platform_21 |
| DGL902 | Alk1_platform_17 | BMPRII_platform_22 |
| DGL903 | Alk1_platform_17 | BMPRII_platform_23 |
| DGL904 | Alk1_platform_17 | BMPRII_platform_25 |
| DGL905 | Alk1_platform_18 | BMPRII_platform_17 |
| DGL906 | Alk1_platform_18 | BMPRII_platform_18 |
| DGL907 | Alk1_platform_18 | BMPRII_platform_19 |
| DGL908 | Alk1_platform_18 | BMPRII_platform_21 |
| DGL909 | Alk1_platform_18 | BMPRII_platform_22 |
| DGL910 | Alk1_platform_18 | BMPRII_platform_23 |
| DGL911 | Alk1_platform_18 | BMPRII_platform_25 |
| DGL912 | Alk1_platform_19 | BMPRII_platform_17 |
| DGL913 | Alk1_platform_19 | BMPRII_platform_18 |
| DGL914 | Alk1_platform_19 | BMPRII_platform_19 |
| DGL915 | Alk1_platform_19 | BMPRII_platform_21 |
| DGL916 | Alk1_platform_19 | BMPRII_platform_22 |
| DGL917 | Alk1_platform_19 | BMPRII_platform_23 |
| DGL918 | Alk1_platform_19 | BMPRII_platform_25 |

TABLE 7

Additional engineered variants.

| ID | Sequence |
|---|---|
| CH969 (ScFv29_L1_H3_CH) | EVQLLESGGGLVQPGGSLRLSCAASGFTFSDYAMSWVRQAPGKG LEWVANINQSGSEKNYVDSMRGRFTISRDNSKNTLYLQMNSLRA EDTAVYYCAREFDWWGQGTLVTVSSSGGGGSGGGGSGGGGSQSV LAQPPSASGTPGQRVTISCSGSASNIGSNYVYWYQQLPGTAPKL LIYGNNKRPSGVPDRFSGSKSGTSASLAISGLRSEDEADYYCAA WDDSLNGRVFGGGTKLTVLDKTHTCPPCPAPEAAGAPSVFLFPP KPKDTLMISRTPEVTCVVVDVSHEDPEVKFNWYVDGVEVHNAKT KPREEQYNSTYRVVSVLTVLHQDWLNGKEYKCKVSNKALPAPIE KTISKAKGQPREPQVYTLPPCRDELTKNQVSLWCLVKGFYPSDI AVEWESNGQPENNYKTTPPVLDSDGSFFLYSKLTVDKSRWQQGN VFSCSVMHEALHNHYTQKSLSLSPGEPEA (SEQ ID NO: 124) |
| CH970 (scFv29_L2_H3_CH) | EVQLLESGGGLVQPGGSLRLSCAASGFTFSDYAMSWVRQAPGKG LEWVANINQSGSEKNYVDSMRGRFTISRDNSKNTLYLQMNSLRA EDTAVYYCAREFDWWGQGTLVTVSSSGGGGSGGGGSGGGGSQSV LAQPPSASGTPGQRVTISCSGSSSNIGSNYVYWYQQLPGTAPKL LIYGNNKRPAGVPDRFSGSKSGTSASLAISGLRSEDEADYYCAA WDDSLNGRVFGGGTKLTVLDKTHTCPPCPAPEAAGAPSVFLFPP KPKDTLMISRTPEVTCVVVDVSHEDPEVKFNWYVDGVEVHNAKT KPREEQYNSTYRVVSVLTVLHQDWLNGKEYKCKVSNKALPAPIE KTISKAKGQPREPQVYTLPPCRDELTKNQVSLWCLVKGFYPSDI AVEWESNGQPENNYKTTPPVLDSDGSFFLYSKLTVDKSRWQQGN VFSCSVMHEALHNHYTQKSLSLSPGEPEA (SEQ ID NO: 125) |
| CH971 (scFv29_L3_H3_CH) | EVQLLESGGGLVQPGGSLRLSCAASGFTFSDYAMSWVRQAPGKG LEWVANINQSGSEKNYVDSMRGRFTISRDNSKNTLYLQMNSLRA EDTAVYYCAREFDWWGQGTLVTVSSSGGGGGGGGSGGGGSQSVL AQPPSASGTPGQRVTISCSGSSSNIGSNYVYWYQQLPGTAPKLL IYGNNKRPSGVPDRFSGSKSGTSASLAISGLRSEDEADYYCAAW DDSLSGRVFGGGTKLTVLDKTHTCPPCPAPEAAGAPSVFLFPPK |

TABLE 7-continued

Additional engineered variants.

| ID | Sequence |
|---|---|
| | PKDTLMISRTPEVTCVVVDVSHEDPEVKFNWYVDGVEVHNAKTK PREEQYNSTYRVVSVLTVLHQDWLNGKEYKCKVSNKALPAPIEK TISKAKGQPREPQVYTLPPCRDELTKNQVSLWCLVKGFYPSDIA VEWESNGQPENNYKTTPPVLDSDGSFFLYSKLTVDKSRWQQGNV FSCSVMHEALHNHYTQKSLSLSPGEPEA (SEQ ID NO: 126) |
| CH972 (scFv29_L4_H3_CH) | EVQLLESGGGLVQPGGSLRLSCAASGFTFSDYAMSWVRQAPGKG LEWVANINQSGSEKNYVDSMRGRFTISRDNSKNTLYLQMNSLRA EDTAVYYCAREFDWWGQGTLVTVSSSGGGGSGGGGSGGGGSQSV LAQPPSASGTPGQRVTISCSGSASNIGSNYVYWYQQLPGTAPKL LIYGNNKRPAGVPDRFSGSKSGTSASLAISGLRSEDEADYYCAA WDDSLSGRVFGGGTKLTVLDKTHTCPPCPAPEAAGAPSVFLFPP KPKDTLMISRTPEVTCVVVDVSHEDPEVKFNWYVDGVEVHNAKT KPREEQYNSTYRVVSVLTVLHQDWLNGKEYKCKVSNKALPAPIE KTISKAKGQPREPQVYTLPPCRDELTKNQVSLWCLVKGFYPSDI AVEWESNGQPENNYKTTPPVLDSDGSFFLYSKLTVDKSRWQQGN VFSCSVMHEALHNHYTQKSLSLSPGEPEA (SEQ ID NO: 127) |
| CH973 (scFv29_L1_CH) | EVQLLESGGGLVQPGGSLRLSCAASGFTFSSYAMSWVRQAPGKG LEWVANINQDGSEKNYVDSMRGRFTISRDNSKNTLYLQMNSLRA EDTAVYYCAREFDYWGQGTLVTVSSSGGGGSGGGGSGGGGSQSV LAQPPSASGTPGQRVTISCSGSASNIGSNYVYWYQQLPGTAPKL LIYGNNKRPSGVPDRFSGSKSGTSASLAISGLRSEDEADYYCAA WDDSLNGRVFGGGTKLTVLDKTHTCPPCPAPEAAGAPSVFLFPP KPKDTLMISRTPEVTCVVVDVSHEDPEVKFNWYVDGVEVHNAKT KPREEQYNSTYRVVSVLTVLHQDWLNGKEYKCKVSNKALPAPIE KTISKAKGQPREPQVYTLPPCRDELTKNQVSLWCLVKGFYPSDI AVEWESNGQPENNYKTTPPVLDSDGSFFLYSKLTVDKSRWQQGN VFSCSVMHEALHNHYTQKSLSLSPGEPEA (SEQ ID NO: 128) |
| CH974 (scFv29_L2_CH) | EVQLLESGGGLVQPGGSLRLSCAASGFTFSSYAMSWVRQAPGKG LEWVANINQDGSEKNYVDSMRGRFTISRDNSKNTLYLQMNSLRA EDTAVYYCAREFDYWGQGTLVTVSSSGGGGSGGGGSGGGGSQSV LAQPPSASGTPGQRVTISCSGSSSNIGSNYVYWYQQLPGTAPKL LIYGNNKRPAGVPDRFSGSKSGTSASLAISGLRSEDEADYYCAA WDDSLNGRVFGGGTKLTVLDKTHTCPPCPAPEAAGAPSVFLFPP KPKDTLMISRTPEVTCVVVDVSHEDPEVKFNWYVDGVEVHNAKT KPREEQYNSTYRVVSVLTVLHQDWLNGKEYKCKVSNKALPAPIE KTISKAKGQPREPQVYTLPPCRDELTKNQVSLWCLVKGFYPSDI AVEWESNGQPENNYKTTPPVLDSDGSFFLYSKLTVDKSRWQQGN VFSCSVMHEALHNHYTQKSLSLSPGEPEA (SEQ ID NO: 129) |
| CH975 (scFv29_L3_CH) | EVQLLESGGGLVQPGGSLRLSCAASGFTFSSYAMSWVRQAPGKG LEWVANINQDGSEKNYVDSMRGRFTISRDNSKNTLYLQMNSLRA EDTAVYYCAREFDYWGQGTLVTVSSSGGGGSGGGGSGGGGSQSV LAQPPSASGTPGQRVTISCSGSSSNIGSNYVYWYQQLPGTAPKL LIYGNNKRPSGVPDRFSGSKSGTSASLAISGLRSEDEADYYCAA WDDSLSGRVFGGGTKLTVLDKTHTCPPCPAPEAAGAPSVFLFPP KPKDTLMISRTPEVTCVVVDVSHEDPEVKFNWYVDGVEVHNAKT KPREEQYNSTYRVVSVLTVLHQDWLNGKEYKCKVSNKALPAPIE KTISKAKGQPREPQVYTLPPCRDELTKNQVSLWCLVKGFYPSDI AVEWESNGQPENNYKTTPPVLDSDGSFFLYSKLTVDKSRWQQGN VFSCSVMHEALHNHYTQKSLSLSPGEPEA (SEQ ID NO: 130) |
| CH976 (scFv29_L4_CH) | EVQLLESGGGLVQPGGSLRLSCAASGFTFSSYAMSWVRQAPGKG LEWVANINQDGSEKNYVDSMRGRFTISRDNSKNTLYLQMNSLRA EDTAVYYCAREFDYWGQGTLVTVSSSGGGGSGGGGSGGGGSQSV LAQPPSASGTPGQRVTISCSGSASNIGSNYVYWYQQLPGTAPKL LIYGNNKRPAGVPDRFSGSKSGTSASLAISGLRSEDEADYYCAA WDDSLSGRVFGGGTKLTVLDKTHTCPPCPAPEAAGAPSVFLFPP KPKDTLMISRTPEVTCVVVDVSHEDPEVKFNWYVDGVEVHNAKT |

TABLE 7-continued

Additional engineered variants.

| ID | Sequence |
|---|---|
| | KPREEQYNSTYRVVSVLTVLHQDWLNGKEYKCKVSNKALPAPIE KTISKAGQPREPQVYTLPPCRDELTKNQVSLWCLVKGFYPSDI AVEWESNGQPENNYKTTPPVLDSDGSFFLYSKLTVDKSRWQQGN VFSCSVMHEALHNHYTQKSLSLSPGEPEA (SEQ ID NO: 131) |
| CH977 (scFv36_L1_CH) | EVQLLESGGGLVQPGGSLRLSCAASGFTFSDYYMTWIRQAPGKG LEWVSSISGGSTYYADSRKGRFTISRDNSENTLYLQMNSLRAED TAVYYCARDFGVAGWFGQYGMDVWGQGTLVTVSSGGGGSGGGGS GGGGSQSVLTQPPSASGTPGQRVTISCTGSASNIGAGYDVHWYQ QLPGTAPKLLIYRSNQRPSGVPDRFSGSKSGTSASLAISGLRSE DEADYYCSSYAGNYNLVFGGGTKLTVLDKTHTCPPCPAPEAAGA PSVFLFPPKPKDTLMISRTPEVTCVVVDVSHEDPEVKFNWYVDG VEVHNAKTKPREEQYNSTYRVVSVLTVLHQDWLNGKEYKCKVSN KALPAPIEKTISKAGQPREPQVCTLPPSRDELTKNQVSLSCAV KGFYPSDIAVEWESNGQPENNYKTTPPVLDSDGSFFLVSKLTVD KSRWQQGNVFSCSVMHEALHNHYTQKSLSLSPGWSHPQFEK (SEQ ID NO: 132) |
| CH978 (scFv36_L2_CH) | EVQLLESGGGLVQPGGSLRLSCAASGFTFSDYYMTWIRQAPGKG LEWVSSISGGSTYYADSRKGRFTISRDNSENTLYLQMNSLRAED TAVYYCARDFGVAGWFGQYGMDVWGQGTLVTVSSGGGGSGGGGS GGGGSQSVLTQPPSASGTPGQRVTISCTGSSSNIGAGYDVHWYQ QLPGTAPKLLIYRSNQRPAGVPDRFSGSKSGTSASLAISGLRSE DEADYYCSSYAGNYNLVFGGGTKLTVLDKTHTCPPCPAPEAAGA PSVFLFPPKPKDTLMISRTPEVTCVVVDVSHEDPEVKFNWYVDG VEVHNAKTKPREEQYNSTYRVVSVLTVLHQDWLNGKEYKCKVSN KALPAPIEKTISKAGQPREPQVCTLPPSRDELTKNQVSLSCAV KGFYPSDIAVEWESNGQPENNYKTTPPVLDSDGSFFLVSKLTVD KSRWQQGNVFSCSVMHEALHNHYTQKSLSLSPGWSHPQFEK (SEQ ID NO: 133) |
| CH979 (scFv36_L3_CH) | EVQLLESGGGLVQPGGSLRLSCAASGFTFSDYYMTWIRQAPGKG LEWVSSISGGSTYYADSRKGRFTISRDNSENTLYLQMNSLRAED TAVYYCARDFGVAGWFGQYGMDVWGQGTLVTVSSGGGGSGGGGS GGGGSQSVLTQPPSASGTPGQRVTISCTGSSSNIGAGYDVHWYQ QLPGTAPKLLIYRSNQRPSGVPDRFSGSKSGTSASLAISGLRSE DEADYYCSSYAGLYNLVFGGGTKLTVLDKTHTCPPCPAPEAAGA PSVFLFPPKPKDTLMISRTPEVTCVVVDVSHEDPEVKFNWYVDG VEVHNAKTKPREEQYNSTYRVVSVLTVLHQDWLNGKEYKCKVSN KALPAPIEKTISKAGQPREPQVCTLPPSRDELTKNQVSLSCAV KGFYPSDIAVEWESNGQPENNYKTTPPVLDSDGSFFLVSKLTVD KSRWQQGNVFSCSVMHEALHNHYTQKSLSLSPGWSHPQFEK (SEQ ID NO: 134) |
| CH980 (scFv36_L4_CH) | EVQLLESGGGLVQPGGSLRLSCAASGFTFSDYYMTWIRQAPGKG LEWVSSISGGSTYYADSRKGRFTISRDNSENTLYLQMNSLRAED TAVYYCARDFGVAGWFGQYGMDVWGQGTLVTVSSGGGGSGGGGS GGGGSQSVLTQPPSASGTPGQRVTISCTGSASNIGAGYDVHWYQ QLPGTAPKLLIYRSNQRPAGVPDRFSGSKSGTSASLAISGLRSE DEADYYCSSYAGLYNLVFGGGTKLTVLDKTHTCPPCPAPEAAGA PSVFLFPPKPKDTLMISRTPEVTCVVVDVSHEDPEVKFNWYVDG VEVHNAKTKPREEQYNSTYRVVSVLTVLHQDWLNGKEYKCKVSN KALPAPIEKTISKAGQPREPQVCTLPPSRDELTKNQVSLSCAV KGFYPSDIAVEWESNGQPENNYKTTPPVLDSDGSFFLVSKLTVD KSRWQQGNVFSCSVMHEALHNHYTQKSLSLSPGWSHPQFEK (SEQ ID NO: 135) |

These binders were then tested using an ELISA assay. High binding plates (Corning, 9018) were coated with either 2 ug/ml of human BMPRII protein (Sino Biological, #10551-H08H) or 2 μg/ml of human ALK1 protein (Sino Biological, #10066-H08H) overnight at 40. The plates were then washed three times with wash buffer (R & D Systems, WA126). The plates were blocked with 1% BSA in PBS for one hour at room temperature, then blocked with 1% BSA and 2 μg/ml of goat anti-human IgG (Jackson ImmunoResearch, 109-005-190) in PBS for another hour at room temperature. The plates were then washed three times with wash buffer and DGL antibodies or controls, which were diluted with PBS and 0.1% BSA. The antibodies were incubated for one hour at room temperature and then the plates were washed three times with wash buffer. The plates were then incubated with mouse anti-human IgG Fc secondary—HRP (diluted with PBS/0.1% BSA); 100 ul per well at 2 μg/ml and incubated at room temperature for one hour. The plate was washed three times in wash buffer and then 100 ul TMB (R & D Systems, DY9998B, substrate reagent pack). After the wells turn blue, 50 ul of stop solution (R & D Systems, DY994) was added to each well and the absorbance of the plate was read at 450 nm. results can be found in Table 8.

TABLE 8

Binding of optimized ALK1 and BMPRII bispecific antibodies.

| Name | Abs450 100 nM (Alk1 ELISA) | Abs450 10 nM (Alk1 ELISA) | Abs450 1 nM (Alk1 ELISA) | Abs450 100 nM (BMPRII ELISA) | Abs450 10 nM (BMPRII ELISA) | Abs450 1 nM (BMPRII ELISA) |
|---|---|---|---|---|---|---|
| DGL621 | 1.58 | 0.95 | 0.17 | 0.33 | 0.22 | 0.21 |
| DGL622 | 1.58 | 0.75 | 0.15 | 0.50 | 0.36 | 0.37 |
| DGL623 | 1.43 | 0.61 | 0.14 | 0.31 | 0.20 | 0.18 |
| DGL624 | 1.54 | 1.21 | 0.25 | 0.93 | 0.24 | 0.16 |
| DGL625 | 0.11 | 0.07 | 0.07 | 1.21 | 0.35 | 0.17 |
| DGL626 | 0.06 | 0.07 | 0.06 | 0.71 | 0.25 | 0.17 |
| DGL627 | 0.07 | 0.07 | 0.05 | 0.66 | 0.22 | 0.15 |
| DGL628 | 0.52 | 0.12 | 0.05 | 0.80 | 0.27 | 0.17 |
| DGL629 | 0.08 | 0.08 | 0.08 | 0.90 | 0.29 | 0.18 |
| DGL630 | 0.08 | 0.07 | 0.07 | 0.53 | 0.31 | 0.30 |
| DGL631 | 0.70 | 0.19 | 0.07 | 0.97 | 0.65 | 0.61 |
| DGL632 | 0.06 | 0.05 | 0.06 | 0.88 | 0.46 | 0.46 |
| DGL633 | 1.42 | 0.78 | 0.15 | 0.37 | 0.14 | 0.12 |
| DGL634 | 0.10 | 0.06 | 0.05 | 0.40 | 0.19 | 0.12 |
| DGL635 | 1.17 | 0.29 | 0.09 | 1.17 | 0.33 | 0.15 |
| DGL636 | 1.45 | 0.56 | 0.11 | 0.20 | 0.16 | 0.14 |
| DGL637 | 1.48 | 0.77 | 0.16 | 0.27 | 0.17 | 0.17 |
| DGL638 | 1.02 | 0.22 | 0.05 | 0.23 | 0.22 | 0.17 |
| DGL639 | 1.39 | 0.46 | 0.09 | 0.49 | 0.35 | 0.34 |
| DGL640 | 1.40 | 0.47 | 0.09 | 0.43 | 0.30 | 0.30 |
| DGL641 | 0.83 | 0.15 | 0.07 | 0.90 | 0.43 | 0.33 |
| DGL642 | 0.50 | 0.09 | 0.08 | 0.51 | 0.55 | 0.53 |
| DGL643 | 0.71 | 0.13 | 0.04 | 0.26 | 0.23 | 0.3 |
| DGL644 | 0.54 | 0.10 | 0.06 | 0.17 | 0.20 | 0.23 |
| DGL645 | 0.59 | 0.13 | 0.07 | 0.16 | 0.21 | 0.23 |
| DGL646 | 0.80 | 0.15 | 0.06 | 0.34 | 0.22 | 0.25 |
| DGL647 | 0.84 | 0.16 | 0.07 | 1.90 | 0.51 | 0.25 |
| DGL648 | 0.80 | 0.17 | 0.08 | 0.77 | 0.33 | 0.24 |
| DGL649 | 0.81 | 0.18 | 0.07 | 0.76 | 0.32 | 0.30 |
| DGL650 | 0.65 | 0.15 | 0.08 | 0.79 | 0.49 | 0.54 |

Example 6. DiscoverX Data for Variants

The bispecific antibodies were screened for agonist activity as described in Example 2. Data reported (RLU) is the average of two replicates at the highest concentration tested. Antibodies were compared to the natural ligand, BMP9 on every plate.

TABLE 9

Agonist activity of exemplary bispecific antibodies

| DGL | Description | Emax (RLU) | % Emax BMP9 |
|---|---|---|---|
| DGL621 | ALK1_platform_1_B_8 | 1091500 | 30 |
| DGL622 | ALK1_platform_2_B_8 | 936000 | 25 |
| DGL623 | ALK1_platform_3_B_8 | 1108500 | 30 |
| DGL624 | ALK1_platform_4_B_36 | 1550500 | 42 |
| DGL625 | ALK1_platform_5_B_36 | 615000 | 17 |
| DGL626 | ALK1_platform_6_B_36 | 258000 | 7 |
| DGL627 | ALK1_platform_7_B_36 | 502500 | 14 |
| DGL628 | ALK1_platform_8_B_36 | 883500 | 24 |
| DGL629 | ALK1_platform_9_B_36 | 424500 | 12 |
| DGL630 | ALK1_platform_10_B_8 | 168000 | 5 |
| DGL631 | ALK1_platform_11_B_8 | 470000 | 13 |
| DGL632 | ALK1_platform_12_B_8 | 130000 | 4 |
| DGL633 | ALK1_platform_13_B_8 | 585800 | 32 |
| DGL634 | ALK1_platform_14_B_8 | 288300 | 16 |
| DGL635 | BMPRII_platform_1_B29 | 2614800 | 141 |
| DGL636 | BMPRII_platform_2_B29 | 361800 | 20 |
| DGL637 | BMPRII_platform_3_B29 | 382300 | 21 |
| DGL638 | BMPRII_platform_4_B29 | 1474800 | 80 |
| DGL639 | BMPRII_platform_5_B29 | 752300 | 41 |
| DGL640 | BMPRII_platform_6_B29 | 1532800 | 83 |
| DGL641 | BMPRII_platform_7_B1 | 1407800 | 76 |
| DGL642 | BMPRII_platform_8_B1 | 255300 | 14 |
| DGL643 | BMPRII_platform_9_B1 | 246300 | 13 |

TABLE 9-continued

Agonist activity of exemplary bispecific antibodies

| DGL | Description | Emax (RLU) | % Emax BMP9 |
|---|---|---|---|
| DGL644 | BMPRII_platform_10_B1 | 153400 | 8 |
| DGL645 | BMPRII_platform_11_B1 | 352650 | 19 |
| DGL646 | BMPRII_platform_12_B1 | 332700 | 18 |
| DGL647 | BMPRII_platform_13_B1 | 1455250 | 79 |
| DGL648 | BMPRII_platform_14v2_B1 | 1448250 | 78 |
| DGL649 | BMPRII_platform_15_B1 | 648250 | 35 |
| DGL650 | BMPRII_platform_16_B1 | 801250 | 43 |
| DGL651 | ALK1_platform_15_B_36 | 17617667 | 72 |
| DGL652 | ALK1_platform_16_B_36 | 1484266.667 | 60 |
| DGL653 | ALK1_platform_17_B_36 | 1433766.667 | 58 |
| DGL654 | BMPRII_platform_17_B29 | 1871266.667 | 76 |
| DGL655 | BMPRII_platform_18_B29 | 437266.6667 | 18 |
| DGL656 | BMPRII_platform_19_B29 | 1355266.667 | 55 |
| DGL730 | BMPRII_platform_20_B36_Alk1_scFv29_BsAb | 342493.75 | 22 |
| DGL731 | BMPRII_platform_21_B36_Alk1_scFv29_BsAb | 1559493.75 | 100 |
| DGL732 | BMPRII_platform_22_B36_Alk1_scFv29_BsAb | 844993.75 | 54 |
| DGL733 | BMPRII_platform_23_B36_Alk1_scFv29_BsAb | 1654493.75 | 106 |
| DGL734 | BMPRII_platform_24 B36_Alk1_scFv29_BsAb | 216993.75 | 14 |
| DGL735 | BMPRII_platform_25_B36_Alk1_scFv29_BsAb | 1062493.75 | 68 |
| DGL736 | ALK1_platform_18_B29_BMPRII_scFv36_BsAb | 1131493.75 | 73 |
| DGL737 | ALK1_platform_19_B29_BMPRII_scFv36_BsAb | 1200493.75 | 77 |
| DGL860 | ALK1_platform_15_BMPRII_Platform_17 | 2011075 | 79 |
| DGL861 | ALK1_platform_16_BMPRII_Platform_17 | 2084075 | 81 |
| DGL862 | ALK1_platform_17_BMPRII_Platform_17 | 2131075 | 83 |
| DGL863 | ALK1_platform_15_BMPRII_Platform_18 | 603575 | 24 |
| DGL864 | ALK1_platform_16_BMPRII_Platform_18 | 553075 | 22 |
| DGL865 | ALK1_platform_17_BMPRII_Platform_18 | 755075 | 30 |
| DGL866 | ALK1_platform_15_BMPRII_Platform_19 | 1147575 | 45 |
| DGL867 | ALK1_platform_16_BMPRII_Platform_19 | 1479075 | 58 |
| DGL868 | ALK1_platform_17_BMPRII_Platform_19 | 1707075 | 67 |

TABLE 10

Agonist activity of exemplary bispecific antibodies

| DGL | Description | Emax (RLU) | % Emax BMP9 |
|---|---|---|---|
| DGL869 | scFv29_L1_H3_CH | 1436575 | 56 |
| DGL870 | scFv29_L2_H3_CH | 1423575 | 56 |
| DGL871 | scFv29_L3_H3_CH | 1593075 | 62 |
| DGL872 | scFv29_L4_H3_CH | 1456075 | 57 |
| DGL873 | scFv29_L1_CH | 1545575 | 60 |
| DGL874 | scFv29_L2_CH | 1558075 | 61 |
| DGL875 | scFv29_L3_CH | 1656575 | 65 |
| DGL876 | scFv29_L4_CH | 1568575 | 61 |
| DGL877 | scFv36_L1_CH | 1950075 | 76 |
| DGL878 | scFv36_L2_CH | 1880075 | 73 |
| DGL879 | scFv36_L3_CH | 1806575 | 71 |
| DGL880 | scFv36_L4_CH | 1682575 | 66 |

TABLE 11

Agonist activity of exemplary bispecific antibodies

| DGL | Description | Emax (RLU) | % Emax BMP9 |
|---|---|---|---|
| DGL893 | Alk_platform_15_BMPRII_platform_21 | 551775 | 20 |
| DGL894 | Alk_platform_15_BMPRII_platform_22 | 383225 | 14 |
| DGL895 | Alk_platform_15_BMPRII_platform_23 | 715275 | 26 |
| DGL896 | Alk_platform_15_BMPRII_platform_25 | 281725 | 10 |

TABLE 11-continued

Agonist activity of exemplary bispecific antibodies

| DGL | Description | Emax (RLU) | % Emax BMP9 |
|---|---|---|---|
| DGL897 | Alk1_platform_16_BMPRII_platform_21 | 700775 | 26 |
| DGL898 | Alk1_platform_16_BMPRII_platform_22 | 509125 | 19 |
| DGL899 | Alk1_platform_16_BMPRII_platform_23 | 812275 | 30 |
| DGL900 | Alk1_platform_16_BMPRII_platform_25 | 332675 | 12 |
| DGL901 | Alk1_platform_17_BMPRII_platform_21 | 799775 | 29 |
| DGL902 | Alk1_platform_17_BMPRII_platform_22 | 528925 | 19 |
| DGL903 | Alk1_platform_17_BMPRII_platform_23 | 917775 | 34 |
| DGL904 | Alk1_platform_17_BMPRII_platform_25 | 474575 | 17 |
| DGL905 | Alk1_platform_18_BMPRII_platform_17 | 972275 | 36 |
| DGL906 | Alk1_platform_18_BMPRII_platform_18 | −41075 | −2 |
| DGL907 | Alk1_platform_18_BMPRII_platform_19 | 320825 | 12 |
| DGL908 | Alk1_platform_18_BMPRII_platform_21 | 1234775 | 45 |
| DGL909 | Alk1_platform_18_BMPRII_platform_22 | 663275 | 24 |
| DGL910 | Alk1_platform_18_BMPRII_platform_23 | 1328775 | 49 |
| DGL911 | Alk1_platform_18_BMPRII_platform_25 | 520775 | 19 |
| DGL912 | Alk1_platform_19_BMPRII_platform_17 | 909775 | 33 |
| DGL913 | Alk1_platform_19_BMPRII_platform_18 | 8425 | 0 |
| DGL914 | Alk1_platform_19_BMPRII_platform_19 | 556775 | 20 |
| DGL915 | Alk1_platform_19_BMPRII_platform_21 | 123975 | 5 |
| DGL916 | Alk1_platform_19_BMPRII_platform_22 | 1114275 | 41 |
| DGL917 | Alk1_platform_19_BMPRII_platform_23 | 469475 | 17 |
| DGL918 | Alk1_platform_19_BMPRII_platform_25 | 1243275 | 46 |

Example 7. Engineering of scFv Containing Bispecific Agonist Antibodies with Optimized Hinges Agonist activity of heteromeric antibodies with modified hinges identified by the DIAGONAL platform was also tested. A variant of DGL288, DGL809, was designed with hinge 1. DGL809 was designed, expressed, and purified as described above. Heteromeric antibodies were tested using the DiscoverX assay. DGL809 outperformed the parental DGL288, as seen in Table 12 (average values across two different experiment is shown), which shows the activity level relative to BMP9 at 100 nM antibody concentration.

TABLE 12

Agonist activity of exemplary bispecific antibodies

| DGL | Hinge | % Emax BMP9 |
|---|---|---|
| DGL288 | Hinge 6 | 72 |
| DGL809 | Hinge 1 | 79 |

Example 8. Engineering Bispecific Agonist Antibodies with Optimized Linkers in DVD-Ig Format An alternative way to rigidify agonist antibodies is to optimize the linkers between IgG and additional variable domains in the DVD-Ig format. To pursue this route, the agonist activity of heteromeric antibodies with modified VH to IgG hinge linkers identified by the DIAGONAL platform was tested. Variants of DGL292, DGL810, DGL811, and DGL812, were designed, expressed, and purified as described above. Heteromeric antibodies were tested using the DiscoverX assay where variants outperformed the parental DGL292, as seen in Table 14 (average values across two different experiment is shown).

TABLE 13

Linkers used in DVD-Ig format

| DGL | VH1-VH2 linker | VL1-VL2 linker |
|---|---|---|
| DGL292 | PAPNLLGGP (SEQ ID NO: 157) | PAPNLLGGP (SEQ ID NO: 157) |
| DGL810 | PLAP (SEQ ID NO: 2) | PLAP (SEQ ID NO: 2) |
| DGL811 | PLAP (SEQ ID NO: 2) | PAPNLLGGP (SEQ ID NO: 157) |
| DGL812 | PAPNLLGGP (SEQ ID NO: 157) | PLAP (SEQ ID NO: 2) |

TABLE 14

Agonist activity in DVD-Ig format

| DGL | % Emax BMP9 |
|---|---|
| DGL292 | 57 |
| DGL810 | 76 |
| DGL811 | 73 |
| DGL812 | 62 |

TABLE 15

Sequences

| ID | Sequence |
|---|---|
| DGL288 | EVQLLESGGGLVQPGGSLRLSCAASGFTFSDYYMTWIRQAPGKGLEWVS SISGGSTYYADSRKGRFTISRDNSENTLYLQMNSLRAEDTAVYYCARDF GVAGWFGQYGMDVWGQGTLVTVSSGGGGSGGGGSGGGGSQSVLTQPPSA SGTPGQRVTISCTGSSSNIGAGYDVHWYQQLPGTAPKLLIYRSNQRPSG VPDRFSGSKSGTSASLAISGLRSEDEADYYCSSYAGNYNLVFGGGTKLT VLDKGPSVFPLAPEPKSSEVQLLESGGGLVQPGGSLRLSCAASGFTFSS YAMSWVRQAPGKGLEWVANINQDGSEKNYVDSMRGRFTISRDNSKNTLY LQMNSLRAEDTAVYYCAREFDYWGQGTLVTVSSGGGGSGGGGSGGGGS QSVLAQPPSASGTPGQRVTISCSGSSSNIGSNYVYWYQQLPGTAPKLLI YGNNKRPSGVPDRFSGSKSGTSASLAISGLRSEDEADYYCAAWDDSLNG RVFGGGTKLTVLDKTHTCPPCPAPEAAGAPSVFLFPPKPKDTLMISRTP EVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSF FLYSKLTVDKSRWQQGNVFSCSVMHEALHNHYTQKSLSLSPG (SEQ ID NO: 147) |
| DGL809 | EVQLLESGGGLVQPGGSLRLSCAASGFTFSDYYMTWIRQAPGKGLEWVS SISGGSTYYADSRKGRFTISRDNSENTLYLQMNSLRAEDTAVYYCARDF GVAGWFGQYGMDVWGQGTLVTVSSGGGGSGGGGSGGGGSQSVLTQPPSA SGTPGQRVTISCTGSSSNIGAGYDVHWYQQLPGTAPKLLIYRSNQRPSG VPDRFSGSKSGTSASLAISGLRSEDEADYYCSSYAGNYNLVFGGGTKLT VLDKGPSVFPLAPEPKSSEVQLLESGGGLVQPGGSLRLSCAASGFTFSS YAMSWVRQAPGKGLEWVANINQDGSEKNYVDSMRGRFTISRDNSKNTLY LQMNSLRAEDTAVYYCAREFDYWGQGTLVTVSSGGGGSGGGGSGGGGS QSVLAQPPSASGTPGQRVTISCSGSSSNIGSNYVYWYQQLPGTAPKLLI YGNNKRPSGVPDRFSGSKSGTSASLAISGLRSEDEADYYCAAWDDSLNG RVFGGGTKLTVLCPPCPAPEAAGAPSVFLFPPKPKDTLMISRTPEVTCV |

TABLE 15-continued

| | Sequences |
|---|---|

| ID | Sequence |
|---|---|

VVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTK
NQVSLTCLVKGFYPSDIAVEWESNGQPENNYKTTPPVLDSDGSFFLYSK
LTVDKSRWQQGNVFSCSVMHEALHNHYTQKSLSLSPG (SEQ ID NO:
148)

DGL292_HC  EVQLLESGGGLVQPGGSLRLSCAASGFTFSDYYMTWIRQAPGKGLEWVS
SISGGSTYYADSRKGRFTISRDNSENTLYLQMNSLRAEDTAVYYCARDF
GVAGWFGQYGMDVWGQGTLVTVSSPAPNLLGGPEVQLLESGGGLVQPGG
SLRLSCAASGFTFSSYAMSWVRQAPGKGLEWVANINQDGSEKNYVDSMR
GRFTISRDNSKNTLYLQMNSLRAEDTAVYYCAREFDYWGQGTLVTVTSS
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPEAAGAPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPG (SEQ ID NO:
149)

DGL292_LC  QSVLTQPPSASGTPGQRVTISCTGSSSNIGAGYDVHWYQQLPGTAPKLL
IYRSNQRPSGVPDRFSGSKSGTSASLAISGLRSEDEADYYCSSYAGNYN
LVFGGGTKLTVLPAPNLLGGPQSVLAQPPSASGTPGQRVTISCSGSSSN
IGSNYVYWYQQLPGTAPKLLIYGNNKRPSGVPDRFSGSKSGTSASLAIS
GLRSEDEADYYCAAWDDSLNGRVFGGGTKLTVLGQPKAAPSVTLFPPSS
EELQANKATLVCLISDFYPGAVTVAWKADSSPVKAGVETTTPSKQSNNK
YAASSYLSLTPEQWKSHRSYSCQVTHEGSTVEKTVAPTECS (SEQ ID
NO: 150)

DGL810_HC  EVQLLESGGGLVQPGGSLRLSCAASGFTFSDYYMTWIRQAPGKGLEWVS
SISGGSTYYADSRKGRFTISRDNSENTLYLQMNSLRAEDTAVYYCARDF
GVAGWFGQYGMDVWGQGTLVTVSSPLAPEVQLLESGGGLVQPGGSLRLS
CAASGFTFSSYAMSWVRQAPGKGLEWVANINQDGSEKNYVDSMRGRFTI
SRDNSKNTLYLQMNSLRAEDTAVYYCAREFDYWGQGTLVTVTSSASTKG
PSVFPLAPSSKSTSGGTAALGCLVKDYFPEPVTVSWNSGALTSGVHTFP
AVLQSSGLYSLSSVVTVPSSSLGTQTYICNVNHKPSNTKVDKKVEPKSC
DKTHTCPPCPAPEAAGAPSVFLFPPKPKDTLMISRTPEVTCVVVDVSHE
DPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSR
WQQGNVFSCSVMHEALHNHYTQKSLSLSPG (SEQ ID NO: 151)

DGL810_LC  QSVLTQPPSASGTPGQRVTISCTGSSSNIGAGYDVHWYQQLPGTAPKLL
IYRSNQRPSGVPDRFSGSKSGTSASLAISGLRSEDEADYYCSSYAGNYN
LVFGGGTKLTVLPLAPQSVLAQPPSASGTPGQRVTISCSGSSSNIGSNY
VYWYQQLPGTAPKLLIYGNNKRPSGVPDRFSGSKSGTSASLAISGLRSE
DEADYYCAAWDDSLNGRVFGGGTKLTVLGQPKAAPSVTLFPPSSEELQA
NKATLVCLISDFYPGAVTVAWKADSSPVKAGVETTTPSKQSNNKYAASS
YLSLTPEQWKSHRSYSCQVTHEGSTVEKTVAPTECS (SEQ ID NO:
152)

DGL811_HC  EVQLLESGGGLVQPGGSLRLSCAASGFTFSDYYMTWIRQAPGKGLEWVS
SISGGSTYYADSRKGRFTISRDNSENTLYLQMNSLRAEDTAVYYCARDF
GVAGWFGQYGMDVWGQGTLVTVSSPLAPEVQLLESGGGLVQPGGSLRLS
CAASGFTFSSYAMSWVRQAPGKGLEWVANINQDGSEKNYVDSMRGRFTI
SRDNSKNTLYLQMNSLRAEDTAVYYCAREFDYWGQGTLVTVTSSASTKG
PSVFPLAPSSKSTSGGTAALGCLVKDYFPEPVTVSWNSGALTSGVHTFP
AVLQSSGLYSLSSVVTVPSSSLGTQTYICNVNHKPSNTKVDKKVEPKSC
DKTHTCPPCPAPEAAGAPSVFLFPPKPKDTLMISRTPEVTCVVVDVSHE
DPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSR
WQQGNVFSCSVMHEALHNHYTQKSLSLSPG (SEQ ID NO: 153)

DGL811_LC  QSVLTQPPSASGTPGQRVTISCTGSSSNIGAGYDVHWYQQLPGTAPKLL
IYRSNQRPSGVPDRFSGSKSGTSASLAISGLRSEDEADYYCSSYAGNYN
LVFGGGTKLTVLPAPNLLGGPQSVLAQPPSASGTPGQRVTISCSGSSSN
IGSNYVYWYQQLPGTAPKLLIYGNNKRPSGVPDRFSGSKSGTSASLAIS
GLRSEDEADYYCAAWDDSLNGRVFGGGTKLTVLGQPKAAPSVTLFPPSS
EELQANKATLVCLISDFYPGAVTVAWKADSSPVKAGVETTTPSKQSNNK
YAASSYLSLTPEQWKSHRSYSCQVTHEGSTVEKTVAPTECS (SEQ ID
NO: 154)

DGL812_HC  EVQLLESGGGLVQPGGSLRLSCAASGFTFSDYYMTWIRQAPGKGLEWVS
SISGGSTYYADSRKGRFTISRDNSENTLYLQMNSLRAEDTAVYYCARDF
GVAGWFGQYGMDVWGQGTLVTVSSPAPNLLGGPEVQLLESGGGLVQPGG

TABLE 15-continued

Sequences

| ID | Sequence |
|---|---|
| | SLRLSCAASGFTFSSYAMSWVRQAPGKGLEWVANINQDGSEKNYVDSMR<br>GRFTISRDNSKNTLYLQMNSLRAEDTAVYYCAREFDYWGQGTLVTVTSS<br>ASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKKV<br>EPKSCDKTHTCPPCPAPEAAGAPSVFLFPPKPKDTLMISRTPEVTCVVV<br>DVSHEDPEVKFNWYVDGVEVHNAKTKPREEQYNSTYRVVSVLTVLHQDW<br>LNGKEYKCKVSNKALPAPIEKTISKAKGQPREPQVYTLPPSRDELTKNQ<br>VSLTCLVKGFYPSDIAVEWESNGQPENNYKTTPPVLDSDGSFFLYSKLT<br>VDKSRWQQGNVFSCSVMHEALHNHYTQKSLSLSPG (SEQ ID NO:<br>155) |
| DGL812_LC | QSVLTQPPSASGTPGQRVTISCTGSSSNIGAGYDVHWYQQLPGTAPKLL<br>IYRSNQRPSGVPDRFSGSKSGTSASLAISGLRSEDEADYYCSSYAGNYN<br>LVFGGGTKLTVLPLAPQSVLAQPPSASGTPGQRVTISCSGSSSNIGSNY<br>VYWYQQLPGTAPKLLIYGNNKRPSGVPDRFSGSKSGTSASLAISGLRSE<br>DEADYYCAAWDDSLNGRVFGGGTKLTVLGQPKAAPSVTLFPPSSEELQA<br>NKATLVCLISDFYPGAVTVAWKADSSPVKAGVETTTPSKQSNNKYAASS<br>YLSLTPEQWKSHRSYSCQVTHEGSTVEKTVAPTECS (SEQ ID NO:<br>156) |

TABLE 16

Sequences

| ID | Sequence |
|---|---|
| CH1118_HC | EVQLLESGGGLVQPGGSLRLSCAASGFTFSDYYMTWIRQAPGKGLEWVSSI<br>SGGSTYYADSRKGRFTISRDNSENTLYLQMNSLRAEDTAVYYCARDFGVAG<br>WFGQYGMDVWGQGTLVTVSSPAPNLLGGPEVQLLESGGGLVQPGGSLRLSC<br>AASGFTFSSYAMSWVRQAPGKGLEWVANINQDGSEKNYVDSMRGRFTISRD<br>NSKNTLYLQMNSLRAEDTAVYYCAREFDYWGQGTLVTVSSASTKGPSVFPL<br>APSSKSTSGGTAALGCLVKDYFPEPVTVSWNSGALTSGVHTFPAVLQSSGL<br>YSLSSVVTVPSSSLGTQTYICNVNHKPSNTKVDKKVEPKSCDKTHTCPPCP<br>APEAAGAPSVFLFPPKPKDTLYITREPEVTCVVVDVSHEDPEVKFNWYVDG<br>VEVHNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVEWES<br>NGQPENNYKTTPPVLDSDGSFFLYSKLTVDKSRWQQGNVFSCSVMHEALHN<br>HYTQKSLSLSPG (SEQ ID NO: 136) |
| CH1119_HC<br>(DGL945<br>HC) | EVQLLESGGGLVQPGGSLRLSCAASGFTFSDYYMTWIRQAPGKGLEWVSSI<br>SGGSTYYADSRKGRFTISRDNSENTLYLQMNSLRAEDTAVYYCARDFGVAG<br>WFGQYGMDVWGQGTLVTVSSPLAPEVQLLESGGGLVQPGGSLRLSCAASGF<br>TFSSYAMSWVRQAPGKGLEWVANINQDGSEKNYVDSMRGRFTISRDNSKNT<br>LYLQMNSLRAEDTAVYYCAREFDYWGQGTLVTVSSASTKGPSVFPLAPSSK<br>STSGGTAALGCLVKDYFPEPVTVSWNSGALTSGVHTFPAVLQSSGLYSLSS<br>VVTVPSSSLGTQTYICNVNHKPSNTKVDKKVEPKSCDKTHTCPPCPAPEAA<br>GAPSVFLFPPKPKDTLYITREPEVTCVVVDVSHEDPEVKFNWYVDGVEVHN<br>AKTKPREEQYNSTYRVVSVLTVLHQDWLNGKEYKCKVSNKALPAPIEKTIS<br>KAKGQPREPQVYTLPPSRDELTKNQVSLTCLVKGFYPSDIAVEWESNGQPE<br>NNYKTTPPVLDSDGSFFLYSKLTVDKSRWQQGNVFSCSVMHEALHNHYTQK<br>SLSLSPG (SEQ ID NO: 137) |
| CH1120_HC<br>(DGL946<br>HC) | EVQLLESGGGLVQPGGSLRLSCAASGFTFSDYYMNWIRQAPGKGLEWVSSI<br>SGGSTYYADSVKGRFTISRDNSENTLYLQMNSLRAEDTAVYYCARDFGVAG<br>WFGQFGMDVWGQGTLVTVSSPLAPEVQLLESGGGLVQPGGSLRLSCAASGF<br>TFSSYWMSWVRQAPGKGLEWVANIKQDGSEKNYVDSMRGRFTISRDNSKNT<br>LYLQMNSLRAEDTAVYYCAREYDYWGQGTLVTVSSASTKGPSVFPLAPSSK<br>STSGGTAALGCLVKDYFPEPVTVSWNSGALTSGVHTFPAVLQSSGLYSLSS<br>VVTVPSSSLGTQTYICNVNHKPSNTKVDKKVEPKSCDKTHTCPPCPAPEAA<br>GAPSVFLFPPKPKDTLYITREPEVTCVVVDVSHEDPEVKFNWYVDGVEVHN<br>AKTKPREEQYNSTYRVVSVLTVLHQDWLNGKEYKCKVSNKALPAPIEKTIS<br>KAKGQPREPQVYTLPPSRDELTKNQVSLTCLVKGFYPSDIAVEWESNGQPE<br>NNYKTTPPVLDSDGSFFLYSKLTVDKSRWQQGNVFSCSVMHEALHNHYTQK<br>SLSLSPG (SEQ ID NO: 138) |
| CH1121_HC<br>(DGL947<br>HC) | EVQLLESGGGLVQPGGSLRLSCAASGFTFSDYYMNWIRQAPGKGLEWVSSI<br>SGGSTYYADSVKGRFTISRDNSENTLYLQMNSLRAEDTAVYYCARDFGVAG<br>WFGQFGMDVWGQGTLVTVSSPLAPEVQLLESGGGLVQPGGSLRLSCAASGF<br>TFSSYWMSWVRQAPGKGLEWVANINQDGSEKYYVDSMRGRFTISRDNSKNT<br>LYLQMNSLRAEDTAVYYCAREYDYWGQGTLVTVSSASTKGPSVFPLAPSSK<br>STSGGTAALGCLVKDYFPEPVTVSWNSGALTSGVHTFPAVLQSSGLYSLSS<br>VVTVPSSSLGTQTYICNVNHKPSNTKVDKKVEPKSCDKTHTCPPCPAPEAA<br>GAPSVFLFPPKPKDTLYITREPEVTCVVVDVSHEDPEVKFNWYVDGVEVHN |

TABLE 16-continued

Sequences

| ID | Sequence |
|---|---|

AKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQK
SLSLSPG (SEQ ID NO: 139)

CH1122_HC
(DGL948
HC)

EVQLLESGGGLVQPGGSLRLSCAASGFTFSDYYMNWIRQAPGKGLEWVSSI
SGGSTYYADSVKGRFTISRDNSENTLYLQMNSLRAEDTAVYYCARDFGVAG
WFGQFGMDVWGQGTLVTVSSPLAPEVQLLESGGGLVQPGGSLRLSCAASGF
TFSSYWMSWVRQAPGKGLEWVANIKQDGSEKNYVDSMRGRFTISRDNSKNT
LYLQMNSLRAEDTAVYYCAREFDFWGQGTLVTVSSASTKGPSVFPLAPSSK
STSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPEAA
GAPSVFLFPPKPKDTLYITREPEVTCVVVDVSHEDPEVKFNWYVDGVEVHN
AKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQK
SLSLSPG (SEQ ID NO: 140)

CH1123_HC
(DGL949
HC)

EVQLLESGGGLVQPGGSLRLSCAASGFTFSDYYMNWIRQAPGKGLEWVSSI
SGGSTYYADSVKGRFTISRDNSENTLYLQMNSLRAEDTAVYYCARDFGVAG
WFGYYGMDVWGQGTLVTVSSPLAPEVQLLESGGGLVQPGGSLRLSCAASGF
TFSSYWMSWVRQAPGKGLEWVANIKQDGSEKNYVDSMRGRFTISRDNSKNT
LYLQMNSLRAEDTAVYYCAREFDFWGQGTLVTVSSASTKGPSVFPLAPSSK
STSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPEAA
GAPSVFLFPPKPKDTLYITREPEVTCVVVDVSHEDPEVKFNWYVDGVEVHN
AKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQK
SLSLSPG (SEQ ID NO: 141)

CH1247
(DGL1146
HC)

EVQLLESGGGLVQPGGSLRLSCAASGFTFSDYYMTWIRQAPGKGLEWVSSI
SGGSTYYADSRKGRFTISRDNSENTLYLQMNSLRAEDTAVYYCARDFGVAG
WFGQYGMDVWGQGTLVTVSSPLAPEVQLLESGGGLVQPGGSLRLSCAASGF
TFSSYAMSWVRQAPGKGLEWVANINQDGSEKNYVDSMRGRFTISRDNSKNT
LYLQMNSLRAEDTAVYYCAREFDYWGQGTLVTVSSASTKGPSVFPLAPSSK
STSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPEAA
GAPSVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPE
NNYKTTPPVLDSDGSFFLYSKLTVDKSRWQQGNVFSCSVLHEALHSHYTQK
SLSLSPG (SEQ ID NO: 142)

CH385_LC

QSVLTQPPSASGTPGQRVTISCTGSSSNIGAGYDVHWYQQLPGTAPKLLIY
RSNQRPSGVPDRFSGSKSGTSASLAISGLRSEDEADYYCSSYAGNYNLVFG
GGTKLTVLPAPNLLGGPQSVLAQPPSASGTPGQRVTISCGSSSNIGSNYV
YWYQQLPGTAPKLLIYGNNKRPSGVPDRFSGSKSGTSASLAISGLRSEDEA
DYYCAAWDDSLNGRVFGGGTKLTVLGQPKAAPSVTLFPPSSEELQANKATL
VCLISDFYPGAVTVAWKADSSPVKAGVETTTPSKQSNNKYAASSYLSLTPE
QWKSHRSYSCQVTHEGSTVEKTVAPTECS (SEQ ID NO: 143)

CH1126_LC

QSVLTQPPSASGTPGQRVTISCTGSSSNIGAGYDVHWYQQLPGTAPKLLIY
RSNQRPSGVPDRFSGSKSGTSASLAISGLRSEDEADYYCSSYAGLYNLVFG
GGTKLTVLPLAPQSVLAQPPSASGTPGQRVTISCGSSSNIGSNYVYWYQQ
LPGTAPKLLIYGNNKRPSGVPDRFSGSKSGTSASLAISGLRSEDEADYYCA
AWDDSLSGRVFGGGTKLTVLGQPKAAPSVTLFPPSSEELQANKATLVCLIS
DFYPGAVTVAWKADSSPVKAGVETTTPSKQSNNKYAASSYLSLTPEQWKSH
RSYSCQVTHEGSTVEKTVAPTECS (SEQ ID NO: 144)

CH1127_LC

EVQLLESGGGLVQPGGSLRLSCAASGFTFSDYYMTWIRQAPGKGLEWVSSI
SGGSTYYADSRKGRFTISRDNSENTLYLQMNSLRAEDTAVYYCARDFGVAG
WFGQYGMDVWGQGTLVTVSSPLAPQSVLAQPPSASGTPGQRVTISCGSSS
NIGSNYVYWYQQLPGTAPKLLIYGNNKRPSGVPDRFSGSKSGTSASLAISG
LRSEDEADYYCAAWDDSLSGRVFGGGTKLTVLGQPKAAPSVTLFPPSSEEL
QANKATLVCLISDFYPGAVTVAWKADSSPVKAGVETTTPSKQSNNKYAASS
YLSLTPEQWKSHRSYSCQVTHEGSTVEKTVAPTECS (SEQ ID NO:
145)

TABLE 16-continued

| Sequences | |
|---|---|
| ID | Sequence |
| CH943_LC (DGL945 LC, DGL946 LC, DGL947 LC, DGL948 LC, DGL949 LC, DGL1146 LC) | QSVLTQPPSASGTPGQRVTISCTGSSSNIGAGYDVHWYQQLPGTAPKLLIY RSNQRPSGVPDRFSGSKSGTSASLAISGLRSEDEADYYCSSYAGNYNLVFG GGTKLTVLPLAPQSVLAQPPSASGTPGQRVTISCSGSSSNIGSNYVYWYQQ LPGTAPKLLIYGNNKRPSGVPDRFSGSKSGTSASLAISGLRSEDEADYYCA AWDDSLNGRVFGGGTKLTVLGQPKAAPSVTLFPPSSEELQANKATLVCLIS DFYPGAVTVAWKADSSPVKAGVETTTPSKQSNNKYAASSYLSLTPEQWKSH RSYSCQVTHEGSTVEKTVAPTECS (SEQ ID NO: 146) |

TABLE 17

| Sequences - CDRs | |
|---|---|
| ID | Sequence |
| DGL945/DGL1146 ALK1 HCDR1 | SYAMS(SEQ ID NO: 158) |
| DGL945/DGL1146 ALK1 HCDR2 | NINQDGSEKNYVDSMRG(SEQ ID NO: 159) |
| DGL945/DGL1146 ALK1 HCDR3 | EFDY(SEQ ID NO: 160) |
| DGL945/DGL1146 BMPRII HCDR1 | DYYMT(SEQ ID NO: 169) |
| DGL945/DGL 1146 BMPRII HCDR2 | SISGGSTYYADSRKG(SEQ ID NO: 170) |
| DGL945/DGL1146 BMPRII HCDR3 | DFGVAGWFGQYGMDV(SEQ ID NO: 171) |
| DGL947 ALK1 HCDR1 | SYWMS(SEQ ID NO: 164) |
| DGL947 ALK1 HCDR2 | NINQDGSEKYYVDSMRG(SEQ ID NO: 165) |
| DGL947 ALK1 HCDR3 | EYDY(SEQ ID NO: 166) |
| DGL947 BMPRII HCDR1 | DYYMN (SEQ ID NO: 175) |
| DGL947 BMPRII HCDR2 | SISGGSTYYADSVKG(SEQ ID NO: 176) |

TABLE 17-continued

| Sequences - CDRs | |
|---|---|
| ID | Sequence |
| DGL947 BMPRII HCDR3 | DFGVAGWFGQFGMDV(SEQ ID NO: 177) |
| DGL949 ALK1 HCDR1 | SYWMS(SEQ ID NO: 164) |
| DGL949 ALK1 HCDR2 | NIKQDGSEKNYVDSMRG(SEQ ID NO: 167) |
| DGL949 ALK1 HCDR3 | EFDF(SEQ ID NO: 168) |
| DGL949 BMPRII HCDR1 | DYYMN(SEQ ID NO: 175) |
| DGL949 BMPRII HCDR2 | SISGGSTYYADSVKG(SEQ ID NO: 176) |
| DGL949 BMPRII HCDR3 | DFGVAGWFGYYGMDV(SEQ ID NO: 179) |
| CH943 ALK1 LCDR1 | SGSSSNIGSNYVY (SEQ ID NO: 161) |
| CH943 ALK1 LCDR2 | GNNKRPS(SEQ ID NO: 162) |
| CH943 ALK1 LCDR3 | AAWDDSLNGRV(SEQ ID NO: 163) |
| CH943 BMPRII LCDR1 | TGSSSNIGAGYDVH(SEQ ID NO: 172) |
| CH943 BMPRII LCDR2 | RSNQRPS(SEQ ID NO: 173) |
| CH943 BMPRII LCDR3 | SSYAGNYNLV(SEQ ID NO: 174) |

TABLE 17

| Sequences - VH/VL | |
|---|---|
| ID | Sequence |
| DGL945/DGL1146 ALK1 VH | EVQLLESGGGLVQPGGSLRLSCAASGFTFSSYAMSWVRQAPGKG LEWVANINQDGSEKNYVDSMRGRFTISRDNSKNTLYLQMNSLRA EDTAVYYCAREFDYWGQGTLVTVSS(SEQ ID NO: 180) |
| DGL945/DGL1146 ALK1 VL | QSVLAQPPSASGTPGQRVTISCSGSSSNIGSNYVYWYQQLPGTA PKLLIYGNNKRPSGVPDRFSGSKSGTSASLAISGLRSEDEADYY CAAWDDSLNGRVFGGGTKLTVL(SEQ ID NO: 181) |
| DGL945/DGL1146 BMPRII VH | EVQLLESGGGLVQPGGSLRLSCAASGFTFSDYYMTWIRQAPGKG LEWVSSISGGSTYYADSRKGRFTISRDNSENTLYLQMNSLRAED TAVYYCARDFGVAGWFGQYGMDVWGQGTLVTVSS(SEQ ID NO: 184) |
| DGL945/DGL1146 BMPRII VL | QSVLTQPPSASGTPGQRVTISCTGSSSNIGAGYDVHWYQQLPGT APKLLIYRSNQRPSGVPDRFSGSKSGTSASLAISGLRSEDEADY YCSSYAGNYNLVFGGGTKLTVL(SEQ ID NO: 185) |

TABLE 17-continued

| Sequences - VH/VL | |
|---|---|
| ID | Sequence |
| DGL947 ALK1 VH | EVQLLESGGGLVQPGGSLRLSCAASGFTFSSYWMSWVRQAPGKG LEWVANINQDGSEKYYVDSMRGRFTISRDNSKNTLYLQMNSLRA EDTAVYYCAREYDYWGQGTLVTVSS (SEQ ID NO: 182) |
| DGL947 ALK1 VL | QSVLAQPPSASGTPGQRVTISCSGSSSNIGSNYVYWYQQLPGTA PKLLIYGNNKRPSGVPDRFSGSKSGTSASLAISGLRSEDEADYY CAAWDDSLNGRVFGGGTKLTVL (SEQ ID NO: 181) |
| DGL947 BMPRII VH | EVQLLESGGGLVQPGGSLRLSCAASGFTFSDYYMNWIRQAPGKG LEWVSSISGGSTYYADSVKGRFTISRDNSENTLYLQMNSLRAED TAVYYCARDFGVAGWFGQFGMDVWGQGTLVTVSS (SEQ ID NO: 186) |
| DGL947 BMPRII VL | QSVLTQPPSASGTPGQRVTISCTGSSSNIGAGYDVHWYQQLPGT APKLLIYRSNQRPSGVPDRFSGSKSGTSASLAISGLRSEDEADY YCSSYAGNYNLVFGGGTKLTVL (SEQ ID NO: 185) |
| DGL949 ALK1 VH | EVQLLESGGGLVQPGGSLRLSCAASGFTFSSYWMSWVRQAPGKG LEWVANIKQDGSEKNYVDSMRGRFTISRDNSKNTLYLQMNSLRA EDTAVYYCAREFDFWGQGTLVTVSS (SEQ ID NO: 183) |
| DGL949 ALK1 VL | QSVLAQPPSASGTPGQRVTISCSGSSSNIGSNYVYWYQQLPGTA PKLLIYGNNKRPSGVPDRFSGSKSGTSASLAISGLRSEDEADYY CAAWDDSLNGRVFGGGTKLTVL (SEQ ID NO: 181) |
| DGL949 BMPRII VH | EVQLLESGGGLVQPGGSLRLSCAASGFTFSDYYMNWIRQAPGKG LEWVSSISGGSTYYADSVKGRFTISRDNSENTLYLQMNSLRAED TAVYYCARDFGVAGWFGYYGMDVWGQGTLVTVSS (SEQ ID NO: 187) |
| DGL949 BMPRII VL | QSVLTQPPSASGTPGQRVTISCTGSSSNIGAGYDVHWYQQLPGT APKLLIYRSNQRPSGVPDRFSGSKSGTSASLAISGLRSEDEADY YCSSYAGNYNLVFGGGTKLTVL (SEQ ID NO: 185) |

Example 9. Screen for Agonistic Activity

The bispecific antibodies were screened for agonist activity. PathHunter U20s ALK-1/BMPR-2 dimerization assay was obtained from DiscoverX Corporation (93-0962C3). These cells use Enzyme Fragment Complementation (EFC) technology using β-galactosidase fragments to evaluate protein-protein interactions. Reporter cells were revived and cultured according to supplier's recommendations. Bispecific antibodies were compared to the natural ligands, BMP9 and BMP10.

To perform the assay, cells were detached and removed from the flask with cell detachment reagent (DiscoverX, 92-0009). Cells were spun at 300 g for four minutes and resuspended at a density of 250K/ml in assay plating media (DiscoverX 93-0563R22A). 20 μl of the suspension were plated/well of a 384 well plate and incubated at 37° C. for 24 hours. Bispecifics were made at 5× the final concentration. 12-point titrations using a 1:10 dilution were done to generate curves. 5 μl of the bispecific was added to the 384 well plate and incubated for three hours. 25 μl of flash detection reagent (DiscoverX, 93-0247) was added/well and the plates were read on a Verilux Skan at 60 minutes. Data was analyzed using PRISM. The results are represented below in Table 17. The data demonstrates that each of the tested bispecific antibodies had robust agonist activity.

TABLE 17

| Agonist activity in DiscoverX assay | |
|---|---|
| DGL | % $E_{max}$ BMP9 |
| DGL292 | 60 |
| DGL945 | 78 |

TABLE 17-continued

| Agonist activity in DiscoverX assay | |
|---|---|
| DGL | % $E_{max}$ BMP9 |
| DGL947 | 47 |
| DGL949 | 42 |
| DGL1146 | 78 |

Example 10. Measurement of Agonistic Activity in Endothelial Cells

HMEC-1 cells were plated at 30K cell/well in 96 well plate in 200 μl complete 10% MCDB growth media and incubated overnight. Approximately 16 hrs later, complete media was replaced with 50 μl serum free MCDB media. Cells were incubated for 4 hrs in serum free media before the addition of 2×DGL tools in 50 ul of serum free MCDB media. After 45 minutes, media was removed and cells were washed once with PBS before addition of lysis buffer from the ELISA kit. Lysates were then analyzed via ELISA following the manufacturer's instructions (Abcam pSMAD1 ELISA AB186036). 12-point titrations using a 1:10 dilution were done to generate curves. As a negative control, an anti-HEL antibody with LALA-PG mutations (BioXCell, CP149) was used. Data was analyzed using PRISM. Data reported is the average of two experiments. The results are represented below in Table 18. The data demonstrates that each of the tested bispecific antibodies had robust agonist activity, as measured through pSMAD1 levels.

TABLE 18

| Agonist activity in endothelial cells | |
| --- | --- |
| DGL | % Emax BMP9 |
| DGL292 | 69 |
| DGL945 | 77 |
| DGL947 | 55 |
| DGL949 | 35 |
| DGL1146 | 79 |

Example 11. Measurement of In Vivo Activity

Figure 4:
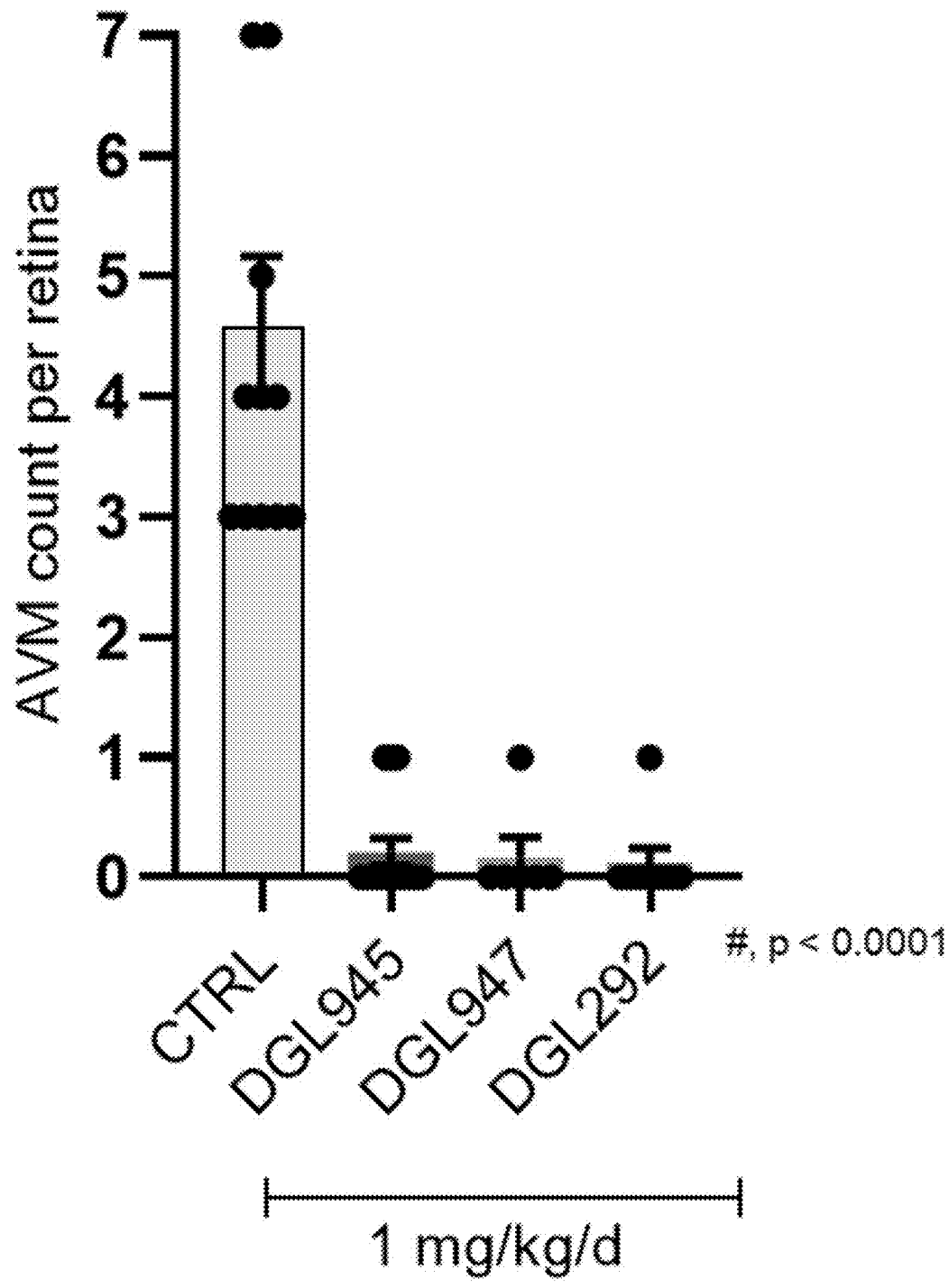
FIG. 4 is a graph depicting arteriovenous malformations (AVMs) in the retina in a HHT mouse model. Mice were treated with control (no bispecific antibody) compared to DGL292, DGL945, and DGL947 (1 mg/kg/day). Mice treated with to DGL292, DGL945, and DGL947 did not form detectable AVMs compared to control.

Antibodies were measured for agonistic activity in a mouse model of HHT wherein circulating BMP9/BMP10 were neutralized by anti-BMP9/10 antibodies (Ruiz S, et al, Scientific Reports, 2016 Nov. 22: 5:37366). These mice develop vascular defects in the postnatal retina. Three animals were dosed with DGL292, DGL945, DGL947 or a negative control antibody (Anti-HEL, LALA-PG, BioXCell, CP149) for two days, P3 and P4, at 1 mg/kg/day. BMP9/10 antibodies were dosed on the same days. Analysis was completed on P6. Retinas were dissected and whole-mount prepared, then stained with both isolectin B4 and SMA to label retinal vasculature and detect arteriovenous malformations (AVMs). Results are shown in FIG. 4. Mice dosed with any ALK1-BMPRII agonist showed a significant reduction in the formation of AVMs, whereas the negative control showed an average of 4.5 AVMs/retina.

Example 12. Analysis of Thermal Stability

Differential scanning calorimetry (DSC) is a thermo-analytical technique used to characterize the thermal stability of protein samples and assess conformational differences between them. Measurements were performed on MicroCal PEAQ DSC (Malvern) for thermal transition midpoint (Tm) and onset of unfolding (TOnset) testing. Samples were diluted to 1 mg/mL with the reference buffer (20 mM Histidine, 8% (w/v) sucrose, 0.02% (w/v) PS80, pH 6.0. 400 μL of respective reference buffers were added into the odd-numbered wells of a 96-well plate and 400 μL of samples were added into the even-numbered wells of the same plate. Experimental parameters were set such that the scan temperature ramped from 10 to 95° C. at a scan rate of 200° C./h. Data analysis was performed in MicroCal PEAQ- DSC automated data analysis software. Melting temperature data is depicted below in Table 19. Surprisingly, it was discovered that DGL947 and DGL949 possessed increased stability, as demonstrated by an increase in both the onset temperature of thermal unfolding (Tonset) and the first unfolding event (Tm1) relative to DGL945 and DGL1146. The variable domains of DGL947 and DGL949 differ from DGL945 and DGL1146 only within the CDRs.

TABLE 19

| Melting temperatures | | | | |
| --- | --- | --- | --- | --- |
| Molecule | $T_{Onset}$ (° C.) | $T_{m1}$ (° C.) | $T_{m2}$ (° C.) | $T_{m3}$ (° C.) |
| DGL945 | 47.1 | 61.7 | 86.7 | NA |
| DGL947 | 59.0 | 71.2 | 87.3 | NA |
| DGL949 | 57.1 | 65.9 | 82.1 | 87.4 |
| DGL1146 | 48.4 | 61.6 | 69.0 | 82.0 |

Example 13. Gene Expression Analysis of HMEC-1 Cells

HMEC-1 cells from ATCC were plated at 30K cells/well of 96 well plate in 100 μl complete growth media (MCDB base, +10% FBS, Pen/Strep, L-glutamine, and hydrocortisone, EGF) overnight. After overnight incubation media was removed and replaced with 50 μl reduced serum media (same as growth but 1% FBS). Cells were allowed to incubate for approximately 4 hours while standard curves of agonists were made in reduced serum media at 2× final concentration. After 4 hours, 50 μl of the antibody or BMP9 was added to cells and allowed to incubate overnight. After overnight incubation, media was removed and RNA lysis buffer from ZYMO was added. RNA was isolated from the cell lysates using a ZYMO 96 RNA isolation kit and RT reaction was performed using Quanta Biosciences kit. qPCR was performed on cDNA using Thermo designed Taqman assays for ID1, Serpine1 and GAPDH as a housekeeping control. Fold change was calculated as DD ct. The results of the gene expression analysis, as shown in Table 20-22, demonstrate that the bispecific antibodies stimulate gene expression of an ALK1 target (ID1) using GAPDH as a housekeeping gene. Table 23-25 is a second experiment, using RPL36AL as the housekeeping gene.

TABLE 20

| On target ID1 fold change over no treatment | | | | | |
| --- | --- | --- | --- | --- | --- |
| | BMP9 | DGL945 | DGL947 | DGL292 | DGL1146 | DGL949 |
| 1 nM | 5.5 | 36.4 | 7.9 | 8.6 | 8.7 | 3.7 |
| 100 pM | 7.8 | 31.8 | 6.9 | 9.0 | 14.8 | 4.0 |
| 10 pM | 1.2 | 11.0 | 3.6 | 2.1 | 5.5 | 3.8 |
| 1 pM | 2.3 | 9.9 | 3.6 | 3.3 | 2.6 | 3.2 |

TABLE 21

| Off target Serpine1 fold change over no treatment | | | | | |
| --- | --- | --- | --- | --- | --- |
| | BMP9 | DGL945 | DGL947 | DGL292 | DGL1146 | DGL949 |
| 1 nM | 1.4 | 2.6 | 1.2 | 1.1 | 1.1 | 1.3 |
| 100 pM | 1.5 | 3.4 | 1.5 | 1.3 | 1.4 | 1.6 |

TABLE 21-continued

| | Off target Serpine1 fold change over no treatment | | | | |
| | BMP9 | DGL945 | DGL947 | DGL292 | DGL1146 | DGL949 |
| --- | --- | --- | --- | --- | --- | --- |
| 10 pM | 1.0 | 3.4 | 1.6 | 1.0 | 1.3 | 1.5 |
| 1 pM | 1.9 | 4.0 | 2.1 | 1.8 | 0.9 | 1.5 |

TABLE 22

| | On target/off target effect | | | | |
| | BMP9 | DGL945 | DGL947 | DGL292 | DGL1146 | DGL949 |
| --- | --- | --- | --- | --- | --- | --- |
| 1 nM | 4.0 | 14.0 | 6.7 | 8.0 | 8.1 | 2.8 |
| 100 pM | 5.2 | 9.4 | 4.6 | 6.9 | 10.7 | 2.6 |
| 10 pM | 1.2 | 3.2 | 2.3 | 2.1 | 4.2 | 2.5 |
| 1 pM | 1.2 | 2.5 | 1.7 | 1.9 | 2.8 | 2.1 |

TABLE 23

| | On target ID1 fold change over no treatment | | | | |
| | BMP9 | DGL945 | DGL947 | DGL292 | DGL1146 | DGL949 |
| --- | --- | --- | --- | --- | --- | --- |
| 1 nM | 9.1 | 2.3 | 1.0 | 2.5 | 1.9 | 0.6 |
| 100 pM | 3.5 | 3.2 | 0.3 | 2.1 | 0.7 | 0.6 |
| 10 pM | 1.0 | 0.4 | 0.3 | 1.7 | 0.4 | 0.2 |
| 1 pM | 0.7 | 0.3 | 0.1 | 0.4 | 0.5 | 0.2 |

TABLE 24

| | Off target Serpine1 fold change over no treatment | | | | |
| | BMP9 | DGL945 | DGL947 | DGL292 | DGL1146 | DGL949 |
| --- | --- | --- | --- | --- | --- | --- |
| 1 nM | 1.2 | 0.3 | 0.3 | 0.4 | 0.2 | 0.2 |
| 100 pM | 0.7 | 0.6 | 0.1 | 0.6 | 0.1 | 0.3 |
| 10 pM | 0.8 | 0.2 | 0.2 | 1.7 | 0.2 | 0.2 |
| 1 pM | 0.4 | 0.2 | 0.1 | 0.2 | 0.3 | 0.1 |

TABLE 25

| | On target/off target effect | | | | |
| | BMP9 | DGL945 | DGL947 | DGL292 | DGL1146 | DGL949 |
| --- | --- | --- | --- | --- | --- | --- |
| 1 nM | 7.8 | 7.7 | 3.9 | 6.2 | 9.5 | 3.4 |
| 100 pM | 4.7 | 5.7 | 2.0 | 3.6 | 5.3 | 2.0 |
| 10 pM | 1.3 | 2.1 | 1.2 | 1.0 | 2.1 | 1.3 |
| 1 pM | 1.8 | 1.3 | 1.1 | 1.7 | 1.5 | 1.3 |

A separate cell line, the TIME cell line, as also used in gene expression analysis. TIME cells (ATCC), which are hTERT-immortalized cells exhibiting endothelial-like morphology, were plated at 30K cells/well of 96 well plate in 100 ul complete growth media (Vascular cell basal media plus microvascular endothelial cell growth kit-VEGF) overnight. After overnight incubation, media was removed and replaced with 50 μl reduced serum media (Growth media diluted 1:10 with Vascular cell basal media). Cells were allowed to incubate for approximately 4 hours while standard curves of agonists were made in reduced serum media at 2× final concentration. After 4 hours, 50 μl of agonist was added to cells and allowed to incubate overnight. After overnight incubation, media was removed and RNA lysis buffer from ZYMO was added. RNA was isolated from the cell lysates using a ZYMO 96 RNA isolation kit and RT reaction was performed using Quanta Biosciences kit. qPCR was performed on CDNA using Thermo designed Taqman assays for ID1, Serpine1 and GAPDH or RPL36AL as a housekeeping control. Fold change was calculated as DD ct. Table 26-27 shows the results using RPL36AL as the housekeeping control.

TABLE 26

| | BMP9 | DGL945 | DGL947 | DGL292 | DGL1146 | DGL949 |
|---|---|---|---|---|---|---|
| | | | On target ID1 fold change over no treatment | | | |
| 1 nM | 6.4 | 7.0 | 4.5 | 12.3 | n.d. | n.d. |
| 100 pM | 1.5 | 4.6 | 0.6 | 4.7 | n.d. | n.d. |
| 10 pM | 0.3 | 1.0 | 0.4 | 0.3 | n.d. | n.d. |
| 1 pM | 0.6 | 0.3 | 0.3 | 0.3 | n.d. | n.d. |

TABLE 27

| | BMP9 | DGL945 | DGL947 | DGL292 | DGL1146 | DGL949 |
|---|---|---|---|---|---|---|
| | | | Off target Serpine1 fold change over no treatment | | | |
| 1 nM | 0.6 | 0.5 | 0.4 | 1.9 | n.d. | n.d. |
| 100 pM | 0.7 | 0.5 | 0.2 | 1.5 | n.d. | n.d. |
| 10 pM | 0.2 | 0.3 | 0.2 | 0.2 | n.d. | n.d. |
| 1 pM | 0.7 | 0.2 | 0.2 | 0.3 | n.d. | n.d. |

TABLE 28

| | BMP9 | DGL945 | DGL947 | DGL292 | DGL1146 | DGL949 |
|---|---|---|---|---|---|---|
| | | | On target/off target effect | | | |
| 1 nM | 11.3 | 14.9 | 11.5 | 6.6 | n.d. | n.d. |
| 100 pM | 2.1 | 9.4 | 4.0 | 3.1 | n.d. | n.d. |
| 10 pM | 1.8 | 2.8 | 1.7 | 1.0 | n.d. | n.d. |
| 1 pM | 0.9 | 1.5 | 1.9 | 1.2 | n.d. | n.d. | n.d.—not determined

Example 14. Stabilization of the ALK1 Receptor on the Surface of Cells

The bispecific antibodies of the disclosure may stabilize the ALK1 receptor complexed with any one of BMPRII, ActRIIA, and ActRIIB on the surface of a cell. Through stabilization of the receptor, signaling may be sustained for longer durations.

To assess ALK1 receptor complex stabilization on the surface of cells, staining may be performed against ALK1 and one or BMPRII, ActRIIA, and ActRIIB. An exemplary protocol is described below, however one of skill in the art will readily recognize alternative approaches for detecting a protein on the surface of a cell. Moreover, the specific parameters outlined in the exemplary protocol (e.g., buffer choice, buffer component concentrations, cell line choice, total cells, antibody concentration, time, temperature, and others) may be adjusted as need to optimize the assay. Staining for ALK1 and BMPRII in MS1 Cells:

Autoclaved coverslips are placed in cell culture 24-well plate, and MS1 cells are seeded onto the coverslips in complete medium, allowing them to adhere overnight. Subsequently, the cells are starved for about 3 hours and then treated with a bispecific antibody disclosed herein (such as DGL288) or an IgG control at a concentration of about 1 µg/mL for 2 hrs. Following treatment, the coverslips are rinsed twice with PBS for about 5 minutes each and fixed in 4% paraformaldehyde for about 10 minutes, followed by another PBS wash.

Next, the cells are permeabilized for about 15 minutes using 0.25% Triton X-100 in PBS and blocked for about 1 hour with a solution containing 5% normal goat serum (Sigma-Aldrich, #G9023-10ML) and 0.25% Triton X-100 in PBS. Primary antibodies, including ALK1 (dilution 1:100, Santacruz #0-101556), BMPRII (dilution 1:100, Invitrogen #MA5-15827), and CD31-AF667 (dilution 1:50, Miltenyi #130-128-736), diluted in a solution of 1% NGS and 0.25% Triton X-100 in PBS, are then applied and allowed to incubate overnight at 4° C. The following day, the coverslips are washed twice with PBS for 5 minutes each and then incubated with secondary antibodies diluted in a solution of 1% NGS and 0.25% Triton X-100 in PBS at a dilution of 1:1000 (Goat anti-rat IgG H+L AF568, Thermo Fisher Scientific, #A-11077; Goat anti-mouse IgG1 AF488, Thermo Fisher Scientific #A-21121). After an additional 3 washes with PBS, the cells are stained with DAPI (BD Biosciences, #564907), followed by 3 more PBS washes. Finally, the coverslips are mounted on glass slides using ProLong™ Diamond Antifade Mountant (Thermo Fisher #P36965). Cell imaging was performed using a confocal Zeiss LSM900 microscope at 63× magnification, and image analysis was conducted using Zenblue Zeiss software.

SEQUENCE LISTING

Sequence total quantity: 223
SEQ ID NO: 1          moltype = AA  length = 9
FEATURE               Location/Qualifiers
source                1..9

-continued

```
                             mol_type = protein
                             organism = synthetic construct
SEQUENCE: 1
PLAPDKTHT                                                        9

SEQ ID NO: 2                 moltype = AA   length = 4
FEATURE                      Location/Qualifiers
source                       1..4
                             mol_type = protein
                             organism = synthetic construct
SEQUENCE: 2
PLAP                                                             4

SEQ ID NO: 3                 moltype = AA   length = 20
FEATURE                      Location/Qualifiers
source                       1..20
                             mol_type = protein
                             organism = synthetic construct
SEQUENCE: 3
GGGGSGGGGS GGGGSGGGGS                                            20

SEQ ID NO: 4                 moltype = AA   length = 7
FEATURE                      Location/Qualifiers
source                       1..7
                             mol_type = protein
                             organism = synthetic construct
SEQUENCE: 4
EKSYGPP                                                          7

SEQ ID NO: 5                 moltype = AA   length = 5
FEATURE                      Location/Qualifiers
source                       1..5
                             mol_type = protein
                             organism = synthetic construct
SEQUENCE: 5
DKTHT                                                            5

SEQ ID NO: 6                 moltype = AA   length = 11
FEATURE                      Location/Qualifiers
source                       1..11
                             mol_type = protein
                             organism = synthetic construct
SEQUENCE: 6
CPPCPAPELL G                                                     11

SEQ ID NO: 7                 moltype = AA   length = 15
FEATURE                      Location/Qualifiers
source                       1..15
                             mol_type = protein
                             organism = synthetic construct
SEQUENCE: 7
PLAPCPPCPA PELLG                                                 15

SEQ ID NO: 8                 moltype = AA   length = 16
FEATURE                      Location/Qualifiers
source                       1..16
                             mol_type = protein
                             organism = synthetic construct
SEQUENCE: 8
DKTHTCPPCP APELLG                                                16

SEQ ID NO: 9                 moltype = AA   length = 18
FEATURE                      Location/Qualifiers
source                       1..18
                             mol_type = protein
                             organism = synthetic construct
SEQUENCE: 9
EKSYGPPCPP CPAPELLG                                              18

SEQ ID NO: 10                moltype = AA   length = 210
FEATURE                      Location/Qualifiers
source                       1..210
                             mol_type = protein
                             organism = synthetic construct
SEQUENCE: 10
GPSVFLFPPK PKDTLMISRT PEVTCVVVDV SHEDPEVKFN WYVDGVEVHN AKTKPREEQY  60
NSTYRVVSVL TVLHQDWLNG KEYKCKVSNK ALPAPIEKTI SKAKGQPREP QVYTLPPSRD  120
ELTKNQVSLT CLVKGFYPSD IAVEWESNGQ PENNYKTTPP VLDSDGSFFL YSKLTVDKSR  180
WQQGNVFSCS VMHEALHNHY TQKSLSLSPG                                   210
```

```
SEQ ID NO: 11                  moltype = AA   length = 225
FEATURE                        Location/Qualifiers
source                         1..225
                               mol_type = protein
                               organism = synthetic construct
SEQUENCE: 11
PLAPCPPCPA PELLGGPSVF LFPPKPKDTL MISRTPEVTC VVVDVSHEDP EVKFNWYVDG   60
VEVHNAKTKP REEQYNSTYR VVSVLTVLHQ DWLNGKEYKC KVSNKALPAP IEKTISKAKG  120
QPREPQVYTL PPSRDELTKN QVSLTCLVKG FYPSDIAVEW ESNGQPENNY KTTPPVLDSD  180
GSFFLYSKLT VDKSRWQQGN VFSCSVMHEA LHNHYTQKSL SLSPG                  225

SEQ ID NO: 12                  moltype = AA   length = 226
FEATURE                        Location/Qualifiers
source                         1..226
                               mol_type = protein
                               organism = synthetic construct
SEQUENCE: 12
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPG                 226

SEQ ID NO: 13                  moltype = AA   length = 228
FEATURE                        Location/Qualifiers
source                         1..228
                               mol_type = protein
                               organism = synthetic construct
SEQUENCE: 13
EKSYGPPCPP CPAPELLGGP SVFLFPPKPK DTLMISRTPE VTCVVVDVSH EDPEVKFNWY   60
VDGVEVHNAK TKPREEQYNS TYRVVSVLTV LHQDWLNGKE YKCKVSNKAL PAPIEKTISK  120
AKGQPREPQV YTLPPSRDEL TKNQVSLTCL VKGFYPSDIA VEWESNGQPE NNYKTTPPVL  180
DSDGSFFLYS KLTVDKSRWQ QGNVFSCSVM HEALHNHYTQ KSLSLSPG               228

SEQ ID NO: 14                  moltype = AA   length = 221
FEATURE                        Location/Qualifiers
source                         1..221
                               mol_type = protein
                               organism = synthetic construct
SEQUENCE: 14
CPPCPAPELL GGPSVFLFPP KPKDTLMISR TPEVTCVVVD VSHEDPEVKF NWYVDGVEVH   60
NAKTKPREEQ YNSTYRVVSV LTVLHQDWLN GKEYKCKVSN KALPAPIEKT ISKAKGQPRE  120
PQVYTLPPSR DELTKNQVSL TCLVKGFYPS DIAVEWESNG QPENNYKTTP PVLDSDGSFF  180
LYSKLTVDKS RWQQGNVFSC SVMHEALHNH YTQKSLSLSP G                      221

SEQ ID NO: 15                  moltype = AA   length = 769
FEATURE                        Location/Qualifiers
source                         1..769
                               mol_type = protein
                               organism = synthetic construct
SEQUENCE: 15
GDEMGTDIQM TQSPSSLSAS VGDRVTITCR ASQSISSYLN WYQQKPGKAP KLLIYAASSL   60
QSGVPSRFSG SGSGTDFTLT ISSLQPEDFA TYYCQQSYST PRTFGQGTKV DIKEGKSSGS  120
GSESKASQVQ LQESGPGLVK PSQTLSLTCT VSGGSISSDD YYWSWIRQTP GKGLEWIGYI  180
YYSGITYYNP SLKSRVTISV DTSKNQFSLK LSSVTAADTA VYYCAREGCN DGVCYNGVFD  240
YWGQGTLVTV SSSGGSGGGG SSGGGGSGGG GSSGGGGDGG GGSGGTQSAL TQPASVSGSP  300
GQSITISCTG TSSDVGGYKS VSWYQQHPGK APKLMIYDVS NRPSGVSDRF SGSKSGNTAS  360
LTISGLQAED EADYYCSSYT SSSSLWVFGG GTKLTVLGEG KSSGSGSESK ASQVQLVQSG  420
AEVKKPGSSV KVSCKASGGT FSSYAISWVR QAPGQGLEWM GRIIPILGIA NYAQKFQGRV  480
TMTEDTSTDT AYMELSSLRS EDTAVYYCAT DLWGVGADWG QGTLVTVSSG SGGGGDGGGG  540
SGDKTHTCPP CPAPELLGGP SVFLFPPKPK DTLMISRTPE VTCVVVDVSH EDPEVKFNWY  600
VDGVEVHNAK TKPREEQYNS TYRVVSVLTV LHQDWLNGKE YKCKVSNKAL PAPIEKTISK  660
AKGQPREPQV YTLPPSREEL TKNQVSLTCL VKGFYPSDIA VEWESNGQPE NNYKTTPPVL  720
DSDGSFFLYS KLTVDKSRWQ QGNVFSCSVM HEALHNHYTQ KSLSLSPGS             769

SEQ ID NO: 16                  moltype = AA   length = 477
FEATURE                        Location/Qualifiers
source                         1..477
                               mol_type = protein
                               organism = synthetic construct
SEQUENCE: 16
EVQLLESGGG LVQPGGSLRL SCAASGFTFS IYAMSWVRQA PGKGLEWVSA ISGSGGSTYY   60
ADSVKGRFTI SRDNSKNTLY LQMNSLRAED TAVYYCARDF DYWGQGTLVT VTSSGGGGSG  120
GGGSGGGGSQ SVLTQPPSAS GTPGQRVTIS CSGGSSNIGS NYVYWYQQLP GTAPKLLIYG  180
NINRPSGVPD RFSGSKSGTS ASLAISGLRS EDEADYYCAA WDDSLNGRVF GGGTKLTVLG  240
GGGSGGGGSG GGGSGVECPP CPAPPVAGPS VFLFPPKPKD TLMISRTPEV TCVVVDVSHE  300
DPEVQFNWYV DGVEVHNAKT KPREEQFNST FRVVSVLTVV HQDWLNGKEY KCKVSNKGLP  360
APIEKTISKT KGQPREPQVY TLPPCREEMT KNQVSLWCLV KGFYPSDIAV EWESNGQPEN  420
NYKTTPPMLD SDGSFFLYSK LTVDKSRWQQ GNVFSCSVMH EALHNHYTQK SLSLSPG     477
```

```
SEQ ID NO: 17              moltype = AA   length = 487
FEATURE                    Location/Qualifiers
source                     1..487
                           mol_type = protein
                           organism = synthetic construct
SEQUENCE: 17
EVQLLESGGG LVQPGGSLRL SCAASGFTFS NAWMNWVRQA PGKGLEWVSS ISSSSSYIYY   60
ADSVKGRFTI SRDNSKNTLY LQMNSLRAED TAVYYCARAV AAGGMFWGLD QWGQGTLVTV  120
TSSGGGGSGG GGSGGGGSQS VLTQPPSASG TPGQRVTISC SGSRSNIGSN SVHWYQQLPG  180
TAPKLLIYGN SNRPSGVPDR FSGSKSGTSA SLAISGLRSE DEADYYCQSY DSSLNDHVVF  240
GGGTKLTVLG GGGSGGGGSG GGGSGVECPP CPAPPVAGPS VFLFPPKPKD TLMISRTPEV  300
TCVVVDVSHE DPEVQFNWYV DGVEVHNAKT KPREEQFNST FRVVSVLTVV HQDWLNGKEY  360
KCKVSNKGLP APIEKTISKT KGQPREPQVC TLPPSREEMT KNQVSLSCAV KGFYPSDIAV  420
EWESNGQPEN NYKTTPPMLD SDGSFFLVSK LTVDKSRWQQ GNVFSCSVMH EALHNHYTQK  480
SLSLSPG                                                            487

SEQ ID NO: 18              moltype = AA   length = 477
FEATURE                    Location/Qualifiers
source                     1..477
                           mol_type = protein
                           organism = synthetic construct
SEQUENCE: 18
EVQLLESGGG LVQPGGSLRL SCAASGFTFS SYAMSWVRQA PGKGLEWVAN INQDGSEKNY   60
VDSMRGRFTI SRDNSKNTLY LQMNSLRAED TAVYYCAREF DYWGQGTLVT VTSSGGGGSG  120
GGGSGGGGSQ SVLAQPPSAS GTPGQRVTIS CSGSSSNIGS NYVYWYQQLP GTAPKLLIYG  180
NNKRPSGVPD RFSGSKSGTS ASLAISGLRS EDEADYYCAA WDDSLNGRVF GGGTKLTVLG  240
GGGSGGGGSG GGGSGVECPP CPAPPVAGPS VFLFPPKPKD TLMISRTPEV TCVVVDVSHE  300
DPEVQFNWYV DGVEVHNAKT KPREEQFNST FRVVSVLTVV HQDWLNGKEY KCKVSNKGLP  360
APIEKTISKT KGQPREPQVY TLPPCREEMT KNQVSLWCLV KGFYPSDIAV EWESNGQPEN  420
NYKTTPPMLD SDGSFFLYSK LTVDKSRWQQ GNVFSCSVMH EALHNHYTQK SLSLSPG     477

SEQ ID NO: 19              moltype = AA   length = 485
FEATURE                    Location/Qualifiers
source                     1..485
                           mol_type = protein
                           organism = synthetic construct
SEQUENCE: 19
EVQLLESGGG LVQPGGSLRL SCAASGFTFS DYYMTWIRQA PGKGLEWVSS ISGGSTYYAD   60
SRKGRFTISR DNSENTLYLQ MNSLRAEDTA VYYCARDFGV AGWFGQYGMD VWGQGTLVTV  120
SSGGGGSGGG GSGGGGSQSV LTQPPSASGT PGQRVTISCT GSSSNIGAGY DVHWYQQLPG  180
TAPKLLIYRS NQRPSGVPDR FSGSKSGTSA SLAISGLRSE DEADYYCSSY AGNYNLVFGG  240
GTKLTVLGGG GSGGGGSGGG GSGVECPPCP APPVAGPSVF LFPPKPKDTL MISRTPEVTC  300
VVVDVSHEDP EVQFNWYVDG VEVHNAKTKP REEQFNSTFR VVSVLTVVHQ DWLNGKEYKC  360
KVSNKGLPAP IEKTISKTKG QPREPQVCTL PPSREEMTKN QVSLSCAVKG FYPSDIAVEW  420
ESNGQPENNY KTTPPMLDSD GSFFLVSKLT VDKSRWQQGN VFSCSVMHEA LHNHYTQKSL  480
SLSPG                                                              485

SEQ ID NO: 20              moltype = AA   length = 477
FEATURE                    Location/Qualifiers
source                     1..477
                           mol_type = protein
                           organism = synthetic construct
SEQUENCE: 20
EVQLLESGGG LVQPGGSLRL SCAASGFTFS IYAMSWVRQA PGKGLEWVSA ISGSGGSTYY   60
ADSVKGRFTI SRDNSKNTLY LQMNSLRAED TAVYYCARDF DYWGQGTLVT VTSSGGGGSG  120
GGGSGGGGSQ SVLTQPPSAS GTPGQRVTIS CSGSSSNIGS NYVYWYQQLP GTAPKLLIYG  180
NINRPSGVPD RFSGSKSGTS ASLAISGLRS EDEADYYCAA WDDSLNGRVF GGGTKLTVLG  240
GGGSGGGGSG GGGSGVECPP CPAPPVAGPS VFLFPPKPKD TLMISRTPEV TCVVVDVSHE  300
DPEVQFNWYV DGVEVHNAKT KPREEQFNST FRVVSVLTVV HQDWLNGKEY KCKVSNKGLP  360
APIEKTISKT KGQPREPQVY TLPPCREEMT KNQVSLWCLV KGFYPSDIAV EWESNGQPEN  420
NYKTTPPMLD SDGSFFLYSK LTVDKSRWQQ GNVFSCSVMH EALHNHYTQK SLSLSPG     477

SEQ ID NO: 21              moltype = AA   length = 477
FEATURE                    Location/Qualifiers
source                     1..477
                           mol_type = protein
                           organism = synthetic construct
SEQUENCE: 21
EVQLLESGGG LVQPGGSLRL SCAASGFTFS IYAMSWVRQA PGKGLEWVSA ISGSGGSTYY   60
ADSVKGRFTI SRDNSKNTLY LQMNSLRAED TAVYYCARDF DYWGQGTLVT VTSSGGGGSG  120
GGGSGGGGSQ SVLTQPPSAS GTPGQRVTIS CSGSSSNIGS NYVYWYQQLP GTAPKLLIYG  180
NINRPSGVPD RFSGSKSGTS ASLAISGLRS EDEADYYCAA WDDSLNGRVF GGGTKLTVLG  240
GGGSGGGGSG GGGSGVECPP CPAPPVAGPS VFLFPPKPKD TLMISRTPEV TCVVVDVSHE  300
DPEVQFNWYV DGVEVHNAKT KPREEQFNST FRVVSVLTVV HQDWLNGKEY KCKVSNKGLP  360
APIEKTISKT KGQPREPQVC TLPPSREEMT KNQVSLSCAV KGFYPSDIAV EWESNGQPEN  420
NYKTTPPMLD SDGSFFLVSK LTVDKSRWQQ GNVFSCSVMH EALHNHYTQK SLSLSPG     477

SEQ ID NO: 22              moltype = AA   length = 487
```

```
FEATURE              Location/Qualifiers
source               1..487
                     mol_type = protein
                     organism = synthetic construct
SEQUENCE: 22
EVQLLESGGG LVQPGGSLRL SCAASGFTFS NAWMNWVRQA PGKGLEWVSS ISSSSSYIYY   60
ADSVKGRFTI SRDNSKNTLY LQMNSLRAED TAVYYCARAV AAGGMFWGLD QWGQGTLVTV  120
TSSGGGGSGG GGSGGGGSQS VLTQPPSASG TPGQRVTISC SGSRSNIGSN SVHWYQQLPG  180
TAPKLLIYGN SNRPSGVPDR FSGSKSGTSA SLAISGLRSE DEADYYCQSY DSSLNDHVVF  240
GGGTKLTVLG GGGSGGGGSG GGGSGVECPP CPAPPVAGPS VFLFPPKPKD TLMISRTPEV  300
TCVVVDVSHE DPEVQFNWYV DGVEVHNAKT KPREEQFNST FRVVSVLTVV HQDWLNGKEY  360
KCKVSNKGLP APIEKTISKT KGQPREPQVY TLPPCREEMT KNQVSLWCLV KGFYPSDIAV  420
EWESNGQPEN NYKTTPPMLD SDGSFFLYSK LTVDKSRWQQ GNVFSCSVMH EALHNHYTQK  480
SLSLSPG                                                             487

SEQ ID NO: 23        moltype = AA  length = 487
FEATURE              Location/Qualifiers
source               1..487
                     mol_type = protein
                     organism = synthetic construct
SEQUENCE: 23
EVQLLESGGG LVQPGGSLRL SCAASGFTFS NAWMNWVRQA PGKGLEWVSS ISSSSSYIYY   60
ADSVKGRFTI SRDNSKNTLY LQMNSLRAED TAVYYCARAV AAGGMFWGLD QWGQGTLVTV  120
TSSGGGGSGG GGSGGGGSQS VLTQPPSASG TPGQRVTISC SGSRSNIGSN SVHWYQQLPG  180
TAPKLLIYGN SNRPSGVPDR FSGSKSGTSA SLAISGLRSE DEADYYCQSY DSSLNDHVVF  240
GGGTKLTVLG GGGSGGGGSG GGGSGVECPP CPAPPVAGPS VFLFPPKPKD TLMISRTPEV  300
TCVVVDVSHE DPEVQFNWYV DGVEVHNAKT KPREEQFNST FRVVSVLTVV HQDWLNGKEY  360
KCKVSNKGLP APIEKTISKT KGQPREPQVC TLPPSREEMT KNQVSLSCAV KGFYPSDIAV  420
EWESNGQPEN NYKTTPPMLD SDGSFFLVSK LTVDKSRWQQ GNVFSCSVMH EALHNHYTQK  480
SLSLSPG                                                             487

SEQ ID NO: 24        moltype = AA  length = 477
FEATURE              Location/Qualifiers
source               1..477
                     mol_type = protein
                     organism = synthetic construct
SEQUENCE: 24
EVQLLESGGG LVQPGGSLRL SCAASGFTFS SYAMSWVRQA PGKGLEWVAN INQDGSEKNY   60
VDSMRGRFTI SRDNSKNTLY LQMNSLRAED TAVYYCAREF DYWGQGTLVT VTSSGGGGSG  120
GGGSGGGGSQ SVLAQPPSAS GTPGQRVTIS CSGSSSNIGS NYVYWYQQLP GTAPKLLIYG  180
NNKRPSGVPD RFSGSKSGTS ASLAISGLRS EDEADYYCAA WDDSLNGRVF GGGTKLTVLG  240
GGGSGGGGSG GGGSGVECPP CPAPPVAGPS VFLFPPKPKD TLMISRTPEV TCVVVDVSHE  300
DPEVQFNWYV DGVEVHNAKT KPREEQFNST FRVVSVLTVV HQDWLNGKEY KCKVSNKGLP  360
APIEKTISKT KGQPREPQVY TLPPCREEMT KNQVSLWCLV KGFYPSDIAV EWESNGQPEN  420
NYKTTPPMLD SDGSFFLYSK LTVDKSRWQQ GNVFSCSVMH EALHNHYTQK SLSLSPG     477

SEQ ID NO: 25        moltype = AA  length = 477
FEATURE              Location/Qualifiers
source               1..477
                     mol_type = protein
                     organism = synthetic construct
SEQUENCE: 25
EVQLLESGGG LVQPGGSLRL SCAASGFTFS SYAMSWVRQA PGKGLEWVAN INQDGSEKNY   60
VDSMRGRFTI SRDNSKNTLY LQMNSLRAED TAVYYCAREF DYWGQGTLVT VTSSGGGGSG  120
GGGSGGGGSQ SVLAQPPSAS GTPGQRVTIS CSGSSSNIGS NYVYWYQQLP GTAPKLLIYG  180
NNKRPSGVPD RFSGSKSGTS ASLAISGLRS EDEADYYCAA WDDSLNGRVF GGGTKLTVLG  240
GGGSGGGGSG GGGSGVECPP CPAPPVAGPS VFLFPPKPKD TLMISRTPEV TCVVVDVSHE  300
DPEVQFNWYV DGVEVHNAKT KPREEQFNST FRVVSVLTVV HQDWLNGKEY KCKVSNKGLP  360
APIEKTISKT KGQPREPQVC TLPPSREEMT KNQVSLSCAV KGFYPSDIAV EWESNGQPEN  420
NYKTTPPMLD SDGSFFLVSK LTVDKSRWQQ GNVFSCSVMH EALHNHYTQK SLSLSPG     477

SEQ ID NO: 26        moltype = AA  length = 485
FEATURE              Location/Qualifiers
source               1..485
                     mol_type = protein
                     organism = synthetic construct
SEQUENCE: 26
EVQLLESGGG LVQPGGSLRL SCAASGFTFS DYYMTWIRQA PGKGLEWVSS ISGGSTYYAD   60
SRKGRFTISR DNSENTLYLQ MNSLRAEDTA VYYCARDFGV AGWFGQYGMD VWGQGTLVTV  120
SSGGGGSGGG GSGGGGSQSV LTQPPSASGT PGQRVTISCT GSSSNIGAGY DVHWYQQLPG  180
TAPKLLIYRS NQRPSGVPDR FSGSKSGTSA SLAISGLRSE DEADYYCSSY AGNYNLVFGG  240
GTKLTVLGGG GSGGGGSGGG GSGVECPPCP APPVAGPSVF LFPPKPKDTL MISRTPEVTC  300
VVVDVSHEDP EVQFNWYVDG VEVHNAKTKP REEQFNSTFR VVSVLTVVHQ DWLNGKEYKC  360
KVSNKGLPAP IEKTISKTKG QPREPQVYTL PPCREEMTKN QVSLWCLVKG FYPSDIAVEW  420
ESNGQPENNY KTTPPMLDSD GSFFLYSKLT VDKSRWQQGN VFSCSVMHEA LHNHYTQKSL  480
SLSPG                                                               485

SEQ ID NO: 27        moltype = AA  length = 485
FEATURE              Location/Qualifiers
```

```
source                      1..485
                            mol_type = protein
                            organism = synthetic construct
SEQUENCE: 27
EVQLLESGGG LVQPGGSLRL SCAASGFTFS DYYMTWIRQA PGKGLEWVSS ISGGGSTYYAD    60
SRKGRFTISR DNSENTLYLQ MNSLRAEDTA VYYCARDFGV AGWFGQYGMD VWGQGTLVTV    120
SSGGGGSGGG GSGGGGSQSV LTQPPSASGT PGQRVTISCT GSSSNIGAGY DVHWYQQLPG    180
TAPKLLIYRS NQRPSGVPDR FSGSKSGTSA SLAISGLRSE DEADYYCSSY AGNYNLVFGG    240
GTKLTVLGGG GSGGGGSGGG GSGVECPPCP APPVAGPSVF LFPPKPKDTL MISRTPEVTC    300
VVVDVSHEDP EVQFNWYVDG VEVHNAKTKP REEQFNSTFR VVSVLTVVHQ DWLNGKEYKC    360
KVSNKGLPAP IEKTISKTKG QPREPQVCTL PPSREEMTKN QVSLSCAVKG FYPSDIAVEW    420
ESNGQPENNY KTTPPMLDSD GSFFLVSKLT VDKSRWQQGN VFSCSVMHEA LHNHYTQKSL    480
SLSPG                                                               485

SEQ ID NO: 28                moltype = AA   length = 469
FEATURE                      Location/Qualifiers
source                       1..469
                             mol_type = protein
                             organism = synthetic construct
SEQUENCE: 28
EVQLLESGGG LVQPGGSLRL SCAASGFTFS IYAMSWVRQA PGKGLEWVSA ISGSGGSTYY    60
ADSVKGRFTI SRDNSKNTLY LQMNSLRAED TAVYYCARDF DYWGQGTLVT VTSSGGGGSG    120
GGGSGGGGSQ SVLTQPPSAS GTPGQRVTIS CSGSSSNIGS NYVYWYQQLP GTAPKLLIYG    180
NINRPSGVPD RFSGSKSGTS ASLAISGLRS EDEADYYCAA WDDSLNGRVF GGGTKLTVLD    240
KTHTCPPCPA PEAAGAPSVF LFPPKPKDTL MISRTPEVTC VVVDVSHEDP EVKFNWYVDG    300
VEVHNAKTKP REEQYNSTYR VVSVLTVLHQ DWLNGKEYKC KVSNKALPAP IEKTISKAKG    360
QPREPQVYTL PPCRDELTKN QVSLWCLVKG FYPSDIAVEW ESNGQPENNY KTTPPVLDSD    420
GSFFLYSKLT VDKSRWQQGN VFSCSVMHEA LHNHYTQKSL SLSPGEPEA              469

SEQ ID NO: 29                moltype = AA   length = 483
FEATURE                      Location/Qualifiers
source                       1..483
                             mol_type = protein
                             organism = synthetic construct
SEQUENCE: 29
EVQLLESGGG LVQPGGSLRL SCAASGFTFS NAWMNWVRQA PGKGLEWVSS ISSSSSYIYY    60
ADSVKGRFTI SRDNSKNTLY LQMNSLRAED TAVYYCARAV AAGGMFWGLD QWGQGTLVTV    120
TSSGGGGSGG GGSGGGGSQS VLTQPPSASG TPGQRVTISC SGSRSNIGSN SVHWYQQLPG    180
TAPKLLIYGN SNRPSGVPDR FSGSKSGTSA SLAISGLRSE DEADYYCQSY DSSLNDHVVF    240
GGGTKLTVLD KTHTCPPCPA PEAAGAPSVF LFPPKPKDTL MISRTPEVTC VVVDVSHEDP    300
EVKFNWYVDG VEVHNAKTKP REEQYNSTYR VVSVLTVLHQ DWLNGKEYKC KVSNKALPAP    360
IEKTISKAKG QPREPQVCTL PPSRDELTKN QVSLSCAVKG FYPSDIAVEW ESNGQPENNY    420
KTTPPVLDSD GSFFLVSKLT VDKSRWQQGN VFSCSVMHEA LHNHYTQKSL SLSPGWSHPQ    480
FEK                                                                483

SEQ ID NO: 30                moltype = AA   length = 464
FEATURE                      Location/Qualifiers
source                       1..464
                             mol_type = protein
                             organism = synthetic construct
SEQUENCE: 30
EVQLLESGGG LVQPGGSLRL SCAASGFTFS IYAMSWVRQA PGKGLEWVSA ISGSGGSTYY    60
ADSVKGRFTI SRDNSKNTLY LQMNSLRAED TAVYYCARDF DYWGQGTLVT VTSSGGGGSG    120
GGGSGGGGSQ SVLTQPPSAS GTPGQRVTIS CSGSSSNIGS NYVYWYQQLP GTAPKLLIYG    180
NINRPSGVPD RFSGSKSGTS ASLAISGLRS EDEADYYCAA WDDSLNGRVF GGGTKLTVLC    240
PPCPAPEAAG APSVFLFPPK PKDTLMISRT PEVTCVVVDV SHEDPEVKFN WYVDGVEVHN    300
AKTKPREEQY NSTYRVVSVL TVLHQDWLNG KEYKCKVSNK ALPAPIEKTI SKAKGQPREP    360
QVYTLPPCRD ELTKNQVSLW CLVKGFYPSD IAVEWESNGQ PENNYKTTPP VLDSDGSFFL    420
YSKLTVDKSR WQQGNVFSCS VMHEALHNHY TQKSLSLSPG EPEA                   464

SEQ ID NO: 31                moltype = AA   length = 478
FEATURE                      Location/Qualifiers
source                       1..478
                             mol_type = protein
                             organism = synthetic construct
SEQUENCE: 31
EVQLLESGGG LVQPGGSLRL SCAASGFTFS NAWMNWVRQA PGKGLEWVSS ISSSSSYIYY    60
ADSVKGRFTI SRDNSKNTLY LQMNSLRAED TAVYYCARAV AAGGMFWGLD QWGQGTLVTV    120
TSSGGGGSGG GGSGGGGSQS VLTQPPSASG TPGQRVTISC SGSRSNIGSN SVHWYQQLPG    180
TAPKLLIYGN SNRPSGVPDR FSGSKSGTSA SLAISGLRSE DEADYYCQSY DSSLNDHVVF    240
GGGTKLTVLC PPCPAPEAAG APSVFLFPPK PKDTLMISRT PEVTCVVVDV SHEDPEVKFN    300
WYVDGVEVHN AKTKPREEQY NSTYRVVSVL TVLHQDWLNG KEYKCKVSNK ALPAPIEKTI    360
SKAKGQPREP QVCTLPPSRD ELTKNQVSLS CAVKGFYPSD IAVEWESNGQ PENNYKTTPP    420
VLDSDGSFFL VSKLTVDKSR WQQGNVFSCS VMHEALHNHY TQKSLSLSPG WSHPQFEK    478

SEQ ID NO: 32                moltype = AA   length = 468
FEATURE                      Location/Qualifiers
source                       1..468
                             mol_type = protein
```

```
                         organism = synthetic construct
SEQUENCE: 32
EVQLLESGGG LVQPGGSLRL SCAASGFTFS IYAMSWVRQA PGKGLEWVSA ISGSGGSTYY   60
ADSVKGRFTI SRDNSKNTLY LQMNSLRAED TAVYYCARDF DYWGQGTLVT VTSSGGGGSG  120
GGGSGGGGSQ SVLTQPPSAS GTPGQRVTIS CSGSSSNIGS NYVYWYQQLP GTAPKLLIYG  180
NINRPSGVPD RFSGSKSGTS ASLAISGLRS EDEADYYCAA WDDSLNGRVF GGGTKLTVLP  240
LAPCPPCPAP EAAGAPSVFL FPPKPKDTLM ISRTPEVTCV VVDVSHEDPE VKFNWYVDGV  300
EVHNAKTKPR EEQYNSTYRV VSVLTVLHQD WLNGKEYKCK VSNKALPAPI EKTISKAKGQ  360
PREPQVYTLP PCRDELTKNQ VSLWCLVKGF YPSDIAVEWE SNGQPENNYK TTPPVLDSDG  420
SFFLYSKLTV DKSRWQQGNV FSCSVMHEAL HNHYTQKSLS LSPGEPEA              468

SEQ ID NO: 33          moltype = AA  length = 482
FEATURE                Location/Qualifiers
source                 1..482
                       mol_type = protein
                       organism = synthetic construct
SEQUENCE: 33
EVQLLESGGG LVQPGGSLRL SCAASGFTFS NAWMNWVRQA PGKGLEWVSS ISSSSSYIYY   60
ADSVKGRFTI SRDNSKNTLY LQMNSLRAED TAVYYCARAV AAGGMFWGLD QWGQGTLVTV  120
TSSGGGGSGG GGSGGGGSQS VLTQPPSASG TPGQRVTISC SGSRSNIGSN SVHWYQQLPG  180
TAPKLLIYGN SNRPSGVPDR FSGSKSGTSA SLAISGLRSE DEADYYCQSY DSSLNDHVVF  240
GGGTKLTVLP LAPCPPCPAP EAAGAPSVFL FPPKPKDTLM ISRTPEVTCV VVDVSHEDPE  300
VKFNWYVDGV EVHNAKTKPR EEQYNSTYRV VSVLTVLHQD WLNGKEYKCK VSNKALPAPI  360
EKTISKAKGQ PREPQVCTLP PSRDELTKNQ VSLSCAVKGF YPSDIAVEWE SNGQPENNYK  420
TTPPVLDSDG SFFLVSKLTV DKSRWQQGNV FSCSVMHEAL HNHYTQKSLS LSPGWSHPQF  480
EK                                                              482

SEQ ID NO: 34          moltype = AA  length = 469
FEATURE                Location/Qualifiers
source                 1..469
                       mol_type = protein
                       organism = synthetic construct
SEQUENCE: 34
EVQLLESGGG LVQPGGSLRL SCAASGFTFS SYAMSWVRQA PGKGLEWVAN INQDGSEKNY   60
VDSMRGRFTI SRDNSKNTLY LQMNSLRAED TAVYYCAREF DYWGQGTLVT VTSSGGGGSG  120
GGGSGGGGSQ SVLAQPPSAS GTPGQRVTIS CSGSSSNIGS NYVYWYQQLP GTAPKLLIYG  180
NNKRPSGVPD RFSGSKSGTS ASLAISGLRS EDEADYYCAA WDDSLNGRVF GGGTKLTVLD  240
KTHTCPPCPA PEAAGAPSVF LFPPKPKDTL MISRTPEVTC VVVDVSHEDP EVKFNWYVDG  300
VEVHNAKTKP REEQYNSTYR VVSVLTVLHQ DWLNGKEYKC KVSNKALPAP IEKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGEPEA             469

SEQ ID NO: 35          moltype = AA  length = 481
FEATURE                Location/Qualifiers
source                 1..481
                       mol_type = protein
                       organism = synthetic construct
SEQUENCE: 35
EVQLLESGGG LVQPGGSLRL SCAASGFTFS DYYMTWIRQA PGKGLEWVSS ISGGSTYYAD   60
SRKGRFTISR DNSENTLYLQ MNSLRAEDTA VYYCARDFGV AGWFGQYGMD VWGQGTLVTV  120
SSGGGGSGG GSGGGGSQSV LTQPPSASGT PGQRVTISCT GSSSNIGAGY DVHWYQQLPG  180
TAPKLLIYRS NQRPSGVPDR FSGSKSGTSA SLAISGLRSE DEADYYCSSY AGNYNLVFGG  240
GTKLTVLDKT HTCPPCPAPE AAGAPSVFLF PPKPKDTLMI SRTPEVTCVV VDVSHEDPEV  300
KFNWYVDGVE VHNAKTKPRE EQYNSTYRVV SVLTVLHQDW LNGKEYKCKV SNKALPAPIE  360
KTISKAKGQP REPQVCTLPP SRDELTKNQV SLSCAVKGFY PSDIAVEWES NGQPENNYKT  420
TPPVLDSDGS FFLVSKLTVD KSRWQQGNVF SCSVMHEALH NHYTQKSLSL SPGWSHPQFE  480
K                                                               481

SEQ ID NO: 36          moltype = AA  length = 464
FEATURE                Location/Qualifiers
source                 1..464
                       mol_type = protein
                       organism = synthetic construct
SEQUENCE: 36
EVQLLESGGG LVQPGGSLRL SCAASGFTFS SYAMSWVRQA PGKGLEWVAN INQDGSEKNY   60
VDSMRGRFTI SRDNSKNTLY LQMNSLRAED TAVYYCAREF DYWGQGTLVT VTSSGGGGSG  120
GGGSGGGGSQ SVLAQPPSAS GTPGQRVTIS CSGSSSNIGS NYVYWYQQLP GTAPKLLIYG  180
NNKRPSGVPD RFSGSKSGTS ASLAISGLRS EDEADYYCAA WDDSLNGRVF GGGTKLTVLC  240
PPCPAPEAAG APSVFLFPPK PKDTLMISRT PEVTCVVVDV SHEDPEVKFN WYVDGVEVHN  300
AKTKPREEQY NSTYRVVSVL TVLHQDWLNG KEYKCKVSNK ALPAPIEKTI SKAKGQPREP  360
QVYTLPPCRD ELTKNQVSLW CLVKGFYPSD IAVEWESNGQ PENNYKTTPP VLDSDGSFFL  420
YSKLTVDKSR WQQGNVFSCS VMHEALHNHY TQKSLSLSPG EPEA                 464

SEQ ID NO: 37          moltype = AA  length = 476
FEATURE                Location/Qualifiers
source                 1..476
                       mol_type = protein
                       organism = synthetic construct
SEQUENCE: 37
```

```
EVQLLESGGG LVQPGGSLRL SCAASGFTFS DYYMTWIRQA PGKGLEWVSS ISGGSTYYAD   60
SRKGRFTISR DNSENTLYLQ MNSLRAEDTA VYYCARDFGV AGWFGQYGMD VWGQGTLVTV  120
SSGGGGSGGG GSGGGGSQSV LTQPPSASGT PGQRVTISCT GSSSNIGAGY DVHWYQQLPG  180
TAPKLLIYRS NQRPSGVPDR FSGSKSGTSA SLAISGLRSE DEADYYCSSY AGNYNLVFGG  240
GTKLTVLCPP CPAPEAAGAP SVFLFPPKPK DTLMISRTPE VTCVVVDVSH EDPEVKFNWY  300
VDGVEVHNAK TKPREEQYNS TYRVVSVLTV LHQDWLNGKE YKCKVSNKAL PAPIEKTISK  360
AKGQPREPQV CTLPPSRDEL TKNQVSLSCA VKGFYPSDIA VEWESNGQPE NNYKTTPPVL  420
DSDGSFFLVS KLTVDKSRWQ QGNVFSCSVM HEALHNHYTQ KSLSLSPGWS HPQFEK      476

SEQ ID NO: 38               moltype = AA   length = 468
FEATURE                     Location/Qualifiers
source                      1..468
                            mol_type = protein
                            organism = synthetic construct
SEQUENCE: 38
EVQLLESGGG LVQPGGSLRL SCAASGFTFS SYAMSWVRQA PGKGLEWVAN INQDGSEKNY   60
VDSMRGRFTI SRDNSKNTLY LQMNSLRAED TAVYYCAREF DYWGQGTLVT VTSSGGGGSG  120
GGGSGGGGSQ SVLAQPPSAS GTPGQRVTIS CSGSSSNIGS NYVYWYQQLP GTAPKLLIYG  180
NNKRPSGVPD RFSGSKSGTS ASLAISGLRS EDEADYYCAA WDDSLNGRVF GGGTKLTVLP  240
LAPCPPCPAP EAAGAPSVFL FPPKPKDTLM ISRTPEVTCV VVDVSHEDPE VKFNWYVDGV  300
EVHNAKTKPR EEQYNSTYRV VSVLTVLHQD WLNGKEYKCK VSNKALPAPI EKTISKAKGQ  360
PREPQVYTLP PCRDELTKNQ VSLWCLVKGF YPSDIAVEWE SNGQPENNYK TTPPVLDSDG  420
SFFLYSKLTV DKSRWQQGNV FSCSVMHEAL HNHYTQKSLS LSPGEPEA              468

SEQ ID NO: 39               moltype = AA   length = 480
FEATURE                     Location/Qualifiers
source                      1..480
                            mol_type = protein
                            organism = synthetic construct
SEQUENCE: 39
EVQLLESGGG LVQPGGSLRL SCAASGFTFS DYYMTWIRQA PGKGLEWVSS ISGGSTYYAD   60
SRKGRFTISR DNSENTLYLQ MNSLRAEDTA VYYCARDFGV AGWFGQYGMD VWGQGTLVTV  120
SSGGGGSGGG GSGGGGSQSV LTQPPSASGT PGQRVTISCT GSSSNIGAGY DVHWYQQLPG  180
TAPKLLIYRS NQRPSGVPDR FSGSKSGTSA SLAISGLRSE DEADYYCSSY AGNYNLVFGG  240
GTKLTVLPLA PCPPCPAPEA AGAPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIEK  360
TISKAKGQPR EPQVCTLPPS RDELTKNQVS LSCAVKGFYP SDIAVEWESN GQPENNYKTT  420
PPVLDSDGSF FLVSKLTVDK SRWQQGNVFS CSVMHEALHN HYTQKSLSLS PGWSHPQFEK  480

SEQ ID NO: 40               moltype = AA   length = 447
FEATURE                     Location/Qualifiers
source                      1..447
                            mol_type = protein
                            organism = synthetic construct
SEQUENCE: 40
EVQLLESGGG LVQPGGSLRL SCAASGFTFS IYAMSWVRQA PGKGLEWVSA ISGSGGSTYY   60
ADSVKGRFTI SRDNSKNTLY LQMNSLRAED TAVYYCARDF DYWGQGTLVT VTSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE AAGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP CRDELTKNQV  360
SLWCLVKGFY PSDIAVEWES NGQPENNYKT TPPVLDSDGS FFLYSKLTVD KSRWQQGNVF  420
SCSVMHEALH NHYTQKSLSL SPGEPEA                                     447

SEQ ID NO: 41               moltype = AA   length = 216
FEATURE                     Location/Qualifiers
source                      1..216
                            mol_type = protein
                            organism = synthetic construct
SEQUENCE: 41
QSVLTQPPSA SGTPGQRVTI SCSGSSSNIG SNYVYWYQQL PGTAPKLLIY GNINRPSGVP   60
DRFSGSKSGT SASLAISGLR SEDEADYYCA AWDDSLNGRV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                          216

SEQ ID NO: 42               moltype = AA   length = 474
FEATURE                     Location/Qualifiers
source                      1..474
                            mol_type = protein
                            organism = synthetic construct
SEQUENCE: 42
EVQLLESGGG LVQPGGSLRL SCAASGFTFS IYAMSWVRQA PGKGLEWVSA ISGSGGSTYY   60
ADSVKGRFTI SRDNSKNTLY LQMNSLRAED TAVYYCARDF DYWGQGTLVT VTSSGGGGSQ  120
GGGSGGGGSQ SVLTQPPSAS GTPGQRVTIS CSGSSSNIGS NYVYWYQQLP GTAPKLLIYG  180
NINRPSGVPD RFSGSKSGTS ASLAISGLRS EDEADYYCAA WDDSLNGRVF GGGTKLTVLD  240
KTHTCPPCPA PEAAGAPSVF LFPPKPKDTL MISRTPEVTC VVVDVSHEDP EVKFNWYVDG  300
VEVHNAKTKP REEQYNSTYR VVSVLTVLHQ DWLNGKEYKC KVSNKALPAP IEKTISKAKG  360
QPREPQVCTL PPSRDELTKN QVSLSCAVKG FYPSDIAVEW ESNGQPENNY KTTPPVLDSD  420
GSFFLVSKLT VDKSRWQQGN VFSCSVMHEA LHNHYTQKSL SLSPGKWSHP QFEK        474
```

```
SEQ ID NO: 43                moltype = AA  length = 456
FEATURE                      Location/Qualifiers
source                       1..456
                             mol_type = protein
                             organism = synthetic construct
SEQUENCE: 43
EVQLLESGGG LVQPGGSLRL SCAASGFTFS NAWMNWVRQA PGKGLEWVSS ISSSSSYIYY   60
ADSVKGRFTI SRDNSKNTLY LQMNSLRAED TAVYYCARAV AAGGMFWGLD QWGQGTLVTV  120
TSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGAPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPC  360
RDELTKNQVS LWCLVKGFYP SDIAVEWESN GQPENNYKTT PPVLDSDGSF FLYSKLTVDK  420
SRWQQGNVFS CSVMHEALHN HYTQKSLSLS PGEPEA                            456

SEQ ID NO: 44                moltype = AA  length = 217
FEATURE                      Location/Qualifiers
source                       1..217
                             mol_type = protein
                             organism = synthetic construct
SEQUENCE: 44
QSVLTQPPSA SGTPGQRVTI SCSGSRSNIG SNSVHWYQQL PGTAPKLLIY GNSNRPSGVP   60
DRFSGSKSGT SASLAISGLR SEDEADYYCQ SYDSSLNDHV VFGGGTKLTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                          217

SEQ ID NO: 45                moltype = AA  length = 484
FEATURE                      Location/Qualifiers
source                       1..484
                             mol_type = protein
                             organism = synthetic construct
SEQUENCE: 45
EVQLLESGGG LVQPGGSLRL SCAASGFTFS NAWMNWVRQA PGKGLEWVSS ISSSSSYIYY   60
ADSVKGRFTI SRDNSKNTLY LQMNSLRAED TAVYYCARAV AAGGMFWGLD QWGQGTLVTV  120
TSSGGGGSGG GGSGGGGSQS VLTQPPSASG TPGQRVTISC SGSRSNIGSN SVHWYQQLPG  180
TAPKLLIYGN SNRPSGVPDR FSGSKSGTSA SLAISGLRSE DEADYYCQSY DSSLNDHVVF  240
GGGTKLTVLD KTHTCPPCPA PEAAGAPSVF LFPPKPKDTL MISRTPEVTC VVVDVSHEDP  300
EVKFNWYVDG VEVHNAKTKP REEQYNSTYR VVSVLTVLHQ DWLNGKEYKC KVSNKALPAP  360
IEKTISKAKG QPREPQVCTL PPSRDELTKN QVSLSCAVKG FYPSDIAVEW ESNGQPENNY  420
KTTPPVLDSD GSFFLVSKLT VDKSRWQQGN VFSCSVMHEA LHNHYTQKSL SLSPGKWSHP  480
QFEK                                                              484

SEQ ID NO: 46                moltype = AA  length = 447
FEATURE                      Location/Qualifiers
source                       1..447
                             mol_type = protein
                             organism = synthetic construct
SEQUENCE: 46
EVQLLESGGG LVQPGGSLRL SCAASGFTFS SYAMSWVRQA PGKGLEWVAN INQDGSEKNY   60
VDSMRGRFTI SRDNSKNTLY LQMNSLRAED TAVYYCAREF DYWGQGTLVT VTSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE AAGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP CRDELTKNQV  360
SLWCLVKGFY PSDIAVEWES NGQPENNYKT TPPVLDSDGS FFLYSKLTVD KSRWQQGNVF  420
SCSVMHEALH NHYTQKSLSL SPGEPEA                                      447

SEQ ID NO: 47                moltype = AA  length = 216
FEATURE                      Location/Qualifiers
source                       1..216
                             mol_type = protein
                             organism = synthetic construct
SEQUENCE: 47
QSVLAQPPSA SGTPGQRVTI SCSGSSSNIG SNYVYWYQQL PGTAPKLLIY GNNKRPSGVP   60
DRFSGSKSGT SASLAISGLR SEDEADYYCA AWDDSLNGRV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                            216

SEQ ID NO: 48                moltype = AA  length = 474
FEATURE                      Location/Qualifiers
source                       1..474
                             mol_type = protein
                             organism = synthetic construct
SEQUENCE: 48
EVQLLESGGG LVQPGGSLRL SCAASGFTFS SYAMSWVRQA PGKGLEWVAN INQDGSEKNY   60
VDSMRGRFTI SRDNSKNTLY LQMNSLRAED TAVYYCAREF DYWGQGTLVT VTSSGGGGSG  120
GGGSGGGGSQ SVLAQPPSAS GTPGQRVTIS CSGSSSNIGS NYVYWYQQLP GTAPKLLIYG  180
NNKRPSGVPD RFSGSKSGTS ASLAISGLRS EDEADYYCAA WDDSLNGRVF GGGTKLTVLD  240
```

```
KTHTCPPCPA PEAAGAPSVF LFPPKPKDTL MISRTPEVTC VVVDVSHEDP EVKFNWYVDG    300
VEVHNAKTKP REEQYNSTYR VVSVLTVLHQ DWLNGKEYKC KVSNKALPAP IEKTISKAKG    360
QPREPQVCTL PPSRDELTKN QVSLSCAVKG FYPSDIAVEW ESNGQPENNY KTTPPVLDSD    420
GSFFLVSKLT VDKSRWQQGN VFSCSVMHEA LHNHYTQKSL SLSPGKWSHP QFEK          474

SEQ ID NO: 49              moltype = AA  length = 455
FEATURE                    Location/Qualifiers
source                     1..455
                           mol_type = protein
                           organism = synthetic construct
SEQUENCE: 49
EVQLLESGGG LVQPGGSLRL SCAASGFTFS DYYMTWIRQA PGKGLEWVSS ISGGSTYYAD    60
SRKGRFTISR DNSENTLYLQ MNSLRAEDTA VYYCARDFGV AGWFGQYGMD VWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPEAA    240
GAPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPCR    360
DELTKNQVSL WCLVKGFYPS DIAVEWESNG QPENNYKTTP PVLDSDGSFF LYSKLTVDKS    420
RWQQGNVFSC SVMHEALHNH YTQKSLSLSP GEPEA                               455

SEQ ID NO: 50              moltype = AA  length = 216
FEATURE                    Location/Qualifiers
source                     1..216
                           mol_type = protein
                           organism = synthetic construct
SEQUENCE: 50
QSVLTQPPSA SGTPGQRVTI SCTGSSSNIG AGYDVHWYQQ LPGTAPKLLI YRSNQRPSGV    60
PDRFSGSKSG TSASLAISGL RSEDEADYYC SSYAGNYNLV FGGGTKLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                             216

SEQ ID NO: 51              moltype = AA  length = 482
FEATURE                    Location/Qualifiers
source                     1..482
                           mol_type = protein
                           organism = synthetic construct
SEQUENCE: 51
EVQLLESGGG LVQPGGSLRL SCAASGFTFS DYYMTWIRQA PGKGLEWVSS ISGGSTYYAD    60
SRKGRFTISR DNSENTLYLQ MNSLRAEDTA VYYCARDFGV AGWFGQYGMD VWGQGTLVTV    120
SSGGGGSGGG GSGGGGSQSV LTQPPSASGT PGQRVTISCT GSSSNIGAGY DVHWYQQLPG    180
TAPKLLIYRS NQRPSGVPDR FSGSKSGTSA SLAISGLRSE DEADYYCSSY AGNYNLVFGG    240
GTKLTVLDKT HTCPPCPAPE AAGAPSVFLF PPKPKDTLMI SRTPEVTCVV VDVSHEDPEV    300
KFNWYVDGVE VHNAKTKPRE EQYNSTYRVV SVLTVLHQDW LNGKEYKCKV SNKALPAPIE    360
KTISKAKGQP REPQVCTLPP SRDELTKNQV SLSCAVKGFY PSDIAVEWES NGQPENNYKT    420
TPPVLDSDGS FFLVSKLTVD KSRWQQGNVF SCSVMHEALH NHYTQKSLSL SPGKWSHPQF    480
EK                                                                  482

SEQ ID NO: 52              moltype = AA  length = 455
FEATURE                    Location/Qualifiers
source                     1..455
                           mol_type = protein
                           organism = synthetic construct
SEQUENCE: 52
EVQLLESGGG LVQPGGSLRL SCAASGFTFS IYAMSWVRQA PGKGLEWVSA ISGSGGSTYY    60
ADSVKGRFTI SRDNSKNTLY LQMNSLRAED TAVYYCARDF DYWGQGTLVT VTSSASVAAP    120
SVFIFPPSDE QLKSGTASVV CLLNNFYPRE AKVQWKVDNA LQSGNSQESV TEQDSKDSTY    180
SLSSTLTLSK ADYEKHKVYA CEVTHQGLSS PVTKSFNRGE CDKTHTCPPC PAPEAAGAPS    240
VFLFPPKPKD TLMISRTPEV TCVVVDVSHE DPEVKFNWYV DGVEVHNAKT KPREEQYNST    300
YRVVSVLTVL HQDWLNGKEY KCKVSNKALP APIEKTISKA KGQPREPQVC TLPPSRDELT    360
KNQVSLSCAV KGFYPSDIAV EWESNGQPEN NYKTTPPVLD SDGSFFLVSK LTVDKSRWQQ    420
GNVFSCSVMH EALHNHYTQK SLSLSPGWSH PQFEK                              455

SEQ ID NO: 53              moltype = AA  length = 215
FEATURE                    Location/Qualifiers
source                     1..215
                           mol_type = protein
                           organism = synthetic construct
SEQUENCE: 53
QSVLTQPPSA SGTPGQRVTI SCSGSSSNIG SNYVYWYQQL PGTAPKLLIY GNINRPSGVP    60
DRFSGSKSGT SASLAISGLR SEDEADYYCA AWDDSLNGRV FGGGTKLTVL SSASTKGPSV    120
FPLAPSSKST SGGTAALGCL VKDYFPEPVT VSWNSGALTS GVHTFPAVLQ SSGLYSLSSV    180
VTVPSSSLGT QTYICNVNHK PSNTKVDKKV EPKSC                              215

SEQ ID NO: 54              moltype = AA  length = 456
FEATURE                    Location/Qualifiers
source                     1..456
                           mol_type = protein
                           organism = synthetic construct
SEQUENCE: 54
```

```
EVQLLESGGG LVQPGGSLRL SCAASGFTFS NAWMNWVRQA PGKGLEWVSS ISSSSSYIYY   60
ADSVKGRFTI SRDNSKNTLY LQMNSLRAED TAVYYCARAV AAGGMFWGLD QWGQGTLVTV  120
TSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGAPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPC  360
RDELTKNQVS LWCLVKGFYP SDIAVEWESN GQPENNYKTT PPVLDSDGSF FLYSKLTVDK  420
SRWQQGNVFS CSVMHEALHN HYTQKSLSLS PGEPEA                           456

SEQ ID NO: 55          moltype = AA  length = 217
FEATURE                Location/Qualifiers
source                 1..217
                       mol_type = protein
                       organism = synthetic construct
SEQUENCE: 55
QSVLTQPPSA SGTPGQRVTI SCSGSRSNIG SNSVHWYQQL PGTAPKLLIY GNSNRPSGVP   60
DRFSGSKSGT SASLAISGLR SEDEADYYCQ SYDSSLNDHV VFGGGTKLTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                          217

SEQ ID NO: 56          moltype = AA  length = 455
FEATURE                Location/Qualifiers
source                 1..455
                       mol_type = protein
                       organism = synthetic construct
SEQUENCE: 56
EVQLLESGGG LVQPGGSLRL SCAASGFTFS SYAMSWVRQA PGKGLEWVAN INQDGSEKNY   60
VDSMRGRFTI SRDNSKNTLY LQMNSLRAED TAVYYCAREF DYWGQGTLVT VTSSASVAAP  120
SVFIFPPSDE QLKSGTASVV CLLNNFYPRE AKVQWKVDNA LQSGNSQESV TEQDSKDSTY  180
SLSSTLTLSK ADYEKHKVYA CEVTHQGLSS PVTKSFNRGE CDKTHTCPPC PAPEAAGAPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVC TLPPSRDELT  360
KNQVSLSCAV KGFYPSDIAV EWESNGQPEN NYKTTPPVLD SDGSFFLVSK LTVDKSRWQQ  420
GNVFSCSVMH EALHNHYTQK SLSLSPGWSH PQFEK                            455

SEQ ID NO: 57          moltype = AA  length = 215
FEATURE                Location/Qualifiers
source                 1..215
                       mol_type = protein
                       organism = synthetic construct
SEQUENCE: 57
QSVLAQPPSA SGTPGQRVTI SCSGSSSNIG SNYVYWYQQL PGTAPKLLIY GNNKRPSGVP   60
DRFSGSKSGT SASLAISGLR SEDEADYYCA AWDDSLNGRV FGGGTKLTVL SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKKV EPKSC                            215

SEQ ID NO: 58          moltype = AA  length = 455
FEATURE                Location/Qualifiers
source                 1..455
                       mol_type = protein
                       organism = synthetic construct
SEQUENCE: 58
EVQLLESGGG LVQPGGSLRL SCAASGFTFS DYYMTWIRQA PGKGLEWVSS ISGGSTYYAD   60
SRKGRFTISR DNSENTLYLQ MNSLRAEDTA VYYCARDFGV AGWFGQYGMD VWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPEAA  240
GAPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPCR  360
DELTKNQVSL WCLVKGFYPS DIAVEWESNG QPENNYKTTP PVLDSDGSFF LYSKLTVDKS  420
RWQQGNVFSC SVMHEALHNH YTQKSLSLSP GEPEA                            455

SEQ ID NO: 59          moltype = AA  length = 216
FEATURE                Location/Qualifiers
source                 1..216
                       mol_type = protein
                       organism = synthetic construct
SEQUENCE: 59
QSVLTQPPSA SGTPGQRVTI SCTGSSSNIG AGYDVHWYQQ LPGTAPKLLI YRSNQRPSGV   60
PDRFSGSKSG TSASLAISGL RSEDEADYYC SSYAGNYNLV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                           216

SEQ ID NO: 60          moltype = AA  length = 730
FEATURE                Location/Qualifiers
source                 1..730
                       mol_type = protein
                       organism = synthetic construct
SEQUENCE: 60
EVQLLESGGG LVQPGGSLRL SCAASGFTFS IYAMSWVRQA PGKGLEWVSA ISGSGGSTYY   60
```

```
ADSVKGRFTI SRDNSKNTLY LQMNSLRAED TAVYYCARDF DYWGQGTLVT VTSSGGGGSG   120
GGGSGGGGSQ SVLTQPPSAS GTPGQRVTIS CSGSSSNIGS NYVYWYQQLP GTAPKLLIYG   180
NINRPSGVPD RFSGSKSGTS ASLAISGLRS EDEADYYCAA WDDSLNGRVF GGGTKLTVLD   240
KGPSVFPLAP EPKSSEVQLL ESGGGLVQPG GSLRLSCAAS GFTFSNAWMN WVRQAPGKGL   300
EWVSSISSSS SYIYYADSVK GRFTISRDNS KNTLYLQMNS LRAEDTAVYY CARAVAAGGM   360
FWGLDQWGQG TLVTVTSSGG GGSGGGGSGG GGSQSVLTQP PSASGTPGQR VTISCSGSRS   420
NIGSNSVHWY QQLPGTAPKL LIYGNSNRPS GVPDRFSGSK SGTSASLAIS GLRSEDEADY   480
YCQSYDSSLN DHVVFGGGTK LTVLDKTHTC PPCPAPEAAG APSVFLFPPK PKDTLMISRT   540
PEVTCVVVDV SHEDPEVKFN WYVDGVEVHN AKTKPREEQY NSTYRVVSVL TVLHQDWLNG   600
KEYKCKVSNK ALPAPIEKTI SKAKGQPREP QVYTLPPSRD ELTKNQVSLT CLVKGFYPSD   660
IAVEWESNGQ PENNYKTTPP VLDSDGSFFL YSKLTVDKSR WQQGNVFSCS VMHEALHNHY   720
TQKSLSLSPG                                                          730

SEQ ID NO: 61          moltype = AA  length = 730
FEATURE                Location/Qualifiers
source                 1..730
                       mol_type = protein
                       organism = synthetic construct
SEQUENCE: 61
EVQLLESGGG LVQPGGSLRL SCAASGFTFS NAWMNWVRQA PGKGLEWVSS ISSSSSYIYY   60
ADSVKGRFTI SRDNSKNTLY LQMNSLRAED TAVYYCARAV AAGGMFWGLD QWGQGTLVTV   120
TSSGGGGSGG GGSGGGGSQS VLTQPPSASG TPGQRVTISC SGSRSNIGSN SVHWYQQLPG   180
TAPKLLIYGN SNRPSGVPDR FSGSKSGTSA SLAISGLRSE DEADYYCQSY DSSLNDHVVF   240
GGGTKLTVLD KGPSVFPLAP EPKSSEVQLL ESGGGLVQPG GSLRLSCAAS GFTFSIYAMS   300
WVRQAPGKGL EWVSAISGSG GSTYYADSVK GRFTISRDNS KNTLYLQMNS LRAEDTAVYY   360
CARDFDYWGQ GTLVTVTSSG GGGSGGGGSG GGGSQSVLTQ PPSASGTPGQ RVTISCSGSS   420
SNIGSNYVYW YQQLPGTAPK LLIYGNINRP SGVPDRFSGS KSGTSASLAI SGLRSEDEAD   480
YYCAAWDDSL NGRVFGGGTK LTVLDKTHTC PPCPAPEAAG APSVFLFPPK PKDTLMISRT   540
PEVTCVVVDV SHEDPEVKFN WYVDGVEVHN AKTKPREEQY NSTYRVVSVL TVLHQDWLNG   600
KEYKCKVSNK ALPAPIEKTI SKAKGQPREP QVYTLPPSRD ELTKNQVSLT CLVKGFYPSD   660
IAVEWESNGQ PENNYKTTPP VLDSDGSFFL YSKLTVDKSR WQQGNVFSCS VMHEALHNHY   720
TQKSLSLSPG                                                          730

SEQ ID NO: 62          moltype = AA  length = 728
FEATURE                Location/Qualifiers
source                 1..728
                       mol_type = protein
                       organism = synthetic construct
SEQUENCE: 62
EVQLLESGGG LVQPGGSLRL SCAASGFTFS SYAMSWVRQA PGKGLEWVAN INQDGSEKNY   60
VDSMRGRFTI SRDNSKNTLY LQMNSLRAED TAVYYCAREF DYWGQGTLVT VTSSGGGGSG   120
GGGSGGGGSQ SVLAQPPSAS GTPGQRVTIS CSGSSSNIGS NYVYWYQQLP GTAPKLLIYG   180
NNKRPSGVPD RFSGSKSGTS ASLAISGLRS EDEADYYCAA WDDSLNGRVF GGGTKLTVLD   240
KGPSVFPLAP EPKSSEVQLL ESGGGLVQPG GSLRLSCAAS GFTFSDYYMT WIRQAPGKGL   300
EWVSSISGGS TYYADSRKGR FTISRDNSEN TLYLQMNSLR AEDTAVYYCA RDFGVAGWFG   360
QYGMDVWGQG TLVTVSSGGG GSGGGGSGGG GSQSVLTQPP SASGTPGQRV TISCTGSSSN   420
IGAGYDVHWY QQLPGTAPKL LIYRSNQRPS GVPDRFSGSK SGTSASLAIS GLRSEDEADY   480
YCSSYAGNYN LVFGGGTKLT VLDKTHTCPP CPAPEAAGAP SVFLFPPKPK DTLMISRTPE   540
VTCVVVDVSH EDPEVKFNWY VDGVEVHNAK TKPREEQYNS TYRVVSVLTV LHQDWLNGKE   600
YKCKVSNKAL PAPIEKTISK AKGQPREPQV YTLPPSRDEL TKNQVSLTCL VKGFYPSDIA   660
VEWESNGQPE NNYKTTPPVL DSDGSFFLYS KLTVDKSRWQ QGNVFSCSVM HEALHNHYTQ   720
KSLSLSPG                                                            728

SEQ ID NO: 63          moltype = AA  length = 728
FEATURE                Location/Qualifiers
source                 1..728
                       mol_type = protein
                       organism = synthetic construct
SEQUENCE: 63
EVQLLESGGG LVQPGGSLRL SCAASGFTFS DYYMTWIRQA PGKGLEWVSS ISGGSTYYAD   60
SRKGRFTISR DNSENTLYLQ MNSLRAEDTA VYYCARDFGV AGWFGQYGMD VWGQGTLVTV   120
SSGGGGSGGG GSGGGGSQSV LTQPPSASGT PGQRVTISCT GSSSNIGAGY DVHWYQQLPG   180
TAPKLLIYRS NQRPSGVPDR FSGSKSGTSA SLAISGLRSE DEADYYCSSY AGNYNLVFGG   240
GTKLTVLDKG PSVFPLAPEP KSSEVQLLES GGGLVQPGGS LRLSCAASGF TFSSYAMSWV   300
RQAPGKGLEW VANINQDGSE KNYVDSMRGR FTISRDNSKN TLYLQMNSLR AEDTAVYYCA   360
REFDYWGQGT LVTVTSSGGG GSGGGGSGGG GSQSVLAQPP SASGTPGQRV TISCSGSSSN   420
IGSNYVYWYQ QLPGTAPKLL IYGNNKRPSG VPDRFSGSKS GTSASLAISG LRSEDEADYY   480
CAAWDDSLNG RVFGGGTKLT VLDKTHTCPP CPAPEAAGAP SVFLFPPKPK DTLMISRTPE   540
VTCVVVDVSH EDPEVKFNWY VDGVEVHNAK TKPREEQYNS TYRVVSVLTV LHQDWLNGKE   600
YKCKVSNKAL PAPIEKTISK AKGQPREPQV YTLPPSRDEL TKNQVSLTCL VKGFYPSDIA   660
VEWESNGQPE NNYKTTPPVL DSDGSFFLYS KLTVDKSRWQ QGNVFSCSVM HEALHNHYTQ   720
KSLSLSPG                                                            728

SEQ ID NO: 64          moltype = AA  length = 724
FEATURE                Location/Qualifiers
source                 1..724
                       mol_type = protein
                       organism = synthetic construct
SEQUENCE: 64
```

-continued

```
EVQLLESGGG LVQPGGSLRL SCAASGFTFS IYAMSWVRQA PGKGLEWVSA ISGSGGSTYY    60
ADSVKGRFTI SRDNSKNTLY LQMNSLRAED TAVYYCARDF DYWGQGTLVT VTSSGGGGSG   120
GGGSGGGGSQ SVLTQPPSAS GTPGQRVTIS CSGSSSNIGS NYVYWYQQLP GTAPKLLIYG   180
NINRPSGVPD RFSGSKSGTS ASLAISGLRS EDEADYYCAA WDDSLNGRVF GGGTKLTVLD   240
KTHTCPPCPA PEAAGAPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPSRDELTKN QVSLTCLVKG FYPSDIAVEW ESNGQPENNY KTTPPVLDSD   420
GSFFLYSKLT VDKSRWQQGN VFSCSVMHEA LHNHYTQKSL SLSPGGGGGS GGGGSEVQLL   480
ESGGGLVQPG GSLRLSCAAS GFTFSNAWMN WVRQAPGKGL EWVSSISSSS SYIYYADSVK   540
GRFTISRDNS KNTLYLQMNS LRAEDTAVYY CARAVAAGGM FWGLDQWGQG TLVTVTSSGG   600
GGGSGGGGSG GGSQSVLTQP PSASGTPGQR VTISCSGSRS NIGSNSVHWY QQLPGTAPKL   660
LIYGNSNRPS GVPDRFSGSK SGTSASLAIS GLRSEDEADY YCQSYDSSLN DHVVFGGGTK   720
LTVL                                                               724

SEQ ID NO: 65              moltype = AA   length = 724
FEATURE                    Location/Qualifiers
source                     1..724
                           mol_type = protein
                           organism = synthetic construct
SEQUENCE: 65
EVQLLESGGG LVQPGGSLRL SCAASGFTFS NAWMNWVRQA PGKGLEWVSS ISSSSSYIYY    60
ADSVKGRFTI SRDNSKNTLY LQMNSLRAED TAVYYCARAV AAGGMFWGLD QWGQGTLVTV   120
TSSGGGGSGG GGSGGGGSQS VLTQPPSASG TPGQRVTISC SGSRSNIGSN SVHWYQQLPG   180
TAPKLLIYGN SNRPSGVPDR FSGSKSGTSA SLAISGLRSE DEADYYCQSY DSSLNDHVVF   240
GGGTKLTVLD KTHTCPPCPA PEAAGAPSVF LFPPKPKDTL MISRTPEVTC VVVDVSHEDP   300
EVKFNWYVDG VEVHNAKTKP REEQYNSTYR VVSVLTVLHQ DWLNGKEYKC KVSNKALPAP   360
IEKTISKAKG QPREPQVYTL PPSRDELTKN QVSLTCLVKG FYPSDIAVEW ESNGQPENNY   420
KTTPPVLDSD GSFFLYSKLT VDKSRWQQGN VFSCSVMHEA LHNHYTQKSL SLSPGGGGGS   480
GGGGSEVQLL ESGGGLVQPG GSLRLSCAAS GFTFSIYAMS WVRQAPGKGL EWVSAISGSG   540
GSTYYADSVK GRFTISRDNS KNTLYLQMNS LRAEDTAVYY CARDFDYWGQ GTLVTVTSSG   600
GGGSGGGGSG GGGSQSVLTQ PPSASGTPGQ RVTISCSGSS NIGSNYVYW YQQLPGTAPK   660
LLIYGNINRP SGVPDRFSGS KSGTSASLAI SGLRSEDEAD YYCAAWDDSL NGRVFGGGTK   720
LTVL                                                               724

SEQ ID NO: 66              moltype = AA   length = 722
FEATURE                    Location/Qualifiers
source                     1..722
                           mol_type = protein
                           organism = synthetic construct
SEQUENCE: 66
EVQLLESGGG LVQPGGSLRL SCAASGFTFS SYAMSWVRQA PGKGLEWVAN INQDGSEKNY    60
VDSMRGRFTI SRDNSKNTLY LQMNSLRAED TAVYYCAREF DYWGQGTLVT VTSSGGGGSG   120
GGGSGGGGSQ SVLAQPPSAS GTPGQRVTIS CSGSSSNIGS NYVYWYQQLP GTAPKLLIYG   180
NNKRPSGVPD RFSGSKSGTS ASLAISGLRS EDEADYYCAA WDDSLNGRVF GGGTKLTVLD   240
KTHTCPPCPA PEAAGAPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPSRDELTKN QVSLTCLVKG FYPSDIAVEW ESNGQPENNY KTTPPVLDSD   420
GSFFLYSKLT VDKSRWQQGN VFSCSVMHEA LHNHYTQKSL SLSPGGGGGS GGGGSEVQLL   480
ESGGGLVQPG GSLRLSCAAS GFTFSDYYMT WIRQAPGKGL EWVSSISGGS TYYADSRKGR   540
FTISRDNSEN TLYLQMNSLR AEDTAVYYCA RDFGVAGWFG QYGMDVWGQG TLVTVSSGGG   600
GSGGGGSGGG GSQSVLTQPP SASGTPGQRV TISCTGSSSN IGAGYDVHWY QQLPGTAPKL   660
LIYRSNQRPS GVPDRFSGSK SGTSASLAIS GLRSEDEADY YCSSYAGNYN LVFGGGTKLT   720
VL                                                                 722

SEQ ID NO: 67              moltype = AA   length = 722
FEATURE                    Location/Qualifiers
source                     1..722
                           mol_type = protein
                           organism = synthetic construct
SEQUENCE: 67
EVQLLESGGG LVQPGGSLRL SCAASGFTFS DYYMTWIRQA PGKGLEWVSS ISGGSTYYAD    60
SRKGRFTISR DNSENTLYLQ MNSLRAEDTA VYYCARDFGV AGWFGQYGMD VWGQGTLVTV   120
SSGGGGSGGG GSGGGGSQSV LTQPPSASGT PGQRVTISCT GSSSNIGAGY DVHWYQQLPG   180
TAPKLLIYRS NQRPSGVPDR FSGSKSGTSA SLAISGLRSE DEADYYCSSY AGNYNLVFGG   240
GTKLTVLDKT HTCPPCPAPE AAGAPSVFLF PPKPKDTLMI SRTPEVTCVV VDVSHEDPEV   300
KFNWYVDGVE HNAKTKPRE EQYNSTYRVV SVLTVLHQDW LNGKEYKCKV SNKALPAPIE   360
KTISKAKGQP REPQVYTLPP SRDELTKNQV SLTCLVKGFY PSDIAVEWES NGQPENNYKT   420
TPPVLDSDGS FFLYSKLTVD KSRWQQGNVF SCSVMHEALH NHYTQKSLSL SPGGGGGSGG   480
GGSEVQLLES GGGLVQPGGS LRLSCAASGF TFSSYAMSWV RQAPGKGLEW VANINQDGSE   540
KNYVDSMRGR FTISRDNSKN TLYLQMNSLR AEDTAVYYCA REFDYWGQGT LVTVTSSGGG   600
GSGGGGSGGG GSQSVLAQPP SASGTPGQRV TISCSGSSSN IGSNYVYWYQ QLPGTAPKLL   660
IYGNNKRPSG VPDRFSGSKS GTSASLAISG LRSEDEADYY CAAWDDSLNG RVFGGGTKLT   720
VL                                                                 722

SEQ ID NO: 68              moltype = AA   length = 575
FEATURE                    Location/Qualifiers
source                     1..575
                           mol_type = protein
                           organism = synthetic construct
```

```
SEQUENCE: 68
EVQLLESGGG LVQPGGSLRL SCAASGFTFS IYAMSWVRQA PGKGLEWVSA ISGSGGGSTYY  60
ADSVKGRFTI SRDNSKNTLY LQMNSLRAED TAVYYCARDF DYWGQGTLVT VTSSPAPNLL   120
GGPEVQLLES GGGLVQPGGS LRLSCAASGF TFSNAWMNWV RQAPGKGLEW VSSISSSSSY   180
IYYADSVKGR FTISRDNSKN TLYLQMNSLR AEDTAVYYCA RAVAAGGMFW GLDQWGQGTL   240
VTVTSSASTK GPSVFPLAPS SKSTSGGTAA LGCLVKDYFP EPVTVSWNSG ALTSGVHTFP   300
AVLQSSGLYS LSSVVTVPSS SLGTQTYICN VNHKPSNTKV DKKVEPKSCD KTHTCPPCPA   360
PEAAGAPSVF LFPPKPKDTL MISRTPEVTC VVVDVSHEDP EVKFNWYVDG VEVHNAKTKP   420
REEQYNSTYR VVSVLTVLHQ DWLNGKEYKC KVSNKALPAP IEKTISKAKG QPREPQVYTL   480
PPSRDELTKN QVSLTCLVKG FYPSDIAVEW ESNGQPENNY KTTPPVLDSD GSFFLYSKLT   540
VDKSRWQQGN VFSCSVMHEA LHNHYTQKSL SLSPG                              575

SEQ ID NO: 69              moltype = AA   length = 336
FEATURE                    Location/Qualifiers
source                     1..336
                           mol_type = protein
                           organism = synthetic construct
SEQUENCE: 69
QSVLTQPPSA SGTPGQRVTI SCSGSSSNIG SNYVYWYQQL PGTAPKLLIY GNINRPSGVP   60
DRFSGSKSGT SASLAISGLR SEDEADYYCA AWDDSLNGRV FGGGTKLTVL PAPNLLGGPQ   120
SVLTQPPSAS GTPGQRVTIS CSGSRSNIGS NSVHWYQQLP GTAPKLLIYG NSNRPSGVPD   180
RFSGSKSGTS ASLAISGLRS EDEADYYCQS YDSSLNDHVV FGGGTKLTVL GQPKAAPSVT   240
LFPPSSEELQ ANKATLVCLI SDFYPGAVTV AWKADSSPVK AGVETTTPSK QSNNKYAASS   300
YLSLTPEQWK SHRSYSCQVT HEGSTVEKTV APTECS                             336

SEQ ID NO: 70              moltype = AA   length = 575
FEATURE                    Location/Qualifiers
source                     1..575
                           mol_type = protein
                           organism = synthetic construct
SEQUENCE: 70
EVQLLESGGG LVQPGGSLRL SCAASGFTFS NAWMNWVRQA PGKGLEWVSS ISSSSSYIYY   60
ADSVKGRFTI SRDNSKNTLY LQMNSLRAED TAVYYCARAV AAGGMFWGLD QWGQGTLVTV   120
TSSPAPNLLG GPEVQLLESG GGLVQPGGSL RLSCAASGF SIYAMSWVR QAPGKGLEWV   180
SAISGSGGST YYADSVKGRF TISRDNSKNT LYLQMNSLRA EDTAVYYCAR DFDYWGQGTL   240
VTVTSSASTK GPSVFPLAPS SKSTSGGTAA LGCLVKDYFP EPVTVSWNSG ALTSGVHTFP   300
AVLQSSGLYS LSSVVTVPSS SLGTQTYICN VNHKPSNTKV DKKVEPKSCD KTHTCPPCPA   360
PEAAGAPSVF LFPPKPKDTL MISRTPEVTC VVVDVSHEDP EVKFNWYVDG VEVHNAKTKP   420
REEQYNSTYR VVSVLTVLHQ DWLNGKEYKC KVSNKALPAP IEKTISKAKG QPREPQVYTL   480
PPSRDELTKN QVSLTCLVKG FYPSDIAVEW ESNGQPENNY KTTPPVLDSD GSFFLYSKLT   540
VDKSRWQQGN VFSCSVMHEA LHNHYTQKSL SLSPG                              575

SEQ ID NO: 71              moltype = AA   length = 336
FEATURE                    Location/Qualifiers
source                     1..336
                           mol_type = protein
                           organism = synthetic construct
SEQUENCE: 71
QSVLTQPPSA SGTPGQRVTI SCSGSRSNIG SNSVHWYQQL PGTAPKLLIY GNSNRPSGVP   60
DRFSGSKSGT SASLAISGLR SEDEADYYCQ SYDSSLNDHV VFGGGTKLTV LPAPNLLGGP   120
QSVLTQPPSA SGTPGQRVTI SCSGSSSNIG SNYVYWYQQL PGTAPKLLIY GNINRPSGVP   180
DRFSGSKSGT SASLAISGLR SEDEADYYCA AWDDSLNGRV FGGGTKLTVL GQPKAAPSVT   240
LFPPSSEELQ ANKATLVCLI SDFYPGAVTV AWKADSSPVK AGVETTTPSK QSNNKYAASS   300
YLSLTPEQWK SHRSYSCQVT HEGSTVEKTV APTECS                             336

SEQ ID NO: 72              moltype = AA   length = 574
FEATURE                    Location/Qualifiers
source                     1..574
                           mol_type = protein
                           organism = synthetic construct
SEQUENCE: 72
EVQLLESGGG LVQPGGSLRL SCAASGFTFS SYAMSWVRQA PGKGLEWVAN INQDGSEKNY   60
VDSMRGRFTI SRDNSKNTLY LQMNSLRAED TAVYYCAREF DYWGQGTLVT VTSSPAPNLL   120
GGPEVQLLES GGGLVQPGGS LRLSCAASGF TFSDYYMTWI RQAPGKGLEW VSSISGGSTY   180
YADSRKGRFT ISRDNSENTL YLQMNSLRAE DTAVYYCARD FGVAGWFGQY GMDVWGQGTL   240
VTVSSASTKG PSVFPLAPSS KSTSGGTAAL GCLVKDYFPE PVTVSWNSGA LTSGVHTFPA   300
VLQSSGLYSL SSVVTVPSSS LGTQTYICNV NHKPSNTKVD KKVEPKSCDK THTCPPCPAP   360
EAAGAPSVFL FPPKPKDTLM ISRTPEVTCV VVDVSHEDPE VKFNWYVDGV EVHNAKTKPR   420
EEQYNSTYRV VSVLTVLHQD WLNGKEYKCK VSNKALPAPI EKTISKAKGQ PREPQVYTLP   480
PSRDELTKNQ VSLTCLVKGF YPSDIAVEWE SNGQPENNYK TTPPVLDSDG SFFLYSKLTV   540
DKSRWQQGNV FSCSVMHEAL HNHYTQKSLS LSPG                               574

SEQ ID NO: 73              moltype = AA   length = 335
FEATURE                    Location/Qualifiers
source                     1..335
                           mol_type = protein
                           organism = synthetic construct
SEQUENCE: 73
QSVLAQPPSA SGTPGQRVTI SCSGSSSNIG SNYVYWYQQL PGTAPKLLIY GNNKRPSGVP   60
```

```
DRFSGSKSGT SASLAISGLR SEDEADYYCA AWDDSLNGRV FGGGTKLTVL PAPNLLGGPQ    120
SVLTQPPSAS GTPGQRVTIS CTGSSSNIGA GYDVHWYQQL PGTAPKLLIY RSNQRPSGVP    180
DRFSGSKSGT SASLAISGLR SEDEADYYCS SYAGNYNLVF GGGTKLTVLG QPKAAPSVTL    240
FPPSSEELQA NKATLVCLIS DFYPGAVTVA WKADSSPVKA GVETTTPSKQ SNNKYAASSY    300
LSLTPEQWKS HRSYSCQVTH EGSTVEKTVA PTECS                              335

SEQ ID NO: 74              moltype = AA  length = 574
FEATURE                    Location/Qualifiers
source                     1..574
                           mol_type = protein
                           organism = synthetic construct
SEQUENCE: 74
EVQLLESGGG LVQPGGSLRL SCAASGFTFS DYYMTWIRQA PGKGLEWVSS ISGGSTYYAD    60
SRKGRFTISR DNSENTLYLQ MNSLRAEDTA VYYCARDFGV AGWFGQYGMD VWGQGTLVTV    120
SSPAPNLLGG PEVQLLESGG GLVQPGGSLR LSCAASGFTF SSYAMSWVRQ APGKGLEWVA    180
NINQDGSEKN YVDSMRGRFT ISRDNSKNTL YLQMNSLRAE DTAVYYCARE FDYWGQGTLV    240
TVTSSASTKG PSVFPLAPSS KSTSGGTAAL GCLVKDYFPE PVTVSWNSGA LTSGVHTFPA    300
VLQSSGLYSL SSVVTVPSSS LGTQTYICNV NHKPSNTKVD KKVEPKSCDK THTCPPCPAP    360
EAAGAPSVFL FPPKPKDTLM ISRTPEVTCV VVDVSHEDPE VKFNWYVDGV EVHNAKTKPR    420
EEQYNSTYRV VSVLTVLHQD WLNGKEYKCK VSNKALPAPI EKTISKAKGQ PREPQVYTLP    480
PSRDELTKNQ VSLTCLVKGF YPSDIAVEWE SNGQPENNYK TTPPVLDSDG SFFLYSKLTV    540
DKSRWQQGNV FSCSVMHEAL HNHYTQKSLS LSPG                              574

SEQ ID NO: 75              moltype = AA  length = 335
FEATURE                    Location/Qualifiers
source                     1..335
                           mol_type = protein
                           organism = synthetic construct
SEQUENCE: 75
QSVLTQPPSA SGTPGQRVTI SCTGSSSNIG AGYDVHWYQQ LPGTAPKLLI YRSNQRPSGV    60
PDRFSGSKSG TSASLAISGL RSEDEADYYC SSYAGNYNLV FGGGTKLTVL PAPNLLGGPQ    120
SVLAQPPSAS GTPGQRVTIS CSGSSSNIGS NYVYWYQQLP GTAPKLLIYG NNKRPSGVPD    180
RFSGSKSGTS ASLAISGLRS EDEADYYCAA WDDSLNGRVF GGGTKLTVLG QPKAAPSVTL    240
FPPSSEELQA NKATLVCLIS DFYPGAVTVA WKADSSPVKA GVETTTPSKQ SNNKYAASSY    300
LSLTPEQWKS HRSYSCQVTH EGSTVEKTVA PTECS                              335

SEQ ID NO: 76              moltype = AA  length = 469
FEATURE                    Location/Qualifiers
source                     1..469
                           mol_type = protein
                           organism = synthetic construct
SEQUENCE: 76
EVQLLESGGG LVQPGGSLRL SCAASGFTFS DYAMSWVRQA PGKGLEWVSA ISGSGGVTYY    60
ADSVKGRFTI SRDNSKNTLY LQMNSLRAED TAVYYCAREF DWWGQGTLVT VTSSGGGGSG    120
GGGSGGGGSQ SVLTQPPSAS GTPGQRVTIS CSGSSSNIGS NYVYWYQQLP GTAPKLLIYG    180
NINRPSGVPD RFSGSKSGTS ASLAISGLRS EDEADYYCAA WDDSLNGRVF GGGTKLTVLD    240
KTHTCPPCPA PEAAGAPSVF LFPPKPKDTL MISRTPEVTC VVVDVSHEDP EVKFNWYVDG    300
VEVHNAKTKP REEQYNSTYR VVSVLTVLHQ DWLNGKEYKC KVSNKALPAP IEKTISKAKG    360
QPREPQVYTL PPCRDELTKN QVSLWCLVKG FYPSDIAVEW ESNGQPENNY KTTPPVLDSD    420
GSFFLYSKLT VDKSRWQQGN VFSCSVMHEA LHNHYTQKSL SLSPGEPEA              469

SEQ ID NO: 77              moltype = AA  length = 469
FEATURE                    Location/Qualifiers
source                     1..469
                           mol_type = protein
                           organism = synthetic construct
SEQUENCE: 77
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCAREF DWWGQGTLVT VTSSGGGGSG    120
GGGSGGGGSQ SVLTQPPSAS GTPGQRVTIS CSGSSSNIGS NYVYWYQQLP GTAPKLLIYG    180
NINRPSGVPD RFSGSKSGTS ASLAISGLRS EDEADYYCAA WDDSLNGRVF GGGTKLTVLD    240
KTHTCPPCPA PEAAGAPSVF LFPPKPKDTL MISRTPEVTC VVVDVSHEDP EVKFNWYVDG    300
VEVHNAKTKP REEQYNSTYR VVSVLTVLHQ DWLNGKEYKC KVSNKALPAP IEKTISKAKG    360
QPREPQVYTL PPCRDELTKN QVSLWCLVKG FYPSDIAVEW ESNGQPENNY KTTPPVLDSD    420
GSFFLYSKLT VDKSRWQQGN VFSCSVMHEA LHNHYTQKSL SLSPGEPEA              469

SEQ ID NO: 78              moltype = AA  length = 469
FEATURE                    Location/Qualifiers
source                     1..469
                           mol_type = protein
                           organism = synthetic construct
SEQUENCE: 78
EVQLLESGGG LVQPGGSLRL SCAASGFTFS DYAMSWVRQA PGKGLEWVSA ISGSGGATYY    60
ADSVKGRFTI SRDNSKNTLY LQMNSLRAED TAVYYCAREF DYWGQGTLVT VTSSGGGGSG    120
GGGSGGGGSQ SVLTQPPSAS GTPGQRVTIS CSGSSSNIGS NYVYWYQQLP GTAPKLLIYG    180
NINRPSGVPD RFSGSKSGTS ASLAISGLRS EDEADYYCAA WDDSLNGRVF GGGTKLTVLD    240
KTHTCPPCPA PEAAGAPSVF LFPPKPKDTL MISRTPEVTC VVVDVSHEDP EVKFNWYVDG    300
VEVHNAKTKP REEQYNSTYR VVSVLTVLHQ DWLNGKEYKC KVSNKALPAP IEKTISKAKG    360
QPREPQVYTL PPCRDELTKN QVSLWCLVKG FYPSDIAVEW ESNGQPENNY KTTPPVLDSD    420
```

-continued

```
GSFFLYSKLT VDKSRWQQGN VFSCSVMHEA LHNHYTQKSL SLSPGEPEA              469

SEQ ID NO: 79          moltype = AA   length = 469
FEATURE                Location/Qualifiers
source                 1..469
                       mol_type = protein
                       organism = synthetic construct
SEQUENCE: 79
EVQLLESGGG LVQPGGSLRL SCAASGFTFS SYAMSWVRQA PGKGLEWVAN INQDGSEKNY   60
VDSMRGRFTI SRDNSKNTLY LQMNSLRAED TAVYYCAREF DYWGQGTLVT VTSSGGGGSG  120
GGGSGGGGSQ SVLAQPPSAS GTPGQRVTIS CSGSSSNIGS NYVYWYQQLP GTAPKLLIYG  180
NNKRPSGVPD RFSGSKSGTS ASLAISGLRS EDEADYYCAA WDDSLNGRVF GGGTKLTVLD  240
KTHTCPPCPA PEAAGAPSVF LFPPKPKDTL MISRTPEVTC VVVDVSHEDP EVKFNWYVDG  300
VEVHNAKTKP REEQYNSTYR VVSVLTVLHQ DWLNGKEYKC KVSNKALPAP IEKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGEPEA              469

SEQ ID NO: 80          moltype = AA   length = 469
FEATURE                Location/Qualifiers
source                 1..469
                       mol_type = protein
                       organism = synthetic construct
SEQUENCE: 80
EVQLLESGGG LVQPGGSLRL SCAASGFTFS SYAMSWVRQA PGKGLEWVAN INQDGSEKNY   60
VDSMRGRFTI SRDNSKNTLY LQMNSLRAED TAVYYCARDY RYWGQGTLVT VTSSGGGGSG  120
GGGSGGGGSQ SVLAQPPSAS GTPGQRVTIS CSGSSSNIGS NYVYWYQQLP GTAPKLLIYG  180
NNKRPSGVPD RFSGSKSGTS ASLAISGLRS EDEADYYCAA WDDSLNGRVF GGGTKLTVLD  240
KTHTCPPCPA PEAAGAPSVF LFPPKPKDTL MISRTPEVTC VVVDVSHEDP EVKFNWYVDG  300
VEVHNAKTKP REEQYNSTYR VVSVLTVLHQ DWLNGKEYKC KVSNKALPAP IEKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGEPEA              469

SEQ ID NO: 81          moltype = AA   length = 469
FEATURE                Location/Qualifiers
source                 1..469
                       mol_type = protein
                       organism = synthetic construct
SEQUENCE: 81
EVQLLESGGG LVQPGGSLRL SCAASGFTFS SYAMSWVRQA PGKGLEWVAN INQDGSEKNY   60
VDSMRGRFTI SRDNSKNTLY LQMNSLRAED TAVYYCAREY KYWGQGTLVT VTSSGGGGSG  120
GGGSGGGGSQ SVLAQPPSAS GTPGQRVTIS CSGSSSNIGS NYVYWYQQLP GTAPKLLIYG  180
NNKRPSGVPD RFSGSKSGTS ASLAISGLRS EDEADYYCAA WDDSLNGRVF GGGTKLTVLD  240
KTHTCPPCPA PEAAGAPSVF LFPPKPKDTL MISRTPEVTC VVVDVSHEDP EVKFNWYVDG  300
VEVHNAKTKP REEQYNSTYR VVSVLTVLHQ DWLNGKEYKC KVSNKALPAP IEKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGEPEA              469

SEQ ID NO: 82          moltype = AA   length = 469
FEATURE                Location/Qualifiers
source                 1..469
                       mol_type = protein
                       organism = synthetic construct
SEQUENCE: 82
EVQLLESGGG LVQPGGSLRL SCAASGFTFS SYAMSWVRQA PGKGLEWVAN INQDGSEKNY   60
VDSMRGRFTI SRDNSKNTLY LQMNSLRAED TAVYYCAREY QYWGQGTLVT VTSSGGGGSG  120
GGGSGGGGSQ SVLAQPPSAS GTPGQRVTIS CSGSSSNIGS NYVYWYQQLP GTAPKLLIYG  180
NNKRPSGVPD RFSGSKSGTS ASLAISGLRS EDEADYYCAA WDDSLNGRVF GGGTKLTVLD  240
KTHTCPPCPA PEAAGAPSVF LFPPKPKDTL MISRTPEVTC VVVDVSHEDP EVKFNWYVDG  300
VEVHNAKTKP REEQYNSTYR VVSVLTVLHQ DWLNGKEYKC KVSNKALPAP IEKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGEPEA              469

SEQ ID NO: 83          moltype = AA   length = 469
FEATURE                Location/Qualifiers
source                 1..469
                       mol_type = protein
                       organism = synthetic construct
SEQUENCE: 83
EVQLLESGGG LVQPGGSLRL SCAASGFTFS SYAMSWVRQA PGKGLEWVAN INQDGSEKNY   60
VDSMRGRFTI SRDNSKNTLY LQMNSLRAED TAVYYCARNY QYWGQGTLVT VTSSGGGGSG  120
GGGSGGGGSQ SVLAQPPSAS GTPGQRVTIS CSGSSSNIGS NYVYWYQQLP GTAPKLLIYG  180
NNKRPSGVPD RFSGSKSGTS ASLAISGLRS EDEADYYCAA WDDSLNGRVF GGGTKLTVLD  240
KTHTCPPCPA PEAAGAPSVF LFPPKPKDTL MISRTPEVTC VVVDVSHEDP EVKFNWYVDG  300
VEVHNAKTKP REEQYNSTYR VVSVLTVLHQ DWLNGKEYKC KVSNKALPAP IEKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGEPEA              469

SEQ ID NO: 84          moltype = AA   length = 469
FEATURE                Location/Qualifiers
```

```
source                    1..469
                          mol_type = protein
                          organism = synthetic construct
SEQUENCE: 84
EVQLLESGGG LVQPGGSLRL SCAASGFTFS SYAMSWVRQA PGKGLEWVAN INQDGSEKNY    60
VDSMRGRFTI SRDNSKNTLY LQMNSLRAED TAVYYCARNY QFWGQGTLVT VTSSGGGGSG   120
GGGSGGGGSQ SVLAQPPSAS GTPGQRVTIS CSGSSSNIGS NYVYWYQQLP GTAPKLLIYG   180
NNKRPSGVPD RFSGSKSGTS ASLAISGLRS EDEADYYCAA WDDSLNGRVF GGGTKLTVLD   240
KTHTCPPCPA PEAAGAPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPCRDELTKN QVSLWCLVKG FYPSDIAVEW ESNGQPENNY KTTPPVLDSD   420
GSFFLYSKLT VDKSRWQQGN VFSCSVMHEA LHNHYTQKSL SLSPGEPEA              469

SEQ ID NO: 85              moltype = AA  length = 469
FEATURE                   Location/Qualifiers
source                    1..469
                          mol_type = protein
                          organism = synthetic construct
SEQUENCE: 85
EVQLLESGGG LVQPGGSLRL SCAASGFTFS IYAMSWVRQA PGKGLEWVSA ISGSGGSTYY    60
ADSVKGRFTI SRDNSKNTLY LQMNSLRAED TAVYYCARDG LYWGQGTLVT VTSSGGGGSG   120
GGGSGGGGSQ SVLTQPPSAS GTPGQRVTIS CSGSSSNIGS NYVYWYQQLP GTAPKLLIYG   180
NINRPSGVPD RFSGSKSGTS ASLAISGLRS EDEADYYCAA WDDSLNGRVF GGGTKLTVLD   240
KTHTCPPCPA PEAAGAPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPCRDELTKN QVSLWCLVKG FYPSDIAVEW ESNGQPENNY KTTPPVLDSD   420
GSFFLYSKLT VDKSRWQQGN VFSCSVMHEA LHNHYTQKSL SLSPGEPEA              469

SEQ ID NO: 86              moltype = AA  length = 469
FEATURE                   Location/Qualifiers
source                    1..469
                          mol_type = protein
                          organism = synthetic construct
SEQUENCE: 86
EVQLLESGGG LVQPGGSLRL SCAASGFTFS IYAMSWVRQA PGKGLEWVSA ISGSGGSTYY    60
ADSVKGRFTI SRDNSKNTLY LQMNSLRAED TAVYYCARNW DYWGQGTLVT VTSSGGGGSG   120
GGGSGGGGSQ SVLTQPPSAS GTPGQRVTIS CSGSSSNIGS NYVYWYQQLP GTAPKLLIYG   180
NINRPSGVPD RFSGSKSGTS ASLAISGLRS EDEADYYCAA WDDSLNGRVF GGGTKLTVLD   240
KTHTCPPCPA PEAAGAPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPCRDELTKN QVSLWCLVKG FYPSDIAVEW ESNGQPENNY KTTPPVLDSD   420
GSFFLYSKLT VDKSRWQQGN VFSCSVMHEA LHNHYTQKSL SLSPGEPEA              469

SEQ ID NO: 87              moltype = AA  length = 469
FEATURE                   Location/Qualifiers
source                    1..469
                          mol_type = protein
                          organism = synthetic construct
SEQUENCE: 87
EVQLLESGGG LVQPGGSLRL SCAASGFTFS IYAMSWVRQA PGKGLEWVSA ISGSGGSTYY    60
ADSVKGRFTI SRDNSKNTLY LQMNSLRAED TAVYYCARNG LYWGQGTLVT VTSSGGGGSG   120
GGGSGGGGSQ SVLTQPPSAS GTPGQRVTIS CSGSSSNIGS NYVYWYQQLP GTAPKLLIYG   180
NINRPSGVPD RFSGSKSGTS ASLAISGLRS EDEADYYCAA WDDSLNGRVF GGGTKLTVLD   240
KTHTCPPCPA PEAAGAPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPCRDELTKN QVSLWCLVKG FYPSDIAVEW ESNGQPENNY KTTPPVLDSD   420
GSFFLYSKLT VDKSRWQQGN VFSCSVMHEA LHNHYTQKSL SLSPGEPEA              469

SEQ ID NO: 88              moltype = AA  length = 469
FEATURE                   Location/Qualifiers
source                    1..469
                          mol_type = protein
                          organism = synthetic construct
SEQUENCE: 88
EVQLLESGGG LVQPGGSLRL SCAASGFTFS IYAMSWVRQA PGKGLEWVSA ISGSGGSTYY    60
ADSVKGRFTI SRDNSKNTLY LQMNSLRAED TAVYYCARNY DFWGQGTLVT VTSSGGGGSG   120
GGGSGGGGSQ SVLTQPPSAS GTPGQRVTIS CSGSSSNIGS NYVYWYQQLP GTAPKLLIYG   180
NINRPSGVPD RFSGSKSGTS ASLAISGLRS EDEADYYCAA WDDSLNGRVF GGGTKLTVLD   240
KTHTCPPCPA PEAAGAPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPCRDELTKN QVSLWCLVKG FYPSDIAVEW ESNGQPENNY KTTPPVLDSD   420
GSFFLYSKLT VDKSRWQQGN VFSCSVMHEA LHNHYTQKSL SLSPGEPEA              469

SEQ ID NO: 89              moltype = AA  length = 469
FEATURE                   Location/Qualifiers
source                    1..469
                          mol_type = protein
                          organism = synthetic construct
SEQUENCE: 89
```

```
EVQLLESGGG LVQPGGSLRL SCAASGFTFS IYAMSWVRQA PGKGLEWVSA ISGSGGGSTYY   60
ADSVKGRFTI SRDNSKNTLY LQMNSLRAED TAVYYCARDY LYWGQGTLVT VTSSGGGGSG   120
GGGSGGGGSQ SVLTQPPSAS GTPGQRVTIS CSGSSSNIGS NYVYWYQQLP GTAPKLLIYG   180
NINRPSGVPD RFSGSKSGTS ASLAISGLRS EDEADYYCAA WDDSLNGRVF GGGTKLTVLD   240
KTHTCPPCPA PEAAGAPSVF LFPPKPKDTL MISRTPEVTC YVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPCRDELTKN QVSLWCLVKG FYPSDIAVEW ESNGQPENNY KTTPPVLDSD   420
GSFFLYSKLT VDKSRWQQGN VFSCSVMHEA LHNHYTQKSL SLSPGEPEA             469

SEQ ID NO: 90            moltype = AA  length = 468
FEATURE                  Location/Qualifiers
source                   1..468
                         mol_type = protein
                         organism = synthetic construct
SEQUENCE: 90
EVQLLESGGG LVQPGGSLRL SCAASGFTFS SYWMSWVRQA PGKGLEWVAN IKQDGSEKNY   60
VDSMRGRFTI SRDNSKNTLY LQMNSLRAED TAVYYCAREY DYWGQGTLVT VTSGGGGSGG   120
GGSGGGGSQS VLAQPPSASG TPGQRVTISC SGSSSNIGSN YVYWYQQLPG TAPKLLIYGN   180
NKRPSGVPDR FSGSKSGTSA SLAISGLRSE DEADYYCAAW DDSLNGRVFG GGTKLTVLDK   240
THTCPPCPAP EAAGAPSVFL FPPKPKDTLM ISRTPEVTCV VVDVSHEDPE VKFNWYVDGV   300
EVHNAKTKPR EEQYNSTYRV VSVLTVLHQD WLNGKEYKCK VSNKALPAPI EKTISKAKGQ   360
PREPQVYTLP PCRDELTKNQ VSLWCLVKGF YPSDIAVEWE SNGQPENNYK TTPPVLDSDG   420
SFFLYSKLTV DKSRWQQGNV FSCSVMHEAL HNHYTQKSLS LSPGEPEA             468

SEQ ID NO: 91            moltype = AA  length = 468
FEATURE                  Location/Qualifiers
source                   1..468
                         mol_type = protein
                         organism = synthetic construct
SEQUENCE: 91
EVQLLESGGG LVQPGGSLRL SCAASGFTFS SYWMSWVRQA PGKGLEWVAN INQDGSEKYY   60
VDSMRGRFTI SRDNSKNTLY LQMNSLRAED TAVYYCAREY DYWGQGTLVT VTSGGGGSGG   120
GGSGGGGSQS VLAQPPSASG TPGQRVTISC SGSSSNIGSN YVYWYQQLPG TAPKLLIYGN   180
NKRPSGVPDR FSGSKSGTSA SLAISGLRSE DEADYYCAAW DDSLNGRVFG GGTKLTVLDK   240
THTCPPCPAP EAAGAPSVFL FPPKPKDTLM ISRTPEVTCV VVDVSHEDPE VKFNWYVDGV   300
EVHNAKTKPR EEQYNSTYRV VSVLTVLHQD WLNGKEYKCK VSNKALPAPI EKTISKAKGQ   360
PREPQVYTLP PCRDELTKNQ VSLWCLVKGF YPSDIAVEWE SNGQPENNYK TTPPVLDSDG   420
SFFLYSKLTV DKSRWQQGNV FSCSVMHEAL HNHYTQKSLS LSPGEPEA             468

SEQ ID NO: 92            moltype = AA  length = 468
FEATURE                  Location/Qualifiers
source                   1..468
                         mol_type = protein
                         organism = synthetic construct
SEQUENCE: 92
EVQLLESGGG LVQPGGSLRL SCAASGFTFS SYWMSWVRQA PGKGLEWVAN IKQDGSEKNY   60
VDSMRGRFTI SRDNSKNTLY LQMNSLRAED TAVYYCAREF DFWGQGTLVT VTSGGGGSGG   120
GGSGGGGSQS VLAQPPSASG TPGQRVTISC SGSSSNIGSN YVYWYQQLPG TAPKLLIYGN   180
NKRPSGVPDR FSGSKSGTSA SLAISGLRSE DEADYYCAAW DDSLNGRVFG GGTKLTVLDK   240
THTCPPCPAP EAAGAPSVFL FPPKPKDTLM ISRTPEVTCV VVDVSHEDPE VKFNWYVDGV   300
EVHNAKTKPR EEQYNSTYRV VSVLTVLHQD WLNGKEYKCK VSNKALPAPI EKTISKAKGQ   360
PREPQVYTLP PCRDELTKNQ VSLWCLVKGF YPSDIAVEWE SNGQPENNYK TTPPVLDSDG   420
SFFLYSKLTV DKSRWQQGNV FSCSVMHEAL HNHYTQKSLS LSPGEPEA             468

SEQ ID NO: 93            moltype = AA  length = 469
FEATURE                  Location/Qualifiers
source                   1..469
                         mol_type = protein
                         organism = synthetic construct
SEQUENCE: 93
EVQLLESGGG LVQPGGSLRL SCAASGFTFS DYAMSWVRQA PGKGLEWVAN INQSGSEKNY   60
VDSMRGRFTI SRDNSKNTLY LQMNSLRAED TAVYYCAREF DWWGQGTLVT VSSSGGGGSG   120
GGGSGGGGSQ SVLAQPPSAS GTPGQRVTIS CSGSSSNIGS NYVYWYQQLP GTAPKLLIYG   180
NNKRPSGVPD RFSGSKSGTS ASLAISGLRS EDEADYYCAA WDDSLNGRVF GGGTKLTVLD   240
KTHTCPPCPA PEAAGAPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPCRDELTKN QVSLWCLVKG FYPSDIAVEW ESNGQPENNY KTTPPVLDSD   420
GSFFLYSKLT VDKSRWQQGN VFSCSVMHEA LHNHYTQKSL SLSPGEPEA             469

SEQ ID NO: 94            moltype = AA  length = 469
FEATURE                  Location/Qualifiers
source                   1..469
                         mol_type = protein
                         organism = synthetic construct
SEQUENCE: 94
EVQLLESGGG LVQPGGSLRL SCAASGFTFS DYAMSWVRQA PGKGLEWVAN INQDGSEKNY   60
VDSMRGRFTI SRDNSKNTLY LQMNSLRAED TAVYYCAREF DWWGQGTLVT VSSSGGGGSG   120
GGGSGGGGSQ SVLAQPPSAS GTPGQRVTIS CSGSSSNIGS NYVYWYQQLP GTAPKLLIYG   180
NNKRPSGVPD RFSGSKSGTS ASLAISGLRS EDEADYYCAA WDDSLNGRVF GGGTKLTVLD   240
```

```
KTHTCPPCPA PEAAGAPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPCRDELTKN QVSLWCLVKG FYPSDIAVEW ESNGQPENNY KTTPPVLDSD   420
GSFFLYSKLT VDKSRWQQGN VFSCSVMHEA LHNHYTQKSL SLSPGEPEA              469

SEQ ID NO: 95              moltype = AA  length = 481
FEATURE                   Location/Qualifiers
source                    1..481
                          mol_type = protein
                          organism = synthetic construct
SEQUENCE: 95
EVQLLESGGG LVQPGGSLRL SCAASGFTFS DYYMTWIRQA PGKGLEWVSS ISGGSTYYAD   60
SRKGRFTISR DNSENTLYLQ MNSLRAEDTA VYYCARDFGV AGWFGQYGMD VWGQGTLVTV   120
SSGGGGSGGG GSGGGGSQSV LTQPPSASGT PGQRVTISCT GSSSNIGAGY DVHWYQQLPG   180
TAPKLLIYRS NQRPSGVPDR FSGSKSGTSA SLAISGLRSE DEADYYCSSY AGNYNLVFGG   240
GTKLTVLDKT HTCPPCPAPE AAGAPSVFLF PPKPKDTLMI SRTPEVTCVV VDVSHEDPEV   300
KFNWYVDGVE VHNAKTKPRE EQYNSTYRVV SVLTVLHQDW LNGKEYKCKV SNKALPAPIE   360
KTISKAKGQP REPQVCTLPP SRDELTKNQV SLSCAVKGFY PSDIAVEWES NGQPENNYKT   420
TPPVLDSDGS FFLVSKLTVD KSRWQQGNVF SCSVMHEALH NHYTQKSLSL SPGWSHPQFE   480
K                                                                   481

SEQ ID NO: 96              moltype = AA  length = 481
FEATURE                   Location/Qualifiers
source                    1..481
                          mol_type = protein
                          organism = synthetic construct
SEQUENCE: 96
EVQLLESGGG LVQPGGSLRL SCAASGFTFS DYYMTWIRQA PGKGLEWVSS ISGGSTYYAD   60
SRKGRFTISR DNSENTLYLQ MNSLRAEDTA VYYCARWETS SGGFGSGGLS HWGQGTLVTV   120
SSGGGGSGGG GSGGGGSQSV LTQPPSASGT PGQRVTISCT GSSSNIGAGY DVHWYQQLPG   180
TAPKLLIYRS NQRPSGVPDR FSGSKSGTSA SLAISGLRSE DEADYYCSSY AGNYNLVFGG   240
GTKLTVLDKT HTCPPCPAPE AAGAPSVFLF PPKPKDTLMI SRTPEVTCVV VDVSHEDPEV   300
KFNWYVDGVE VHNAKTKPRE EQYNSTYRVV SVLTVLHQDW LNGKEYKCKV SNKALPAPIE   360
KTISKAKGQP REPQVCTLPP SRDELTKNQV SLSCAVKGFY PSDIAVEWES NGQPENNYKT   420
TPPVLDSDGS FFLVSKLTVD KSRWQQGNVF SCSVMHEALH NHYTQKSLSL SPGWSHPQFE   480
K                                                                   481

SEQ ID NO: 97              moltype = AA  length = 481
FEATURE                   Location/Qualifiers
source                    1..481
                          mol_type = protein
                          organism = synthetic construct
SEQUENCE: 97
EVQLLESGGG LVQPGGSLRL SCAASGFTFS DYYMTWIRQA PGKGLEWVSS ISGGSTYYAD   60
SRKGRFTISR DNSENTLYLQ MNSLRAEDTA VYYCARLTVD GGGYGSGGLD LWGQGTLVTV   120
SSGGGGSGGG GSGGGGSQSV LTQPPSASGT PGQRVTISCT GSSSNIGAGY DVHWYQQLPG   180
TAPKLLIYRS NQRPSGVPDR FSGSKSGTSA SLAISGLRSE DEADYYCSSY AGNYNLVFGG   240
GTKLTVLDKT HTCPPCPAPE AAGAPSVFLF PPKPKDTLMI SRTPEVTCVV VDVSHEDPEV   300
KFNWYVDGVE VHNAKTKPRE EQYNSTYRVV SVLTVLHQDW LNGKEYKCKV SNKALPAPIE   360
KTISKAKGQP REPQVCTLPP SRDELTKNQV SLSCAVKGFY PSDIAVEWES NGQPENNYKT   420
TPPVLDSDGS FFLVSKLTVD KSRWQQGNVF SCSVMHEALH NHYTQKSLSL SPGWSHPQFE   480
K                                                                   481

SEQ ID NO: 98              moltype = AA  length = 481
FEATURE                   Location/Qualifiers
source                    1..481
                          mol_type = protein
                          organism = synthetic construct
SEQUENCE: 98
EVQLLESGGG LVQPGGSLRL SCAASGFTFS DYYMTWIRQA PGKGLEWVSS ISGGSTYYAD   60
SRKGRFTISR DNSENTLYLQ MNSLRAEDTA VYYCARNEVS GGYYGEFGLS LWGQGTLVTV   120
SSGGGGSGGG GSGGGGSQSV LTQPPSASGT PGQRVTISCT GSSSNIGAGY DVHWYQQLPG   180
TAPKLLIYRS NQRPSGVPDR FSGSKSGTSA SLAISGLRSE DEADYYCSSY AGNYNLVFGG   240
GTKLTVLDKT HTCPPCPAPE AAGAPSVFLF PPKPKDTLMI SRTPEVTCVV VDVSHEDPEV   300
KFNWYVDGVE VHNAKTKPRE EQYNSTYRVV SVLTVLHQDW LNGKEYKCKV SNKALPAPIE   360
KTISKAKGQP REPQVCTLPP SRDELTKNQV SLSCAVKGFY PSDIAVEWES NGQPENNYKT   420
TPPVLDSDGS FFLVSKLTVD KSRWQQGNVF SCSVMHEALH NHYTQKSLSL SPGWSHPQFE   480
K                                                                   481

SEQ ID NO: 99              moltype = AA  length = 481
FEATURE                   Location/Qualifiers
source                    1..481
                          mol_type = protein
                          organism = synthetic construct
SEQUENCE: 99
EVQLLESGGG LVQPGGSLRL SCAASGFTFS DYYMTWIRQA PGKGLEWVSS ISGGSTYYAD   60
SRKGRFTISR DNSENTLYLQ MNSLRAEDTA VYYCARNVTS GGYFGSFGLD LWGQGTLVTV   120
SSGGGGSGGG GSGGGGSQSV LTQPPSASGT PGQRVTISCT GSSSNIGAGY DVHWYQQLPG   180
TAPKLLIYRS NQRPSGVPDR FSGSKSGTSA SLAISGLRSE DEADYYCSSY AGNYNLVFGG   240
```

```
GTKLTVLDKT HTCPPCPAPE AAGAPSVFLF PPKPKDTLMI SRTPEVTCVV VDVSHEDPEV    300
KFNWYVDGVE VHNAKTKPRE EQYNSTYRVV SVLTVLHQDW LNGKEYKCKV SNKALPAPIE    360
KTISKAKGQP REPQVCTLPP SRDELTKNQV SLSCAVKGFY PSDIAVEWES NGQPENNYKT    420
TPPVLDSDGS FFLVSKLTVD KSRWQQGNVF SCSVMHEALH NHYTQKSLSL SPGWSHPQFE    480
K                                                                   481

SEQ ID NO: 100            moltype = AA   length = 481
FEATURE                   Location/Qualifiers
source                    1..481
                          mol_type = protein
                          organism = synthetic construct
SEQUENCE: 100
EVQLLESGGG LVQPGGSLRL SCAASGFTFS DYYMTWIRQA PGKGLEWVSS ISGGGSTYYAD    60
SRKGRFTISR DNSENTLYLQ MNSLRAEDTA VYYCARWETS GGYYGSGGLT IWGQGTLVTV    120
SSGGGGSGGG GSGGGGSQSV LTQPPSASGT PGQRVTISCT GSSSNIGAGY DVHWYQQLPG    180
TAPKLLIYRS NQRPSGVPDR FSGSKSGTSA SLAISGLRSE DEADYYCSSY AGNYNLVFGG    240
GTKLTVLDKT HTCPPCPAPE AAGAPSVFLF PPKPKDTLMI SRTPEVTCVV VDVSHEDPEV    300
KFNWYVDGVE VHNAKTKPRE EQYNSTYRVV SVLTVLHQDW LNGKEYKCKV SNKALPAPIE    360
KTISKAKGQP REPQVCTLPP SRDELTKNQV SLSCAVKGFY PSDIAVEWES NGQPENNYKT    420
TPPVLDSDGS FFLVSKLTVD KSRWQQGNVF SCSVMHEALH NHYTQKSLSL SPGWSHPQFE    480
K                                                                   481

SEQ ID NO: 101            moltype = AA   length = 483
FEATURE                   Location/Qualifiers
source                    1..483
                          mol_type = protein
                          organism = synthetic construct
SEQUENCE: 101
EVQLLESGGG LVQPGGSLRL SCAASGFTFS NAWMNWVRQA PGKGLEWVSS ISSSSSYIYY    60
ADSVKGRFTI SRDNSKNTLY LQMNSLRAED TAVYYCARAV AAGGMFWGLD QWGQGTLVTV    120
TSSGGGGSGG GGSGGGGSQS VLTQPPSASG TPGQRVTISC SGSRSNIGSN SVHWYQQLPG    180
TAPKLLIYGN SNRPSGVPDR FSGSKSGTSA SLAISGLRSE DEADYYCQSY DSSLNDHVVF    240
GGGTKLTVLD KTHTCPPCPA PEAAGAPSVF LFPPKPKDTL MISRTPEVTC VVVDVSHEDP    300
EVKFNWYVDG VEVHNAKTKP REEQYNSTYR VVSVLTVLHQ DWLNGKEYKC KVSNKALPAP    360
IEKTISKAKG QPREPQVCTL PPSRDELTKN QVSLSCAVKG FYPSDIAVEW ESNGQPENNY    420
KTTPPVLDSD GSFFLVSKLT VDKSRWQQGN VFSCSVMHEA LHNHYTQKSL SLSPGWSHPQ    480
FEK                                                                 483

SEQ ID NO: 102            moltype = AA   length = 483
FEATURE                   Location/Qualifiers
source                    1..483
                          mol_type = protein
                          organism = synthetic construct
SEQUENCE: 102
EVQLLESGGG LVQPGGSLRL SCAASGFTFS NAWMNWVRQA PGKGLEWVSS ISSSSSYIYY    60
ADSVKGRFTI SRDNSKNTLY LQMNSLRAED TAVYYCARSN GSGGSTYPLD LWGQGTLVTV    120
TSSGGGGSGG GGSGGGGSQS VLTQPPSASG TPGQRVTISC SGSRSNIGSN SVHWYQQLPG    180
TAPKLLIYGN SNRPSGVPDR FSGSKSGTSA SLAISGLRSE DEADYYCQSY DSSLNDHVVF    240
GGGTKLTVLD KTHTCPPCPA PEAAGAPSVF LFPPKPKDTL MISRTPEVTC VVVDVSHEDP    300
EVKFNWYVDG VEVHNAKTKP REEQYNSTYR VVSVLTVLHQ DWLNGKEYKC KVSNKALPAP    360
IEKTISKAKG QPREPQVCTL PPSRDELTKN QVSLSCAVKG FYPSDIAVEW ESNGQPENNY    420
KTTPPVLDSD GSFFLVSKLT VDKSRWQQGN VFSCSVMHEA LHNHYTQKSL SLSPGWSHPQ    480
FEK                                                                 483

SEQ ID NO: 103            moltype = AA   length = 483
FEATURE                   Location/Qualifiers
source                    1..483
                          mol_type = protein
                          organism = synthetic construct
SEQUENCE: 103
EVQLLESGGG LVQPGGSLRL SCAASGFTFS NAWMNWVRQA PGKGLEWVSS ISSSSSYIYY    60
ADSVKGRFTI SRDNSKNTLY LQMNSLRAED TAVYYCARSN GSGGSDYPLD LWGQGTLVTV    120
TSSGGGGSGG GGSGGGGSQS VLTQPPSASG TPGQRVTISC SGSRSNIGSN SVHWYQQLPG    180
TAPKLLIYGN SNRPSGVPDR FSGSKSGTSA SLAISGLRSE DEADYYCQSY DSSLNDHVVF    240
GGGTKLTVLD KTHTCPPCPA PEAAGAPSVF LFPPKPKDTL MISRTPEVTC VVVDVSHEDP    300
EVKFNWYVDG VEVHNAKTKP REEQYNSTYR VVSVLTVLHQ DWLNGKEYKC KVSNKALPAP    360
IEKTISKAKG QPREPQVCTL PPSRDELTKN QVSLSCAVKG FYPSDIAVEW ESNGQPENNY    420
KTTPPVLDSD GSFFLVSKLT VDKSRWQQGN VFSCSVMHEA LHNHYTQKSL SLSPGWSHPQ    480
FEK                                                                 483

SEQ ID NO: 104            moltype = AA   length = 483
FEATURE                   Location/Qualifiers
source                    1..483
                          mol_type = protein
                          organism = synthetic construct
SEQUENCE: 104
EVQLLESGGG LVQPGGSLRL SCAASGFTFS NAWMNWVRQA PGKGLEWVSS ISSSSSYIYY    60
ADSVKGRFTI SRDNSKNTLY LQMNSLRAED TAVYYCARSN GSGGSTSPLD LWGQGTLVTV    120
TSSGGGGSGG GGSGGGGSQS VLTQPPSASG TPGQRVTISC SGSRSNIGSN SVHWYQQLPG    180
```

```
TAPKLLIYGN SNRPSGVPDR FSGSKSGTSA SLAISGLRSE DEADYYCQSY DSSLNDHVVF    240
GGGTKLTVLD KTHTCPPCPA PEAAGAPSVF LFPPKPKDTL MISRTPEVTC VVVDVSHEDP    300
EVKFNWYVDG VEVHNAKTKP REEQYNSTYR VVSVLTVLHQ DWLNGKEYKC KVSNKALPAP    360
IEKTISKAKG QPREPQVCTL PPSRDELTKN QVSLSCAVKG FYPSDIAVEW ESNGQPENNY    420
KTTPPVLDSD GSFFLVSKLT VDKSRWQQGN VFSCSVMHEA LHNHYTQKSL SLSPGWSHPQ    480
FEK                                                                 483

SEQ ID NO: 105            moltype = AA   length = 483
FEATURE                   Location/Qualifiers
source                    1..483
                          mol_type = protein
                          organism = synthetic construct
SEQUENCE: 105
EVQLLESGGG LVQPGGSLRL SCAASGFTFS NAWMNWVRQA PGKGLEWVSS ISSSSSYIYY     60
ADSVKGRFTI SRDNSKNTLY LQMNSLRAED TAVYYCARAV AGTSMWYGLD QWGQGTLVTV    120
TSSGGGGSGG GGSGGGGSQS VLTQPPSASG TPGQRVTISC SGSRSNIGSN SVHWYQQLPG    180
TAPKLLIYGN SNRPSGVPDR FSGSKSGTSA SLAISGLRSE DEADYYCQSY DSSLNDHVVF    240
GGGTKLTVLD KTHTCPPCPA PEAAGAPSVF LFPPKPKDTL MISRTPEVTC VVVDVSHEDP    300
EVKFNWYVDG VEVHNAKTKP REEQYNSTYR VVSVLTVLHQ DWLNGKEYKC KVSNKALPAP    360
IEKTISKAKG QPREPQVCTL PPSRDELTKN QVSLSCAVKG FYPSDIAVEW ESNGQPENNY    420
KTTPPVLDSD GSFFLVSKLT VDKSRWQQGN VFSCSVMHEA LHNHYTQKSL SLSPGWSHPQ    480
FEK                                                                 483

SEQ ID NO: 106            moltype = AA   length = 483
FEATURE                   Location/Qualifiers
source                    1..483
                          mol_type = protein
                          organism = synthetic construct
SEQUENCE: 106
EVQLLESGGG LVQPGGSLRL SCAASGFTFS NAWMNWVRQA PGKGLEWVSS ISSSSSYIYY     60
ADSVKGRFTI SRDNSKNTLY LQMNSLRAED TAVYYCARAV GASTVYFGLD QWGQGTLVTV    120
TSSGGGGSGG GGSGGGGSQS VLTQPPSASG TPGQRVTISC SGSRSNIGSN SVHWYQQLPG    180
TAPKLLIYGN SNRPSGVPDR FSGSKSGTSA SLAISGLRSE DEADYYCQSY DSSLNDHVVF    240
GGGTKLTVLD KTHTCPPCPA PEAAGAPSVF LFPPKPKDTL MISRTPEVTC VVVDVSHEDP    300
EVKFNWYVDG VEVHNAKTKP REEQYNSTYR VVSVLTVLHQ DWLNGKEYKC KVSNKALPAP    360
IEKTISKAKG QPREPQVCTL PPSRDELTKN QVSLSCAVKG FYPSDIAVEW ESNGQPENNY    420
KTTPPVLDSD GSFFLVSKLT VDKSRWQQGN VFSCSVMHEA LHNHYTQKSL SLSPGWSHPQ    480
FEK                                                                 483

SEQ ID NO: 107            moltype = AA   length = 483
FEATURE                   Location/Qualifiers
source                    1..483
                          mol_type = protein
                          organism = synthetic construct
SEQUENCE: 107
EVQLLESGGG LVQPGGSLRL SCAASGFTFS NAWMNWVRQA PGKGLEWVSS ISSSSSYIYY     60
ADSVKGRFTI SRDNSKNTLY LQMNSLRAED TAVYYCARAV AAGGFFWGLD QWGQGTLVTV    120
TSSGGGGSGG GGSGGGGSQS VLTQPPSASG TPGQRVTISC SGSRSNIGSN SVHWYQQLPG    180
TAPKLLIYGN SNRPSGVPDR FSGSKSGTSA SLAISGLRSE DEADYYCQSY DSSLNDHVVF    240
GGGTKLTVLD KTHTCPPCPA PEAAGAPSVF LFPPKPKDTL MISRTPEVTC VVVDVSHEDP    300
EVKFNWYVDG VEVHNAKTKP REEQYNSTYR VVSVLTVLHQ DWLNGKEYKC KVSNKALPAP    360
IEKTISKAKG QPREPQVCTL PPSRDELTKN QVSLSCAVKG FYPSDIAVEW ESNGQPENNY    420
KTTPPVLDSD GSFFLVSKLT VDKSRWQQGN VFSCSVMHEA LHNHYTQKSL SLSPGWSHPQ    480
FEK                                                                 483

SEQ ID NO: 108            moltype = AA   length = 483
FEATURE                   Location/Qualifiers
source                    1..483
                          mol_type = protein
                          organism = synthetic construct
SEQUENCE: 108
EVQLLESGGG LVQPGGSLRL SCAASGFTFS NAWMNWVRQA PGKGLEWVSS ISSSSSYIYY     60
ADSVKGRFTI SRDNSKNTLY LQMNSLRAED TAVYYCARAV AAGGLFWGLD QWGQGTLVTV    120
TSSGGGGSGG GGSGGGGSQS VLTQPPSASG TPGQRVTISC SGSRSNIGSN SVHWYQQLPG    180
TAPKLLIYGN SNRPSGVPDR FSGSKSGTSA SLAISGLRSE DEADYYCQSY DSSLNDHVVF    240
GGGTKLTVLD KTHTCPPCPA PEAAGAPSVF LFPPKPKDTL MISRTPEVTC VVVDVSHEDP    300
EVKFNWYVDG VEVHNAKTKP REEQYNSTYR VVSVLTVLHQ DWLNGKEYKC KVSNKALPAP    360
IEKTISKAKG QPREPQVCTL PPSRDELTKN QVSLSCAVKG FYPSDIAVEW ESNGQPENNY    420
KTTPPVLDSD GSFFLVSKLT VDKSRWQQGN VFSCSVMHEA LHNHYTQKSL SLSPGWSHPQ    480
FEK                                                                 483

SEQ ID NO: 109            moltype = AA   length = 483
FEATURE                   Location/Qualifiers
source                    1..483
                          mol_type = protein
                          organism = synthetic construct
SEQUENCE: 109
EVQLLESGGG LVQPGGSLRL SCAASGFTFS LAWMNWVRQA PGKGLEWVSS ISSSTSYIYY     60
ADSVKGRFTI SRDNSKNTLY LQMNSLRAED TAVYYCARAV AAGGMFWGLD QWGQGTLVTV    120
```

```
TSSGGGGSGG GGSGGGGSQS VLTQPPSASG TPGQRVTISC SGSRSNIGSN SVHWYQQLPG    180
TAPKLLIYGN SNRPSGVPDR FSGSKSGTSA SLAISGLRSE DEADYYCQSY DSSLNDHVVF    240
GGGTKLTVLD KTHTCPPCPA PEAAGAPSVF LFPPKPKDTL MISRTPEVTC VVVDVSHEDP    300
EVKFNWYVDG VEVHNAKTKP REEQYNSTYR VVSVLTVLHQ DWLNGKEYKC KVSNKALPAP    360
IEKTISKAKG QPREPQVCTL PPSRDELTKN QVSLSCAVKG FYPSDIAVEW ESNGQPENNY    420
KTTPPVLDSD GSFFLVSKLT VDKSRWQQGN VFSCSVMHEA LHNHYTQKSL SLSPGWSHPQ    480
FEK                                                                 483

SEQ ID NO: 110             moltype = AA   length = 483
FEATURE                    Location/Qualifiers
source                     1..483
                           mol_type = protein
                           organism = synthetic construct
SEQUENCE: 110
EVQLLESGGG LVQPGGSLRL SCAASGFTFS LAWMNWVRQA PGKGLEWVSS ISSSTSYIYY    60
ADSVKGRFTI SRDNSKNTLY LQMNSLRAED TAVYYCARAV AAGGFFWGLD QWGQGTLVTV    120
TSSGGGGSGG GGSGGGGSQS VLTQPPSASG TPGQRVTISC SGSRSNIGSN SVHWYQQLPG    180
TAPKLLIYGN SNRPSGVPDR FSGSKSGTSA SLAISGLRSE DEADYYCQSY DSSLNDHVVF    240
GGGTKLTVLD KTHTCPPCPA PEAAGAPSVF LFPPKPKDTL MISRTPEVTC VVVDVSHEDP    300
EVKFNWYVDG VEVHNAKTKP REEQYNSTYR VVSVLTVLHQ DWLNGKEYKC KVSNKALPAP    360
IEKTISKAKG QPREPQVCTL PPSRDELTKN QVSLSCAVKG FYPSDIAVEW ESNGQPENNY    420
KTTPPVLDSD GSFFLVSKLT VDKSRWQQGN VFSCSVMHEA LHNHYTQKSL SLSPGWSHPQ    480
FEK                                                                 483

SEQ ID NO: 111             moltype = AA   length = 481
FEATURE                    Location/Qualifiers
source                     1..481
                           mol_type = protein
                           organism = synthetic construct
SEQUENCE: 111
EVQLLESGGG LVQPGGSLRL SCAASGFTFS DYYMNWIRQA PGKGLEWVSS ISGGSTYYAD    60
SVKGRFTISR DNSENTLYLQ MNSLRAEDTA VYYCARDFGV AGWFGQFGMD VWGQGTLVTV    120
SSGGGGSGGG GSGGGGSQSV LTQPPSASGT PGQRVTISCT GSSSNIGAGY DVHWYQQLPG    180
TAPKLLIYRS NQRPSGVPDR FSGSKSGTSA SLAISGLRSE DEADYYCSSY AGNYNLVFGG    240
GTKLTVLDKT HTCPPCPAPE AAGAPSVFLF PPKPKDTLMI SRTPEVTCVV VDVSHEDPEV    300
KFNWYVDGVE VHNAKTKPRE EQYNSTYRVV SVLTVLHQDW LNGKEYKCKV SNKALPAPIE    360
KTISKAKGQP REPQVCTLPP SRDELTKNQV SLSCAVKGFY PSDIAVEWES NGQPENNYKT    420
TPPVLDSDGS FFLVSKLTVD KSRWQQGNVF SCSVMHEALH NHYTQKSLSL SPGWSHPQFE    480
K                                                                   481

SEQ ID NO: 112             moltype = AA   length = 481
FEATURE                    Location/Qualifiers
source                     1..481
                           mol_type = protein
                           organism = synthetic construct
SEQUENCE: 112
EVQLLESGGG LVQPGGSLRL SCAASGFTFS DSYMSWIRQA PGKGLEWVSS ISGGSTYYAD    60
SVKGRFTISR DNSENTLYLQ MNSLRAEDTA VYYCARDFGV AGYFGQYGMD VWGQGTLVTV    120
SSGGGGSGGG GSGGGGSQSV LTQPPSASGT PGQRVTISCT GSSSNIGAGY DVHWYQQLPG    180
TAPKLLIYRS NQRPSGVPDR FSGSKSGTSA SLAISGLRSE DEADYYCSSY AGNYNLVFGG    240
GTKLTVLDKT HTCPPCPAPE AAGAPSVFLF PPKPKDTLMI SRTPEVTCVV VDVSHEDPEV    300
KFNWYVDGVE VHNAKTKPRE EQYNSTYRVV SVLTVLHQDW LNGKEYKCKV SNKALPAPIE    360
KTISKAKGQP REPQVCTLPP SRDELTKNQV SLSCAVKGFY PSDIAVEWES NGQPENNYKT    420
TPPVLDSDGS FFLVSKLTVD KSRWQQGNVF SCSVMHEALH NHYTQKSLSL SPGWSHPQFE    480
K                                                                   481

SEQ ID NO: 113             moltype = AA   length = 481
FEATURE                    Location/Qualifiers
source                     1..481
                           mol_type = protein
                           organism = synthetic construct
SEQUENCE: 113
EVQLLESGGG LVQPGGSLRL SCAASGFTFS DYYMNWIRQA PGKGLEWVSS ISGGSTYYAD    60
SVKGRFTISR DNSENTLYLQ MNSLRAEDTA VYYCARDFGV AGWFGYYGMD VWGQGTLVTV    120
SSGGGGSGGG GSGGGGSQSV LTQPPSASGT PGQRVTISCT GSSSNIGAGY DVHWYQQLPG    180
TAPKLLIYRS NQRPSGVPDR FSGSKSGTSA SLAISGLRSE DEADYYCSSY AGNYNLVFGG    240
GTKLTVLDKT HTCPPCPAPE AAGAPSVFLF PPKPKDTLMI SRTPEVTCVV VDVSHEDPEV    300
KFNWYVDGVE VHNAKTKPRE EQYNSTYRVV SVLTVLHQDW LNGKEYKCKV SNKALPAPIE    360
KTISKAKGQP REPQVCTLPP SRDELTKNQV SLSCAVKGFY PSDIAVEWES NGQPENNYKT    420
TPPVLDSDGS FFLVSKLTVD KSRWQQGNVF SCSVMHEALH NHYTQKSLSL SPGWSHPQFE    480
K                                                                   481

SEQ ID NO: 114             moltype = AA   length = 481
FEATURE                    Location/Qualifiers
source                     1..481
                           mol_type = protein
                           organism = synthetic construct
SEQUENCE: 114
EVQLLESGGG LVQPGGSLRL SCAASGFTFS DYYMTWIRQA PGKGLEWVSS ISGGSTYYAD    60
```

```
SRKGRFTISR DNSENTLYLQ MNSLRAEDTA VYYCARDYGV AGWFGQYGMD VWGQGTLVTV    120
SSGGGGSGGG GSGGGGSQSV LTQPPSASGT PGQRVTISCT GSSSNIGAGY DVHWYQQLPG    180
TAPKLLIYRS NQRPSGVPDR FSGSKSGTSA SLAISGLRSE DEADYYCSSY AGNYNLVFGG    240
GTKLTVLDKT HTCPPCPAPE AAGAPSVFLF PPKPKDTLMI SRTPEVTCVV VDVSHEDPEV    300
KFNWYVDGVE VHNAKTKPRE EQYNSTYRVV SVLTVLHQDW LNGKEYKCKV SNKALPAPIE    360
KTISKAKGQP REPQVCTLPP SRDELTKNQV SLSCAVKGFY PSDIAVEWES NGQPENNYKT    420
TPPVLDSDGS FFLVSKLTVD KSRWQQGNVF SCSVMHEALH NHYTQKSLSL SPGWSHPQFE    480
K                                                                    481

SEQ ID NO: 115           moltype = AA   length = 481
FEATURE                  Location/Qualifiers
source                   1..481
                         mol_type = protein
                         organism = synthetic construct
SEQUENCE: 115
EVQLLESGGG LVQPGGSLRL SCAASGFTFS DYYMTWIRQA PGKGLEWVSS ISGGSTYYAD     60
SRKGRFTISR DNSENTLYLQ MNSLRAEDTA VYYCARDFGV SGWFGQYGMD VWGQGTLVTV    120
SSGGGGSGGG GSGGGGSQSV LTQPPSASGT PGQRVTISCT GSSSNIGAGY DVHWYQQLPG    180
TAPKLLIYRS NQRPSGVPDR FSGSKSGTSA SLAISGLRSE DEADYYCSSY AGNYNLVFGG    240
GTKLTVLDKT HTCPPCPAPE AAGAPSVFLF PPKPKDTLMI SRTPEVTCVV VDVSHEDPEV    300
KFNWYVDGVE VHNAKTKPRE EQYNSTYRVV SVLTVLHQDW LNGKEYKCKV SNKALPAPIE    360
KTISKAKGQP REPQVCTLPP SRDELTKNQV SLSCAVKGFY PSDIAVEWES NGQPENNYKT    420
TPPVLDSDGS FFLVSKLTVD KSRWQQGNVF SCSVMHEALH NHYTQKSLSL SPGWSHPQFE    480
K                                                                    481

SEQ ID NO: 116           moltype = AA   length = 481
FEATURE                  Location/Qualifiers
source                   1..481
                         mol_type = protein
                         organism = synthetic construct
SEQUENCE: 116
EVQLLESGGG LVQPGGSLRL SCAASGFTFS DYWMTWIRQA PGKGLEWVSS ISGGSTYYAD     60
SRKGRFTISR DNSENTLYLQ MNSLRAEDTA VYYCARDFGV AGWFGQYGMD VWGQGTLVTV    120
SSGGGGSGGG GSGGGGSQSV LTQPPSASGT PGQRVTISCT GSSSNIGAGY DVHWYQQLPG    180
TAPKLLIYRS NQRPSGVPDR FSGSKSGTSA SLAISGLRSE DEADYYCSSY AGNYNLVFGG    240
GTKLTVLDKT HTCPPCPAPE AAGAPSVFLF PPKPKDTLMI SRTPEVTCVV VDVSHEDPEV    300
KFNWYVDGVE VHNAKTKPRE EQYNSTYRVV SVLTVLHQDW LNGKEYKCKV SNKALPAPIE    360
KTISKAKGQP REPQVCTLPP SRDELTKNQV SLSCAVKGFY PSDIAVEWES NGQPENNYKT    420
TPPVLDSDGS FFLVSKLTVD KSRWQQGNVF SCSVMHEALH NHYTQKSLSL SPGWSHPQFE    480
K                                                                    481

SEQ ID NO: 117           moltype = AA   length = 481
FEATURE                  Location/Qualifiers
source                   1..481
                         mol_type = protein
                         organism = synthetic construct
SEQUENCE: 117
EVQLLESGGG LVQPGGSLRL SCAASGFTFS DYYMTWIRQA PGKGLEWVSS ISGGTTYYAD     60
SRKGRFTISR DNSENTLYLQ MNSLRAEDTA VYYCARDFGV AGWFGQYGMD VWGQGTLVTV    120
SSGGGGSGGG GSGGGGSQSV LTQPPSASGT PGQRVTISCT GSSSNIGAGY DVHWYQQLPG    180
TAPKLLIYRS NQRPSGVPDR FSGSKSGTSA SLAISGLRSE DEADYYCSSY AGNYNLVFGG    240
GTKLTVLDKT HTCPPCPAPE AAGAPSVFLF PPKPKDTLMI SRTPEVTCVV VDVSHEDPEV    300
KFNWYVDGVE VHNAKTKPRE EQYNSTYRVV SVLTVLHQDW LNGKEYKCKV SNKALPAPIE    360
KTISKAKGQP REPQVCTLPP SRDELTKNQV SLSCAVKGFY PSDIAVEWES NGQPENNYKT    420
TPPVLDSDGS FFLVSKLTVD KSRWQQGNVF SCSVMHEALH NHYTQKSLSL SPGWSHPQFE    480
K                                                                    481

SEQ ID NO: 118           moltype = AA   length = 481
FEATURE                  Location/Qualifiers
source                   1..481
                         mol_type = protein
                         organism = synthetic construct
SEQUENCE: 118
EVQLLESGGG LVQPGGSLRL SCAASGFTFS DYWMTWIRQA PGKGLEWVSS ISGGTTYYAD     60
SRKGRFTISR DNSENTLYLQ MNSLRAEDTA VYYCARDYGV AGWFGQYGMD VWGQGTLVTV    120
SSGGGGSGGG GSGGGGSQSV LTQPPSASGT PGQRVTISCT GSSSNIGAGY DVHWYQQLPG    180
TAPKLLIYRS NQRPSGVPDR FSGSKSGTSA SLAISGLRSE DEADYYCSSY AGNYNLVFGG    240
GTKLTVLDKT HTCPPCPAPE AAGAPSVFLF PPKPKDTLMI SRTPEVTCVV VDVSHEDPEV    300
KFNWYVDGVE VHNAKTKPRE EQYNSTYRVV SVLTVLHQDW LNGKEYKCKV SNKALPAPIE    360
KTISKAKGQP REPQVCTLPP SRDELTKNQV SLSCAVKGFY PSDIAVEWES NGQPENNYKT    420
TPPVLDSDGS FFLVSKLTVD KSRWQQGNVF SCSVMHEALH NHYTQKSLSL SPGWSHPQFE    480
K                                                                    481

SEQ ID NO: 119           moltype = AA   length = 481
FEATURE                  Location/Qualifiers
source                   1..481
                         mol_type = protein
                         organism = synthetic construct
SEQUENCE: 119
```

```
EVQLLESGGG LVQPGGSLRL SCAASGFTFS DYWMTWIRQA PGKGLEWVSS ISGGTTYYAD    60
SRKGRFTISR DNSENTLYLQ MNSLRAEDTA VYYCARDFGV SGWFGQYGMD VWGQGTLVTV   120
SSGGGGSGGG GSGGGGSQSV LTQPPSASGT PGQRVTISCT GSSSNIGAGY DVHWYQQLPG   180
TAPKLLIYRS NQRPSGVPDR FSGSKSGTSA SLAISGLRSE DEADYYCSSY AGNYNLVFGG   240
GTKLTVLDKT HTCPPCPAPE AAGAPSVFLF PPKPKDTLMI SRTPEVTCVV VDVSHEDPEV   300
KFNWYVDGVE VHNAKTKPRE EQYNSTYRVV SVLTVLHQDW LNGKEYKCKV SNKALPAPIE   360
KTISKAKGQP REPQVCTLPP SRDELTKNQV SLSCAVKGFY PSDIAVEWES NGQPENNYKT   420
TPPVLDSDGS FFLVSKLTVD KSRWQQGNVF SCSVMHEALH NHYTQKSLSL SPGWSHPQFE   480
K                                                                   481

SEQ ID NO: 120         moltype = AA   length = 469
FEATURE                Location/Qualifiers
source                 1..469
                       mol_type = protein
                       organism = synthetic construct
SEQUENCE: 120
EVQLLESGGG LVQPGGSLRL SCAASGFTFS IYAMSWVRQA PGKGLEWVSA ISGSGGSTYY    60
ADSVKGRFTI SRDNSKNTLY LQMNSLRAED TAVYYCARDF DYWGQGTLVT VTSSGGGGSG   120
GGGSGGGGSQ SVLTQPPSAS GTPGQRVTIS CSGSSSNIGS NYVYWYQQLP GTAPKLLIYG   180
NINRPSGVPD RFSGSKSGTS ASLAISGLRS EDEADYYCAA WDDSLNGRVF GGGTKLTVLD   240
KTHTCPPCPA PEAAGAPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPCRDELTKN QVSLWCLVKG FYPSDIAVEW ESNGQPENNY KTTPPVLDSD   420
GSFFLYSKLT VDKSRWQQGN VFSCSVMHEA LHNHYTQKSL SLSPGEPEA               469

SEQ ID NO: 121         moltype = AA   length = 483
FEATURE                Location/Qualifiers
source                 1..483
                       mol_type = protein
                       organism = synthetic construct
SEQUENCE: 121
EVQLLESGGG LVQPGGSLRL SCAASGFTFS NAWMNWVRQA PGKGLEWVSS ISSSSSYIYY    60
ADSVKGRFTI SRDNSKNTLY LQMNSLRAED TAVYYCARAV AAGGMFWGLD QWGQGTLVTV   120
TSSGGGGSGG GSGGGGSQS VLTQPPSASG TPGQRVTISC SGSRSNIGSN SVHWYQQLPG   180
TAPKLLIYGN SNRPSGVPDR FSGSKSGTSA SLAISGLRSE DEADYYCQSY DSSLNDHVVF   240
GGGTKLTVLD KTHTCPPCPA PEAAGAPSVF LFPPKPKDTL MISRTPEVTC VVVDVSHEDP   300
EVKFNWYVDG VEVHNAKTKP REEQYNSTYR VVSVLTVLHQ DWLNGKEYKC KVSNKALPAP   360
IEKTISKAKG QPREPQVCTL PPSRDELTKN QVSLSCAVKG FYPSDIAVEW ESNGQPENNY   420
KTTPPVLDSD GSFFLVSKLT VDKSRWQQGN VFSCSVMHEA LHNHYTQKSL SLSPGWSHPQ   480
FEK                                                                 483

SEQ ID NO: 122         moltype = AA   length = 469
FEATURE                Location/Qualifiers
source                 1..469
                       mol_type = protein
                       organism = synthetic construct
SEQUENCE: 122
EVQLLESGGG LVQPGGSLRL SCAASGFTFS SYAMSWVRQA PGKGLEWVAN INQDGSEKNY    60
VDSMRGRFTI SRDNSKNTLY LQMNSLRAED TAVYYCAREF DYWGQGTLVT VTSSGGGGSG   120
GGGSGGGGSQ SVLAQPPSAS GTPGQRVTIS CSGSSSNIGS NYVYWYQQLP GTAPKLLIYG   180
NNKRPSGVPD RFSGSKSGTS ASLAISGLRS EDEADYYCAA WDDSLNGRVF GGGTKLTVLD   240
KTHTCPPCPA PEAAGAPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPCRDELTKN QVSLWCLVKG FYPSDIAVEW ESNGQPENNY KTTPPVLDSD   420
GSFFLYSKLT VDKSRWQQGN VFSCSVMHEA LHNHYTQKSL SLSPGEPEA               469

SEQ ID NO: 123         moltype = AA   length = 481
FEATURE                Location/Qualifiers
source                 1..481
                       mol_type = protein
                       organism = synthetic construct
SEQUENCE: 123
EVQLLESGGG LVQPGGSLRL SCAASGFTFS DYYMTWIRQA PGKGLEWVSS ISGGSTYYAD    60
SRKGRFTISR DNSENTLYLQ MNSLRAEDTA VYYCARDFGV AGWFGQYGMD VWGQGTLVTV   120
SSGGGGSGGG GSGGGGSQSV LTQPPSASGT PGQRVTISCT GSSSNIGAGY DVHWYQQLPG   180
TAPKLLIYRS NQRPSGVPDR FSGSKSGTSA SLAISGLRSE DEADYYCSSY AGNYNLVFGG   240
GTKLTVLDKT HTCPPCPAPE AAGAPSVFLF PPKPKDTLMI SRTPEVTCVV VDVSHEDPEV   300
KFNWYVDGVE VHNAKTKPRE EQYNSTYRVV SVLTVLHQDW LNGKEYKCKV SNKALPAPIE   360
KTISKAKGQP REPQVCTLPP SRDELTKNQV SLSCAVKGFY PSDIAVEWES NGQPENNYKT   420
TPPVLDSDGS FFLVSKLTVD KSRWQQGNVF SCSVMHEALH NHYTQKSLSL SPGWSHPQFE   480
K                                                                   481

SEQ ID NO: 124         moltype = AA   length = 469
FEATURE                Location/Qualifiers
source                 1..469
                       mol_type = protein
                       organism = synthetic construct
SEQUENCE: 124
EVQLLESGGG LVQPGGSLRL SCAASGFTFS DYAMSWVRQA PGKGLEWVAN INQSGSEKNY    60
```

```
VDSMRGRFTI SRDNSKNTLY LQMNSLRAED TAVYYCAREF DWWGQGTLVT VSSSGGGGSG    120
GGGSGGGGSQ SVLAQPPSAS GTPGQRVTIS CSGSASNIGS NYVYWYQQLP GTAPKLLIYG    180
NNKRPSGVPD RFSGSKSGTS ASLAISGLRS EDEADYYCAA WDDSLNGRVF GGGTKLTVLD    240
KTHTCPPCPA PEAAGAPSVF LFPPKPKDTL MISRTPEVTC VVVDVSHEDP EVKFNWYVDG    300
VEVHNAKTKP REEQYNSTYR VVSVLTVLHQ DWLNGKEYKC SNSNKALPVL IEKTISKAKG    360
QPREPQVYTL PPCRDELTKN QVSLWCLVKG FYPSDIAVEW ESNGQPENNY KTTPPVLDSD    420
GSFFLYSKLT VDKSRWQQGN VFSCSVMHEA LHNHYTQKSL SLSPGEPEA                469

SEQ ID NO: 125              moltype = AA   length = 469
FEATURE                    Location/Qualifiers
source                     1..469
                           mol_type = protein
                           organism = synthetic construct
SEQUENCE: 125
EVQLLESGGG LVQPGGSLRL SCAASGFTFS DYAMSWVRQA PGKGLEWVAN INQSGSEKNY     60
VDSMRGRFTI SRDNSKNTLY LQMNSLRAED TAVYYCAREF DWWGQGTLVT VSSSGGGGSG    120
GGGSGGGGSQ SVLAQPPSAS GTPGQRVTIS CSGSSSNIGS NYVYWYQQLP GTAPKLLIYG    180
NNKRPAGVPD RFSGSKSGTS ASLAISGLRS EDEADYYCAA WDDSLNGRVF GGGTKLTVLD    240
KTHTCPPCPA PEAAGAPSVF LFPPKPKDTL MISRTPEVTC VVVDVSHEDP EVKFNWYVDG    300
VEVHNAKTKP REEQYNSTYR VVSVLTVLHQ DWLNGKEYKC KVSNKALPAP IEKTISKAKG    360
QPREPQVYTL PPCRDELTKN QVSLWCLVKG FYPSDIAVEW ESNGQPENNY KTTPPVLDSD    420
GSFFLYSKLT VDKSRWQQGN VFSCSVMHEA LHNHYTQKSL SLSPGEPEA                469

SEQ ID NO: 126              moltype = AA   length = 469
FEATURE                    Location/Qualifiers
source                     1..469
                           mol_type = protein
                           organism = synthetic construct
SEQUENCE: 126
EVQLLESGGG LVQPGGSLRL SCAASGFTFS DYAMSWVRQA PGKGLEWVAN INQSGSEKNY     60
VDSMRGRFTI SRDNSKNTLY LQMNSLRAED TAVYYCAREF DWWGQGTLVT VSSSGGGGSG    120
GGGSGGGGSQ SVLAQPPSAS GTPGQRVTIS CSGSSSNIGS NYVYWYQQLP GTAPKLLIYG    180
NNKRPSGVPD RFSGSKSGTS ASLAISGLRS EDEADYYCAA WDDSLSGRVF GGGTKLTVLD    240
KTHTCPPCPA PEAAGAPSVF LFPPKPKDTL MISRTPEVTC VVVDVSHEDP EVKFNWYVDG    300
VEVHNAKTKP REEQYNSTYR VVSVLTVLHQ DWLNGKEYKC KVSNKALPAP IEKTISKAKG    360
QPREPQVYTL PPCRDELTKN QVSLWCLVKG FYPSDIAVEW ESNGQPENNY KTTPPVLDSD    420
GSFFLYSKLT VDKSRWQQGN VFSCSVMHEA LHNHYTQKSL SLSPGEPEA                469

SEQ ID NO: 127              moltype = AA   length = 469
FEATURE                    Location/Qualifiers
source                     1..469
                           mol_type = protein
                           organism = synthetic construct
SEQUENCE: 127
EVQLLESGGG LVQPGGSLRL SCAASGFTFS DYAMSWVRQA PGKGLEWVAN INQSGSEKNY     60
VDSMRGRFTI SRDNSKNTLY LQMNSLRAED TAVYYCAREF DWWGQGTLVT VSSSGGGGSG    120
GGGSGGGGSQ SVLAQPPSAS GTPGQRVTIS CSGSASNIGS NYVYWYQQLP GTAPKLLIYG    180
NNKRPAGVPD RFSGSKSGTS ASLAISGLRS EDEADYYCAA WDDSLSGRVF GGGTKLTVLD    240
KTHTCPPCPA PEAAGAPSVF LFPPKPKDTL MISRTPEVTC VVVDVSHEDP EVKFNWYVDG    300
VEVHNAKTKP REEQYNSTYR VVSVLTVLHQ DWLNGKEYKC KVSNKALPAP IEKTISKAKG    360
QPREPQVYTL PPCRDELTKN QVSLWCLVKG FYPSDIAVEW ESNGQPENNY KTTPPVLDSD    420
GSFFLYSKLT VDKSRWQQGN VFSCSVMHEA LHNHYTQKSL SLSPGEPEA                469

SEQ ID NO: 128              moltype = AA   length = 469
FEATURE                    Location/Qualifiers
source                     1..469
                           mol_type = protein
                           organism = synthetic construct
SEQUENCE: 128
EVQLLESGGG LVQPGGSLRL SCAASGFTFS SYAMSWVRQA PGKGLEWVAN INQDGSEKNY     60
VDSMRGRFTI SRDNSKNTLY LQMNSLRAED TAVYYCAREF DYWGQGTLVT VSSSGGGGSG    120
GGGSGGGGSQ SVLAQPPSAS GTPGQRVTIS CSGSASNIGS NYVYWYQQLP GTAPKLLIYG    180
NNKRPSGVPD RFSGSKSGTS ASLAISGLRS EDEADYYCAA WDDSLNGRVF GGGTKLTVLD    240
KTHTCPPCPA PEAAGAPSVF LFPPKPKDTL MISRTPEVTC VVVDVSHEDP EVKFNWYVDG    300
VEVHNAKTKP REEQYNSTYR VVSVLTVLHQ DWLNGKEYKC KVSNKALPAP IEKTISKAKG    360
QPREPQVYTL PPCRDELTKN QVSLWCLVKG FYPSDIAVEW ESNGQPENNY KTTPPVLDSD    420
GSFFLYSKLT VDKSRWQQGN VFSCSVMHEA LHNHYTQKSL SLSPGEPEA                469

SEQ ID NO: 129              moltype = AA   length = 469
FEATURE                    Location/Qualifiers
source                     1..469
                           mol_type = protein
                           organism = synthetic construct
SEQUENCE: 129
EVQLLESGGG LVQPGGSLRL SCAASGFTFS SYAMSWVRQA PGKGLEWVAN INQDGSEKNY     60
VDSMRGRFTI SRDNSKNTLY LQMNSLRAED TAVYYCAREF DYWGQGTLVT VSSSGGGGSG    120
GGGSGGGGSQ SVLAQPPSAS GTPGQRVTIS CSGSSSNIGS NYVYWYQQLP GTAPKLLIYG    180
NNKRPAGVPD RFSGSKSGTS ASLAISGLRS EDEADYYCAA WDDSLNGRVF GGGTKLTVLD    240
KTHTCPPCPA PEAAGAPSVF LFPPKPKDTL MISRTPEVTC VVVDVSHEDP EVKFNWYVDG    300
```

```
VEVHNAKTKP REEQYNSTYR VVSVLTVLHQ DWLNGKEYKC KVSNKALPAP IEKTISKAKG     360
QPREPQVYTL PPCRDELTKN QVSLWCLVKG FYPSDIAVEW ESNGQPENNY KTTPPVLDSD     420
GSFFLYSKLT VDKSRWQQGN VFSCSVMHEA LHNHYTQKSL SLSPGEPEA               469

SEQ ID NO: 130          moltype = AA   length = 469
FEATURE                 Location/Qualifiers
source                  1..469
                        mol_type = protein
                        organism = synthetic construct
SEQUENCE: 130
EVQLLESGGG LVQPGGSLRL SCAASGFTFS SYAMSWVRQA PGKGLEWVAN INQDGSEKNY     60
VDSMRGRFTI SRDNSKNTLY LQMNSLRAED TAVYYCAREF DYWGQGTLVT VSSSGGGGSG     120
GGGSGGGGSQ SVLAQPPSAS GTPGQRVTIS CSGSSSNIGS NYVYWYQQLP GTAPKLLIYG     180
NNKRPSGVPD RFSGSKSGTS ASLAISGLRS EDEADYYCAA WDDSLSGRVF GGGTKLTVLD     240
KTHTCPPCPA PEAAGAPSVF LFPPKPKDTL MISRTPEVTC VVVDVSHEDP EVKFNWYVDG     300
VEVHNAKTKP REEQYNSTYR VVSVLTVLHQ DWLNGKEYKC KVSNKALPAP IEKTISKAKG     360
QPREPQVYTL PPCRDELTKN QVSLWCLVKG FYPSDIAVEW ESNGQPENNY KTTPPVLDSD     420
GSFFLYSKLT VDKSRWQQGN VFSCSVMHEA LHNHYTQKSL SLSPGEPEA               469

SEQ ID NO: 131          moltype = AA   length = 469
FEATURE                 Location/Qualifiers
source                  1..469
                        mol_type = protein
                        organism = synthetic construct
SEQUENCE: 131
EVQLLESGGG LVQPGGSLRL SCAASGFTFS SYAMSWVRQA PGKGLEWVAN INQDGSEKNY     60
VDSMRGRFTI SRDNSKNTLY LQMNSLRAED TAVYYCAREF DYWGQGTLVT VSSSGGGGSG     120
GGGSGGGGSQ SVLAQPPSAS GTPGQRVTIS CSGSASNIGS NYVYWYQQLP GTAPKLLIYG     180
NNKRPAGVPD RFSGSKSGTS ASLAISGLRS EDEADYYCAA WDDSLSGRVF GGGTKLTVLD     240
KTHTCPPCPA PEAAGAPSVF LFPPKPKDTL MISRTPEVTC VVVDVSHEDP EVKFNWYVDG     300
VEVHNAKTKP REEQYNSTYR VVSVLTVLHQ DWLNGKEYKC KVSNKALPAP IEKTISKAKG     360
QPREPQVYTL PPCRDELTKN QVSLWCLVKG FYPSDIAVEW ESNGQPENNY KTTPPVLDSD     420
GSFFLYSKLT VDKSRWQQGN VFSCSVMHEA LHNHYTQKSL SLSPGEPEA               469

SEQ ID NO: 132          moltype = AA   length = 481
FEATURE                 Location/Qualifiers
source                  1..481
                        mol_type = protein
                        organism = synthetic construct
SEQUENCE: 132
EVQLLESGGG LVQPGGSLRL SCAASGFTFS DYYMTWIRQA PGKGLEWVSS ISGGSTYYAD     60
SRKGRFTISR DNSENTLYLQ MNSLRAEDTA VYYCARDFGV AGWFGQYGMD VWGQGTLVTV     120
SSGGGGSGGG GSGGGGSQSV LTQPPSASGT PGQRVTISCT GSASNIGAGY DVHWYQQLPG     180
TAPKLLIYRS NQRPSGVPDR FSGSKSGTSA SLAISGLRSE DEADYYCSSY AGNYNLVFGG     240
GTKLTVLDKT HTCPPCPAPE AAGAPSVFLF PPKPKDTLMI SRTPEVTCVV VDVSHEDPEV     300
KFNWYVDGVE VHNAKTKPRE EQYNSTYRVV SVLTVLHQDW LNGKEYKCKV SNKALPAPIE     360
KTISKAKGQP REPQVCTLPP SRDELTKNQV SLSCAVKGFY PSDIAVEWES NGQPENNYKT     420
TPPVLDSDGS FFLVSKLTVD KSRWQQGNVF SCSVMHEALH NHYTQKSLSL SPGWSHPQFE     480
K                                                                   481

SEQ ID NO: 133          moltype = AA   length = 481
FEATURE                 Location/Qualifiers
source                  1..481
                        mol_type = protein
                        organism = synthetic construct
SEQUENCE: 133
EVQLLESGGG LVQPGGSLRL SCAASGFTFS DYYMTWIRQA PGKGLEWVSS ISGGSTYYAD     60
SRKGRFTISR DNSENTLYLQ MNSLRAEDTA VYYCARDFGV AGWFGQYGMD VWGQGTLVTV     120
SSGGGGSGGG GSGGGGSQSV LTQPPSASGT PGQRVTISCT GSSSNIGAGY DVHWYQQLPG     180
TAPKLLIYRS NQRPAGVPDR FSGSKSGTSA SLAISGLRSE DEADYYCSSY AGNYNLVFGG     240
GTKLTVLDKT HTCPPCPAPE AAGAPSVFLF PPKPKDTLMI SRTPEVTCVV VDVSHEDPEV     300
KFNWYVDGVE VHNAKTKPRE EQYNSTYRVV SVLTVLHQDW LNGKEYKCKV SNKALPAPIE     360
KTISKAKGQP REPQVCTLPP SRDELTKNQV SLSCAVKGFY PSDIAVEWES NGQPENNYKT     420
TPPVLDSDGS FFLVSKLTVD KSRWQQGNVF SCSVMHEALH NHYTQKSLSL SPGWSHPQFE     480
K                                                                   481

SEQ ID NO: 134          moltype = AA   length = 481
FEATURE                 Location/Qualifiers
source                  1..481
                        mol_type = protein
                        organism = synthetic construct
SEQUENCE: 134
EVQLLESGGG LVQPGGSLRL SCAASGFTFS DYYMTWIRQA PGKGLEWVSS ISGGSTYYAD     60
SRKGRFTISR DNSENTLYLQ MNSLRAEDTA VYYCARDFGV AGWFGQYGMD VWGQGTLVTV     120
SSGGGGSGGG GSGGGGSQSV LTQPPSASGT PGQRVTISCT GSSSNIGAGY DVHWYQQLPG     180
TAPKLLIYRS NQRPSGVPDR FSGSKSGTSA SLAISGLRSE DEADYYCSSY AGLYNLVFGG     240
GTKLTVLDKT HTCPPCPAPE AAGAPSVFLF PPKPKDTLMI SRTPEVTCVV VDVSHEDPEV     300
KFNWYVDGVE VHNAKTKPRE EQYNSTYRVV SVLTVLHQDW LNGKEYKCKV SNKALPAPIE     360
KTISKAKGQP REPQVCTLPP SRDELTKNQV SLSCAVKGFY PSDIAVEWES NGQPENNYKT     420
```

```
TPPVLDSDGS FFLVSKLTVD KSRWQQGNVF SCSVMHEALH NHYTQKSLSL SPGWSHPQFE  480
K                                                                               481

SEQ ID NO: 135              moltype = AA   length = 481
FEATURE                     Location/Qualifiers
source                      1..481
                            mol_type = protein
                            organism = synthetic construct
SEQUENCE: 135
EVQLLESGGG LVQPGGSLRL SCAASGFTFS DYYMTWIRQA PGKGLEWVSS ISGGSTYYAD  60
SRKGRFTISR DNSENTLYLQ MNSLRAEDTA VYYCARDFGV AGWFGQYGMD VWGQGTLVTV  120
SSGGGGSGGG GSGGGGSQSV LTQPPSASGT PGQRVTISCT GSASNIGAGY DVHWYQQLPG  180
TAPKLLIYRS NQRPAGVPDR FSGSKSGTSA SLAISGLRSE DEADYYCSSY AGLYNLVFGG  240
GTKLTVLDKT HTCPPCPAPE AAGAPSVFLF PPKPKDTLMI SRTPEVTCVV VDVSHEDPEV  300
KFNWYVDGVE VHNAKTKPRE EQYNSTYRVV SVLTVLHQDW LNGKEYKCKV SNKALPAPIE  360
KTISKAKGQP REPQVCTLPP SRDELTKNQV SLSCAVKGFY PSDIAVEWES NGQPENNYKT  420
TPPVLDSDGS FFLVSKLTVD KSRWQQGNVF SCSVMHEALH NHYTQKSLSL SPGWSHPQFE  480
K                                                                               481

SEQ ID NO: 136              moltype = AA   length = 573
FEATURE                     Location/Qualifiers
source                      1..573
                            mol_type = protein
                            organism = synthetic construct
SEQUENCE: 136
EVQLLESGGG LVQPGGSLRL SCAASGFTFS DYYMTWIRQA PGKGLEWVSS ISGGSTYYAD  60
SRKGRFTISR DNSENTLYLQ MNSLRAEDTA VYYCARDFGV AGWFGQYGMD VWGQGTLVTV  120
SSPAPNLLGG PEVQLLESGG GLVQPGGSLR LSCAASGFTF SSYAMSWVRQ APGKGLEWVA  180
NINQDGSEKN YVDSMRGRFT ISRDNSKNTL YLQMNSLRAE DTAVYYCARE FDYWGQGTLV  240
TVSSASTKGP SVFPLAPSSK STSGGTAALG CLVKDYFPEP VTVSWNSGAL TSGVHTFPAV  300
LQSSGLYSLS SVVTVPSSSL GTQTYICNVN HKPSNTKVDK KVEPKSCDKT HTCPPCPAPE  360
AAGAPSVFLF PPKPKDTLYI TREPEVTCVV VDVSHEDPEV KFNWYVDGVE VHNAKTKPRE  420
EQYNSTYRVV SVLTVLHQDW LNGKEYKCKV SNKALPAPIE KTISKAKGQP REPQVYTLPP  480
SRDELTKNQV SLTCLVKGFY PSDIAVEWES NGQPENNYKT TPPVLDSDGS FFLYSKLTVD  540
KSRWQQGNVF SCSVMHEALH NHYTQKSLSL SPG                                        573

SEQ ID NO: 137              moltype = AA   length = 568
FEATURE                     Location/Qualifiers
source                      1..568
                            mol_type = protein
                            organism = synthetic construct
SEQUENCE: 137
EVQLLESGGG LVQPGGSLRL SCAASGFTFS DYYMTWIRQA PGKGLEWVSS ISGGSTYYAD  60
SRKGRFTISR DNSENTLYLQ MNSLRAEDTA VYYCARDFGV AGWFGQYGMD VWGQGTLVTV  120
SSPLAPEVQL LESGGGLVQP GGSLRLSCAA SGFTFSSYAM SWVRQAPGKG LEWVANINQD  180
GSEKNYVDSM RGRFTISRDN SKNTLYLQMN SLRAEDTAVY YCAREFDYWG QGTLVTVSSA  240
STKGPSVFPL APSSKSTSGG TAALGCLVKD YFPEPVTVSW NSGALTSGVH TFPAVLQSSG  300
LYSLSSVVTV PSSSLGTQTY ICNVNHKPSN TKVDKKVEPK SCDKTHTCPP CPAPEAAGAP  360
SVFLFPPKPK DTLYITREPE VTCVVVDVSH EDPEVKFNWY VDGVEVHNAK TKPREEQYNS  420
TYRVVSVLTV LHQDWLNGKE YKCKVSNKAL PAPIEKTISK AKGQPREPQV YTLPPSRDEL  480
TKNQVSLTCL VKGFYPSDIA VEWESNGQPE NNYKTTPPVL DSDGSFFLYS KLTVDKSRWQ  540
QGNVFSCSVM HEALHNHYTQ KSLSLSPG                                              568

SEQ ID NO: 138              moltype = AA   length = 568
FEATURE                     Location/Qualifiers
source                      1..568
                            mol_type = protein
                            organism = synthetic construct
SEQUENCE: 138
EVQLLESGGG LVQPGGSLRL SCAASGFTFS DYYMNWIRQA PGKGLEWVSS ISGGSTYYAD  60
SVKGRFTISR DNSENTLYLQ MNSLRAEDTA VYYCARDFGV AGWFGQFGMD VWGQGTLVTV  120
SSPLAPEVQL LESGGGLVQP GGSLRLSCAA SGFTFSSYWM SWVRQAPGKG LEWVANIKQD  180
GSEKNYVDSM RGRFTISRDN SKNTLYLQMN SLRAEDTAVY YCAREYDYWG QGTLVTVSSA  240
STKGPSVFPL APSSKSTSGG TAALGCLVKD YFPEPVTVSW NSGALTSGVH TFPAVLQSSG  300
LYSLSSVVTV PSSSLGTQTY ICNVNHKPSN TKVDKKVEPK SCDKTHTCPP CPAPEAAGAP  360
SVFLFPPKPK DTLYITREPE VTCVVVDVSH EDPEVKFNWY VDGVEVHNAK TKPREEQYNS  420
TYRVVSVLTV LHQDWLNGKE YKCKVSNKAL PAPIEKTISK AKGQPREPQV YTLPPSRDEL  480
TKNQVSLTCL VKGFYPSDIA VEWESNGQPE NNYKTTPPVL DSDGSFFLYS KLTVDKSRWQ  540
QGNVFSCSVM HEALHNHYTQ KSLSLSPG                                              568

SEQ ID NO: 139              moltype = AA   length = 568
FEATURE                     Location/Qualifiers
source                      1..568
                            mol_type = protein
                            organism = synthetic construct
SEQUENCE: 139
EVQLLESGGG LVQPGGSLRL SCAASGFTFS DYYMNWIRQA PGKGLEWVSS ISGGSTYYAD  60
SVKGRFTISR DNSENTLYLQ MNSLRAEDTA VYYCARDFGV AGWFGQFGMD VWGQGTLVTV  120
SSPLAPEVQL LESGGGLVQP GGSLRLSCAA SGFTFSSYWM SWVRQAPGKG LEWVANINQD  180
```

```
GSEKYYVDSM RGRFTISRDN SKNTLYLQMN SLRAEDTAVY YCAREYDYWG QGTLVTVSSA   240
STKGPSVFPL APSSKSTSGG TAALGCLVKD YFPEPVTVSW NSGALTSGVH TFPAVLQSSG   300
LYSLSSVVTV PSSSLGTQTY ICNVNHKPSN TKVDKKVEPK SCDKTHTCPP CPAPEAAGAP   360
SVFLFPPKPK DTLYITREPE VTCVVVDVSH EDPEVKFNWY VDGVEVHNAK TKPREEQYNS   420
TYRVVSVLTV LHQDWLNGKE YKCKVSNKAL PAPIEKTISK AKGQPREPQV YTLPPSRDEL   480
TKNQVSLTCL VKGFYPSDIA VEWESNGQPE NNYKTTPPVL DSDGSFFLYS KLTVDKSRWQ   540
QGNVFSCSVM HEALHNHYTQ KSLSLSPG                                      568

SEQ ID NO: 140          moltype = AA   length = 568
FEATURE                 Location/Qualifiers
source                  1..568
                        mol_type = protein
                        organism = synthetic construct
SEQUENCE: 140
EVQLLESGGG LVQPGGSLRL SCAASGFTFS DYYMNWIRQA PGKGLEWVSS ISGGSTYYAD   60
SVKGRFTISR DNSENTLYLQ MNSLRAEDTA VYYCARDFGV AGWFGQFGMD VWGQGTLVTV   120
SSPLAPEVQL LESGGGLVQP GGSLRLSCAA SGFTFSSYWM SWVRQAPGKG LEWVANIKQD   180
GSEKNYVDSM RGRFTISRDN SKNTLYLQMN SLRAEDTAVY YCAREFDFWG QGTLVTVSSA   240
STKGPSVFPL APSSKSTSGG TAALGCLVKD YFPEPVTVSW NSGALTSGVH TFPAVLQSSG   300
LYSLSSVVTV PSSSLGTQTY ICNVNHKPSN TKVDKKVEPK SCDKTHTCPP CPAPEAAGAP   360
SVFLFPPKPK DTLYITREPE VTCVVVDVSH EDPEVKFNWY VDGVEVHNAK TKPREEQYNS   420
TYRVVSVLTV LHQDWLNGKE YKCKVSNKAL PAPIEKTISK AKGQPREPQV YTLPPSRDEL   480
TKNQVSLTCL VKGFYPSDIA VEWESNGQPE NNYKTTPPVL DSDGSFFLYS KLTVDKSRWQ   540
QGNVFSCSVM HEALHNHYTQ KSLSLSPG                                      568

SEQ ID NO: 141          moltype = AA   length = 568
FEATURE                 Location/Qualifiers
source                  1..568
                        mol_type = protein
                        organism = synthetic construct
SEQUENCE: 141
EVQLLESGGG LVQPGGSLRL SCAASGFTFS DYYMNWIRQA PGKGLEWVSS ISGGSTYYAD   60
SVKGRFTISR DNSENTLYLQ MNSLRAEDTA VYYCARDFGV AGWFGYYGMD VWGQGTLVTV   120
SSPLAPEVQL LESGGGLVQP GGSLRLSCAA SGFTFSSYWM SWVRQAPGKG LEWVANIKQD   180
GSEKNYVDSM RGRFTISRDN SKNTLYLQMN SLRAEDTAVY YCAREFDFWG QGTLVTVSSA   240
STKGPSVFPL APSSKSTSGG TAALGCLVKD YFPEPVTVSW NSGALTSGVH TFPAVLQSSG   300
LYSLSSVVTV PSSSLGTQTY ICNVNHKPSN TKVDKKVEPK SCDKTHTCPP CPAPEAAGAP   360
SVFLFPPKPK DTLYITREPE VTCVVVDVSH EDPEVKFNWY VDGVEVHNAK TKPREEQYNS   420
TYRVVSVLTV LHQDWLNGKE YKCKVSNKAL PAPIEKTISK AKGQPREPQV YTLPPSRDEL   480
TKNQVSLTCL VKGFYPSDIA VEWESNGQPE NNYKTTPPVL DSDGSFFLYS KLTVDKSRWQ   540
QGNVFSCSVM HEALHNHYTQ KSLSLSPG                                      568

SEQ ID NO: 142          moltype = AA   length = 568
FEATURE                 Location/Qualifiers
source                  1..568
                        mol_type = protein
                        organism = synthetic construct
SEQUENCE: 142
EVQLLESGGG LVQPGGSLRL SCAASGFTFS DYYMTWIRQA PGKGLEWVSS ISGGSTYYAD   60
SRKGRFTISR DNSENTLYLQ MNSLRAEDTA VYYCARDFGV AGWFGQYGMD VWGQGTLVTV   120
SSPLAPEVQL LESGGGLVQP GGSLRLSCAA SGFTFSSYAM SWVRQAPGKG LEWVANINQD   180
GSEKNYVDSM RGRFTISRDN SKNTLYLQMN SLRAEDTAVY YCAREFDYWG QGTLVTVSSA   240
STKGPSVFPL APSSKSTSGG TAALGCLVKD YFPEPVTVSW NSGALTSGVH TFPAVLQSSG   300
LYSLSSVVTV PSSSLGTQTY ICNVNHKPSN TKVDKKVEPK SCDKTHTCPP CPAPEAAGAP   360
SVFLFPPKPK DTLMISRTPE VTCVVVDVSH EDPEVKFNWY VDGVEVHNAK TKPREEQYNS   420
TYRVVSVLTV LHQDWLNGKE YKCKVSNKAL PAPIEKTISK AKGQPREPQV YTLPPSRDEL   480
TKNQVSLTCL VKGFYPSDIA VEWESNGQPE NNYKTTPPVL DSDGSFFLYS KLTVDKSRWQ   540
QGNVFSCSVL HEALHSHYTQ KSLSLSPG                                      568

SEQ ID NO: 143          moltype = AA   length = 335
FEATURE                 Location/Qualifiers
source                  1..335
                        mol_type = protein
                        organism = synthetic construct
SEQUENCE: 143
QSVLTQPPSA SGTPGQRVTI SCTGSSSNIG AGYDVHWYQQ LPGTAPKLLI YRSNQRPSGV   60
PDRFSGSKSG TSASLAISGL RSEDEADYYC SSYAGNYNLV FGGGTKLTVL PAPNLLGGPQ   120
SVLAQPPSAS GTPGQRVTIS CSGSSSNIGS NYVYWYQQLP GTAPKLLIYG NNKRPSGVPD   180
RFSGSKSGTS ASLAISGLRS EDEADYYCAA WDDSLNGRVF GGGTKLTVLG QPKAAPSVTL   240
FPPSSEELQA NKATLVCLIS DFYPGAVTVA WKADSSPVKA GVETTTPSKQ SNNKYAASSY   300
LSLTPEQWKS HRSYSCQVTH EGSTVEKTVA PTECS                             335

SEQ ID NO: 144          moltype = AA   length = 330
FEATURE                 Location/Qualifiers
source                  1..330
                        mol_type = protein
                        organism = synthetic construct
SEQUENCE: 144
QSVLTQPPSA SGTPGQRVTI SCTGSSSNIG AGYDVHWYQQ LPGTAPKLLI YRSNQRPSGV   60
```

```
PDRFSGSKSG TSASLAISGL RSEDEADYYC SSYAGLYNLV FGGGTKLTVL PLAPQSVLAQ  120
PPSASGTPGQ RVTISCSGSS SNIGSNYVYW YQQLPGTAPK LLIYGNNKRP SGVPDRFSGS  180
KSGTSASLAI SGLRSEDEAD YYCAAWDDSL SGRVFGGGTK LTVLGQPKAA PSVTLFPPSS  240
EELQANKATL VCLISDFYPG AVTVAWKADS SPVKAGVETT TPSKQSNNKY AASSYLSLTP  300
EQWKSHRSYS CQVTHEGSTV EKTVAPTECS                                   330

SEQ ID NO: 145          moltype = AA  length = 342
FEATURE                 Location/Qualifiers
source                  1..342
                        mol_type = protein
                        organism = synthetic construct
SEQUENCE: 145
EVQLLESGGG LVQPGGSLRL SCAASGFTFS DYYMTWIRQA PGKGLEWVSS ISGGSTYYAD  60
SRKGRFTISR DNSENTLYLQ MNSLRAEDTA VYYCARDFGV AGWFGQYGMD VWGQGTLVTV  120
SSPLAPQSVL AQPPSASGTP GQRVTISCSG SSSNIGSNYV YWYQQLPGTA PKLLIYGNNK  180
RPSGVPDRFS GSKSGTSASL AISGLRSEDE ADYYCAAWDD SLSGRVFGGG TKLTVLGQPK  240
AAPSVTLFPP SSEELQANKA TLVCLISDFY PGAVTVAWKA DSSPVKAGVE TTTPSKQSNN  300
KYAASSYLSL TPEQWKSHRS YSCQVTHEGS TVEKTVAPTE CS                     342

SEQ ID NO: 146          moltype = AA  length = 330
FEATURE                 Location/Qualifiers
source                  1..330
                        mol_type = protein
                        organism = synthetic construct
SEQUENCE: 146
QSVLTQPPSA SGTPGQRVTI SCTGSSSNIG AGYDVHWYQQ LPGTAPKLLI YRSNQRPSGV  60
PDRFSGSKSG TSASLAISGL RSEDEADYYC SSYAGNYNLV FGGGTKLTVL PLAPQSVLAQ  120
PPSASGTPGQ RVTISCSGSS SNIGSNYVYW YQQLPGTAPK LLIYGNNKRP SGVPDRFSGS  180
KSGTSASLAI SGLRSEDEAD YYCAAWDDSL NGRVFGGGTK LTVLGQPKAA PSVTLFPPSS  240
EELQANKATL VCLISDFYPG AVTVAWKADS SPVKAGVETT TPSKQSNNKY AASSYLSLTP  300
EQWKSHRSYS CQVTHEGSTV EKTVAPTECS                                   330

SEQ ID NO: 147          moltype = AA  length = 728
FEATURE                 Location/Qualifiers
source                  1..728
                        mol_type = protein
                        organism = synthetic construct
SEQUENCE: 147
EVQLLESGGG LVQPGGSLRL SCAASGFTFS DYYMTWIRQA PGKGLEWVSS ISGGSTYYAD  60
SRKGRFTISR DNSENTLYLQ MNSLRAEDTA VYYCARDFGV AGWFGQYGMD VWGQGTLVTV  120
SSGGGGSGGG GSGGGGSQSV LTQPPSASGT PGQRVTISCT GSSSNIGAGY DVHWYQQLPG  180
TAPKLLIYRS NQRPSGVPDR FSGSKSGTSA SLAISGLRSE DEADYYCSSY AGNYNLVFGG  240
GTKLTVLDKG PSVFPLAPEP KSSEVQLLES GGGLVQPGGS LRLSCAASGF TFSSYAMSWV  300
RQAPGKGLEW VANINQDGSE KNYVDSMRGR FTISRDNSKN TLYLQMNSLR AEDTAVYYCA  360
REFDYWGQGT LVTVTSSGGG GSGGGGSGGG GSQSVLAQPP SASGTPGQRV TISCSGSSSN  420
IGSNYVYWYQ QLPGTAPKLL IYGNNKRPSG VPDRFSGSKS GTSASLAISG LRSEDEADYY  480
CAAWDDSLNG RVFGGGTKLT VLDKTHTCPP CPAPEAAGAP SVFLFPPKPK DTLMISRTPE  540
VTCVVVDVSH EDPEVKFNWY VDGVEVHNAK TKPREEQYNS TYRVVSVLTV LHQDWLNGKE  600
YKCKVSNKAL PAPIEKTISK AKGQPREPQV YTLPPSRDEL TKNQVSLTCL VKGFYPSDIA  660
VEWESNGQPE NNYKTTPPVL DSDGSFFLYS KLTVDKSRWQ QGNVFSCSVM HEALHNHYTQ  720
KSLSLSPG                                                          728

SEQ ID NO: 148          moltype = AA  length = 723
FEATURE                 Location/Qualifiers
source                  1..723
                        mol_type = protein
                        organism = synthetic construct
SEQUENCE: 148
EVQLLESGGG LVQPGGSLRL SCAASGFTFS DYYMTWIRQA PGKGLEWVSS ISGGSTYYAD  60
SRKGRFTISR DNSENTLYLQ MNSLRAEDTA VYYCARDFGV AGWFGQYGMD VWGQGTLVTV  120
SSGGGGSGGG GSGGGGSQSV LTQPPSASGT PGQRVTISCT GSSSNIGAGY DVHWYQQLPG  180
TAPKLLIYRS NQRPSGVPDR FSGSKSGTSA SLAISGLRSE DEADYYCSSY AGNYNLVFGG  240
GTKLTVLDKG PSVFPLAPEP KSSEVQLLES GGGLVQPGGS LRLSCAASGF TFSSYAMSWV  300
RQAPGKGLEW VANINQDGSE KNYVDSMRGR FTISRDNSKN TLYLQMNSLR AEDTAVYYCA  360
REFDYWGQGT LVTVTSSGGG GSGGGGSGGG GSQSVLAQPP SASGTPGQRV TISCSGSSSN  420
IGSNYVYWYQ QLPGTAPKLL IYGNNKRPSG VPDRFSGSKS GTSASLAISG LRSEDEADYY  480
CAAWDDSLNG RVFGGGTKLT VLCPPCPAPE AAGAPSVFLF PPKPKDTLMI SRTPEVTCVV  540
VDVSHEDPEV KFNWYVDGVE VHNAKTKPRE EQYNSTYRVV SVLTVLHQDW LNGKEYKCKV  600
SNKALPAPIE KTISKAKGQP REPQVYTLPP SRDELTKNQV SLTCLVKGFY PSDIAVEWES  660
NGQPENNYKT TPPVLDSDGS FFLYSKLTVD KSRWQQGNVF SCSVMHEALH NHYTQKSLSL  720
SPG                                                               723

SEQ ID NO: 149          moltype = AA  length = 574
FEATURE                 Location/Qualifiers
source                  1..574
                        mol_type = protein
                        organism = synthetic construct
SEQUENCE: 149
EVQLLESGGG LVQPGGSLRL SCAASGFTFS DYYMTWIRQA PGKGLEWVSS ISGGSTYYAD  60
```

```
SRKGRFTISR DNSENTLYLQ MNSLRAEDTA VYYCARDFGV AGWFGQYGMD VWGQGTLVTV    120
SSPAPNLLGG PEVQLLESGG GLVQPGGSLR LSCAASGFTF SSYAMSWVRQ APGKGLEWVA    180
NINQDGSEKN YVDSMRGRFT ISRDNSKNTL YLQMNSLRAE DTAVYYCARE FDYWGQGTLV    240
TVTSSASTKG PSVFPLAPSS KSTSGGTAAL GCLVKDYFPE PVTVSWNSGA LTSGVHTFPA    300
VLQSSGLYSL SSVVTVPSSS LGTQTYICNV NHKPSNTKVD KKVEPKSCDK THTCPPCPAP    360
EAAGAPSVFL FPPKPKDTLM ISRTPEVTCV VVDVSHEDPE VKFNWYVDGV EVHNAKTKPR    420
EEQYNSTYRV VSVLTVLHQD WLNGKEYKCK VSNKALPAPI EKTISKAKGQ PREPQVYTLP    480
PSRDELTKNQ VSLTCLVKGF YPSDIAVEWE SNGQPENNYK TTPPVLDSDG SFFLYSKLTV    540
DKSRWQQGNV FSCSVMHEAL HNHYTQKSLS LSPG                                574

SEQ ID NO: 150              moltype = AA   length = 335
FEATURE                     Location/Qualifiers
source                      1..335
                            mol_type = protein
                            organism = synthetic construct
SEQUENCE: 150
QSVLTQPPSA SGTPGQRVTI SCTGSSSNIG AGYDVHWYQQ LPGTAPKLLI YRSNQRPSGV    60
PDRFSGSKSG TSASLAISGL RSEDEADYYC SSYAGNYNLV FGGGTKLTVL PAPNLLGGPQ    120
SVLAQPPSAS GTPGQRVTIS CSGSSSNIGS NYVYWYQQLP GTAPKLLIYG NNKRPSGVPD    180
RFSGSKSGTS ASLAISGLRS EDEADYYCAA WDDSLNGRVF GGGTKLTVLG QPKAAPSVTL    240
FPPSSEELQA NKATLVCLIS DFYPGAVTVA WKADSSPVKA GVETTTPSKQ SNNKYAASSY    300
LSLTPEQWKS HRSYSCQVTH EGSTVEKTVA PTECS                               335

SEQ ID NO: 151              moltype = AA   length = 569
FEATURE                     Location/Qualifiers
source                      1..569
                            mol_type = protein
                            organism = synthetic construct
SEQUENCE: 151
EVQLLESGGG LVQPGGSLRL SCAASGFTFS DYYMTWIRQA PGKGLEWVSS ISGGSTYYAD    60
SRKGRFTISR DNSENTLYLQ MNSLRAEDTA VYYCARDFGV AGWFGQYGMD VWGQGTLVTV    120
SSPLAPEVQL LESGGGLVQP GGSLRLSCAA SGFTFSSYAM SWVRQAPGKG LEWVANINQD    180
GSEKNYVDSM RGRFTISRDN SKNTLYLQMN SLRAEDTAVY YCAREFDYWG QGTLVTVTSS    240
ASTKGPSVFP LAPSSKSTSG GTAALGCLVK DYFPEPVTVS WNSGALTSGV HTFPAVLQSS    300
GLYSLSSVVT VPSSSLGTQT YICNVNHKPS NTKVDKKVEP KSCDKTHTCP PCPAPEAAGA    360
PSVFLFPPKP KDTLMISRTP EVTCVVVDVS HEDPEVKFNW YVDGVEVHNA KTKPREEQYN    420
STYRVVSVLT VLHQDWLNGK EYKCKVSNKA LPAPIEKTIS KAKGQPREPQ VYTLPPSRDE    480
LTKNQVSLTC LVKGFYPSDI AVEWESNGQP ENNYKTTPPV LDSDGSFFLY SKLTVDKSRW    540
QQGNVFSCSV MHEALHNHYT QKSLSLSPG                                      569

SEQ ID NO: 152              moltype = AA   length = 330
FEATURE                     Location/Qualifiers
source                      1..330
                            mol_type = protein
                            organism = synthetic construct
SEQUENCE: 152
QSVLTQPPSA SGTPGQRVTI SCTGSSSNIG AGYDVHWYQQ LPGTAPKLLI YRSNQRPSGV    60
PDRFSGSKSG TSASLAISGL RSEDEADYYC SSYAGNYNLV FGGGTKLTVL PLAPQSVLAQ    120
PPSASGTPGQ RVTISCSGSS SNIGSNYVYW YQQLPGTAPK LLIYGNNKRP SGVPDRFSGS    180
KSGTSASLAI SGLRSEDEAD YYCAAWDDSL NGRVFGGGTK LTVLGQPKAA PSVTLFPPSS    240
EELQANKATL VCLISDFYPG AVTVAWKADS SPVKAGVETT TPSKQSNNKY AASSYLSLTP    300
EQWKSHRSYS CQVTHEGSTV EKTVAPTECS                                     330

SEQ ID NO: 153              moltype = AA   length = 569
FEATURE                     Location/Qualifiers
source                      1..569
                            mol_type = protein
                            organism = synthetic construct
SEQUENCE: 153
EVQLLESGGG LVQPGGSLRL SCAASGFTFS DYYMTWIRQA PGKGLEWVSS ISGGSTYYAD    60
SRKGRFTISR DNSENTLYLQ MNSLRAEDTA VYYCARDFGV AGWFGQYGMD VWGQGTLVTV    120
SSPLAPEVQL LESGGGLVQP GGSLRLSCAA SGFTFSSYAM SWVRQAPGKG LEWVANINQD    180
GSEKNYVDSM RGRFTISRDN SKNTLYLQMN SLRAEDTAVY YCAREFDYWG QGTLVTVTSS    240
ASTKGPSVFP LAPSSKSTSG GTAALGCLVK DYFPEPVTVS WNSGALTSGV HTFPAVLQSS    300
GLYSLSSVVT VPSSSLGTQT YICNVNHKPS NTKVDKKVEP KSCDKTHTCP PCPAPEAAGA    360
PSVFLFPPKP KDTLMISRTP EVTCVVVDVS HEDPEVKFNW YVDGVEVHNA KTKPREEQYN    420
STYRVVSVLT VLHQDWLNGK EYKCKVSNKA LPAPIEKTIS KAKGQPREPQ VYTLPPSRDE    480
LTKNQVSLTC LVKGFYPSDI AVEWESNGQP ENNYKTTPPV LDSDGSFFLY SKLTVDKSRW    540
QQGNVFSCSV MHEALHNHYT QKSLSLSPG                                      569

SEQ ID NO: 154              moltype = AA   length = 335
FEATURE                     Location/Qualifiers
source                      1..335
                            mol_type = protein
                            organism = synthetic construct
SEQUENCE: 154
QSVLTQPPSA SGTPGQRVTI SCTGSSSNIG AGYDVHWYQQ LPGTAPKLLI YRSNQRPSGV    60
PDRFSGSKSG TSASLAISGL RSEDEADYYC SSYAGNYNLV FGGGTKLTVL PAPNLLGGPQ    120
SVLAQPPSAS GTPGQRVTIS CSGSSSNIGS NYVYWYQQLP GTAPKLLIYG NNKRPSGVPD    180
```

```
RFSGSKSGTS ASLAISGLRS EDEADYYCAA WDDSLNGRVF GGGTKLTVLG QPKAAPSVTL      240
FPPSSEELQA NKATLVCLIS DFYPGAVTVA WKADSSPVKA GVETTTPSKQ SNNKYAASSY      300
LSLTPEQWKS HRSYSCQVTH EGSTVEKTVA PTECS                                 335

SEQ ID NO: 155              moltype = AA   length = 574
FEATURE                     Location/Qualifiers
source                      1..574
                            mol_type = protein
                            organism = synthetic construct
SEQUENCE: 155
EVQLLESGGG LVQPGGSLRL SCAASGFTFS DYYMTWIRQA PGKGLEWVSS ISGGSTYYAD      60
SRKGRFTISR DNSENTLYLQ MNSLRAEDTA VYYCARDFGV AGWFGQYGMD VWGQGTLVTV      120
SSPAPNLLGG PEVQLLESGG GLVQPGGSLR LSCAASGFTF SSYAMSWVRQ APGKGLEWVA      180
NINQDGSEKN YVDSMRGRFT ISRDNSKNTL YLQMNSLRAE DTAVYYCARE FDYWGQGTLV      240
TVTSSASTKG PSVFPLAPSS KSTSGGTAAL GCLVKDYFPE PVTVSWNSGA LTSGVHTFPA      300
VLQSSGLYSL SSVVTVPSSS LGTQTYICNV NHKPSNTKVD KKVEPKSCDK THTCPPCPAP      360
EAAGAPSVFL FPPKPKDTLM ISRTPEVTCV VVDVSHEDPE VKFNWYVDGV EVHNAKTKPR      420
EEQYNSTYRV VSVLTVLHQD WLNGKEYKCK VSNKALPAPI EKTISKAKGQ PREPQVYTLP      480
PSRDELTKNQ VSLTCLVKGF YPSDIAVEWE SNGQPENNYK TTPPVLDSDG SFFLYSKLTV      540
DKSRWQQGNV FSCSVMHEAL HNHYTQKSLS LSPG                                  574

SEQ ID NO: 156              moltype = AA   length = 330
FEATURE                     Location/Qualifiers
source                      1..330
                            mol_type = protein
                            organism = synthetic construct
SEQUENCE: 156
QSVLTQPPSA SGTPGQRVTI SCTGSSSNIG AGYDVHWYQQ LPGTAPKLLI YRSNQRPSGV      60
PDRFSGSKSG TSASLAISGL RSEDEADYYC SSYAGNYNLV FGGGTKLTVL PLAPQSVLAQ      120
PPSASGTPGQ RVTISCSGSS SNIGSNYVYW YQQLPGTAPK LLIYGNNKRP SGVPDRFSGS      180
KSGTSASLAI SGLRSEDEAD YYCAAWDDSL NGRVFGGGTK LTVLGQPKAA PSVTLFPPSS      240
EELQANKATL VCLISDFYPG AVTVAWKADS SPVKAGVETT TPSKQSNNKY AASSYLSLTP      300
EQWKSHRSYS CQVTHEGSTV EKTVAPTECS                                       330

SEQ ID NO: 157              moltype = AA   length = 9
FEATURE                     Location/Qualifiers
source                      1..9
                            mol_type = protein
                            organism = synthetic construct
SEQUENCE: 157
PAPNLLGGP                                                              9

SEQ ID NO: 158              moltype = AA   length = 5
FEATURE                     Location/Qualifiers
source                      1..5
                            mol_type = protein
                            organism = synthetic construct
SEQUENCE: 158
SYAMS                                                                 5

SEQ ID NO: 159              moltype = AA   length = 17
FEATURE                     Location/Qualifiers
source                      1..17
                            mol_type = protein
                            organism = synthetic construct
SEQUENCE: 159
NINQDGSEKN YVDSMRG                                                     17

SEQ ID NO: 160              moltype = AA   length = 4
FEATURE                     Location/Qualifiers
source                      1..4
                            mol_type = protein
                            organism = synthetic construct
SEQUENCE: 160
EFDY                                                                  4

SEQ ID NO: 161              moltype = AA   length = 13
FEATURE                     Location/Qualifiers
source                      1..13
                            mol_type = protein
                            organism = synthetic construct
SEQUENCE: 161
SGSSSNIGSN YVY                                                         13

SEQ ID NO: 162              moltype = AA   length = 7
FEATURE                     Location/Qualifiers
source                      1..7
                            mol_type = protein
                            organism = synthetic construct
```

```
SEQUENCE: 162
GNNKRPS                                                                7

SEQ ID NO: 163          moltype = AA  length = 11
FEATURE                 Location/Qualifiers
source                  1..11
                        mol_type = protein
                        organism = synthetic construct
SEQUENCE: 163
AAWDDSLNGR V                                                           11

SEQ ID NO: 164          moltype = AA  length = 5
FEATURE                 Location/Qualifiers
source                  1..5
                        mol_type = protein
                        organism = synthetic construct
SEQUENCE: 164
SYWMS                                                                  5

SEQ ID NO: 165          moltype = AA  length = 17
FEATURE                 Location/Qualifiers
source                  1..17
                        mol_type = protein
                        organism = synthetic construct
SEQUENCE: 165
NINQDGSEKY YVDSMRG                                                     17

SEQ ID NO: 166          moltype = AA  length = 4
FEATURE                 Location/Qualifiers
source                  1..4
                        mol_type = protein
                        organism = synthetic construct
SEQUENCE: 166
EYDY                                                                   4

SEQ ID NO: 167          moltype = AA  length = 17
FEATURE                 Location/Qualifiers
source                  1..17
                        mol_type = protein
                        organism = synthetic construct
SEQUENCE: 167
NIKQDGSEKN YVDSMRG                                                     17

SEQ ID NO: 168          moltype = AA  length = 4
FEATURE                 Location/Qualifiers
source                  1..4
                        mol_type = protein
                        organism = synthetic construct
SEQUENCE: 168
EFDF                                                                   4

SEQ ID NO: 169          moltype = AA  length = 5
FEATURE                 Location/Qualifiers
source                  1..5
                        mol_type = protein
                        organism = synthetic construct
SEQUENCE: 169
DYYMT                                                                  5

SEQ ID NO: 170          moltype = AA  length = 15
FEATURE                 Location/Qualifiers
source                  1..15
                        mol_type = protein
                        organism = synthetic construct
SEQUENCE: 170
SISGGSTYYA DSRKG                                                       15

SEQ ID NO: 171          moltype = AA  length = 15
FEATURE                 Location/Qualifiers
source                  1..15
                        mol_type = protein
                        organism = synthetic construct
SEQUENCE: 171
DFGVAGWFGQ YGMDV                                                       15

SEQ ID NO: 172          moltype = AA  length = 14
FEATURE                 Location/Qualifiers
source                  1..14
                        mol_type = protein
```

-continued

```
                        organism = synthetic construct
SEQUENCE: 172
TGSSSNIGAG YDVH                                                14

SEQ ID NO: 173          moltype = AA   length = 7
FEATURE                 Location/Qualifiers
source                  1..7
                        mol_type = protein
                        organism = synthetic construct
SEQUENCE: 173
RSNQRPS                                                        7

SEQ ID NO: 174          moltype = AA   length = 10
FEATURE                 Location/Qualifiers
source                  1..10
                        mol_type = protein
                        organism = synthetic construct
SEQUENCE: 174
SSYAGNYNLV                                                     10

SEQ ID NO: 175          moltype = AA   length = 5
FEATURE                 Location/Qualifiers
source                  1..5
                        mol_type = protein
                        organism = synthetic construct
SEQUENCE: 175
DYYMN                                                          5

SEQ ID NO: 176          moltype = AA   length = 15
FEATURE                 Location/Qualifiers
source                  1..15
                        mol_type = protein
                        organism = synthetic construct
SEQUENCE: 176
SISGGSTYYA DSVKG                                               15

SEQ ID NO: 177          moltype = AA   length = 15
FEATURE                 Location/Qualifiers
source                  1..15
                        mol_type = protein
                        organism = synthetic construct
SEQUENCE: 177
DFGVAGWFGQ FGMDV                                               15

SEQ ID NO: 178          moltype = AA   length = 5
FEATURE                 Location/Qualifiers
source                  1..5
                        mol_type = protein
                        organism = synthetic construct
SEQUENCE: 178
SCDKT                                                          5

SEQ ID NO: 179          moltype = AA   length = 15
FEATURE                 Location/Qualifiers
source                  1..15
                        mol_type = protein
                        organism = synthetic construct
SEQUENCE: 179
DFGVAGWFGY YGMDV                                               15

SEQ ID NO: 180          moltype = AA   length = 113
FEATURE                 Location/Qualifiers
source                  1..113
                        mol_type = protein
                        organism = synthetic construct
SEQUENCE: 180
EVQLLESGGG LVQPGGSLRL SCAASGFTFS SYAMSWVRQA PGKGLEWVAN INQDGSEKNY  60
VDSMRGRFTI SRDNSKNTLY LQMNSLRAED TAVYYCAREF DYWGQGTLVT VSS        113

SEQ ID NO: 181          moltype = AA   length = 110
FEATURE                 Location/Qualifiers
source                  1..110
                        mol_type = protein
                        organism = synthetic construct
SEQUENCE: 181
QSVLAQPPSA SGTPGQRVTI SCSGSSSNIG SNYVYWYQQL PGTAPKLLIY GNNKRPSGVP  60
DRFSGSKSGT SASLAISGLR SEDEADYYCA AWDDSLNGRV FGGGTKLTVL          110

SEQ ID NO: 182          moltype = AA   length = 113
```

-continued

```
FEATURE                Location/Qualifiers
source                 1..113
                       mol_type = protein
                       organism = synthetic construct
SEQUENCE: 182
EVQLLESGGG LVQPGGSLRL SCAASGFTFS SYWMSWVRQA PGKGLEWVAN INQDGSEKYY  60
VDSMRGRFTI SRDNSKNTLY LQMNSLRAED TAVYYCAREY DYWGQGTLVT VSS         113

SEQ ID NO: 183         moltype = AA   length = 113
FEATURE                Location/Qualifiers
source                 1..113
                       mol_type = protein
                       organism = synthetic construct
SEQUENCE: 183
EVQLLESGGG LVQPGGSLRL SCAASGFTFS SYWMSWVRQA PGKGLEWVAN IKQDGSEKNY  60
VDSMRGRFTI SRDNSKNTLY LQMNSLRAED TAVYYCAREF DFWGQGTLVT VSS         113

SEQ ID NO: 184         moltype = AA   length = 122
FEATURE                Location/Qualifiers
source                 1..122
                       mol_type = protein
                       organism = synthetic construct
SEQUENCE: 184
EVQLLESGGG LVQPGGSLRL SCAASGFTFS DYYMTWIRQA PGKGLEWVSS ISGGSTYYAD  60
SRKGRFTISR DNSENTLYLQ MNSLRAEDTA VYYCARDFGV AGWFGQYGMD VWGQGTLVTV  120
SS                                                                 122

SEQ ID NO: 185         moltype = AA   length = 110
FEATURE                Location/Qualifiers
source                 1..110
                       mol_type = protein
                       organism = synthetic construct
SEQUENCE: 185
QSVLTQPPSA SGTPGQRVTI SCTGSSSNIG AGYDVHWYQQ LPGTAPKLLI YRSNQRPSGV  60
PDRFSGSKSG TSASLAISGL RSEDEADYYC SSYAGNYNLV FGGGTKLTVL            110

SEQ ID NO: 186         moltype = AA   length = 122
FEATURE                Location/Qualifiers
source                 1..122
                       mol_type = protein
                       organism = synthetic construct
SEQUENCE: 186
EVQLLESGGG LVQPGGSLRL SCAASGFTFS DYYMNWIRQA PGKGLEWVSS ISGGSTYYAD  60
SVKGRFTISR DNSENTLYLQ MNSLRAEDTA VYYCARDFGV AGWFGQFGMD VWGQGTLVTV  120
SS                                                                 122

SEQ ID NO: 187         moltype = AA   length = 122
FEATURE                Location/Qualifiers
source                 1..122
                       mol_type = protein
                       organism = synthetic construct
SEQUENCE: 187
EVQLLESGGG LVQPGGSLRL SCAASGFTFS DYYMNWIRQA PGKGLEWVSS ISGGSTYYAD  60
SVKGRFTISR DNSENTLYLQ MNSLRAEDTA VYYCARDFGV AGWFGYYGMD VWGQGTLVTV  120
SS                                                                 122

SEQ ID NO: 188         moltype = AA   length = 6
FEATURE                Location/Qualifiers
source                 1..6
                       mol_type = protein
                       organism = synthetic construct
SEQUENCE: 188
GGGGSG                                                               6

SEQ ID NO: 189         moltype = AA   length = 5
FEATURE                Location/Qualifiers
source                 1..5
                       mol_type = protein
                       organism = synthetic construct
SEQUENCE: 189
GGSGG                                                                5

SEQ ID NO: 190         moltype = AA   length = 10
FEATURE                Location/Qualifiers
source                 1..10
                       mol_type = protein
                       organism = synthetic construct
SEQUENCE: 190
GGGGSGGGGS                                                          10
```

-continued

```
SEQ ID NO: 191              moltype = AA   length = 9
FEATURE                     Location/Qualifiers
source                      1..9
                            mol_type = protein
                            organism = synthetic construct
SEQUENCE: 191
GGSGGGGSG                                                            9

SEQ ID NO: 192              moltype = AA   length = 10
FEATURE                     Location/Qualifiers
source                      1..10
                            mol_type = protein
                            organism = synthetic construct
SEQUENCE: 192
GGSGGGGSGS                                                           10

SEQ ID NO: 193              moltype = AA   length = 13
FEATURE                     Location/Qualifiers
source                      1..13
                            mol_type = protein
                            organism = synthetic construct
SEQUENCE: 193
GGSGGGGSGG GGS                                                       13

SEQ ID NO: 194              moltype = AA   length = 14
FEATURE                     Location/Qualifiers
source                      1..14
                            mol_type = protein
                            organism = synthetic construct
SEQUENCE: 194
GGGGSGGGGS GGGG                                                      14

SEQ ID NO: 195              moltype = AA   length = 15
FEATURE                     Location/Qualifiers
source                      1..15
                            mol_type = protein
                            organism = synthetic construct
SEQUENCE: 195
GGGGSGGGGS GGGGS                                                     15

SEQ ID NO: 196              moltype = AA   length = 27
FEATURE                     Location/Qualifiers
source                      1..27
                            mol_type = protein
                            organism = synthetic construct
SEQUENCE: 196
RADAAAAGGG GSGGGGSGGG GSGGGGS                                        27

SEQ ID NO: 197              moltype = AA   length = 6
FEATURE                     Location/Qualifiers
source                      1..6
                            mol_type = protein
                            organism = synthetic construct
SEQUENCE: 197
ASTKGP                                                               6

SEQ ID NO: 198              moltype = AA   length = 13
FEATURE                     Location/Qualifiers
source                      1..13
                            mol_type = protein
                            organism = synthetic construct
SEQUENCE: 198
ASTKGPSVFP LAP                                                       13

SEQ ID NO: 199              moltype = AA   length = 5
FEATURE                     Location/Qualifiers
source                      1..5
                            mol_type = protein
                            organism = synthetic construct
SEQUENCE: 199
TVAAP                                                                5

SEQ ID NO: 200              moltype = AA   length = 6
FEATURE                     Location/Qualifiers
source                      1..6
                            mol_type = protein
                            organism = synthetic construct
SEQUENCE: 200
```

-continued

```
RTVAAP                                                          6

SEQ ID NO: 201           moltype = AA   length = 12
FEATURE                  Location/Qualifiers
source                   1..12
                         mol_type = protein
                         organism = synthetic construct

SEQUENCE: 201
TVAAPSVFIF PP                                                   12

SEQ ID NO: 202           moltype = AA   length = 13
FEATURE                  Location/Qualifiers
source                   1..13
                         mol_type = protein
                         organism = synthetic construct

SEQUENCE: 202
RTVAAPSVFI FPP                                                  13

SEQ ID NO: 203           moltype = AA   length = 16
FEATURE                  Location/Qualifiers
source                   1..16
                         mol_type = protein
                         organism = synthetic construct

SEQUENCE: 203
AKTTPKLEEG EFSEAR                                               16

SEQ ID NO: 204           moltype = AA   length = 17
FEATURE                  Location/Qualifiers
source                   1..17
                         mol_type = protein
                         organism = synthetic construct

SEQUENCE: 204
AKTTPKLEEG EFSEARV                                              17

SEQ ID NO: 205           moltype = AA   length = 9
FEATURE                  Location/Qualifiers
source                   1..9
                         mol_type = protein
                         organism = synthetic construct

SEQUENCE: 205
AKTTPKLGG                                                       9

SEQ ID NO: 206           moltype = AA   length = 10
FEATURE                  Location/Qualifiers
source                   1..10
                         mol_type = protein
                         organism = synthetic construct

SEQUENCE: 206
SAKTTPKLGG                                                      10

SEQ ID NO: 207           moltype = AA   length = 6
FEATURE                  Location/Qualifiers
source                   1..6
                         mol_type = protein
                         organism = synthetic construct

SEQUENCE: 207
SAKTTP                                                          6

SEQ ID NO: 208           moltype = AA   length = 6
FEATURE                  Location/Qualifiers
source                   1..6
                         mol_type = protein
                         organism = synthetic construct

SEQUENCE: 208
RADAAP                                                          6

SEQ ID NO: 209           moltype = AA   length = 9
FEATURE                  Location/Qualifiers
source                   1..9
                         mol_type = protein
                         organism = synthetic construct

SEQUENCE: 209
RADAAPTVS                                                       9

SEQ ID NO: 210           moltype = AA   length = 12
FEATURE                  Location/Qualifiers
source                   1..12
                         mol_type = protein
                         organism = synthetic construct
```

```
SEQUENCE: 210
RADAAAAGGP GS                                                          12

SEQ ID NO: 211        moltype = AA  length = 18
FEATURE               Location/Qualifiers
source                1..18
                      mol_type = protein
                      organism = synthetic construct
SEQUENCE: 211
SAKTTPKLEE GEFSEARV                                                    18

SEQ ID NO: 212        moltype = AA  length = 5
FEATURE               Location/Qualifiers
source                1..5
                      mol_type = protein
                      organism = synthetic construct
SEQUENCE: 212
ADAAP                                                                   5

SEQ ID NO: 213        moltype = AA  length = 12
FEATURE               Location/Qualifiers
source                1..12
                      mol_type = protein
                      organism = synthetic construct
SEQUENCE: 213
ADAAPTVSIF PP                                                          12

SEQ ID NO: 214        moltype = AA  length = 6
FEATURE               Location/Qualifiers
source                1..6
                      mol_type = protein
                      organism = synthetic construct
SEQUENCE: 214
QPKAAP                                                                  6

SEQ ID NO: 215        moltype = AA  length = 13
FEATURE               Location/Qualifiers
source                1..13
                      mol_type = protein
                      organism = synthetic construct
SEQUENCE: 215
QPKAAPSVTL FPP                                                         13

SEQ ID NO: 216        moltype = AA  length = 6
FEATURE               Location/Qualifiers
source                1..6
                      mol_type = protein
                      organism = synthetic construct
SEQUENCE: 216
AKTTPP                                                                  6

SEQ ID NO: 217        moltype = AA  length = 13
FEATURE               Location/Qualifiers
source                1..13
                      mol_type = protein
                      organism = synthetic construct
SEQUENCE: 217
AKTTPPSVTP LAP                                                         13

SEQ ID NO: 218        moltype = AA  length = 6
FEATURE               Location/Qualifiers
source                1..6
                      mol_type = protein
                      organism = synthetic construct
SEQUENCE: 218
AKTTAP                                                                  6

SEQ ID NO: 219        moltype = AA  length = 13
FEATURE               Location/Qualifiers
source                1..13
                      mol_type = protein
                      organism = synthetic construct
SEQUENCE: 219
AKTTAPSVYP LAP                                                         13

SEQ ID NO: 220        moltype = AA  length = 15
FEATURE               Location/Qualifiers
source                1..15
                      mol_type = protein
```

```
                        organism = synthetic construct
SEQUENCE: 220
GENKVEYAPA LMALS                                                15

SEQ ID NO: 221          moltype = AA   length = 15
FEATURE                 Location/Qualifiers
source                  1..15
                        mol_type = protein
                        organism = synthetic construct
SEQUENCE: 221
GPAKELTPLK EAKVS                                                15

SEQ ID NO: 222          moltype = AA   length = 15
FEATURE                 Location/Qualifiers
source                  1..15
                        mol_type = protein
                        organism = synthetic construct
SEQUENCE: 222
GHEAAAVMQV QYPAS                                                15

SEQ ID NO: 223          moltype = AA   length = 6
FEATURE                 Location/Qualifiers
source                  1..6
                        mol_type = protein
                        organism = synthetic construct
SEQUENCE: 223
KSCDKT                                                          6
```

The invention claimed is:

1. A multispecific binding protein comprising at least a first polypeptide chain and a second polypeptide chain, wherein said first polypeptide chain comprises a first variable heavy chain domain (VH1) linked to a second variable heavy chain domain (VH2) via at least one modified hinge region and wherein said second polypeptide chain comprises a first variable light chain domain (VL1) linked to a second variable light chain domain (VL2), wherein:

the VH1 binds specifically to BMPRII and the VH2 binds specifically to ALK1; or the VH1 binds specifically to ALK1 and the VH2 binds specifically to BMPRII;

and wherein the VH1 or VH2 binding to ALK1 comprises an HCDR1 amino acid sequence of SYWMS (SEQ ID NO:164), an HCDR2 amino acid sequence of NINQDGSEKYYVDSMRG (SEQ ID NO:165), and an HCDR3 amino acid sequence of EYDY (SEQ ID NO:166); and the VL binding to ALK1 comprises an LCDR1 amino acid sequence of SGSSSNIGSNYVY (SEQ ID NO:161), an LCDR2 amino acid sequence of GNNKRPS (SEQ ID NO:162), and an LCDR3 amino acid sequence of AAWDDSLNGRV (SEQ ID NO: 163); and the VH1 or VH2 binding to BMPRII comprises an HCDR1 amino acid sequence of DYYMN (SEQ ID NO:175), an HCDR2 amino acid sequence of SISGG-STYYADSVKG (SEQ ID NO: 176), and an HCDR3 amino acid sequence of DFGVAGWFGQFGMDV (SEQ ID NO: 177); and the VL binding to BMPRII comprises an LCDR1 amino acid sequence of TGSSSNIGAGYDVH (SEQ ID NO:172), an LCDR2 amino acid sequence of RSNQRPS (SEQ ID NO: 173), and an LCDR3 amino acid sequence of SSYAG-NYNLV (SEQ ID NO:174).

2. The multispecific binding protein of claim 1, wherein the VL1 is linked to the VL2 via at least one modified hinge region.

3. The multispecific binding protein of claim 1, wherein one or both of VH1 and VH2 is truncated at the C-terminal end.

4. The multispecific binding protein of claim 3, wherein the C-terminal end is truncated by at least one residue.

5. The multispecific binding protein of claim 3, wherein the C-terminal end is truncated by at least two residues.

6. The multispecific binding protein of claim 3, wherein the SS amino acid residues of the C-terminal end are deleted.

7. The multispecific binding protein of claim 1, wherein the first polypeptide chain is of the formula VH1-HX1-VH2-C-Fc, wherein:

VH1 is the first heavy chain variable domain;

VH2 is the second heavy chain variable domain;

C is a heavy chain constant domain;

HX1 is a modified hinge region linker; and

Fc is an Fc region; and the second polypeptide chain is of the formula VL1-LX1-VL2-C, wherein:

VL1 is the first light chain variable domain;

VL2 is v second light chain variable domain;

C is a light chain constant domain; and

LX1 is a modified hinge region linker.

8. The multispecific binding protein of claim 1, wherein the modified hinge region comprises; i) an upper hinge region of up to 7 amino acids in length or is absent; and ii) a lower hinge region.

9. The multispecific binding protein of claim 1, wherein the modified hinge region comprises or consists of an amino acid sequence of PLAP (SEQ ID NO:2) or PAPNLLGGP (SEQ ID NO:157).

10. The multispecific binding protein of claim 1, comprising at least a first polypeptide chain and a second polypeptide chain, wherein said first polypeptide chain comprises a first variable heavy chain domain (VH1) linked to a second variable heavy chain domain (VH2) and wherein said second polypeptide chain comprises a first variable light chain domain (VL1) linked to a second variable light chain domain (VL2), wherein:

the VH1 binds specifically to BMPRII and the VH2 binds specifically to ALK1; or the VH1 binds specifically to ALK1 and the VH2 binds specifically to BMPRII and, wherein:

the VH binding to ALK1 comprises an amino acid sequence of EVQLLESGGGLVQPGGSLRLS-CAASGFTFSSYWMSWVRQAPGKGLEWVAN-INQDGSEK YYVDSMRGRFTISRDNSKNT-LYLQMNSLRAEDTAVYYCAREYDYWGQGTLVTVSS (SE Q ID NO: 182), or an amino acid sequence with at least 90% identity thereto; and the VL binding to ALK1 comprises an amino acid sequence of QSVLAQPP-SASGTPGQRVTISCSGSSSNIG-SNYVYWYQQLPGTAPKLLIYGNNKRPSGVP DRFSGSKSGTSASLAISGLRSEDEADYY-CAAWDDSLNGRVFGGGTKLTVL (SEQ ID NO: 181), or an amino acid sequence with at least 90% identity thereto; and/or the VH binding to BMPRII comprises an amino acid sequence of EVQLLESGGGLVQPGGSLRLS-CAASGFTFSDYYMNWIRQAPGKGLEWVSSIS-GGSTYYA DSVKGRFTISRDNSENTLYLQMNSL-RAEDTAVYYCARDFGVAGWFGQFGMDVWGQGT LVTVSS (SEQ ID NO:186), or an amino acid sequence with at least 90% identity thereto; and the VL binding to BMPRII comprises an amino acid sequence of QSVLTQPP-SASGTPGQRVTISCTGSSSNI-GAGYDVHWYQQLPGTAPKLLIYRSNQRPSGV PDRFSGSKSGTSASLAISGLRSEDEADYYCSSY-AGNYNLVFGGGTKLTVL (SEQ ID NO: 185), or an amino acid sequence with at least 90% identity thereto.

11. The multispecific binding protein of claim 10, wherein:

the VH binding to BMPRII comprises an amino acid sequence of EVQLLESGGGLVQPGGSLRLS-CAASGFTFSDYYMNWIRQAPGKGLEWVSSIS-GGSTYYA DSVKGRFTISRDNSENTLYLQMNSL-RAEDTAVYYCARDFGVAGWFGQFGMDVWGQGT LVTVSS (SEQ ID NO:186), or an amino acid sequence with at least 90% identity thereto; and the VL binding to BMPRII comprises an amino acid sequence of QSVLTQPP-SASGTPGQRVTISCTGSSSNI-GAGYDVHWYQQLPGTAPKLLIYRSNQRPSGV PDRFSGSKSGTSASLAISGLRSEDEADYYCSSY-AGNYNLVFGGGTKLTVL (SEQ ID NO: 185), or an amino acid sequence with at least 90% identity thereto.

12. The multispecific binding protein of claim 1, wherein the first polypeptide chain comprises an amino acid sequence of SEQ ID NO: 139, and the second polypeptide chain comprises an amino acid sequence of SEQ ID NO: 146.

13. A multispecific binding protein comprising a first polypeptide chain and a second polypeptide chain, wherein the first polypeptide chain and second polypeptide chain each comprise, from N-terminus to C-terminus, a first single chain variable fragment (scFv) linked to a second scFv, wherein:

the first scFv binds specifically to BMPRII and the second scFv binds specifically to ALK1; or the first scFv binds specifically to ALK1 and the second scFv binds specifically to BMPRII;

wherein the scFv binding to ALK1 comprises a VH domain and a VL domain the VH domain comprising an HCDR1 amino acid sequence of SYWMS (SEQ ID NO:164), an HCDR2 amino acid sequence of NINQDGSEKYYVDSMRG (SEQ ID NO:165), and an HCDR3 amino acid sequence of EYDY (SEQ ID NO:166); and the VL domain comprising an an LCDR1 amino acid sequence of SGSSSNIGSNYVY (SEQ ID NO:161), an LCDR2 amino acid sequence of GNNK-RPS (SEQ ID NO:162), and an LCDR3 amino acid sequence of AAWDDSLNGRV (SEQ ID NO:163) and wherein the scFv binding to BMPRII comprises a VH domain comprising an HCDR1 amino acid sequence of DYYMN (SEQ ID NO:175), an HCDR2 amino acid sequence of SISGGSTYYADSVKG (SEQ ID NO:176), and an HCDR3 amino acid sequence of DFGVAGWFGQFGMDV (SEQ ID NO:177); and a VL domain comprising an LCDR1 amino acid sequence of TGSSSNIGAGYDVH (SEQ ID NO:172), an LCDR2 amino acid sequence of RSNQRPS (SEQ ID NO:173), and an LCDR3 amino acid sequence of SSYAGNYNLV (SEQ ID NO: 174).

14. The multispecific binding protein of claim 13, wherein the first scFv is linked to the second scFv via at least one modified hinge region.

15. The multispecific binding protein of claim 1, wherein the first polypeptide chain further comprises a heavy chain constant region.

16. The multispecific binding protein of claim 15, wherein the heavy chain constant region comprises an alanine (A) at amino acid positions 234, 235, and/or 237, according to EU numbering.

17. A multispecific binding protein comprising at least a first binding moiety and a second binding moiety, wherein said first binding moiety comprises a first variable heavy chain domain (VH1) and first variable light chain domain (VL1), and the second binding moiety comprising a second variable heavy chain domain (VH2) and a second variable light chain domain (VL2), wherein:

the VH1 binds specifically to BMPRII and the VH2 binds specifically to ALK1; or the VH1 binds specifically to ALK1 and the VH2 binds specifically to BMPRII;

and wherein the VH1 or VH2 binding to ALK1 comprises an HCDR1 amino acid sequence of SYWMS (SEQ ID NO:164), an HCDR2 amino acid sequence of NINQDGSEKYYVDSMRG (SEQ ID NO:165), and an HCDR3 amino acid sequence of EYDY (SEQ ID NO:166); and the VL binding to ALK1 comprises an LCDR1 amino acid sequence of SGSSSNIGSNYVY (SEQ ID NO:161), an LCDR2 amino acid sequence of GNNKRPS (SEQ ID NO:162), and an LCDR3 amino acid sequence of AAWDDSLNGRV (SEQ ID NO: 163); and the VH1 or VH2 binding to BMPRII comprises an HCDR1 amino acid sequence of DYYMN (SEQ ID NO:175), an HCDR2 amino acid sequence of SISGG-STYYADSVKG (SEQ ID NO: 176), and an HCDR3 amino acid sequence of DFGVAGWFGQFGMDV (SEQ ID NO: 177); and the VL1 or VL2 binding to BMPRII comprises an LCDR1 amino acid sequence of TGSSSNIGAGYDVH (SEQ ID NO:172), an LCDR2 amino acid sequence of RSNQRPS (SEQ ID NO: 173), and an LCDR3 amino acid sequence of SSYAG-NYNLV (SEQ ID NO:174), and wherein the multispecific binding protein further comprises a heavy chain constant region wherein the heavy chain constant region comprises heterodimerization mutations to promote heterodimerization of the first binding moiety with the second binding moiety.

18. The multispecific binding protein of claim 17, wherein the heterodimerization mutations are Knob-in-Hole (KIH) mutations.

19. The multispecific binding protein of claim 18, wherein the first heavy chain constant region comprises an amino acid substitution at position 366, 368, or 407 which produced a hole, and the second heavy chain constant region comprises an amino acid substitution at position 366 which produce a knob.

20. The multispecific binding protein of claim 19, wherein the first heavy chain constant region comprises the amino acid substitution T366S, L368A, or Y407V, and the second heavy chain constant region comprises the amino acid substitution T366W.

21. The multispecific binding protein of claim 17, wherein the heterodimerization mutations are charge stabilization mutations.

22. The multispecific binding protein of claim 21, wherein the first heavy chain constant region comprises the amino acid substitution N297K, and the second heavy chain constant region comprises the amino acid substitution N297D.

23. The multispecific binding protein of claim 21, wherein the first heavy chain constant region comprises the amino acid substitution T299K, and the second heavy chain constant region comprises the amino acid substitution T299D.

24. The multispecific binding protein of claim 17, wherein the heterodimerization mutations comprise an engineered disulfide bond.

25. The multispecific binding protein of claim 24, wherein the engineered disulfide bond is formed by a first heavy chain constant region comprising the amino acid substitution Y349C, and a second heavy chain constant region comprising the amino acid substitution S354C.

26. The multispecific binding protein of claim 24, wherein the engineered disulfide bond is formed by a C-terminal extension peptide fused to the C-terminus of each of the first heavy chain constant region and the second heavy chain constant region.

27. The multispecific binding protein of claim 17, wherein at least one heavy chain constant region comprises one or more mutations to promote increased half-life.

28. The multispecific binding protein of claim 27, wherein at least one heavy chain constant region comprises one or more substitutions at amino acid positions 428 or 434, according to EU numbering.

29. The multispecific binding protein of claim 28, wherein at least one heavy chain constant region comprises a M428L and N434S substitution, according to EU numbering.

30. A pharmaceutical composition comprising the multispecific binding protein of claim 1 and a pharmaceutically acceptable carrier.

\* \* \* \* \*